US006403320B1

(12) United States Patent
Read et al.

(10) Patent No.: US 6,403,320 B1
(45) Date of Patent: *Jun. 11, 2002

(54) SUPPORT BOUND PROBES AND METHODS OF ANALYSIS USING THE SAME

(75) Inventors: J. Leighton Read; Stephen P. A. Fodor, both of Palo Alto; Lubert Stryer, Stanford, all of CA (US); Michael C. Pirrung, Chapel Hill, NC (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/684,377

(22) Filed: Oct. 5, 2000

Related U.S. Application Data

(63) Continuation of application No. 09/557,875, filed on Apr. 24, 2000, which is a continuation of application No. 09/056,927, filed on Apr. 8, 1998, now Pat. No. 6,197,506, which is a continuation of application No. 08/670,118, filed on Jun. 25, 1996, now Pat. No. 5,800,992, which is a division of application No. 08/168,904, filed on Dec. 15, 1993, now abandoned, which is a continuation of application No. 07/624,114, filed on Dec. 6, 1990, now abandoned, which is a continuation-in-part of application No. 07/492,462, filed on Mar. 7, 1990, now Pat. No. 5,143,854, and a continuation-in-part of application No. 07/362,901, filed on Jun. 7, 1989, now abandoned, application No. 09/684,377, which is a continuation-in-part of application No. 08/348,471, filed on Nov. 30, 1994, which is a continuation of application No. 07/805,727, filed on Dec. 6, 1991, now Pat. No. 5,424,186, which is a continuation-in-part of application No. 07/624,120, filed on Dec. 6, 1990, which is a continuation-in-part of application No. 07/492,462, filed on Mar. 7, 1990, now Pat. No. 5,143,854, which is a continuation-in-part of application No. 07/362,901, filed on Jun. 7, 1989, now abandoned.

(51) Int. Cl.[7] ............................................. C12Q 1/68
(52) U.S. Cl. ..................................... 435/6; 435/7.1
(58) Field of Search ........................... 435/6, 91.2, 7.1

(56) References Cited

U.S. PATENT DOCUMENTS

| | | |
|---|---|---|
| 3,730,844 A | 5/1973 | Gilham et al. ......... 195/103.5 R |
| 3,849,137 A | 11/1974 | Barzynski et al. ............. 96/97 |
| 3,862,056 A | 1/1975 | Hartman .................... 252/511 |
| 3,939,350 A | 2/1976 | Kronick et al. ............. 250/365 |
| 4,072,576 A | 2/1978 | Arwin et al. ......... 195/103.5 R |
| 4,121,222 A | 10/1978 | Diebold et al. ................ 347/7 |
| 4,180,739 A | 12/1979 | Abu-Shumays ......... 250/461 R |
| 4,216,245 A | 8/1980 | Johnson .................... 427/2.13 |
| 4,238,757 A | 12/1980 | Schenck ....................... 357/25 |
| 4,269,933 A | 5/1981 | Pazos ......................... 430/291 |
| 4,314,821 A | 2/1982 | Rice ......................... 23/230 B |
| 4,327,073 A | 4/1982 | Huang ........................... 424/1 |
| 4,339,528 A | 7/1982 | Goldman ................... 430/323 |
| 4,342,905 A | 8/1982 | Fujii et al. .................. 250/201 |
| 4,373,071 A | 2/1983 | Itakura ....................... 525/375 |
| 4,395,486 A | 7/1983 | Wilson et al. ................. 435/6 |
| 4,405,771 A | 9/1983 | Jagur ......................... 528/266 |
| 4,444,878 A | 4/1984 | Paulus ........................... 435/7 |
| 4,444,892 A | 4/1984 | Malmros ..................... 436/528 |
| 4,448,534 A | 5/1984 | Wertz et al. ................. 356/435 |
| 4,458,066 A | 7/1984 | Caruthers et al. ............. 536/27 |
| 4,477,556 A | 10/1984 | Dueber et al. ............. 430/281 |
| 4,478,967 A | 10/1984 | Eian et al. .................... 524/86 |
| 4,483,920 A | 11/1984 | Gillespie et al. ............... 435/6 |
| 4,500,707 A | 2/1985 | Caruthers et al. ............. 536/27 |
| 4,500,919 A | 2/1985 | Schreiber ..................... 358/78 |
| 4,516,833 A | 5/1985 | Fusek .................... 350/162.12 |
| 4,517,338 A | 5/1985 | Urdea et al. ............. 525/54.11 |
| 4,533,682 A | 8/1985 | Tortorello et al. .......... 523/414 |
| 4,537,861 A | 8/1985 | Elings et al. ............... 436/518 |
| 4,542,102 A | 9/1985 | Dattagupta et al. ............ 435/6 |
| 4,555,490 A | 11/1985 | Merril ......................... 436/86 |
| 4,556,643 A | 12/1985 | Paau et al. ..................... 435/5 |
| 4,562,157 A | 12/1985 | Lowe et al. ................. 435/291 |
| 4,563,419 A | 1/1986 | Ranki et al. .................... 435/6 |
| 4,569,967 A | 2/1986 | Kornreich et al. ....... 525/54.11 |
| 4,580,895 A | 4/1986 | Patel ........................... 356/39 |
| 4,584,277 A | 4/1986 | Ullman ....................... 436/501 |
| 4,588,682 A | 5/1986 | Groet et al. .................... 435/6 |
| 4,591,570 A | 5/1986 | Chang ....................... 435/7.24 |
| 4,598,049 A | 7/1986 | Zelinka et al. .............. 422/116 |
| 4,613,566 A | 9/1986 | Potter ............................ 435/6 |
| 4,624,915 A | 11/1986 | Schindler et al. .............. 435/4 |
| 4,626,684 A | 12/1986 | Landa ......................... 250/328 |
| 4,631,211 A | 12/1986 | Houghten .................... 428/35 |
| 4,637,861 A | 1/1987 | Krull et al. ................. 204/1 T |
| 4,656,127 A | 4/1987 | Mundy ........................... 435/6 |

(List continued on next page.)

FOREIGN PATENT DOCUMENTS

| | | |
|---|---|---|
| CA | 1284931 | 6/1991 |
| DE | 2242394 | 3/1974 |
| DE | 3440141 | 5/1986 |

(List continued on next page.)

OTHER PUBLICATIONS

Ballard et al., "Imaging Genes, Chromosomes and Nuclear Structures Using Laser–Scanning Confocal Microscopy," SPIE, *Bioimaging and Two–Dimensional Spectroscopy*, 1205:1–10, conference held Jan. 18–19, 1990, Los Angeles, CA., abstract also included (1990).

Burns et al., "Scanning Silt Aperture Confocal Microscopy for Three–Dimensional Imaging," *Scanning*, 12:156–160 (1990).

Frank et al., "Facile and rapid 'spot–synthesis' of large numbers of peptides on membrane sheets," *Proc. 21st European Pept. Symp.*, Platja D'Oro, Spain, Sep 2–8, 1990.

(List continued on next page.)

Primary Examiner—Eggerton A. Campbell
(74) Attorney, Agent, or Firm—Philip L. McGarrigle; Joseph Liebschuetz; Lisa Treannie

(57) ABSTRACT

The present invention provides methods and apparatus for sequencing, fingerprinting and mapping biological macromolecules, typically biological polymers. The methods make use of a plurality of sequence specific recognition reagents which can also be used for classification of biological samples, and to characterize their sources.

131 Claims, 27 Drawing Sheets

U.S. PATENT DOCUMENTS

| | | |
|---|---|---|
| 4,670,380 A | 6/1987 | Dattagupta ................... 435/6 |
| 4,677,054 A | 6/1987 | White et al. ................... 435/6 |
| 4,681,859 A | 7/1987 | Kramer ...................... 436/501 |
| 4,683,195 A | 7/1987 | Mullis et al. ................. 435/6 |
| 4,683,202 A | 7/1987 | Mullis ......................... 435/91 |
| 4,689,405 A | 8/1987 | Frank et al. ................... 536/27 |
| 4,704,353 A | 11/1987 | Humphries et al. ............ 435/4 |
| 4,711,955 A | 12/1987 | Ward et al. ................... 536/29 |
| 4,713,326 A | 12/1987 | Dattagupta et al. ............ 435/6 |
| 4,713,347 A | 12/1987 | Mitchell et al. ............ 436/501 |
| 4,715,413 A | 12/1987 | Backlund et al. ............ 141/94 |
| 4,715,929 A | 12/1987 | Ogawa ..................... 156/643 |
| 4,716,106 A | 12/1987 | Chiswell ...................... 435/6 |
| 4,719,179 A | 1/1988 | Barany .................... 435/172.1 |
| 4,719,615 A | 1/1988 | Feyrer et al. ............... 369/284 |
| 4,722,906 A | 2/1988 | Guire ........................ 436/501 |
| 4,728,502 A | 3/1988 | Hamill ...................... 422/116 |
| 4,728,591 A | 3/1988 | Clark et al. ................... 430/5 |
| 4,731,325 A | 3/1988 | Palva et al. ................... 435/6 |
| 4,737,344 A | 4/1988 | Koizumi et al. ............ 422/100 |
| 4,755,458 A | 7/1988 | Rabbani et al. ................ 435/5 |
| 4,758,727 A | 7/1988 | Tomei et al. ............ 250/458.1 |
| 4,762,881 A | 8/1988 | Kauer ..................... 525/54.11 |
| 4,766,062 A | 8/1988 | Diamond et al. ............. 435/6 |
| 4,767,700 A | 8/1988 | Wallace ........................ 435/6 |
| 4,777,019 A | 10/1988 | Dandekar ................... 422/68 |
| 4,780,504 A | 10/1988 | Buendia et al. .......... 525/54.11 |
| 4,786,170 A | 11/1988 | Groebler ................... 356/318 |
| 4,786,684 A | 11/1988 | Glass ....................... 525/54.1 |
| 4,794,150 A | 12/1988 | Steel ....................... 525/54.11 |
| 4,808,508 A | 2/1989 | Platzer ...................... 430/143 |
| 4,810,869 A | 3/1989 | Yabe et al. ................. 250/201 |
| 4,811,062 A | 3/1989 | Tabata et al. ............... 356/152 |
| 4,811,218 A | 3/1989 | Hunkapiller et al. ........ 204/461 |
| 4,812,512 A | 3/1989 | Buendia et al. .......... 525/54.11 |
| 4,820,630 A | 4/1989 | Taub ........................... 435/5 |
| 4,822,566 A | 4/1989 | Newman ..................... 422/68 |
| 4,833,092 A | 5/1989 | Geysen ...................... 436/501 |
| 4,844,617 A | 7/1989 | Kelderman et al. ......... 356/372 |
| 4,846,552 A | 7/1989 | Veldkamp et al. ....... 350/162.2 |
| 4,849,513 A | 7/1989 | Smith et al. ................. 536/27 |
| 4,855,225 A | 8/1989 | Fung et al. ..................... 435/6 |
| 4,865,990 A | 9/1989 | Stead et al. ................. 435/803 |
| 4,868,103 A | 9/1989 | Stavrianopoulos et al. .... 435/5 |
| 4,874,500 A | 10/1989 | Madou et al. .............. 204/412 |
| 4,877,745 A | 10/1989 | Hayes et al. ................ 436/166 |
| 4,886,741 A | 12/1989 | Schwartz ...................... 435/5 |
| 4,888,278 A | 12/1989 | Singer et al. ................... 435/6 |
| 4,921,805 A | 5/1990 | Gebeyehu et al. ........... 435/270 |
| 4,923,901 A | 5/1990 | Koester et al. ............... 521/53 |
| 4,925,785 A | 5/1990 | Wang et al. ................... 435/6 |
| 4,931,384 A | 6/1990 | Layton et al. ............. 435/7.31 |
| 4,946,942 A | 8/1990 | Fuller et al. ................ 530/335 |
| 4,965,188 A | 10/1990 | Mullis et al. .................. 435/6 |
| 4,973,493 A | 11/1990 | Guire ............................ 427/2 |
| 4,979,959 A | 12/1990 | Guire ......................... 623/66 |
| 4,981,783 A | 1/1991 | Augenlicht .................... 435/6 |
| 4,981,985 A | 1/1991 | Kaplan et al. ................ 556/50 |
| 4,984,100 A | 1/1991 | Takayama et al. ........... 360/49 |
| 4,987,065 A | 1/1991 | Stavrianopoulos et al. .... 435/5 |
| 4,988,617 A | 1/1991 | Landegren et al. ............ 435/6 |
| 4,992,383 A | 2/1991 | Farnsworth ................. 436/89 |
| 4,994,373 A | 2/1991 | Stavrianopoulos et al. .... 435/5 |
| 5,002,867 A | 3/1991 | Macevicz ...................... 435/6 |
| 5,006,464 A | 4/1991 | Chu et al. ................... 435/7.1 |
| 5,011,770 A | 4/1991 | Kung et al. .................... 435/6 |
| 5,013,669 A | 5/1991 | Peters, Jr. et al. .......... 436/518 |
| 5,021,550 A | 6/1991 | Zeiger ....................... 530/334 |
| 5,026,773 A | 6/1991 | Steel ....................... 525/54.11 |
| 5,026,840 A | 6/1991 | Dattagupta et al. ........... 536/27 |
| 5,028,525 A | 7/1991 | Gray et al. ..................... 435/6 |
| 5,028,545 A | 7/1991 | Soini .......................... 436/501 |
| 5,037,882 A | 8/1991 | Steel ....................... 525/54.11 |
| 5,043,265 A | 8/1991 | Tanke et al. ................... 435/6 |
| 5,047,524 A | 9/1991 | Andrus et al. ................ 536/27 |
| 5,064,754 A | 11/1991 | Mills ............................. 435/6 |
| 5,077,085 A | 12/1991 | Schnur et al. ................ 427/98 |
| 5,077,210 A | 12/1991 | Eigler et al. ................ 435/176 |
| 5,079,600 A | 1/1992 | Schnur et al. ................. 357/4 |
| 5,081,584 A | 1/1992 | Omichinski et al. ........ 364/497 |
| 5,082,830 A | 1/1992 | Brakel et al. ................. 514/44 |
| 5,091,652 A | 2/1992 | Mathies et al. .......... 250/458.1 |
| 5,096,807 A | 3/1992 | Leaback ........................ 435/6 |
| 5,100,626 A | 3/1992 | Levin ......................... 422/100 |
| 5,100,777 A | 3/1992 | Chang ..................... 435/7.24 |
| 5,112,962 A | 5/1992 | Letsinger et al. ............. 536/27 |
| 5,141,813 A | 8/1992 | Nelson ...................... 428/402 |
| 5,143,854 A | 9/1992 | Pirrung et al. .............. 436/518 |
| 5,149,625 A | 9/1992 | Church et al. ................. 435/6 |
| 5,153,319 A | 10/1992 | Caruthers et al. ............. 536/27 |
| 5,164,319 A | 11/1992 | Hafeman et al. ......... 435/287.1 |
| 5,171,695 A | 12/1992 | Ekins ......................... 436/501 |
| 5,188,963 A | 2/1993 | Stapleton ................. 435/288.3 |
| 5,192,980 A | 3/1993 | Dixon et al. ................ 356/326 |
| 5,200,051 A | 4/1993 | Cozzette et al. ............. 204/403 |
| 5,202,231 A | 4/1993 | Drmanac et al. ............... 435/6 |
| 5,206,137 A | 4/1993 | Ip et al. ......................... 435/6 |
| 5,215,882 A | 6/1993 | Bahl et al. ..................... 435/6 |
| 5,215,889 A | 6/1993 | Schultz ....................... 435/41 |
| 5,219,726 A | 6/1993 | Evans .......................... 435/6 |
| 5,225,326 A | 7/1993 | Bresser et al. ................. 435/6 |
| 5,232,829 A | 8/1993 | Longiaru et al. ............... 435/6 |
| 5,235,028 A | 8/1993 | Barany et al. .............. 528/335 |
| 5,242,974 A | 9/1993 | Holmes .................... 525/54.11 |
| 5,252,743 A | 10/1993 | Barrett et al. ............ 548/303.7 |
| 5,256,549 A | 10/1993 | Urdea et al. ................... 435/91 |
| 5,258,506 A | 11/1993 | Urdea et al. ............... 536/23.1 |
| 5,306,641 A | 4/1994 | Saccocio ..................... 436/85 |
| 5,310,893 A | 5/1994 | Erlich et al. .............. 536/24.31 |
| 5,324,633 A | 6/1994 | Fodor et al. ................... 435/6 |
| 5,328,824 A | 7/1994 | Ward et al. .................... 435/6 |
| 5,348,855 A | 9/1994 | Dattagupta et al. ............ 435/6 |
| 5,384,261 A | 1/1995 | Winkler et al. ............. 436/518 |
| 5,405,783 A | 4/1995 | Pirrung et al. .............. 436/518 |
| 5,424,186 A | 6/1995 | Fodor et al. ................... 435/6 |
| 5,424,188 A | 6/1995 | Schneider et al. ............. 435/6 |
| 5,432,099 A | 7/1995 | Ekins ......................... 436/518 |
| 5,436,327 A | 7/1995 | Southern et al. ......... 536/25.34 |
| 5,445,934 A | 8/1995 | Fodor et al. ................... 435/6 |
| 5,447,841 A | 9/1995 | Gray et al. .................... 435/6 |
| 5,474,796 A | 12/1995 | Brennan .................... 427/2.13 |
| 5,486,452 A | 1/1996 | Gordon et al. ................. 435/5 |
| 5,489,507 A | 2/1996 | Chehab ......................... 435/6 |
| 5,489,678 A | 2/1996 | Fodor et al. ................ 536/22.1 |
| 5,492,806 A | 2/1996 | Drmanac et al. ............... 435/5 |
| 5,494,810 A | 2/1996 | Barany et al. ............ 435/91.52 |
| 5,510,270 A | 4/1996 | Fodor et al. ................ 436/518 |
| 5,525,464 A | 6/1996 | Drmanac et al. ............... 435/6 |
| 5,527,681 A | 6/1996 | Holmes ....................... 435/6 |
| 5,552,270 A | 9/1996 | Khrapko et al. ............... 435/6 |
| 5,556,961 A | 9/1996 | Foote et al. ................ 536/27.1 |
| 5,561,071 A | 10/1996 | Hollenberg et al. ............ 437/1 |
| 5,569,584 A | 10/1996 | Augenlicht .................... 435/6 |
| 5,571,639 A | 11/1996 | Hubbell et al. ............... 430/5 |
| 5,593,839 A | 1/1997 | Hubbell et al. ................ 435/6 |
| 5,599,720 A | 2/1997 | Ekins ......................... 436/501 |
| 5,604,099 A | 2/1997 | Erlich et al. ................... 435/6 |
| 5,643,728 A | 7/1997 | Slater et al. ................... 435/6 |
| 5,653,939 A | 8/1997 | Hollis et al. ................. 422/50 |
| 5,667,667 A | 9/1997 | Southern ................... 205/687 |
| 5,667,972 A | 9/1997 | Drmanac et al. ............... 435/6 |

| | | | | | |
|---|---|---|---|---|---|
| 5,695,940 A | 12/1997 | Drmanac et al. ............... 435/6 | JP | 63-223557 | 9/1988 |
| 5,698,393 A | 12/1997 | Macioszek et al. ............ 435/5 | JP | 1-233447 | 9/1989 |
| 5,700,637 A | 12/1997 | Southern ........................ 435/6 | NO | P 913186 | 8/1991 |
| 5,707,806 A | 1/1998 | Shuber ........................... 435/6 | WO | WO 84/03151 | 8/1984 |
| 5,744,305 A | 4/1998 | Fodor et al. .................... 435/6 | WO | WO 84/03564 | 9/1984 |
| 5,776,737 A | 7/1998 | Dunn ........................ 435/91.1 | WO | WO 85/01051 | 3/1985 |
| 5,777,888 A | 7/1998 | Rine et al. .................. 364/496 | WO | WO 86/00991 | 2/1986 |
| 5,800,992 A | 9/1998 | Fodor et al. .................... 435/6 | WO | WO 86/06487 | 11/1986 |
| 5,807,522 A | 9/1998 | Brown et al. ................. 422/50 | WO | WO 87/05942 | 10/1987 |
| 5,830,645 A | 11/1998 | Pinkel et al. ................... 435/6 | WO | WO 88/01058 | 2/1988 |
| 5,843,767 A | 12/1998 | Beattie .................... 435/287.1 | WO | WO 88/04777 | 6/1988 |
| 5,846,708 A | 12/1998 | Hollis et al. ................... 435/6 | WO | WO 89/05616 | 6/1989 |
| 5,869,237 A | 2/1999 | Ward et al. .................... 435/6 | WO | WO 89/08834 | 9/1989 |
| 5,871,697 A | 2/1999 | Rothberg et al. .......... 422/68.1 | WO | WO 89/10977 | 11/1989 |
| 5,972,619 A | 10/1999 | Drmanac et al. ............... 435/6 | WO | WO 89/11548 | 11/1989 |
| 6,018,041 A | 1/2000 | Drmanac et al. .......... 536/24.3 | WO | WO 89/12819 | 12/1989 |
| 6,025,136 A | 2/2000 | Drmanac et al. ............... 435/6 | WO | WO 90/00626 | 1/1990 |
| 6,040,166 A | 3/2000 | Erlich et al. ................. 435/194 | WO | WO 90/00887 | 2/1990 |
| 6,054,270 A | 4/2000 | Southern ........................ 435/6 | WO | WO 90/15070 | 2/1990 |
| | | | WO | WO 90/03382 | 4/1990 |

FOREIGN PATENT DOCUMENTS

| | | |
|---|---|---|
| DE | 3505287 | 3/1988 |
| EP | 046 083 | 2/1982 |
| EP | 088 636 | 9/1983 |
| EP | 103 197 | 3/1984 |
| EP | 127 438 | 12/1984 |
| EP | 063 810 | 3/1986 |
| EP | 174 879 | 3/1986 |
| EP | 194 132 | 9/1986 |
| EP | 228 075 | 7/1987 |
| EP | 233 403 | 8/1987 |
| EP | 245 662 | 11/1987 |
| EP | 268 237 | 5/1988 |
| EP | 130 523 | 6/1988 |
| EP | 281 927 | 9/1988 |
| EP | 228 310 | 10/1988 |
| EP | 288 310 | 10/1988 |
| EP | 304 202 | 2/1989 |
| EP | 307 476 | 3/1989 |
| EP | 319 012 | 6/1989 |
| EP | 328 256 | 8/1989 |
| EP | 333 561 | 9/1989 |
| EP | 337 498 | 10/1989 |
| EP | 386 229 | 4/1990 |
| EP | 373 203 | 6/1990 |
| EP | 392 546 | 10/1990 |
| EP | 142 299 | 12/1990 |
| EP | 400 920 | 12/1990 |
| EP | 173 339 | 1/1992 |
| EP | 171 150 | 3/1992 |
| EP | 237 362 | 3/1992 |
| EP | 185 547 | 6/1992 |
| EP | 260 634 | 6/1992 |
| EP | 232 967 | 4/1993 |
| EP | 235 726 | 5/1993 |
| EP | 476 014 | 8/1994 |
| EP | 225 807 | 10/1994 |
| EP | 717 113 | 6/1996 |
| EP | 721 016 | 7/1996 |
| EP | 535 242 | 9/1997 |
| EP | 848 067 | 6/1998 |
| EP | 619 321 | 1/1999 |
| FR | 2559783 | 3/1988 |
| GB | 2156074 | 3/1988 |
| GB | 2196476 | 4/1988 |
| GB | 8810400.5 | 5/1988 |
| GB | 2233654 | 1/1991 |
| GB | 2248840 | 9/1992 |
| JP | 49-110601 | 10/1974 |
| JP | 60-248669 | 12/1985 |
| JP | 63-084499 | 4/1988 |

| | | |
|---|---|---|
| WO | WO 90/04652 | 5/1990 |
| WO | WO 90/05789 | 5/1990 |
| WO | WO 90/07582 | 7/1990 |
| WO | WO 91/00868 | 1/1991 |
| WO | WO 91/04266 | 4/1991 |
| WO | WO 91/07087 | 5/1991 |
| WO | WO 92/16655 | 1/1992 |
| WO | WO 92/10092 | 6/1992 |
| WO | WO 92/10588 | 6/1992 |
| WO | WO 93/02992 | 2/1993 |
| WO | WO 93/09668 | 5/1993 |
| WO | WO 88/01302 | 6/1993 |
| WO | WO 93/11262 | 6/1993 |
| WO | WO 93/17126 | 9/1993 |
| WO | WO 93/22456 | 11/1993 |
| WO | WO 93/22480 | 11/1993 |
| WO | WO 95/00530 | 1/1995 |
| WO | WO 95/11995 | 5/1995 |
| WO | WO 95/33846 | 12/1995 |
| WO | WO 96/23078 | 8/1996 |
| WO | WO 97/10365 | 3/1997 |
| WO | WO 97/17317 | 5/1997 |
| WO | WO 97/19410 | 5/1997 |
| WO | WO 97/27317 | 7/1997 |
| WO | WO 97/29212 | 8/1997 |
| WO | WO 97/31256 | 8/1997 |
| WO | WO 97/45559 | 12/1997 |
| WO | WO 98/03673 | 1/1998 |
| WO | WO 98/31836 | 7/1998 |
| YU | P-570/87 | 4/1987 |
| YU | 18617/87 | 9/1987 |

OTHER PUBLICATIONS

Southern et al., "Parallel synthesis and analysis of large numbers of related chemical compounds: applications to oligonucleotides," *J. Biotechnology*, 35:217–227 (1994).

Burns et al., "Scanning Slit Aperture Confocal Microscopy for Three–Dimensional Imaging," Scanning, vol. 12, 156–160 (1990).

Ballard, S., "Imaging Genes, Chromosomes and Nuclear Structures using Laser–Scanning Confocal Microscopy," SPIE, vol. 1205, 2–10 (1990).

Sequencing by Hybridization Workshop, listing of participants and workshop presentation summaries, from workshop held Nov. 19–20, 1991.

"A Sequencing Reality Check," *Science*, 242:1245 (1988).

"Affymax raises $25 million to develop high–speed drug discovery system," *Biotechnology News*, 10(3):7–8 (1990).

"Preparation of fluorescent–labeled DNA and its use as a probe in molecular hybridization," *Bioorg Khim*, 12(11):1508–1513 (1986).

Abbott et al., "Manipulation of the Wettability of Surfaces on the 0.1–to 1–Micrometer Scale Through Micromachining and Molecular Self–Assembly," *Science*, 257:1380–1382 (1992).

Adams et al., "Complementary DNA Sequencing: Expressed Sequence Tags and Human Genome Project," *Science*, 252(5013):1651–1656 (1991).

Adams et al., "Photolabile Chelators That "Cage" Calcium with Improved Speed of Release and Pre–Photolysis Affinity," *J. Gen. Physiol.*, p. 9a (12/86).

Adams et al., "Biologically Useful Chelators That Take Up $Ca2^{+upon\ Illumination},$" *J. Am. Chem. Soc.*, 111:7957–7968 (1989).

Ajayaghosh et al., "Solid–Phase Synthesis of N–Methyl– and N–Ethylamides of Peptides Using Photolytically Detachable ((3–Nitro–4((alkylamino)methyl)benzamido)methyl)polystyrene Resin," *J.Org.Chem.*, 55(9):2826–2829 (1990).

Ajayaghosh et al., "Solid–phase synthesis of C–terminal peptide amides using a photoremovable α–methylphenacylamido anchoring linkage," *Proc. Ind. Natl. Sci. (Chem.Sci.)*, 100(5):389–396 (1988).

Ajayaghosh et al., "Polymer–supported Solid–phase Synthesis of C–Terminal Peptide N–Methylamides Using a Modified Photoremovable 3–Nitro–4–N–methylaminomethylpolystyrene Support," *Ind.J.Chem.*, 27B:1004–1008 (1988).

Ajayaghosh et al., "Polymer–Supported Synthesis of Protected Peptide Segments on a Photosensitive o–Nitro(α–Methyl)Bromobenzyl Resin," *Tetrahedron*, 44(21):6661–6666 (1988).

Amit et al., "Photosensitive Protecting Groups of Amino Sugars and Their Use in Glycoside Synthesis. 2–Nitrobenzyloxycarbonylamino and 6–Nitroveratryloxycarbonylamino Derivatives," *J.Org.Chem.*, 39(2):192–196 (1974).

Amit et al., "Photosensitive Protecting Groups—A Review," *Israel J. Chem.*, 12(1–2):103–113 (1974).

Anand et al., "A 3.5 genome equivalent multi access YAC library: construction, characterisation, screening and storage," *Nuc. Acids Res.*, 18(8):1951–1956 (1990).

Anderson et al., "Quantitative Filter Hybridisation," chapter 3 from *Nucleic Acid Hybridization a practical approach*, pp. 73–111, Hames et al., eds., IRL Press (1985).

Applied Biosystems. Model 431A Peptide Synthesizer User's manual, Sections 2 and 6, (Aug. 15, 1989).

Arnold et al., "A Novel Universal Support for DNA & RNA Synthesis," abstract from *Federation Proceedings*, 43(7):abstract No. 3669 (1984).

Atherton et al., Solid Phase Peptide Synthesis: A Practical Approach, IRL Press, (1989), tbl. of cont., pp. vii–ix.

Augenlicht et al., "Cloning and Screening of Sequences Expressed in a Mouse Colon Tumor," *Cancer Research*, 42:1088–1093 (1982).

Augenlicht et al., "Expression of Cloned Sequences in Biopsies of Human Colonic Tissue and in Colonic Carcinoma Cells Induced to Differentiate in Vitro," *Cancer Res.*, 47:6017–6021 (1987).

Bains, W., "Hybridization Methods for DNA Sequencing," *Genomics*, 11(2):294–301 (1991).

Bains et al., "A Novel Method for Nucleic Acid Sequence Determination," *J.Theor.Biol.*, 135:303–307 (1988).

Bains, W., "Alternative Routes Through the Genome," *Biotechnology*, 8:1251–1256 (1988).

Balachander et al., "Functionalized Siloxy–Anchored Monolayers with Exposed Amino, Azido, Bromo, or Cyano Groups," *Tetrahed. Ltrs.*, 29(44):5593–5594 (1988).

Baldwin et al., "New Photolabile Phosphate Protecting Groups," *Tetrahed.*, 46(19):6879–6884 (1990).

Bannwarth et al., "Laboratory Methods, A System for the Simultaneous Chemical synthesis of Different DNA Fragments on Solid Support," *DNA*, 5(5):413–419 (1986).

Bannwarth, W., "Gene Technology: a Challenge for a Chemist," *CHIMIA*, 41(9):302–317 (1987).

Barany, F., "Genetic disease detection and DNA amplification using cloned thermostable ligase," *PNAS*, 88:189–193 (1991).

Barltrop et al., "Photosensitive Protective Groups," *Chemical Communications*, pp. 822–823 (1966).

Baringa, M., "Will 'DNA Chip' Speed Genome Initiative," *Science*, 253:1489 (1985).

Bart et al., "Microfabricated Electrohydrodynamic Pumps," *Sensors and Actuators*, A21–A23:193–197 (1990).

Bartsh et al., "Cloning of mRNA sequences from the human colon: Preliminary characterisation of defined mRNAs in normal and neoplastic tissues," *Br.J.Can.*, 54:791–798 (1986).

Baum, R., "Fledgling firm targets drug discovery process," *Chem. Eng. News*, p. 10–11 (1990).

Beltz et al., "Isolation of Multigene Families and Determination of Homologies by Filter Hybridization Methods," *Methods in Enzymology*, 100:266–285 (1983).

Benschop, Chem. Abstracts 114(26):256643 (1991).

Bhatia et al., "New Approach To Producing Patterned Biomolecular Assemblies," *J. American Chemical Society*, 114:4432–4433 (1992).

Biorad Chromatography Electrophoresis Immunochemistry Molecular Biology HPLC catalog M 1987 pp. 182.

Blawas et al., "Step–and–Repeat Photopatterning of Protein Features Using Caged–Biotin–BSA: Characterization and Resolution," *Langmuir*, 14(15):4243–4250 (1998).

Blawas, A.S., "Photopatterning of Protein Features using Caged–biotin–Bovine Serum Albumin," dissertation for Ph.D at Duke University in 1998.

Bos et al., "Amino–acid substitutions at codon 13 of the N–ras oncogene in human acute myeloid leukaemia," *Nature*, 315:726–730 (1985).

Boyle et al., "Differential distribution of long and short interspersed element sequences in the mouse genome: Chromosome karyotyping by fluorescence in situ hybridization," *PNAS*, 87:7757–7761 (1990).

Brock et al., "Rapid fluorescence detection of in situ hybridization with biotinylated bovine herpervirus–1 DNA probes," *J. Veterinary Diagnostic Invest.*, 1:34–38 (1989).

Burgi et al., "Optimization in Sample Stacking for High–Performance Capillary Electrophoresis," *Anal. Chem.*, 63:2042–2047 (1991).

Cameron et al., "Photogeneration of Organic Bases from o–Nitrobenzyl–Derived Carbamates," *J. Am. Chem. Soc.*, 113:4303–4313 (1991).

Carrano et al., "A High–Resolution, Fluorescence–Based, Semiautomated Method for DNA Fingerprinting," *Genomics*, 4:129–136 (1989).

Caruthers, M.H., "Gene Synthesis Machines: DNA Chemistry and Its Uses," *Science*, 230:281–285 (1985).

Chatterjee et al., "Inducible Alkylation of DNA Using an Oligonucleotide–Quinone Conjugate," *Am. J. Chem. Soc.*, 112:6397–6399 (1990).

Chee et al., "Accessing Genetic Information with High–Density DNA Arrays," *Science*, 274:610–614 (1996).

Chehab et al., "Detection of sicle cell anaemia mutation by colour DNA amplification," *Lancet*, 335:15–17 (1990).

Chehab et al., "Detection of specific DNA sequences by fluorescence amplification: A color complementation assay," *PNAS*, 86:9178–9182 (1989).

Chetverin et al., "Oligonucleotide Arrays: New Concepts and Possibilities," *Biotechnology*, 12:1093–1099 (1994).

Church et al., "Multiplex DNA sequencing," *Science*, 240:185–188 (1988).

Church et al., "Genomic sequencing," *PNAS*, 81:1991–1995 (1984).

Clevite Corp., Piezoelectric Technology, Data for Engineers.

Corbett et al., "Reaction of Nitroso Aromatics with Glyoxylic Acid. A New Path to Hydroxamic Acids," *J. Org. Chem.*, 45:2834–2839 (1980).

Coulsen et al., "Toward a physical map of the genome of the nematode *Caenorhabditis elegans*," *PNAS*, 83:7821–7825 (1986).

Craig et al., "Ordering of cosmid clones covering the Herpes simples virus type 1 (HSV–1) genome: a test case for fingerprinting by hybridization," *Nuc. Acid. Res.*, 18(9):2653–2660 (1990).

Cummings et al., "Photoactivable Fluorphores. 1. Synthesis and Photoactivation of o–Nitrobenzyl–Quenched Fluorescent Carbamates," *Tetrahedron Letters*, 29(1):65–68 (1988).

Dattagupta et al., "Rapid identification of Microorganisms by Nucleic Acid Hybridization after Labeling the Test Sample," *Anal. Biochem.*, 177:85–89 (1989).

Dattagupta et al., "Nucleic Acid Hybridization: a Rapid Method for the Diagnosis of Infectious Diseases," *Perspectives in Antiinfective Therapy*, eds. Jackson et al., pp. 241–247 (1988).

Dower et al., "The Search for Molecular Diversity (II): Recombinant and Synthetic Randomized Peptide Libraries," *Ann. Rep. Med. Chem.*, 26:271–280 (1991).

Diggelmann, "Investigating the VLSIPS synthesis process," Sep. 9, 1994.

Di Mauro et al., "DNA Technology in Chip Construction," *Adv. Mater.*, 5(5):384–386 (1993).

Drmanac et al., "An Algorithm for the DNA Sequence Generation from k–Tuple Word Contents of the Minimal Number of Random Fragments," *J. Biomol.Struct. Dyn.*, 8(5):1085–1102 (1991).

Drmanac et al., "Partial Sequencing by Oligo–Hybridization Concept and Applications in Genome Analysis," 1st Int. Conf. Electrophor., Supercomp., Hum. Genome pp. 60–74 (1990).

Drmanac et al., "Sequencing by Oligonucleotide Hybridization: A Promising Framework in Decoding of the Genome Program?," 1st Int. Conf. Electrophor., Supercomp., Hum. Genome pp. 47–59 (1990).

Drmanac et al., "Laboratory Methods, Reliable Hybridization of Oligonucleotides as Short as Six Nucleotides," *DNA and Cell Biol.*, 9(7):527–534 (1990).

Drmanac et al., "Sequencing of Megabase Plus DNA by Hybridization: theory of the Method," *Genomics*, 4:114–128 (1989).

Dramanac et al., "Sequencing of Megabase Plus DNA by Hybridization: Theory of the Method," abstract of presentation given at Cold Spring Harbor Symposium on Genome Mapping and Sequencing, Apr. 27, 1988 thru May 1, 1988.

Dulcey et al., "Deep UV Photochemistry of Chemisorbed Monolayers: Patterned Coplanar Molecular Assemblies," *Science*, 252:551–554 (1991).

Duncan et al., "Affinity Chromatography of a Sequence–Specific DNA Binding Protein Using Teflon–Linked Oligonucleotides," *Analytical Biochemistry*, 169:104–108 (1988).

Effenhauser et al., "Glass Chips for High–speed Capillary Electrophoresis Separations with Submicrometer Plate Heights," Anal. Chem., 65:2637–2642 (1993).

Effenhauser et al., "High–Speed Separation of Antisense Oligonucleotides on a Micromachined Capillary Electrophoresis Device," *Anal. Chem.*, 66:2949–2953 (1994).

Ekins et al., "High Specific Activity Chemiluminescent and Fluorescent Markers: their Potential Application to High Sensitivity and 'Multi–analyte' Immunoassays," *J. Bioluminescence Chemiluminescence*, 4:59–78 (1989).

Ekins et al., "Development of Microspot Multi–Analyte Ratiometric Immunoassay Using dual Fluorescent–Labelled Antibodies," *Anal. Chemica Acta*, 227:73–96 (1989).

Ekins et al., "Multianalyte Microspot Immunoassay–Microanalytical 'Compact Disk' of the Future," *Clin. Chem.*, 37(11):1955–1967 (1991).

Ekins, R.P., "Multi–analyte immunoassay*," *J. Pharmaceut. Biomedical Analysis*, 7(2):155–168 (1989).

Ekins et al., "Fluorescence Spectroscopy and its Application to a New Generation of High Sensitivity, Multi–Microspot, Multianalyte, Immunoassay," *Clin. Chim. Acta*, 194:91–114 (1990).

Elder, J.K., "Analysis of DNA Oligonucleotide Hybridization Data by Maximum Entropy," in *Maximun Entropy and Bayesian Methods*, eds. Mohammad–Djafari and Demoment, Kluwer, Dordrecht, pp. 363–371 (1992).

Ellis, R.W., "The Application of Synthetic Oligonucleotides to Molecular Biology," *Pharmaceutical Research*, 3(4):195–207 (1986).

Evans et al., "Microfabrication for Automation of Molecular processes in Human Genome Analysis," *Clin. Chem.*, 41(11):1681 (1995).

Evans et al., "Physical mapping of complex genomes by cosmid multiplex analysis," *PNAS*, 86:5030–5034 (1989).

Ezaki et al., "Small–Scale DNA Preparation for Rapid Genetic Identification of Campylobacter Species without Radioisotope," *Microbiol. Immunology*, 32(2):141–150 (1988).

Fan et al., "Mapping small DNA sequences by fluorescence in situ hybridization directly on banded metaphase chromosomes," PNAS, 87(16):6223–6227 (1990).

Fan et al., "Micromachining of Capillary Electrophoresis Injectors and Separators on Glass Chips and Evaluation of Flow at Capillary Intersections," Anal. Chem., 66:177–184 (1994).

Feinberg et al., Addendum to "A technique for Radiolabeling DNA Restriction Endonuclease Fragments to High Specific Activity," *Anal. Biochem.*, 137:266–267 (1984).

Fettinger et al., "Stacked modules for micro flow systems in chemical analysis: concept and studies using an enlarged model," *Sensors and Actuators*, B17:19–25 (1993).

Flanders et al., "A new interferometric alignment technique," *App. Phys Ltrs.*, 31(7):426–429 (1977).

Fodor et al., "Multiplexed biochemical assays with biological chips," *Nature,* 364:555–556 (1993).

Fodor et al., "Light–directed, Spatially Addressable Parallel Chemical Synthesis," *Science,* 251:767–773 (1991).

Forman et al., "Thermodynamics of Duplex Formation and Mismatch Discrimination on Photolithographically Synthesized Oligonucleotide Arrays," chapter 13 pp. 206–228 from *Molecular Modeling of Nucleic Acids,* ACS Symposium Series 682, 4/13–17/97, Leontis et al., eds.

Frank et al., "Simultaneous Multiple Peptide Synthesis Under Continuous flow Conditions on Cellulose Paper Discs as Segmental Solid Supports," *Tetrahedron,* 44(19):6031–6040 (1988).

Frank et al., "Automation of DNA Sequencing Reactions and Related Techniques: A Workstation for Micromanipulation of Liquids," *Bio/Technology,* 6:1211–1212 (1988).

Frank et al., "Simultaneous Synthesis and Biological Applications of DNA Fragments: An Efficient and Complete Methodology," *Methods in Enzymology,* 154:221–250 (1987).

Fuhr et al., "Traveling wave–driven microfabricated electrohydrodynamic pumps for liquids," *J. Micromech. Microeng.,* 4:217–226 (1994).

Fuller et al., "Urethane–Protected Amino Acid N–Carboxy Anhydrides and Their Use in Peptide Synthesis," *J. Amer. Chem. Soc.,* 112(20):7414–7416 (1990).

Furka et al., "General method for rapid synthesis of multi-component peptide mixtures," *Int. J. Peptide Protein Res.,* 37:487–493 (1991).

Furka et al., "Cornucopia of Peptides by Synthesis," 14th Int. Congress of Biochem. abst#FR:013, 7/10–15/88 Prague, Czechoslovakia.

Furka et al., "More Peptides by Less Labour," abst. 288, Int. Symp. Med. Chem., Budapest Hungary 8/15–19/88.

Gait, eds., pp. 1–115 from *Oligonucleotide Synthesis: A Practical Approach,* IRL Press, (1984).

Gazard et al., "Lithographic Technique Using Radiation–Induced Grafting of Acrylic Acid into Poly(Methyl Methacrylate) Films," *Polymer Engineering and Science,* 20(16):1069–1072 (1980).

Gergen et al., "Filter replicas and permanent collections of recombinant DNA plasmids," *Nuc. Acids Res.,* 7(8):2115–2137 (1979).

Getzoff et al., "Mechanisms of Antibody Binding to a Protein," *Science,* 235:1191–1196 (1987).

Geysen et al., "Strategies for epitope analysis using peptide synthesis," *J. Immunol. Meth.,* 102:259–274 (1987).

Geysen et al., "Use of peptide synthesis to probe viral antigens for epitopes to a resolution of a single amino acid," *PNAS,* 81:3998–4002 (1984).

Geysen et al., "A synthetic strategy for epitope mapping," from Peptides: Chem. & Biol., Proc. of 10th Am. Peptide Symp., 5/23–28/87, pp. 519–523, (1987).

Geysen, "Antigen–antibody interactions at the molecular level: adventures in peptide synthesis," *Immunol. Today,* 6(12):364–369 (1985).

Geysen et al., "Cognitive Features of Continuous Antigenic Determinants," from Synthetic Peptides: Approaches to Biological Probes, pp. 19–30, (1989).

Geysen et al., "Chemistry of Antibody Binding to a Protein," *Science,* 235:1184–1190 (1987).

Geysen et al., "The delineation of peptides able to mimic assembled epitopes," 1986 CIBA Symp., pp. 130–149.

Geysen et al., "Cognitive Features of Continuous Antigenic Determinants," *Mol. Recognit.,* 1(1):1–10 (1988).

Geysen et al., "A Prio Ri Delineation of a Peptide Which Mimics A Discontinuous Antigenic Determinant," *Mol. Immunol.,* 23(7):709–715 (1986).

Ghosh et al., "Covalent attachment of oligonucleotides to solid supports," *Nuc. Acids Res.,* 15(13):5353–5373 (1987).

Gilon et al., "Backbone Cyclization: A New Method for Conferring Conformational Constraint on Peptides," *Biopolymers,* 31(6):745–750 (1991).

Gingeras et al., "Hybridization properties of immobilized nucleic acids," *Nuc. Acids Res.,* 15(13):5373–5390 (87).

Gummerlock et al., "RAS Enzyme–Linked Immunoblot Assay Discriminates p21 Species: A Technique to Dissect Gene Family Expression," *Anal. Biochem.,* 180:158–168 (1989).

Gurney et al., "Activation of potassium current by rapid photochemically generated step increases of intracellular calcium in rat sympathetic neurons," *PNAS,* 84:3496–3500 (1987).

Haase et al., "Detection of Two Viral Genomes in Single Cells by Double–Label Hybridization in Situ and Color Microradioautography," *Science,* 227:189–192 (1985).

Hacia, et al., "Two color hybridization analysis using high density oligonucleotide arrays and energy transfer dyes," *Nuc. Acids Res.,* 26(16):3865–3866 (1998).

Hack, M.L., "Conics Formed to Make Fluid & Industrial Gas Micromachines," *Genetic Engineering News,* 15(18):1, 29 (1995).

Hagedorn et al., "Pumping of Water Solutions in Microfabricated Electrohydrodynamic Systems," from Micro Electro Mechanical Systems conference in Travemunde Germany (1992).

Hames et al., *Nuclear acid hybridization, a practical approach,* cover page and table of contents (1985).

Hanahan et al., "Plasmid Screening at High Colony Density," *Meth. Enzymology,* 100:333–342 (1983).

Hanahan et al., "Plasmid screening at high colony density," *Gene,* 10:63–67 (1980).

Haridasan et al., "Peptide Synthesis using Photolytically Cleavable 2–Nitrobenzyloxycarbonyl Protecting Group," *Proc. Indian Natn. Sci. Adad.,* 53A(6):717–728 (1987).

Harrison et al., "Capillary Electrophoresis and Sample Injection Systems Integrated on a Planar Glass Chip," *Anal. Chem.,* 64:1926–1932 (1992).

Harrison et al., "Micromachining a Miniatured Capillary Electrophoresis–Based Chemical Analysis System on a Chip," *Science,* 261:895–897 (1993).

Harrison et al., "Towards minaturized electrophoresis and chemical analysis systems on silicon: an alternative to chemical sensors*," *Sensors and Actuators,* B10:107–116 (1993).

Harrison et al., "Rapid separation of fluorescein derivatives using a micromachined capillary electrophoresis system," *Analytica Chemica Acta,* 283:361–366 (1993).

Hellberg et al., "Minimum analogue peptide sets (MAPS) for quantitative structure–activity relationships," *Int. J. Peptide Res.,* 37:414–424 (1991).

Hilser et al., "Protein and peptide mobility in capillary zone electrophoresis, A comparison of existing models and further analysis," *J. Chromatography,* 630:329–336 (1993).

Ho et al., "Highly Stable Biosensor Using an Artificial Enzyme," *Anal. Chem.,* 59:536–537 (1987).

Hochgeschwender et al., "Preferential expression of a defined T–cell receptor β–chain gene in hapten–specific cytotoxic T–cell clones," *Nature*, 322:376–378 (1986).

Hodgson, J., "Assays A La Photolithography," *Biotech.*, 9:419 (1991).

Hodgson et al., "Hybridization probe size control: optimized 'oligolabelling'," *Nuc. Acids Res.*, 15(15):6295 (1987).

Hopman et al., "Bi–color detection of two target DNAs by non–radioactive in situ hybridization*," *Histochem.*, 85:1–4 (1986).

Iwamura et al., "1–Pyrenylmethyl Esters, Photolabile Protecting Groups for Carboxylic Acids," *Tetrahedron Ltrs.*, 28(6):679–682 (1987).

Iwamura et al., "1–(α–Diazobenzyl)pyrene: A Reagent for Photolabile and Fluorescent Protection of Carboxyl Groups of Amino Acids and Peptides," *Synlett*, p. 35–36 (1991).

Jacobson et al., "Effects of Injection Schemes and Column Geometry on the Performance of Microchip Electrophoresis Devices," *Anal. Chem.*, 66:1107–1113 (1994).

Jacobsen et al., "Open Channel Electrochromatography on a Microchip," *Anal. chem.*, 66:2369–2373 (1994).

Jacobson et al., "Microchip Capillary Electrophoresis with an Integrated Postcolumn Reactor" *Anal. Chem.*, 66:3472–3476 (1994).

Jacobson et al., "Precolumn Reactions with Electrophoretic Analysis Integrated on a Microchip," *Anal. Chem.*, 66:4127–4132 (1994).

Jacobson et al., "Microfabricated chemical measurement systems," *Nature Medicine*, 1(10):1093–1096 (1995).

Jacobsen et al., "Fused Quartz Substrates for Microchip Electrophoresis," *Anal. chem.*, 67:2059–2063 (1995).

Jacobson et al., "High–Speed Separations on a Microchip," *Anal. Chem.*, 66:1114–1118 (1994).

Jacobson et al., "Microchip electrophoresis with sample stacking," *Electrophoresis*, 16:481–486 (1995).

Jayakumari, "Peptide synthesis in a triphasic medium catalysed by papain immobilized in a crosslinked polystyrene support," *Indian J. Chemistry*, 29B:514–517 (1990).

Jovin et al., "Luminescence Digital Imaging Microscopy," *Ann. Rev. Biophys. Biophys. Chem.*, 18:271–308 (1989).

Kafatos et al., "Determination of nucleic acid sequence homologies and relative concentrations by a dot hybridization procedure," *Nuc. Acids Res.*, 7(6):1541–1553 (1979).

Kaiser et al., "Peptide and Protein Synthesis by Segment Synthesis–Condensation," *Science*, 243:187–192 (1989).

Kaplan et al., "Photolabile chelators for the rapid photorelease of divalent cations," *PNAS*, 85:6571–6575 (1988).

Karube, "Micro–biosensors based on silicon fabrication technology," chapter 25 from Biosensors:Fundamentals and Applications, Turner et al., eds., Oxford Publ., 1987, pp. 471–480 (1987).

Kates et al., "A Novel, Convenient, Three–dimensional Orthogonal Strategy for Solid–Phase Synthesis of Cyclic Peptides 1–3," *Tetrahed. Letters*, 34(10):1549–1552 (1993).

Kerkof et al., "A Procedure for Making Simultaneous Determinations of the Relative Levels of Gene Transcripts in Tissues of Cells," *Anal. Biochem.*, 188:349–355 (1990).

Khrapko et al., "An Oligonucleotide hybridization approach to DNA sequencing," *FEBS Lett.*, 256(1,2):118–122 (1989).

Khrapko et al., "A method for DNA sequencing by hybridization with oligonucleotide matrix," *DNA Seq. Map.*, 1:375–388 (1991).

Kidd et al., "$\alpha_1$–Antitrypsin deficiency detection by direct analysis of the mutation in the gene," *Nature*, 304:230–234 (1983).

Kievits et al., "Rapid subchromosomal localization of cosmids by nonradioactive in situ hybridization," *Cytogenetics Cell Genetics*, 53(2–3):134–136 (1990).

Kimura et al., "An Immobilized Enzyme Membrane Fabrication Method using an Ink Jet Nozzle," *Biosensors*, 4:41–52 (1988).

Kimura et al., "An Integrated SOS/FET Multi–Biosensor," *Sensors & Actuators*, 9:373–387 (1986).

Kitazawa et al., "In situ DNA–RNA hybridization using in vivo bromodeoxyuridine–labeled DNA probe," *Histochemistry*, 92:195–199 (1989).

Kleinfeld et al., "Controlled Outgrowth of Dissociated Neurons on Patterned Substrates," *J. Neurosci.*, 8(11):4098–4120 (1988).

Knight, P., "Materials and Methods/Microsequencers for Proteins and Oligosaccharides," *Bio/Tech.*, 7:1075–76 (1989).

Kohara et al., "The Physical Map of the Whole *E. coli* Chromosome: Application of a New Strategy for Rapid Analysis and Sorting of a Large Genomic Library," *Cell*, 50:495–508 (1987).

Krile et al., "Multiplex holography with chirp–modulated binary phase–coded reference–beam masks," *Applied Opt.*, 18(1):52–56 (1979).

Labat, I., "Subfragments as an informative characteristic of the DNA molecule—computer simulation," research report submitted to the University of Belgrade College of Natural Sciences and Mathematics, (1988).

Lander et al., "Genomic Mapping by Fingerprinting Randon Clones: A Mathematical Analysis," *Genomics*, 2:231–239 (1988).

Lainer et al., "Human Lymphocyte Subpopulations Identified by Using Three–Color Immunofluorescence and Flow Cytometry of Analysis: Correlation of Leu–2, Leu–3, Leu–7, Leu–8, and Leu–11 Clee Surface Antigen Expression," *Journal of Immunology*, 132(1):151–156 (1984).

Lam et al., "A new type of synthetic peptide library for identifying ligand–binding activity," *Nature*, 354:82–84 (1991).

Laskey et al., "Messenger RNA prevalance in sea urchin embryos measured with cloned cDNAs," *PNAS*, 77(9):5317–5321 (1980).

Lee et al., "synthesis of a Polymer Surface Containing Covalently Attached Triethoxysilane Functionality Adhesion to Glass," *Macromolecules*, 21:3353–3356 (1988).

Lehrach et al., "Labeling oligonucleotides to high specific activity(I)," *Nuc. Acids Res.*, 17(12):4605–4610 (89).

Lehrach et al., "Phage Vectors—EMBL Series," *Meth. Enzymology*, 153:103–115 (1987).

Lehrach et al., "Hybridization Fingerprinting in Genome Mapping and Sequencing," *Genome Analysis vol. 1:Genetic and Physical Mapping*, Cold Spring Harbor Laboratory Press, pp. 39–81 (1990).

Levy, M.F., "Preparing Additive Printed Circuits," *IBM Tech. Discl. Bull.*, 9(11):1473 (1967).

Lewin, Benjamin, eds., *Genes*, third edition, John Wiley & Sons, cover page, preface and table of contents, (1987).

Lichter et al., "High–Resolution Mapping of Human Chromosome 11 by in Situ hybridization with Cosmid Clones," *Science*, 247:64–69 (1990).

Lichter et al., "Fluorescence in situ hybridization with Alu and L1 polymerase chain reaction probes for rapid characterization of human chromosomes in hybrid cell lines," *PNAS*, 87:6634–6638 (1990).

Lichter et al., "Rapid detection of human chromosome 21 aberrations by in situ hybridization," *PNAS*, 85:9664–9668 (1988).

Lichter et al., "Is non–isotopic in situ hybridization finally coming of age," *Nature*, 345:93–94 (1990).

Lieberman et al., "A Light source Smaller Than the Optical Wavelength," *Science*, 247:59–61 (1990).

Lipshutz et al., "U sing Oligonucleotide Probe Arrays To Access Genetic Diversity," *BioTech.*, 19(3):442–7 (1995).

Little, P.,. "Clone maps made simple," *Nature*, 346:611–612 (1990).

Liu et al., "Sequential Injection Analysis in Capillary Format with an Electroosmotic Pump," *Talanta*, 41(11):1903–1910 (1994).

Lockhart et al., "Expression monitoring by hybridization to high–density oligonucleotide arrays," *Nat. Biotech.*, 14:1675–1680 (1996).

Logue et al., "General Approaches to Mask Design for Binary Optics," SPIE, 1052:19–24 (1989).

Loken et al., "three–color Immunofluorescence Analysis of Leu Antigens on Human Peripheral Blood Using Two Lasers on a Fluorescence–Activated Cell Sorter," *Cymoetry*, 5:151–158 (1984).

Love et al., "Screening of λ Library for Differentially Expressed Genes Using in Vitro Transcripts," *Anal. Biochem.*, 150:429–441 (1985).

Lowe, C.R., "Biosensors," *Trends in Biotech.*, 2:59–65 (1984).

Lowe, C.R., "An Introduction to the Concepts and Technology of Biosensors," *Biosensors*, 1:3–16 (1985).

Lowe, C.R., Biotechnology and Crop Improvement and Protection, BCPC Publications, pp. 131–138 (1986).

Lowe et al., "Solid–Phase Optoelectronic Biosensors," *Methods in Enzymology*, 137:338–347 (1988).

Lowe, C.R., "Biosensors," *Phil. Tran. R. Soc. Lond.*, 324:487–496 (1989).

Lu et al., "Differential screening of murine ascites cDNA libraries by means of in vitro transcripts of cell–cycle–phase–specific cDNA and digital image processing," *Gene*, 86:185–192 (1990).

Luo, J. et al., "Improving the fidelity of *Thermus thermophilus* DNA ligase," *Nuc. Acids Res.*, 24(14):3071–3078 (1996).

Lysov et al., "A new method for determining the DNA nucleotide sequence by hybridization with oligonucleotides," *Doklady Biochem.*, 303(1–6):436–438 (1989).

Lysov et al., "DNA Sequencing by Oligonucleotide Hybridization," First International Conference on Electrophoresis, Supercomputing and the Human Genome, 4/10–13/90 p. 157.

MacDonald et al., "A Rapid ELISA for Measuring Insulin in Large Number of Research Samples," *Metabolism*, 38(5):450–452 (1989).

Mairanovsky, V.G., "Electron–Deprotection–Electrochemical Removal of Protecting Groups**," *Agnew. Chem. Int. Ed. Engl.*, 15(5):281–292 (1976).

Manz et al., "Miniaturized Total Chemical Analysis Systems: a Novel Concept for Chemical Sensing," *Sensors and Actuators*, B1:244–248 (1990).

Manz et al., "Micromachining of monocrystalline silicon and glass for chemical analysis systems, A look into next century's technology or just a fashionable craze?," *Trends in Analytical Chem.*, 10(5):144–149 (1991).

Manz et al., "Planar chips technology for miniaturization and integration of separation techniques into monitoring systems, Capillary electrophoresis on a chip," *J. Chromatography*, 593:253–258 (1992).

Manz et al., "Planar Chips Technology for Miniaturization of Separation Systems: A Developing Perspective in Chemical Monitoring," chapter 1, 1–64 (1993).

Manz et al., "Electroosmotic pumping and electrophoretic separations for miniaturized chemical analysis systems," *J. Micromech. Microeng.*, 4:257–265 (1994).

Masiakowski et al., "Cloning of cDNA sequences of hormone–regulated genes from the MCF–7 human breast cancer cell line," *Nuc. Acids Res.*, 10(24):7895–7903 (1982).

Matsumoto et al., "Preliminary Investigation of Micropumping Based on Electrical Control of Interfacial Tension," IEEE, pp. 105–110 (1990).

Matsuzawa et al., "Containment and growth of neuroblastoma cells on chemically patterned substrates," *J. Neurosci. Meth.*, 50:253–260 (1993).

Matthes et al., "Simultaneous rapid chemical synthesis of over one hundred oligonucleotides on a microscale," *EMBO J.*, 3(4):801–805 (1984).

McCray et al., "Properties and Uses of Photoreactive Caged Compounds," *Ann. Rev. Biophys. Biophys. Chem.*, 18:239–270 (1989).

McGall et al, "The Efficiency of Light–Directed Synthesis of DNA Arrays on Glass Substrates," *J. American Chem. Soc.*, 119(22):5081–5090 (1997).

McGillis, VLSI Technology, Sze, eds., Chapter 7, "Lithography," pp. 267–301 (1983).

McMurray, J.S., "Solid Phase Synthesis of a Cyclic Peptide Using Fmoc Chemistry," *Tetrahedron Letters*, 32(52):7679–7682 (1991).

Meinkoth et al., "Review: Hybridization of Nucleic Acids Immobilized on solid Supports," *Analytical Biochem.*, 138:267–284 (1984).

Melcher et al., "Traveling–Wave Bulk Electroconvection Induced across a Temperature Gradient," *Physics of Fluids*, 10(6):1178–1185 (1967).

Merrifield, R.B., "Solid Phase peptide Synthesis. I. The Synthesis of a Tetrapeptide," *J.Am.Chem.Soc.*, 85:2149–2154 (1963).

Michiels et al., "Molecular approaches to genome analysis: a strategy for the construction of ordered overlapping clone libraries," *CABIOS*, 3(3):203–10 (1987).

Mirzabekov, A.D., "DNA sequencing by hybridization—a megasequencing method and a diagnostic tool?," *TIBTECH*, 12:27–32 (1994).

Miyada et al., "Oligonucleotide Hybridization Techniques," *Meth. Enzymology*, 154:94–107 (1987).

Monaco et al., "Human Genome Linking with Cosmids and Yeast Artificial Chromosomes", abstract from CSHS, p. 50, (1989).

Morita et al., "Direct pattern fabrication on silicone resin by vapor phase electron beam polymerization," *J.Vac.Sci.Technol.*, B1(4):1171–1173 (1983).

Morrison et al., "Solution–Phase Detection of Polynucleotides Using Interacting Fluorescent Labels and Competitive Hybridization," *Anal. Biochem.*, 183:231–244 (1989).

Munegumi et al., "thermal Synthesis of Polypeptides from N–Boc–Amino Acid (Aspartic Acid, β–Aminoglutaric Acid) Anhydrides," *Chem. Letters,* pp. 1643–1646 (1988).

Mutter et al., "Impact of Conformation on the Synthetic Strategies for Peptide Sequences," pp. 217–228 from Chemistry of Peptides and Proteins, vol. 1, Proceedings of the Third USSR–FRG Symp., in USSR (1982).

Nakamori et al., "A Simple and Useful Method for Simultaneous Screening of Elevated Levels of Expression of a Variety of Oncogenes in Malignant Cells," *Jpn. J. Cancer Res.,* 79:1311–1317 (1988).

Nederlof et al., "Multiple Fluorescence In Situ Hybridization," *Cytometry,* 11:126–131 (1990).

Nederlof et al., "Three–Color Fluorescence In Situ Hybridization for the Simultaneous Detection of Multiple Nucleic Acid Sequences," *Cytometry,* 10:20–27 (1989).

Nizetic et al., "An improved bacterial colony lysis procedure enables direct DNA hybridisation using short (10, 11 bases) oligonucleotides to cosmids," *Nuc. Acids Res.,* 19(1):182 (1990).

Nizetic et al., "Construction, arraying, and high–density screening of large insert libraries of human chromosomes X and 21: their potential use as reference libraries," *PNAS,* 88:3233–3237 (1991).

Nyborg, W., "Acoustic Streaming," chapter 11 pp. 265–329 from Physical Acoustics, Principles and Methods, Mason, eds., vol. II, part B, Academic Press, New York and London (1965).

Ocvirk et al., "High Performance Liquid Chromatography Partially Integrated onto a Silicon Chip," *Analyt. Meth. Instrumentation,* 2(2):74–82 (1995).

Ohtsuka et al., "Studies on transfer ribonucleic acids and related compounds. IX Ribonucleic oligonucleotide synthesis using a photosensitive 0–nitrobenzyl protection at the 2'–hydroxl group," *Nuc. Acids Res.,* 1(10):1351–1357 (1974).

Olefirowicz et al., "Capillary Electrophoresis for Sampling Single Nerve Cells," *Chimia,* 45(4):106–108 (1991).

Olson et al., "Random–clone strategy for genomic restriction mapping in yeast," *PNAS,* 83:7826–7830 (1986).

Patchornik et al., "Photosensitive Protecting Groups," *J.Am.Chem.Soc.,* 92(21):6333–6335 (1970).

Patent Abstracts of Japan from EPO, Abst. 13:557, JP 1–233 447 (1989).

Pease et al., "Light–generated oligonucleotide arrays for rapid DNA sequence analysis," *PNAS,*91:5022–26 (1994).

Pevzner, P.A., "DNA Physical Mapping and Alternating Eulerian Cycles in Colored Grapes," *Algorithmica,* 13(1–2):77–105 (1995).

Pevzner, et al., "Multiple Filtration and Approximate Pattern Matching," *Algorithmica,* 13(1–2):135–154 (1995).

Pevzner et al., "Generalized Sequence Alignment and Duality," *Adv. Applied Math.,* 14:139–171 (1993).

Pevzner, P.A., "1–Tuple DNA Sequencing: Computer Analysis," *J. Biomol. Struct. Dynam.,* 7(1):63–69 (1989).

Pfahler et al., "Liquid Transport in Micron and Submicron Channels," *Sensors and Actuators,* A21–A23:431–4 (90).

Pfeifer et al., "Genomic Sequencing and Methylation Analysis by Ligation Mediated PCR," *Science,* 246:810–813 (1989).

Pidgeon et al., "Immobilized Artificial Membrane Chromatography: Supports Composed of Membrane Lipids," *Anal. Biochem.,* 176:36–47 (89).

Pillai, V.N., "Photoremovable Protecting Groups in Organic Synthesis," *Synthesis,* pp. 1–26 (1980).

Pillai et al., "3–Nitro–4–Aminomethylbenzoylderivate von Polyethylenglykolen: Eine neue Klasse von Photosensitiven loslichen Polymeren Tragern zur Synthese von C–terminalen Peptidamiden," *Tetrah. ltr.,* #36 p. 3409–3412 (1979).

Pillai et al., "Synthetic Hydrophilic Polymers, Biomedical and Chemical Applications," *Naturwissenschaften,* 68:558–566 (1981).

Pirrung et al., "Proofing of Photolithographic DNA Synthesis with 3'.5'–Dimethoxybenzoinyloxycarbonyl–Protected Deoxynucleoside Phosphoramidites," *J. Org. Chem.,* 63(2):241–246 (1998).

Pirrung et al., "Comparison of Methods for Photochemical Phosphoramidite–Based DNA Synthesis," *J. Org. Chem.,* 60:6270–6276 (1995).

Ploax et al., "Cyclization of peptides on a solid support," *Int. J. Peptide Protein Research,* 29:162–169 (1987).

Polsky–Cynkin et al.,"Use of DNA Immobilized on Plastic and Agarose Supports to Detect DNA by Sandwich Hybridization," *Clin. Chem.,* 31(9):1428–1443 (1985).

Poustka et al., "Molecular Approaches to Mammalian Genetics," Cold Spring Harbor Symposia on Quantitive Biology, 51:131–139 (1986).

Purushothaman et al., "Synthesis of 4,5–diarylimidazoline–2 thiones and their photoconversion to bis(4, 5–diarylimidazol–2–yl) sulphides," *Ind. J. Chem.,* 29B:18–21 (1990).

Quesada et al., "High–Sensitivity DNA Detection with a Laser–Exited Confocal Fluorescence Gel Scanner," *Biotechniques,* 10:616 (1991).

Reichmanis et al., *J. Polymer Sci. Polymer Chem. Edition,* 23:1–8 (1985).

Renz et al., "A colorimetric method for DNA hybridization," *Nuc. Acids Res.,* 12(8):3435–3445 (1984).

Richter et al., "An Electrohydrodynamic Micropump," *IEEE,* pp. 99–104 (1990).

Richter et al., "Electrodynamic Pumping and Flow Measurement," *IEEE,* pp. 271–276 (1991).

Richter et al., "A Micromachined electrohydrodynamic (EHD) pump," *Sensors and Actuators,* A29:159–168 (91).

Robertson et al., "A General and Efficient Route for Chemical Aminoacylation of Transfer RNAs," *J. Am. Chem. Soc.,* 113:2722–2729 (1991).

Rodda et al., "The Antibody Response to Myoglobin–I. Systematic Synthesis of Myglobin Peptides Reveals Location and Substructure of Species–Dependent Continuous Antigenic Determinants," *Mol. Immunol.,* 23(6):603–610 (1986).

Rodgers, R.P., "Data Processing of Immunoassay Results," Manual of Clin. Lab. Immunol., 3rd ed., ch. 15, pp. 82–87 (1986).

|  | P | A | S | G |  |
|---|---|---|---|---|---|
| L | L<u>P</u>GFL | L<u>A</u>GFL | L<u>S</u>GFL | L<u>G</u>GFL | L |
| F | <u>F</u>PGFL | <u>F</u>AGFL | <u>F</u>SGFL | <u>F</u>GGFL | F |
| W | <u>W</u>PGFL | <u>W</u>AGFL | <u>W</u>SGFL | <u>W</u>GGFL | W |
| Y | <u>Y</u>PGFL | <u>Y</u>AGFL | <u>Y</u>SGFL | <u>Y</u>GGFL | Y |

L SET

FIGURE 22A

|  | p | a | s | G |  |
|---|---|---|---|---|---|
| Y | Y<u>p</u>GFL | Y<u>a</u>GFL | Y<u>s</u>GFL | Y<u>G</u>GFL | Y |
| f | <u>f</u>pGFL | <u>f</u>aGFL | <u>f</u>sGFL | <u>f</u>GGFL | f |
| w | <u>w</u>pGFL | <u>w</u>aGFL | <u>w</u>sGFL | <u>w</u>GGFL | w |
| y | <u>y</u>pGFL | <u>y</u>aGFL | <u>y</u>sGFL | <u>y</u>GGFL | y |

D SET

FIGURE 22B

SUPPORT BOUND PROBES AND METHODS OF ANALYSIS USING THE SAME

CROSS-REFERENCE TO RELATED APPLICATION

The present application is a continuation of U.S. Ser. No. 09/557,875 filed Apr. 24, 2000, which is a continuation of U.S. Ser. No. 09/056,927 filed Apr. 8, 1998 now U.S. Pat. No. 6,197,506 which is a continuation of U.S. Ser. No. 08/670,118 filed Jun. 25, 1996, (now U.S. Pat. No. 5,800, 992), which is a divisional of U.S. Ser. No. 08/168,904 filed Dec. 15, 1993 now abandoned, which is a continuation of U.S. Ser. No. 07/624,114, filed Dec. 6, 1990 (all incorporated by reference) now abandoned, which is a continuation-in-part of commonly assigned patent applications Pirrung et al., U.S. Ser. No. 07/362,901 (VLSIPS parent) filed on Jun. 7, 1989 now abandoned; and Pirrung et al., U.S. Ser. No. 07/492,462 (VLSIPS CIP), filed on Mar. 7, 1990 (now U.S. Pat. No. 5,143,854), which are hereby incorporated herein by reference. The present application is also a continuation-in-part of U.S. Ser. No. 08/348,471 filed Nov. 30, 1994, which is a continuation of U.S. Ser. No. 07/805,727 filed Dec. 6, 1991 (now U.S. Pat. No. 5,424,186), which is a continuation-in-part of U.S. Ser. No. 07/624,120, filed Dec. 6, 1990, which is a continuation-in-part of U.S. Ser. No. 07/492,462, filed Mar. 7, 1990 (now U.S. Pat. No. 5,143, 854), which is a continuation-in-part of U.S. Ser. No. 07/362,901, filed Jun. 7, 1989 now abandoned. Additional commonly assigned applications Barrett et al., U.S. Ser. No. 07/435,316 (caged biotin parent) filed Nov. 13, 1989; and Barrett et al., U.S. Ser. No. 07/612,671 (caged biotin CIP), filed Nov. 13, 1990 are also incorporated herein by reference. Additional applications Pirrung et al., U.S. Ser. No. 07/624,120 (now abandoned) a divisional of which has issued as U.S. Pat. No. 5,744,101 and Dower et al., U.S. Ser. No. 07/626,730 (now U.S. Pat. No. 5,547,839), which are also commonly assigned and filed on the same day as this application, are also hereby incorporated herein by reference.

BACKGROUND OF THE INVENTION

The present invention relates to the sequencing, fingerprinting, and mapping of polymers, particularly biological polymers. The inventions may be applied, for example, in the sequencing, fingerprinting, or mapping of nucleic acids, polypeptides, oligosaccharides, and synthetic polymers.

The relationship between structure and function of macromolecules is of fundamental importance in the understanding of biological systems. These relationships are important to understanding, for example, the functions of enzymes, structural proteins, and signalling proteins, ways in which cells communicate with each other, as well as mechanisms of cellular control and metabolic feedback.

Genetic information is critical in continuation of life processes. Life is substantially informationally based and its genetic content controls the growth and reproduction of the organism and its complements. Polypeptides, which are critical features of all living systems, are encoded by the genetic material of the cell. In particular, the properties of enzymes, functional proteins, and structural proteins are determined by the sequence of amino acids which make them up. As structure and function are integrally related, many biological functions may be explained by elucidating the underlying the structural features which provide those functions. For this reason, it has become very important to determine the genetic sequences of nucleotides which encode the enzymes, structural proteins, and other effectors of biological functions. In addition to segments of nucleotides which encode polypeptides, there are many nucleotide sequences which are involved in control and regulation of gene expression.

The human genome project is directed toward determining the complete sequence the genome of the human organism. Although such a sequence would not correspond to the sequence of any specific individual, it would provide significant information as to the general organization and specific sequences contained within segments from particular individuals. It would also provide mapping information which is very useful for further detailed studies. However, the need for highly rapid, accurate, and inexpensive sequencing technology is nowhere more apparent than in a demanding sequencing project such as this. To complete the sequencing of a human genome would require the determination of approximately $3 \times 10^9$, or 3 billion base pairs.

The procedures typically used today for sequencing include the Sanger dideoxy method, see, e.g., Sanger et al. (1977) *Proc. Natl. Acad. Sci. USA*, 74:5463–5467, or the Maxam and Gilbert method, see, e.g., Maxam et al., (1980) *Methods in Enzymology*, 65:499–559. The Sanger method utilizes enzymatic elongation procedures with chain terminating nucleotides. The Maxam and Gilbert method uses chemical reactions exhibiting specificity of reaction to generate nucleotide specific cleavages. Both methods require a practitioner to perform a large number of complex manual manipulations. These manipulations usually require isolating homogeneous DNA fragments, elaborate and tedious preparing of samples, preparing a separating gel, applying samples to the gel, electrophoresing the samples into this gel, working up the finished gel, and analyzing the results of the procedure.

Thus, a less expensive, highly reliable, and labor efficient means for sequencing biological macromolecules is needed. A substantial reduction in cost and increase in speed of nucleotide sequencing would be very much welcomed. In particular, an automated system would improve the reproducibility and accuracy of procedures. The present invention satisfies these and other needs.

SUMMARY OF THE INVENTION

The present invention provides improved methods useful for de novo sequencing of an unknown polymer sequence, for verification of known sequences, for fingerprinting polymers, and for mapping homologous segments within a sequence. By reducing the number of manual manipulations required and automating most of the steps, the speed, accuracy, and reliability of these procedures are greatly enhanced.

The production of a substrate having a matrix of positionally defined regions with attached reagents exhibiting known recognition specificity can be used for the sequence analysis of a polymer. Although most directly applicable to sequencing, the present invention is also applicable to fingerprinting, mapping, and general screening of specific interactions. The VLSIPS substrates will be applied to evaluating other polymers, e.g., carbohydrates, polypeptides, hydrocarbon synthetic polymers, and the like. For these non-polynucleotides, the sequence specific reagents will usually be antibodies specific for a particular subunit sequence.

The present invention also provides a means to automate sequencing manipulations. The automation of the substrate production method and of the scan and analysis steps minimizes the need for human intervention. This simplifies the tasks and promotes reproducibility.

The present invention provides a composition comprising a plurality of positionally distinguishable sequence specific reagents attached to a solid substrate, which reagents are capable of specifically binding to a predetermined subunit sequence of a preselected multi-subunit length having at least three subunits, said reagents representing substantially all possible sequences of said preselected length. In some embodiments, the subunit sequence is a polynucleotide or a polypeptide, in others the preselected multi-subunit length is five subunits and the subunit sequence is a polynucleotide sequence. In other embodiments, the specific reagent is an oligonucleotide of at least about five nucleotides. Alternatively, the specific reagent is a monoclonal antibody. Usually the specific reagents are all attached to a single solid substrate, and the reagents comprise about 3000 different sequences. In other embodiments, the reagents represents at least about 25% of the possible subsequences of said preselected length. Usually, the reagents are localized in regions of the substrate having a density of at least 25 regions per square centimeter, and often the substrate has a surface area of less than about 4 square centimeters.

The present invention also provides methods for analyzing a sequence of a polynucleotide or a polypeptide, said method comprising the step of:
  a) exposing said polynucleotide or polypeptide to a composition as described.

It also provides useful methods for identifying or comparing a target sequence with a reference, said method comprising the step of:
  a) exposing said target sequence to a composition as described;
  b) determining the pattern of positions of the reagents which specifically interact with the target sequence; and
  c) comparing the pattern with the pattern exhibited by the reference when exposed to the composition.

The present invention also provides methods for sequencing a segment of a polynucleotide comprising the steps of:
  a) combining:
    i) a substrate comprising a plurality of chemically synthesized and positionally distinguishable oligonucleotides capable of recognizing defined oligonucleotide sequences; and
    ii) a target polynucleotide; thereby forming high fidelity matched duplex structures of complementary subsequences of known sequence; and
  b) determining which of said reagents have specifically interacted with subsequences in said target polynucleotide.

In one embodiment, the segment is substantially the entire length of said polynucleotide.

The invention also provides methods for sequencing a polymer, said method comprising the steps of:
  a) preparing a plurality of reagents which each specifically bind to a subsequence of preselected length;
  b) positionally attaching each of said reagents to one or more solid phase substrates, thereby producing substrates of positionally definable sequence specific probes;
  c) combining said substrates with a target polymer whose sequence is to be determined; and
  d) determining which of said reagents have specifically interacted with subsequences in said target polymer.

In one embodiment, the substrates are beads. Preferably, the plurality of reagents comprise substantially all possible subsequences of said preselected length found in said target. In another embodiment, the solid phase substrate is a single substrate having attached thereto reagents recognizing substantially all possible subsequences of preselected length found in said target.

In another embodiment, the method further comprises the step of analyzing a plurality of said recognized subsequences to assemble a sequence of said target polymer. In a bead embodiment, at least some of the plurality of substrates have one subsequence specific reagent attached thereto, and the substrates are coded to indicate the sequence specificity of said reagent.

The present invention also embraces a method of using a fluorescent nucleotide to detect interactions with oligonucleotide probes of known sequence, said method comprising:
  a) attaching said nucleotide to a target unknown polynucleotide sequence, and
  b) exposing said target polynucleotide sequence to a collection of positionally defined oligonucleotide probes of known sequences to determine the sequences of said probes which interact with said target.

In a further refinement, an additional step is included of:
  a) collating said known sequences to determine the overlaps of said known sequences to determine the sequence of said target sequence.

A method of mapping a plurality of sequences relative to one another is also provided, the method comprising:
  a) preparing a substrate having a plurality of positionally attached sequence specific probes are attached;
  b) exposing each of said sequences to said substrate, thereby determining the patterns of interaction between said sequence specific probes and said sequences; and
  c) determining the relative locations of said sequence specific probe interactions on said sequences to determine the overlaps and order of said sequences.

In one refinement, the sequence specific probes are oligonucleotides, applicable to where the target sequences are nucleic acid sequences.

In the nucleic acid sequencing application, the steps of the sequencing process comprise:
  a) producing a matrix substrate having known positionally defined regions of known sequence specific oligonucleotide probes;
  b) hybridizing a target polynucleotide to the positions on the matrix so that each of the positions which contain oligonucleotide probes complementary to a sequence on the target hybridize to the target molecule;
  c) detecting which positions have bound the target, thereby determining sequences which are found on the target; and
  d) analyzing the known sequences contained in the target to determine sequence overlaps and assembling the sequence of the target therefrom.

The enablement of the sequencing process by hybridization is based in large part upon the ability to synthesize a large number (e.g., to virtually saturate) of the possible overlapping sequence segments and distinguishing those probes which hybridize with fidelity from those which have mismatched bases, and to analyze a highly complex pattern of hybridization results to determine the overlap regions.

The detecting of the positions which bind the target sequence would typically be through a fluorescent label on the target. Although a fluorescent label is probably most convenient, other sorts of labels, e.g., radioactive, enzyme linked, optically detectable, or spectroscopic labels may be used. Because the oligonucleotide probes are positionally defined, the location of the hybridized duplex will directly translate to the sequences which hybridize. Thus, upon analysis of the positions provides a collection of subsequences found within the target sequence. These subsequences are matched with respect to their overlaps so as to assemble an intact target sequence.

In one preferred embodiment, linker molecules are provided on a substrate. A terminal end of the linker molecules is provided with a reactive functional group protected with a photoremovable protective group. Using lithographic methods, the photoremovable protective group is exposed to light and removed from the linker molecules in first selected regions. The substrate is then washed or otherwise contacted with a first monomer that reacts with exposed functional groups on the linker molecules. In a preferred embodiment, the monomer is an amino acid containing a photoremovable protective group at its amino or carboxy terminus and the linker molecule terminates in an amino or carboxy acid group bearing a photoremovable protective group.

A second set of selected regions is, thereafter, exposed to light and the photoremovable protective group on the linker molecule/protected amino acid is removed at the second set of regions. The substrate is then contacted with a second monomer containing a photoremovable protective group for reaction with exposed functional groups. This process is repeated to selectively apply monomers until polymers of a desired length and desired chemical sequence are obtained. Photolabile groups are then optionally removed and the sequence is, thereafter, optionally capped. Side chain protective groups, if present, are also removed.

An improved method and apparatus for the preparation of polymers is disclosed. The method and apparatus may be applied to synthesize a variety of polymers at known locations on a substrate. The method could be used to synthesize up to about $10^6$ or more different sequences per cm² at known locations in some embodiments.

The method enables greater ease in peptide synthesis because the physical separation of reagents is not required when growing polymer chains. The chains themselves are separated by different physical locations on the substrate, but the entire substrate is exposed to the various reagents as the synthesis is conducted. Differential reaction is achieved by selectively exposing reactive functional groups to, e.g., light, electric currents, or another spatially localized activator. Remaining areas on the substrate remain unreacted.

By using the lithographic techniques disclosed herein, it is possible to direct light to relatively small and precisely known locations on the substrate. It is, therefore, possible to synthesize polymers of a known chemical sequence at known locations on the substrate.

The resulting substrate will have a variety of uses including, for example, screening large numbers of polymers for biological activity. To screen for biological activity, the substrate is exposed to one or more receptors such as antibody whole cells, receptors on vesicles, lipids, or any one of a variety of other receptors. The receptors are preferably labeled with, for example, a fluorescent marker, radioactive marker, or a labeled antibody reactive with the receptor. The location of the marker on the substrate is detected with, for example, photon detection or autoradiographic techniques. Through knowledge of the sequence of the material at the location where binding is detected, it is possible to quickly determine which sequence binds with the receptor and, therefore, the technique can be used to screen large numbers of peptides. Other possible applications of the inventions herein include diagnostics in which various antibodies for particular receptors would be placed on a substrate and, for example, blood sera would be screened for immune deficiencies. Still further applications include, for example, selective "doping" of organic materials in semiconductor devices, and the like.

In connection with one aspect of the invention an improved reactor system for synthesizing polymers is also disclosed. The reactor system includes a substrate mount which engages a substrate around a periphery thereof. The substrate mount provides for a reactor space between the substrate and the mount through or into which reaction fluids are pumped or flowed. A mask is placed on or focused on the substrate and illuminated so as to deprotect selected regions of the substrate in the reactor space. A monomer is pumped through the reactor space or otherwise contacted with the substrate and reacts with the deprotected regions. By selectively deprotecting regions on the substrate and flowing predetermined monomers through the reactor space, desired polymers at known locations may be synthesized.

Improved detection apparatus and methods are also disclosed. The detection method and apparatus utilize a substrate having a large variety of polymer sequences at known locations on a surface thereof. The substrate is exposed to a fluorescently labeled receptor which binds to one or more of the polymer sequences. The substrate is placed in a microscope detection apparatus for identification of locations where binding takes place. The microscope detection apparatus includes a monochromatic or polychromatic light source for directing light at the substrate, means for detecting fluoresced light from the substrate, and means for determining a location of the fluoresced light. The means for detecting light fluoresced on the substrate may in some embodiments include a photon counter. The means for determining a location of the fluoresced light may include an x/y translation table for the substrate. Translation of the slide and data collection are recorded and managed by an appropriately programmed digital computer.

A further understanding of the nature and advantages of the inventions herein may be realized by reference to the remaining portions of the specification and the attached drawings.

BRIEF DESCRIPTION OF THE DRAWINGS

FIG. 19C illustrates a 500×500 µm mask which has been focused on the substrate according to FIG. 12A while FIG. 19D illustrates a 50×50 µm mask placed in direct contact with the substrate in accord with FIG. 12B;.

FIGS. 22A and 22B illustrate the mapping of sixteen sequences synthesized on two different glass slides;

GLOSSARY

Figure 1:
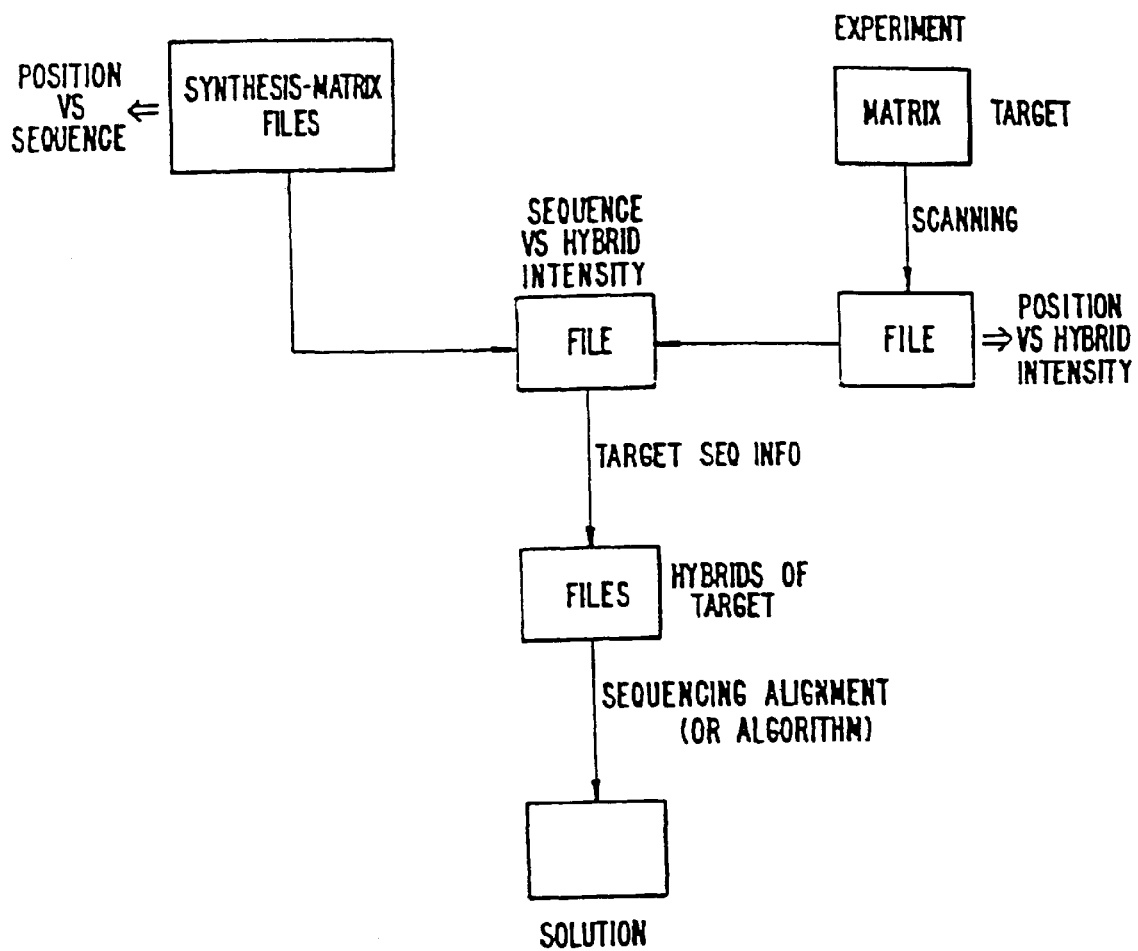
FIG. 1 illustrates a flow chart for sequence, fingerprint, or mapping analysis.

The following terms are intended to have the following general meanings as they are used herein:

1. Complementary

Refers to the topological compatibility or matching together of interacting surfaces of a ligand molecule and its receptor. Thus, the receptor and its ligand can be described as complementary, and furthermore, the contact surface characteristics are complementary to each other.

2. Epitope

The portion of an antigen molecule which is delineated by the area of interaction with the subclass of receptors known as antibodies.

3. Ligand

A ligand is a molecule that is recognized by a particular receptor. Examples of ligands that can be investigated by this invention include, but are not restricted to, agonists and antagonists for cell membrane receptors, toxins and venoms, viral epitopes, hormones (e.g., opiates, steroids, etc.), hormone receptors, peptides, enzymes, enzyme substrates, cofactors, drugs, lectins, sugars, oligonucleotides, nucleic acids, oligosaccharides, proteins, and monoclonal antibodies.

4. Monomer

A member of the set of small molecules which can be joined together to form a polymer. The set of monomers includes but is not restricted to, for example, the set of common L-amino acids, the set of D-amino acids, the set of synthetic amino acids, the set of nucleotides and the set of pentoses and hexoses. As used herein, monomers refers to any member of a basis set for synthesis of a polymer. For example, dimers of L-amino acids form a basis set of 400 monomers for synthesis of polypeptides. Different basis sets of monomers may be used at successive steps in the synthesis of a polymer.

5. Peptide

A polymer in which the monomers are alpha amino acids and which are joined together through amide bonds and alternatively referred to as a polypeptide. In the context of this specification it should be appreciated that the amino acids may be the L-optical isomer or the D-optical isomer. Peptides are more than two amino acid monomers long, and often more than 20 amino acid monomers long. Standard abbreviations for amino acids are used (e.g., P for proline). These abbreviations are included in Stryer, *Biochemistry*, Third Ed., 1988, which is incorporated herein by reference for all purposes.

6. Radiation

Energy which may be selectively applied including energy having a wavelength of between $10^{-14}$ and $10^4$ meters including, for example, electron beam radiation, gamma radiation, x-ray radiation, ultra-violet radiation, visible light, infrared radiation, microwave radiation, and radio waves. "Irradiation" refers to the application of radiation to a surface.

7. Receptor

A molecule that has an affinity for a given ligand. Receptors may be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex.

Other examples of receptors which can be investigated by this invention include but are not restricted to:

a) Microorganism Receptors

Determination of ligands which bind to receptors, such as specific transport proteins or enzymes essential to survival of microorganisms, is useful in a new class of antibiotics. Of particular value would be antibiotics against opportunistic fungi, protozoa, and those bacteria resistant to the antibiotics in current use.

b) Enzymes

For instance, the binding site of enzymes such as the enzymes responsible for cleaving neurotransmitters; determination of ligands which bind to certain receptors to modulate the action of the enzymes which cleave the different neurotransmitters is useful in the development of drugs which can be used in the treatment of disorders of neurotransmission.

c) Antibodies

For instance, the invention may be useful in investigating the ligand-binding site on the antibody molecule which combines with the epitope of an antigen of interest; determining a sequence that mimics an antigenic epitope may lead to the development of vaccines of which the immunogen is based on one or more of such sequences or lead to the development of related diagnostic agents or compounds useful in therapeutic treatments such as for autoimmune diseases (e.g., by blocking the binding of the "self" antibodies).

d) Nucleic Acids

Sequences of nucleic acids may be synthesized to establish DNA or RNA binding sequences.

e) Catalytic Polypeptides

Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant. Catalytic polypeptides are described in, for example, U.S. application Ser. No. 404,920, which is incorporated herein by reference for all purposes.

f) Hormone Receptors

For instance, the receptors for insulin and growth hormone. Determination of the ligands which bind with high affinity to a receptor is useful in the development of, for example, an oral replacement of the daily injections which diabetics must take to relieve the symptoms of diabetes, and in the other case, a replacement for the scarce human growth hormone which can only be obtained from cadavers or by recombinant DNA technology. Other examples are the vasoconstrictive hormone receptors; determination of those ligands which bind to a receptor may lead to the development of drugs to control blood pressure.

g) Opiate Receptors

Determination of ligands which bind to the opiate receptors in the brain is useful in the development of less-addictive replacements for morphine and related drugs.

8. Substrate

A material having a rigid or semi-rigid surface. In many embodiments, at least one surface of the substrate will be substantially flat, although in some embodiments it may be desirable to physically separate synthesis regions for different polymers with, for example, wells, raised regions, etched trenches, or the like. According to other embodiments, small beads may be provided on the surface which may be released upon completion of the synthesis.

9. Protective Group

A material which is bound to a monomer unit and which may be spatially removed upon selective exposure to an activator such as electromagnetic radiation. Examples of protective groups with utility herein include Nitroveratryloxy carbonyl, Nitrobenzyloxy carbonyl, Dimethyl dimethoxybenzyloxy carbonyl, 5-Bromo-7-nitroindolinyl, o-Hydroxy-á-methyl cinnamoyl, and 2-Oxymethylene anthraquinone. Other examples of activators include ion beams, electric fields, magnetic fields, electron beams, x-ray, and the like.

10. Predefined Region

A predefined region is a localized area on a surface which is, was, or is intended to be activated for formation of a polymer. The predefined region may have any convenient shape, e.g., circular, rectangular, elliptical, wedge-shaped, etc. For the sake of brevity herein, "predefined regions" are sometimes referred to simply as "regions."

11. Substantially Pure

A polymer is considered to be "substantially pure" within a predefined region of a substrate when it exhibits characteristics that distinguish it from other predefined regions. Typically, purity will be measured in terms of biological activity or function as a result of uniform sequence. Such characteristics will typically be measured by way of binding with a selected ligand or receptor.

DESCRIPTION OF THE PREFERRED EMBODIMENTS

I. Overall Description
  A. general
  B. VLSIPS substrates
  C. binary masking
  D. applications
  E. detection methods and apparatus
  F. data analysis
II. Theoretical Analysis
  A. simple n-mer structure; theory
  B. complications
  C. non-polynucleotide embodiments
III. Polynucleotide Sequencing
  A. preparation of substrate matrix
  B. labeling target polynucleotide
  C. hybridization conditions
  D. detection; VLSIPS scanning
  E. analysis
  F. substrate reuse
  G. non-polynucleotide aspects
IV. Fingerprinting
  A. general
  B. preparation of substrate matrix
  C. labeling target nucleotides
  D. hybridization conditions
  E. detection; VLSIPS scanning
  F. analysis
  G. substrate reuse
  H. non-polynucleotide aspects
V. Mapping
  A. general
  B. preparation of substrate matrix
  C. labeling
  D. hybridization/specific interaction
  E. detection
  F. analysis
  G. substrate reuse
  H. non-polynucleotide aspects
VI. Additional Screening
  A. specific interactions
  B. sequence comparisons
  C. categorizations
  D. statistical correlations
VII. Formation of Substrate
  A. instrumentation
  B. binary masking
  C. synthetic methods
  D. surface immobilization
VIII. Hybridization/Specific Interaction
  A. general
  B. important parameters
IX. Detection Methods
  A. labeling techniques
  B. scanning system
X. Data Analysis
  A. general
  B. hardware
  C. software
XI. Substrate Reuse
  A. removal of label
  B. storage and preservation
  C. processes to avoid degradation of oligomers XII. Integrated Sequencing Strategy
A. initial mapping strategy
B. selection of smaller clones
C. actual sequencing procedures
XIII. Commercial Applications
A. sequencing
B. fingerprinting
C. mapping I. Overall Description A. General The present invention relies in part on the ability to synthesize or attach specific recognition reagents at known locations on a substrate, typically a single substrate. In particular, the present invention provides the ability to prepare a substrate having a very high density matrix pattern of positionally defined specific recognition reagents. The reagents are capable of interacting with their specific targets while attached to the substrate, e.g., solid phase interactions, and by appropriate labeling of these targets, the sites of the interactions between the target and the specific reagents may be derived. Because the reagents are positionally defined, the sites of the interactions will define the specificity of each interaction. As a result, a map of the patterns of interactions with specific reagents on the substrate is convertible into information on the specific interactions taking place, e.g., the recognized features. Where the specific reagents recognize a large number of possible features, this system allows the determination of the combination of specific interactions which exist on the target molecule. Where the number of features is sufficiently large, the identical same combination, or pattern, of features is sufficiently unlikely that a particular target molecule may often be uniquely defined by its features. In the extreme, the features may actually be the subunit sequence of the target molecule, and a given target sequence may be uniquely defined by its combination of features.

In particular, the methodology is applicable to sequencing polynucleotides. The specific sequence recognition reagents will typically be oligonucleotide probes which hybridize with specificity to subsequences found on the target sequence. A sufficiently large number of those probes allows the fingerprinting of a target polynucleotide or the relative mapping of a collection of target polynucleotides, as described in greater detail below.

In the high resolution fingerprinting provided by a saturating collection of probes which include all possible subsequences of a given size, e.g., 10-mers, collating of all the subsequences and determination of specific overlaps will be derived and the entire sequence can usually be reconstructed.

Although a polynucleotide sequence analysis is a preferred embodiment, for which the specific reagents are most easily accessible, the invention is also applicable to analysis of other polymers, including polypeptides, carbohydrates, and synthetic polymers, including α-, β-, and ω-amino acids, polyurethanes, polyesters, polycarbonates, polyureas, polyamides, polyethyleneimines, polyarylene sulfides, polysiloxanes, polyimides, polyacetates, and mixed polymers. Various optical isomers, e.g., various D- and L-forms of the monomers, may be used.

Sequence analysis will take the form of complete sequence determination, to the level of the sequence of individual subunits along the entire length of the target sequence. Sequence analysis also takes the form of sequence homology, e.g., less than absolute subunit resolution, where "similarity" in the sequence will be detectable, or the form of selective sequences of homology interspersed at specific or irregular locations.

In either case, the sequence is determinable at selective resolution or at particular locations. Thus, the hybridization method will be useful as a means for identification, e.g., a "fingerprint", much like a Southern hybridization method is used. It is also useful to map particular target sequences.

B. VLSIPS Substrates

The invention is enabled by the development of technology to prepare substrates on which specific reagents may be either positionally attached or synthesized. In particular, the very large scale immobilized polymer synthesis (VLSIPS) technology allows for the very high density production of an enormous diversity of reagents mapped out in a known matrix pattern on a substrate. These reagents specifically recognize subsequences in a target polymer and bind thereto, producing a map of positionally defined regions of interaction. These map positions are convertible into actual features recognized, and thus would be present in the target molecule of interest.

As indicated, the sequence specific recognition reagents will often be oligonucleotides which hybridize with fidelity and discrimination to the target sequence. For use with other polymers, monoclonal or polyclonal antibodies having high sequence specificity will often be used.

In the generic sense, the VLSIPS technology allows the production of a substrate with a high density matrix of positionally mapped regions with specific recognition reagents attached at each distinct region. By use of protective groups which can be positionally removed, or added, the regions can be activated or deactivated for addition of particular reagents or compounds. Details of the protection are described below and in related application U.S. Ser. No. 07/492,462 (VLSIPS CIP). In a preferred embodiment, photosensitive protecting agents will be used and the regions of activation or deactivation may be controlled by electro-optical and optical methods, similar to many of the processes used in semiconductor wafer and chip fabrication.

In the nucleic acid nucleotide sequencing application, a VLSIPS substrate is synthesized having positionally defined oligonucleotide probes. See U.S. Ser. No. 07/492,462 (VLSIPS CIP); and U.S. Ser. No. 07/624,120, (automated VLSIPS). By use of masking technology and photosensitive synthetic subunits, the VLSIPS apparatus allows for the stepwise synthesis of polymers according to a positionally defined matrix pattern. Each oligonucleotide probe will be synthesized at known and defined positional locations on the substrate. This forms a matrix pattern of known relationship between position and specificity of interaction. The VLSIPS technology allows the production of a very large number of different oligonucleotide probes to be simultaneously and automatically synthesized including numbers in excess of about $10^2$, $10^3$, $10^4$, $10^5$, $10^6$, or even more, and at densities of at least about $10^2$, $10^3/cm^2$, $10^4/cm^2$, $10^5/cm^2$ and up to $10^6/cm^2$ or more. This application discloses methods for synthesizing polymers on a silicon or other suitably derivatized substrate, methods and chemistry for synthesizing specific types of biological polymers on those substrates, apparatus for scanning and detecting whether interaction has occurred at specific locations on the substrate, and various other technologies related to the use of a high density very large scale immobilized polymer substrate. In particular, sequencing, fingerprinting, and mapping applications are discussed herein in detail, though related technologies are described in simultaneously filed applications U.S. Ser. No. 07/624,1200 (automated VLSIPS) and U.S. Ser. No. 07/626,730, (sequencing by synthesis), each of which is hereby incorporated herein by reference.

In other embodiments, antibody probes will be generated which specifically recognize particular subsequences found on a polymer. Antibodies would be generated which are specific for recognizing a three contiguous amino acid sequence, and monoclonal antibodies may be preferred. Optimally, these antibodies would not recognize any sequences other than the specific three amino acid stretch desired and the binding affinity should be insensitive to flanking or remote sequences found on a target molecule. Likewise, antibodies specific for particular carbohydrate linkages or sequences will be generated. A similar approach could be used for preparing specific reagents which recognize other polymer subunit sequences. These reagents would typically be site specifically localized to a substrate matrix pattern where the regions are closely packed.

These reagents could be individually attached at specific sites on the substrate in a matrix by an automated procedure where the regions are positionally targeted by some other specific mechanism, e.g., one which would allow the entire collection of reagents to be attached to the substrate in a single reaction. Each reagent could be separately attached to a specific oligonucleotide sequence by an automated procedure. This would produce a collection of reagents where, e.g., each monoclonal antibody would have a unique oligonucleotide sequence attached to it. By virtue of a VLSIPS substrate which has different complementary oligonucleotides synthesized on it, each monoclonal antibody would specifically be bound only at that site on the substrate where the complementary oligonucleotide has been synthesized. A crosslinking step would fix the reagent to the substrate. See, e.g., Dattagupta et al. (1985) U.S. Pat. No. 4,542,102 and (1987) U.S. Pat. No. 4,713,326; and Chatterjee, M. et al. (1990) *J. Am. Chem. Soc.* 112:6397–6399, which are hereby incorporated herein by reference. This allows a high density positionally specific collection of specific recognition reagents, e.g., monoclonal antibodies, to be immobilized to a solid substrate using an automated system.

The regions which define particular reagents will usually be generated by selective protecting groups which may be activated or deactivated. Typically the protecting group will be bound to a monomer subunit or spatial region, and can be spatially affected by an activator, such as electromagnetic radiation. Examples of protective groups with utility herein include nitroveratryl oxycarbonyl (NVOC), nitrobenzyl oxycarbony (NBOC), dimethyl dimethoxy benzyloxy carbonyl, 5-bromo-7-nitroindolinyl, O-hydroxy-α-methyl cinnamoyl, and 2-oxymethylene anthraquinone. Examples of activators include ion beams, electric fields, magnetic fields, electron beams, x-ray, and other forms of electromagnetic radiation.

The present invention provides methods and apparatus for the preparation and use of a substrate having a plurality of polymer sequences in predefined regions. The invention is described herein primarily with regard to the preparation of molecules containing sequences of amino acids, but could readily be applied in the preparation of other polymers. Such polymers include, for example, both linear and cyclic polymers of nucleic acids, polysaccharides, phospholipids, and peptides having either α-, β-, or ω-amino acids, heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be apparent upon review of this disclosure. In a preferred embodiment, the invention herein is used in the synthesis of peptides.

The prepared substrate may, for example, be used in screening a variety of polymers as ligands for binding with a receptor, although it will be apparent that the invention could be used for the synthesis of a receptor for binding with a ligand. The substrate disclosed herein will have a wide variety of other uses. Merely by way of example, the invention herein can be used in determining peptide and nucleic acid sequences which bind to proteins, finding sequence-specific binding drugs, identifying epitopes recognized by antibodies, and evaluation of a variety of drugs for clinical and diagnostic applications, as well as combinations of the above.

The invention preferably provides for the use of a substrate "S" with a surface. Linker molecules "L" are optionally provided on a surface of the substrate. The purpose of the linker molecules, in some embodiments, is to facilitate receptor recognition of the synthesized polymers.

Optionally, the linker molecules may be chemically protected for storage purposes. A chemical storage protective group such as t-BOC (t-butoxycarbonyl) may be used in some embodiments. Such chemical protective groups would be chemically removed upon exposure to, for example, acidic solution and would serve to protect the surface during storage and be removed prior to polymer preparation.

On the substrate or a distal end of the linker molecules, a functional group with a protective group $P_0$ is provided. The protective group $P_0$ may be removed upon exposure to radiation, electric fields, electric currents, or other activators to expose the functional group.

In a preferred embodiment, the radiation is ultraviolet (UV), infrared (IR), or visible light. As more fully described below, the protective group may alternatively be an electrochemically-sensitive group which may be removed in the presence of an electric field. In still further alternative embodiments, ion beams, electron beams, or the like may be used for deprotection.

In some embodiments, the exposed regions and, therefore, the area upon which each distinct polymer sequence is synthesized are smaller than about 1 $cm^2$ or less than 1 $mm^2$. In preferred embodiments the exposed area is less than about 10,000 $\mu m^2$ or, more preferably, less than 100 $\mu m^2$ and may, in some embodiments, encompass the binding site for as few as a single molecule. Within these regions, each polymer is preferably synthesized in a substantially pure form.

Concurrently or after exposure of a known region of the substrate to light, the surface is contacted with a first monomer unit $M_1$ which reacts with the functional group which has been exposed by the deprotection step. The first monomer includes a protective group $P_1$. $P_1$ may or may not be the same as $P_0$.

Accordingly, after a first cycle, known first regions of the surface may comprise the sequence:

$S$-$L$-$M_1$-$P_1$ while remaining regions of the surface comprise the sequence:

$S$-$L$-$P_1$.

Thereafter, second regions of the surface (which may include the first region) are exposed to light and contacted with a second monomer $M_2$ (which may or may not be the same as $M_1$) having a protective group $P_2$. $P_2$ may or may not be the same as $P_0$ and $P_1$. After this second cycle, different regions of the substrate may comprise one or more of the following sequences:

$S$-$L$-$M_1$-$M_2$-$P_2$
$S$-$L$-$M_2$-$P_2$

S-L-$M_1$-$P_1$ and/or

S-L-$P_0$.

The above process is repeated until the substrate includes desired polymers of desired lengths. By controlling the locations of the substrate exposed to light and the reagents exposed to the substrate following exposure, the location of each sequence will be known.

Thereafter, the protective groups are removed from some or all of the substrate and the sequences are, optionally, capped with a capping unit C. The process results in a substrate having a surface with a plurality of polymers of the following general formula:

$$S\text{-}[L]\text{-}(M_i)\text{-}(M_j)\text{-}(M_k) \ldots (M_x)\text{-}[C]$$

where square brackets indicate optional groups, and $M_i \ldots M_x$ indicates any sequence of monomers. The number of monomers could cover a wide variety of values, but in a preferred embodiment they will range from 2 to 100.

In some embodiments a plurality of locations on the substrate polymers are to contain a common monomer subsequence. For example, it may be desired to synthesize a sequence S-$M_1$-$M_2$-$M_3$ at first locations and a sequence S-$M_4$-$M_2$-$M_3$ at second locations. The process would commence with irradiation of the first locations followed by contacting with $M_1$-P, resulting in the sequence S-$M_1$-P at the first location. The second locations would then be irradiated and contacted with $M_4$-P, resulting in the sequence S-$M_4$-P at the second locations. Thereafter both the first and second locations would be irradiated and contacted with the dimer $M_2$-$M_3$, resulting in the sequence S-$M_1$-$M_2$-$M_3$ at the first locations and S-$M_4$-$M_2$-$M_3$ at the second locations. Of course, common subsequences of any length could be utilized including those in a range of 2 or more monomers, 2 to 100 monomers, 2 to 20 monomers, and a most preferred range of 2 to 3 monomers.

According to other embodiments, a set of masks is used for the first monomer layer and, thereafter, varied light wavelengths are used for selective deprotection. For example, in the process discussed above, first regions are first exposed through a mask and reacted with a first monomer having a first protective group $P_1$, which is removable upon exposure to a first wavelength of light (e.g., IR). Second regions are masked and reacted with a second monomer having a second protecive group $P_2$, which is removable upon exposure to a second wavelength of light (e.g., UV). Thereafter, masks become unnecessary in the synthesis because the entire substrate may be exposed alternatively to the first and second wavelengths of light in the deprotection cycle.

The polymers prepared on a substrate according to the above methods will have a variety of uses including, for example, screening for biological activity. In such screening activities, the substrate containing the sequences is exposed to an unlabeled or labeled receptor such as an antibody, receptor on a cell, phospholipid vesicle, or any one of a variety of other receptors. In one preferred embodiment the polymers are exposed to a first, unlabeled receptor of interest and, thereafter, exposed to a labeled receptor-specific recognition element, which is, for example, an antibody. This process will provide signal amplification in the detection stage.

The receptor molecules may bind with one or more polymers on the substrate. The presence of the labeled receptor and, therefore, the presence of a sequence which binds with the receptor is detected in a preferred embodiment through the use of autoradiography, detection of fluorescence with a charge-coupled device, fluorescence microscopy, or the like. The sequence of the polymer at the locations where the receptor binding is detected may be used to determine all or part of a sequence which is complementary to the receptor.

Use of the invention herein is illustrated primarily with reference to screening for biological activity. The invention will, however, find many other uses. For example, the invention may be used in information storage (e.g., on optical disks), production of molecular electronic devices, production of stationary phases in separation sciences, production of dyes and brightening agents, photography, and in immobilization of cells, proteins, lectins, nucleic acids, polysaccharides and the like in patterns on a surface via molecular recognition of specific polymer sequences. By synthesizing the same compound in adjacent, progressively differing concentrations, a gradient will be established to control chemotaxis or to develop diagnostic dipsticks which, for example, titrate an antibody against an increasing amount of antigen. By synthesizing several catalyst molecules in close proximity, more efficient multistep conversions may be achieved by "coordinate immobilization." Coordinate immobilization also may be used for electron transfer systems, as well as to provide both structural integrity and other desirable properties to materials such as lubrication, wetting, etc.

According to-alternative embodiments, molecular biodistribution or pharmacokinetic properties may be examined. For example, to assess resistance to intestinal or serum proteases, polymers may be capped with a fluorescent tag and exposed to biological fluids of interest.

III. Polymer Synthesis

FIG. 1 illustrates one embodiment of the invention disclosed herein in which a substrate 2 is shown in cross-section. Essentially, any conceivable substrate may be employed in the invention. The substrate may be biological, nonbiological, organic, inorganic, or a combination of any of these, existing as particles, strands, precipitates, gels, sheets, tubing, spheres, containers, capillaries, pads, slices, films, plates, slides, etc. The substrate may have any convenient shape, such as a disc, square, sphere, circle, etc. The substrate is preferably flat but may take on a variety of alternative surface configurations. For example, the substrate may contain raised or depressed regions on which the synthesis takes place. The substrate and its surface preferably form a rigid support on which to carry out the reactions described herein. The substrate and its surface is also chosen to provide appropriate light-absorbing characteristics. For instance, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoro-ethylene, (poly) vinylidenedifluoride, polystyrene, polycarbonate, or combinations thereof. Other substrate materials will be readily apparent to those of skill in the art upon review of this disclosure. In a preferred embodiment the substrate is flat glass or single-crystal silicon with surface relief features of less than 10 Å.

According to some embodiments, the surface of the substrate is etched using well known techniques to provide for desired surface features. For example, by way of the formation of trenches, v-grooves, mesa structures, or the like, the synthesis regions may be more closely placed within the focus point of impinging light, be provided with reflective "mirror" structures for maximization of light collection from fluorescent sources, or the like.

Surfaces on the solid substrate will usually, though not always, be composed of the same material as the substrate.

Thus, the surface may be composed of any of a wide variety of materials, for example, polymers, plastics, resins, polysaccharides, silica or silica-based materials, carbon, metals, inorganic glasses, membranes, or any of the above-listed substrate materials. In some embodiments the surface may provide for the use of caged binding members which are attached firmly to the surface of the substrate in accord with the teaching of copending application Ser. No. 404,920, previously incorporated herein by reference. Preferably, the surface will contain reactive groups, which could be carboxyl, amino, hydroxyl, or the like. Most preferably, the surface will be optically transparent and will have surface Si—OH functionalities, such as are found on silica surfaces.

The surface 4 of the substrate is preferably provided with a layer of linker molecules 6, although it will be understood that the linker molecules are not required elements of the invention. The linker molecules are preferably of sufficient length to permit polymers in a completed substrate to interact freely with molecules exposed to the substrate. The linker molecules should be 6–50 atoms long to provide sufficient exposure. The linker molecules may be, for example, aryl acetylene, ethylene glycol oligomers containing 2–10 monomer units, diamines, diacids, amino acids, or combinations thereof. Other linker molecules may be used in light of this disclsoure.

According to alternative embodiments, the linker molecules are selected based upon their hydrophilic/hydrophobic properties to improve presentation of synthesized polymers to certain receptors. For example, in the case of a hydrophilic receptor, hydrophilic linker molecules will be preferred so as to permit the receptor to more closely approach the synthesized polymer.

According to another alternative embodiment, linker molecules are also provided with a photocleavable group at an intermediate position. The photocleavable group is preferably cleavable at a wavelength different from the protective group. This enables removal of the various polymers following completion of the synthesis by way of exposure to the different wavelengths of light.

The linker molecules can be attached to the substrate via carbon-carbon bonds using, for example, (poly) trifluorochloroethylene surfaces, or preferably, by siloxane bonds (using, for example, glass or silicon oxide surfaces). Siloxane bonds with the surface of the substrate may be formed in one embodiment via reactions of linker molecules bearing trichlorosilyl groups. The linker molecules may optionally be attached in an ordered array, i.e., as parts of the head groups in a polymerized Langmuir Blodgett film. In alternative embodiments, the linker molecules are adsorbed to the surface of the substrate.

The linker molecules and monomers used herein are provided with a functional group to which is bound a protective group. Preferably, the protective group is on the distal or terminal end of the linker molecule opposite the substrate. The protective group may be either a negative protective group (i.e., the protective group renders the linker molecules less reactive with a monomer upon exposure) or a positive protective group (i.e., the protective group renders the linker molecules more reactive with a monomer upon exposure). In the case of negative protective groups an additional step of reactivation will be required. In some embodiments, this will be done by heating.

The protective group on the linker molecules may be selected from a wide variety of positive light-reactive groups preferably including nitro aromatic compounds such as o-nitrobenzyl derivatives or benzylsulfonyl. In a preferred embodiment, 6-nitroveratryloxy-carbonyl (NVOC), 2-nitrobenzyloxycarbonyl (NBOC) or α,α-dimethyl-dimethoxybenzyloxycarbonyl (DDZ) is used. In one embodiment, a nitro aromatic compound containing a benzylic hydrogen ortho to the nitro group is used, i.e., a chemical of the form:

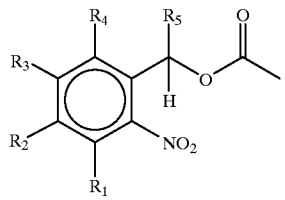

where $R_1$ is alkoxy, alkyl, halo, aryl, alkenyl, or hydrogen; $R_2$ is alkoxy, alkyl, halo, aryl, nitro, or hydrogen; $R_3$ is alkoxy, alkyl, halo, nitro, aryl, or hydrogen; $R_4$ is alkoxy, alkyl, hydrogen, aryl, halo, or nitro; and $R_5$ is alkyl, alkynyl, cyano, alkoxy, hydrogen, halo, aryl, or alkenyl. Other materials which may be used include o-hydroxy-α-methyl cinnamoyl derivatives. Photoremovable protective groups are described in, for example, Patchornik, *J. Am. Chem. Soc.* (1970) 92:6333 and Amit et al., *J. Org. Chem.* (1974) 39:192, both of which are incorporated herein by reference.

In an alternative embodiment the positive reactive group is activated for reaction with reagents in solution. For example, a 5-bromo-7-nitro indoline group, when bound to a carbonyl, undergoes reaction upon exposure to light at 420 nm.

In a second alternative embodiment, the reactive group on the linker molecule is selected from a wide variety of negative light-reactive groups including a cinammate group.

Alternatively, the reactive group is activated or deactivated by electron beam lithography, x-ray lithography, or-any-other radiation. Suitable reactive groups for electron beam lithography include sulfonyl. Other methods may be used including, for example, exposure to a current source. Other reactive groups and methods of activation may be used in light of this disclosure.

Figure 5:
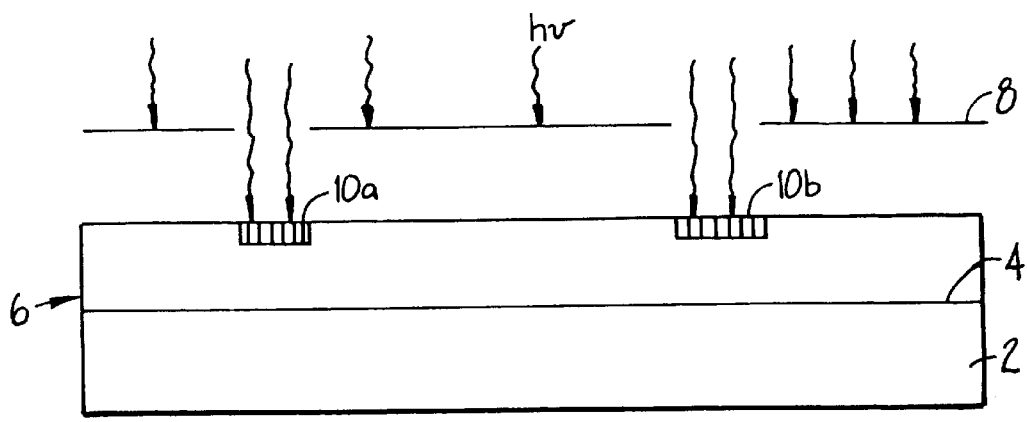
FIG. 5 illustrates masking and irradiation of a substrate at a first location. The substrate is shown in cross-section.

As shown in FIG. 5, the linking molecules are preferably exposed to, for example, light through a suitable mask 8 using photolithographic techniques of the type known in the semiconductor industry and described in, for example, Sze, *VLSI Technology*, McGraw-Hill (1983), and Mead et al., *Introduction to VLSI Systems*, Addison-Wesley (1980), which are incorporated herein by reference for all purposes. The light may be directed at either the surface containing the protective groups or at the back of the-substrate, so long as the substrate is transparent to the wavelength of light needed for removal of the protective groups. In the embodiment shown in FIG. 5, light is directed at the surface of the substrate containing the protective groups. FIG. 5 illustrates the use of such masking techniques as they are applied to a positive reactive group so as to activate linking molecules and expose functional groups in areas 10a and 10b.

The mask 8 is in one embodiment a transparent support material selectively coated with a layer of opaque material. Portions of the opaque material are removed, leaving opaque material in the precise pattern desired on the substrate surface. The mask is brought into close proximity with, imaged on, or brought directly into contact with the substrate surface as shown in FIG. 5. "Openings" in the mask correspond to locations on the substrate where it is desired to remove photoremovable protective groups from the substrate. Alignment may be performed using conventional alignment techniques in which alignment marks (not shown) are used to accurately overlay successive masks with previous patterning steps, or more sophisticated techniques may be used. For example, interferometric techniques such as the one described in Flanders et al., "A New Interferometric Alignment Technique," *App. Phys. Lett.* (1977) 31:426–428, which is incorporated herein by reference, may be used.

To enhance contrast of light applied to the substrate, it is desirable to provide contrast enhancement materials between the mask and the substrate according to some embodiments. This contrast enhancement layer may comprise a molecule which is decomposed by light such as guinone diazid or a material which is transiently bleached at the wavelength of interest. Transient bleaching of materials will allow greater penetration where light is applied, thereby enhancing contrast. Alternatively, contrast enhancement may be provided by way of a cladded fiber optic bundle.

The light may be from a conventional incandescent source, a laser, a laser diode, or the like. If non-collimated sources of light are used it may be desirable to provide a thick- or multi-layered mask to prevent spreading of the light onto the substrate. It may, further, be desirable in some embodiments to utilize groups which are sensitive to different wavelengths to control synthesis. For example, by using groups which are sensitive to different wavelengths, it is possible to select branch positions in the synthesis of a polymer or eliminate certain masking steps. Several reactive groups along with their corresponding wavelengths for deprotection are provided in Table 1.

TABLE 1

| Group | Approximate Deprotection Wavelength |
|---|---|
| Nitroveratryloxy carbonyl (NVOC) | UV (300–400 nm) |
| Nitrobenzyloxy carbonyl (NBOC) | UV (300–350 nm) |
| Dimethyl dimethoxybenzyloxy carbonyl | UV (280–300 nm) |
| 5-Bromo-7-nitroindolinyl | UV (420 nm) |
| o-Hydroxy-α-methyl cinnamoyl | UV (300–350 nm) |
| 2-Oxymethylene anthraquinone | UV (350 nm) |

While the invention is illustrated primarily herein by way of the use of a mask to illuminate selected regions the substrate, other techniques may also be used. For example, the substrate may be translated under a modulated laser or diode light source. Such techniques are discussed in, for example, U.S. Pat. No. 4,719,615 (Feyrer et al.), which is incorporated herein by reference. In alternative embodiments a laser galvanometric scanner is utilized. In other embodiments, the synthesis may take place on or in contact with a conventional liquid crystal (referred to herein as a "light valve") or fiber optic light sources. By appropriately modulating liquid crystals, light may be selectively controlled so as to permit light to contact selected regions of the substrate. Alternatively, synthesis may take place on the end of a series of optical fibers to which light is selectively applied. Other means of controlling the location of light exposure will be apparent to those of skill in the art.

The substrate may be irradiated either in contact or not in contact with a solution (not shown) and is, preferably, irradiated in contact with a solution. The solution contains reagents to prevent the by-products formed by irradiation from interfering with synthesis of the polymer according to some embodiments. Such by-products might include, for example, carbon dioxide, nitrosocarbonyl compounds, styrene derivatives, indole derivatives, and products of their photochemical reactions. Alternatively, the solution may contain reagents used to match the index of refraction of the substrate. Reagents added to the solution may further include, for example, acidic or basic buffers, thiols, substituted hydrazines and hydroxylamines, reducing agents (e.g., NADH) or reagents known to react with a given functional group (e.g., aryl nitroso+glyoxylic acid→aryl formhydroxamate+$CO_2$).

Figure 6:
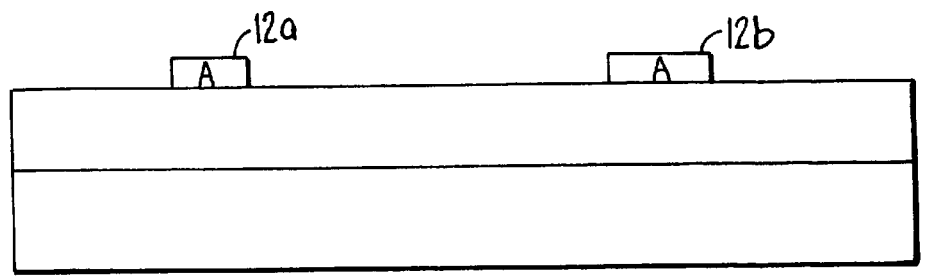
FIG. 6 illustrates the substrate after application of a monomer "A"

Either concurrently with or after the irradiation step, the linker molecules are washed or otherwise contacted with a first monomer, illustrated by "A" in regions 12a and 12b in FIG. 6. The first monomer reacts with the activated functional groups of the linkage molecules which have been exposed to light. The first monomer, which is preferably an amino acid, is also provided with a photoprotective group. The photoprotective group on the monomer may be the same as or different than the protective group used in the linkage molecules, and may be selected from any of the above-described protective groups. In one embodiment, the protective groups for the A monomer is selected from the group NBOC and NVOC.

Figure 7:
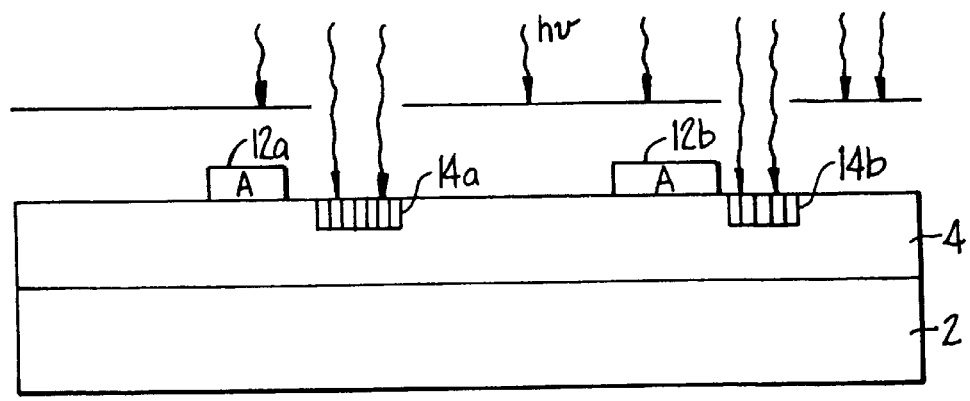
FIG. 7 illustrates irradiation of the substrate at a second location.

As shown in FIG. 7 the process of irradiating is thereafter repeated, with a mask repositioned so as to remove linkage protective groups and expose functional groups in regions 14a and 14b which are illustrated as being regions which were protected in the previous masking step. As an alternative to repositioning of the first mask, in many embodiments a second mask will be utilized. In other alternative embodiments, some steps may provide for illuminating a common region in successive steps. As shown in FIG. 7, it may be desirable to provide separation between irradiated regions. For example, separation of about 1–5 $\mu$m may be appropriate to account for alignment tolerances.

Figure 8:
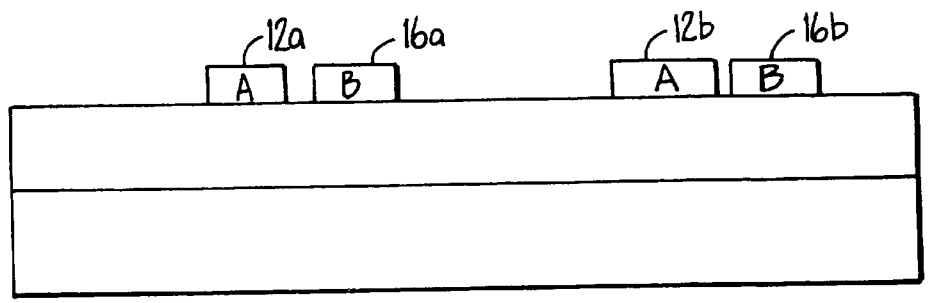
FIG. 8 illustrates the substrate after application of monomer "B"
Figure 10:
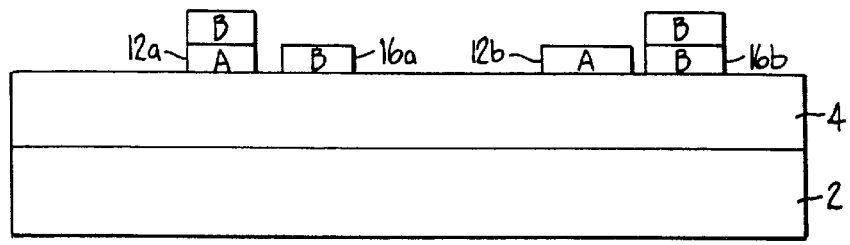
FIG. 10 illustrates the substrate after a second application of "B"

As shown in FIG. 8, the substrate is then exposed to a second protected monomer "B," producing B regions 16a and 16b. Thereafter, the substrate is again masked so as to remove the protective groups and expose reactive groups on A region 12a and B region 16b. The substrate is again exposed to monomer B, resulting in the formation of the structure shown in FIG. 10. The dimers B-A and B-B have been produced on the substrate.

Figure 11:
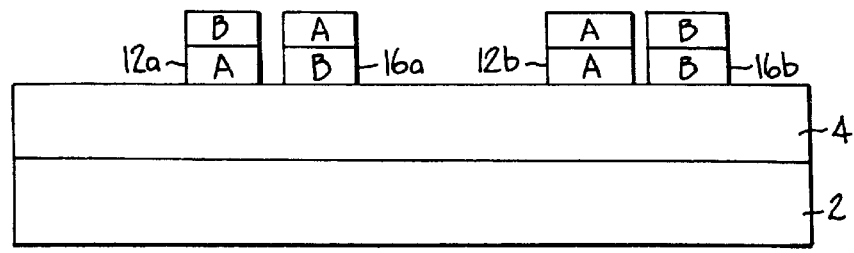
FIG. 11 illustrates a completed substrate.

A subsequent series of masking and contacting steps similar to those described above with A (not shown) provides the structure shown in FIG. 11. The process provides all possible dimers of B and A, i.e., B-A, A-B, A-A, and B-B.

The substrate, the area of synthesis, and the area for synthesis of each individual polymer could be of any size or shape. For example, squares, ellipsoids, rectangles, triangles, circles, or portions thereof, along with irregular geometric shapes, may be utilized. Duplicate synthesis areas may also be applied to a single substrate for purposes of redundancy.

In one embodiment the regions 12 and 16 on the substrate will have a surface area of between about 1 $cm^2$ and $10^{-10}$ $cm^2$. In some embodiments the regions 12 and 16 have areas of less than about $10^{-10}$ $cm^2$, $10^{-2}$ $cm^2$, $10^{-3}$ $cm^2$, $10^{-4}$ $cm^2$, $10^{-5}$ $cm^2$, $10^{-6}$ $cm^2$, $10^{-7}$ $cm^2$, $10^{-8}$ $cm^2$, or $10^{-10}$ $cm^2$. In a preferred embodiment, the regions 12 and 16 are between about 10×10 $\mu$m and 500×500 $\mu$m.

In some embodiments a single substrate supports more than about 10 different monomer sequences and perferably more than about 100 different monomer sequences, although in some embodiments more than about $10^3$, $10^4$, $10_5$, $10^6$, $10^7$, or $10^8$ different sequences are provided on a substrate. Of course, within a region of the substrate in which a monomer sequence is synthesized, it is preferred that the monomer sequence be substantially pure. In some embodiments, regions of the substrate contain polymer sequences which are at least about 1%, 5%, 10%, 15%, 20%, 25%, 30%, 35%, 40%, 45%, 50%, 60%, 70%, 80%, 90%, 95%, 96%, 97%, 98%, or 99% pure.

According to some embodiments, several sequences are intentionally provided within a single region so as to provide an initial screening for biological activity, after which materials within regions exhibiting significant binding are further evaluated.

IV. Details of One Embodiment of a Reactor System

Figure 12A:
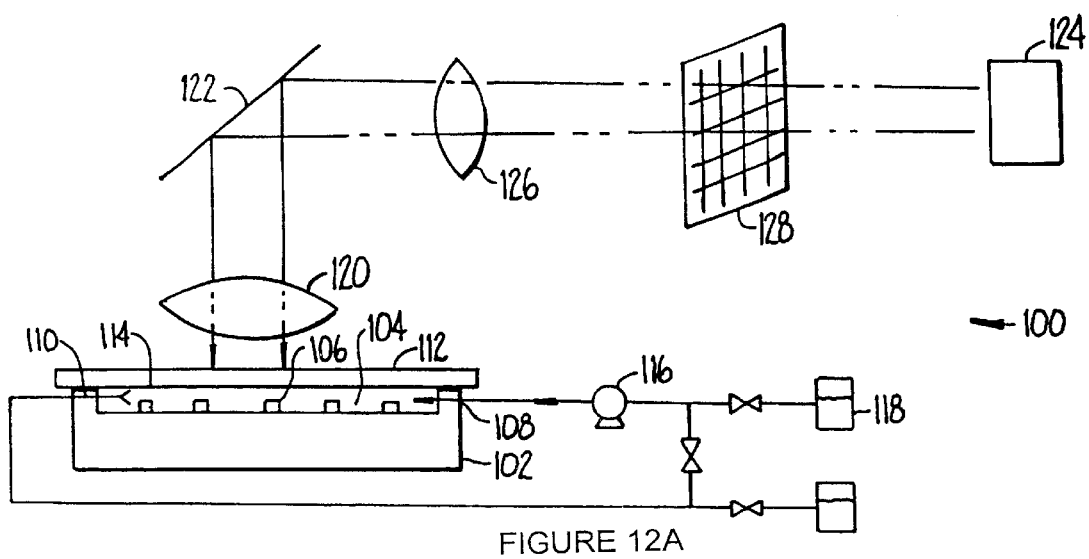
FIGS. 12A and 12B illustrate alternative embodiments of a reactor system for forming a plurality of polymers on a substrate.

FIG. 12A schematically illustrates a preferred embodiment of a reactor system 100 for synthesizing polymers on the prepared substrate in accordance with one aspect of the invention. The reactor system includes a body 102 with a cavity 104 on a surface thereof. In preferred embodiments the cavity 104 is between about 50 and 1000 µm deep with a depth of about 500 µm preferred.

The bottom of the cavity is preferably provided with an array of ridges 106 which extend both into the plane of the Figure and parallel to the plane of the Figure. The ridges are preferably about 50 to 200 µm deep and spaced at about 2 to 3 mm. The purpose of the ridges is to generate turbulent flow for better mixing. The bottom surface of the cavity is preferably light absorbing so as to prevent reflection of impinging light.

A substrate 112 is mounted above the cavity 104. The substrate is provided along its bottom surface 114 with a photoremovable protective group such as NVOC with or without an intervening linker molecule. The substrate is preferably transparent to a wide spectrum of light, but in some embodiments is transparent only at a wavelength at which the protective group may be removed (such as UV in the case of NVOC). The substrate in some embodiments is a conventional microscope glass slide or cover slip. The substrate is preferably as thin as possible, while still providing adequate physical support. Preferably, the substrate is less than about 1 mm thick, more preferably less than 0.5 mm thick, more preferably less than 0.1 mm thick, and most preferably less than 0.05 mm thick. In alternative preferred embodiments, the substrate is quartz or silicon.

The substrate and the body serve to seal the cavity except for an inlet port 108 and an outlet port 110. The body and the substrate may be mated for sealing in some embodiments with one or more gaskets. According to a preferred embodiment, the body is provided with two concentric gaskets and the intervening space is held at vacuum to ensure mating of the substrate to the gaskets.

Fluid is pumped through the inlet port into the cavity by way of a pump 116 which may be, for example, a model no. B-120-S made by Eldex Laboratories. Selected fluids are circulated into the cavity by the pump, through the cavity, and out the outlet for recirculation or disposal. The reactor may be subjected to ultrasonic radiation and/or heated to aid in agitation in some embodiments.

Above the substrate 112, a lens 120 is provided which may be, for example, a 2" 100 mm focal length fused silica lens. For the sake of a compact system, a reflective mirror 122 may be provided for directing light from a light source 124 onto the substrate. Light source 124 may be, for example, a Xe(Hg) light source manufactured by Oriel and having model no. 66024. A second lens 126 may be provided for the purpose of projecting a mask image onto the substrate in combination with lens 112. This form of lithography is referred to herein as projection printing. As will be apparent from this disclosure, proximity printing and the like may also be used according to some embodiments.

Light from the light source is permitted to reach only selected locations on the substrate as a result of mask 128.

Mask 128 may be, for example, a glass slide having etched chrome thereon. The mask 128 in one embodiment is provided with a grid of transparent locations and opaque locations. Such masks may be manufactured by, for example, Photo Sciences, Inc. Light passes freely through the transparent regions of the mask, but is reflected from or absorbed by other regions. Therefore, only selected regions of the substrate are exposed to light.

As discussed above, light valves (LCD's) may be used as an alternative to conventional masks to selectively expose regions of the substrate. Alternatively, fiber optic faceplates such as those available from Schott Glass, Inc, may be used for the purpose of contrast enhancement of the mask or as the sole means of restricting the region to which light is applied. Such faceplates would be placed directly above or on the substrate in the reactor shown in FIG. 8A. In still further embodiments, flys-eye lenses, tapered fiber optic faceplates, or the like, may be used for contrast enhancement.

In order to provide for illumination of regions smaller than a wavelength of light, more elaborate techniques may be utilized. For example, according to one preferred embodiment, light is directed at the substrate by way of molecular microcrystals on the tip of, for example, micropipettes. Such devices are disclosed in Lieberman et al., "A Light Source Smaller Than the Optical Wavelength," *Science* (1990) 247:59–61, which is incorporated herein by reference for all purposes.

In operation, the substrate is placed on the cavity and sealed thereto. All operations in the process of preparing the substrate are carried out in a room lit primarily or entirely by light of a wavelength outside of the light range at which the protective group is removed. For example, in the case of NVOC, the room should be lit with a conventional dark room light which provides little or no UV light. All operations are preferably conducted at about room temperature.

A first, deprotection fluid (without a monomer) is circulated through the cavity. The solution preferably is of 5 mM sulfuric acid in dioxane solution which serves to keep exposed amino groups protonated and decreases their reactivity with photolysis by-products. Absorptive materials such as N,N-diethylamino 2,4-dinitrobenzene, for example, may be included in the deprotection fluid which serves to absorb light and prevent reflection and unwanted photolysis.

The slide is, thereafter, positioned in a light raypath from the mask such that first locations on the substrate are illuminated and, therefore, deprotected. In preferred embodiments the substrate is illuminated for between about 1 and 15 minutes with a preferred illumination time of about 10 minutes at 10–20 mW/cm$^2$ with 365 nm light. The slides are neutralized (i.e., brought to a pH of about 7) after photolysis with, for example, a solution of di-isopropylethylamine (DIEA) in methylene chloride for about 5 minutes.

The first monomer is then placed at the first locations on the substrate. After irradiation, the slide is removed, treated in bulk, and then reinstalled in the flow cell. Alternatively, a fluid containing the first monomer, preferably also protected by a protective group, is circulated through the cavity by way of pump 116. If, for example, it is desired to attach the amino acid Y to the substrate at the first locations, the amino acid Y (bearing a protective group on its α-nitrogen), along with reagents used to render the monomer-reactive, and/or a carrier, is circulated from a storage container 118, through the pump, through the cavity, and back to the inlet of the pump.

The monomer carrier solution is, in a preferred embodiment, formed by mixing of a first solution (referred to herein as solution "A") and a second solution (referred to herein as solution "B"). Table 2 provides an illustration of a mixture which may be used for solution A.

TABLE 2

Representative Monomer Carrier Solution "A"

| | |
|---|---|
| 100 mg | NVOC amino protected amino acid |
| 37 mg | HOBT (1-Hydroxybenzotriazole) |
| 250 μl | DMF (Dimethylformamide) |
| 86 μl | DIEA (Diisopropylethylamine) |

The composition of solution B is illustrated in Table 3. Solutions A and B are mixed and allowed to react at room temperature for about 8 minutes, then diluted with 2 ml of DMF, and 500 μl are applied to the surface of the slide or the solution is circulated through the reactor system and allowed to react for about 2 hours at room temperature. The slide is then washed with DMF, methylene chloride and ethanol.

TABLE 3

Representative Monomer Carrier Solution "B"

| | |
|---|---|
| 250 μl | DMF |
| 111 mg | BOP (Benzotriazolyl-n-oxy-tris (dimethylamino) phosphoniumhexafluorophosphate) |

As the solution containing the monomer to be attached is circulated through the cavity, the amino acid or other monomer will react at its carboxy terminus with amino groups on the regions of the substrate which have been deprotected. Of course, while the invention is illustrated by way of circulation of the monomer through the cavity, the invention could be practiced by way of removing the slide from the reactor and submersing it in an appropriate monomer solution.

After addition of the first monomer, the solution containing the first amino acid is then purged from the system. After circulation of a sufficient amount of the DMF/methylene chloride such that removal of the amino acid can be assured (e.g., about 50× times the volume of the cavity and carrier lines), the mask or substrate is repositioned, or a new mask is utilized such that second regions on the substrate will be exposed to light and the light 124 is engaged for a second exposure. This will deprotect second regions on the substrate and the process is repeated until the desired polymer sequences have been synthesized.

The entire derivatized substrate is then exposed to a receptor of interest, preferably labeled with, for example, a fluorescent marker, by circulation of a solution or suspension of the receptor through the cavity or by contacting the surface of the slide in bulk. The receptor will preferentially bind to certain regions of the substrate which contain complementary sequences.

Antibodies are typically suspended in what is commonly referred to as "supercocktail," which may be, for example, a solution of about 1% BSA (bovine serum albumin), 0.5% Tween in PBS (phosphate buffered saline) buffer. The antibodies are diluted into the supercocktail buffer to a final concentration of, for example, about 0.1 to 4 μg/ml.

Figure 12B:
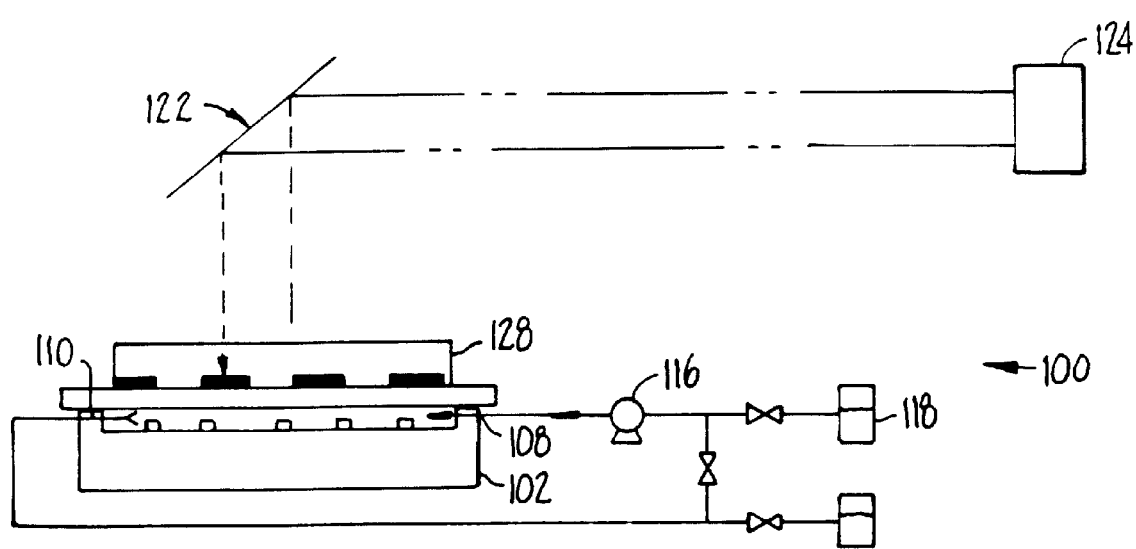

FIG. 12B illustrates an alternative preferred embodiment of the reactor shown in FIG. 8A. According to this embodiment, the mask 128 is placed directly in contact with the substrate. Preferably, the etched portion of the mask is placed face down so as to reduce the effects of light dispersion. According to this embodiment, the imaging lenses 120 and 126 are not necessary because the mask is brought into close proximity with the substrate.

For purposes of increasing the signal-to-noise ratio of the technique, some embodiments of the invention provide for exposure of the substrate to a first labeled or unlabeled receptor followed by exposure of a labeled, second receptor (e.g., an antibody) which binds at multiple sites on the first receptor. If, for example, the first receptor is an antibody derived from a first species of an animal, the second receptor is an antibody derived from a second species directed to epitopes associated with the first species. In the case of a mouse antibody, for example, fluorescently labeled goat antibody or antiserum which is antimouse may be used to bind at multiple sites on the mouse antibody, providing several times the fluorescence compared to the attachment of a single mouse antibody at each binding site. This process may be repeated again with additional antibodies (e.g., goat-mouse-goat, etc.) for further signal amplification.

In preferred embodiments an ordered sequence of masks is utilized. In some embodiments it is possible to use as few as a single mask to synthesize all of the possible polymers of a given monomer set.

If, for example, it is desired to synthesize all 16 dinucleotides from four bases, a 1 cm square synthesis region is divided conceptually into 16 boxes, each 0.25 cm wide. Denote the four monomer units by A, B, C, and D. The first reactions are carried out in four vertical columns, each 0.25 cm wide. The first mask exposes the left-most column of boxes, where A is coupled. The second mask exposes the next column, where B is coupled; followed by a third mask, for the C column; and a final mask that exposes the right-most column, for D. The first, second, third, and fourth masks may be a single mask translated to different locations.

The process is repeated in the horizontal direction for the second unit of the dimer. This time, the masks allow exposure of horizontal rows, again 0.25 cm wide. A, B, C, and D are sequentially coupled using masks that expose horizontal fourths of the reaction area. The resulting substrate contains all 16 dinucleotides of four bases.

The eight masks used to synthesize the dinucleotide are related to one another by translation or rotation. In fact, one mask can be used in all eight steps if it is suitably rotated and translated. For example, in the example above, a mask with a single transparent region could be sequentially used to expose each of the vertical columns, translated 9°, and then sequentially used to allow exposure of the horizontal rows.

Tables 4 and 5 provide a simple computer program in Quick Basic for planning a masking program and a sample output, respectively, for the synthesis of a polymer chain of three monomers ("residues") having three different monomers in the first level, four different monomers in the second level, and five different monomers in the third level in a striped pattern. The output of the program is the number of cells, the number of "stripes" (light regions) on each mask, and the amount of translation required for each exposure of the mask.

TABLE 4

Mask Strategy Program

```
DEFINT A-Z
DIM b(20), w(20), l(500)
F$ = "LPT1:"
OPEN f$ FOR OUTPUT AS #1
jmax = 3         Number of residues
b(1) = 3: b(2) = 4: b(3) = 5      'Number of building blocks for res 1,2,3
g = 1: 1max(1) = 1
FOR j = 1 TO jmax: g= g * b(j): NEXT j
w(0) = 0: w(1) = g / b(1)
```

TABLE 4-continued

Mask Strategy Program

PRINT #1, "MASK2.BAS", DATE$, TIME$: PRINT #1,
PRINT #1, USING "Number of residues=##"; jmax
FOR j = 1 TO jmax
PRINT #1, USING "   Residue ##      ## building blocks"; j; b(j)
NEXT j
PRINT #1, "
PRINT #1, USING "Number of cells=####"; g: PRINT #1,
FOR j = 2 TO jmax
1max(j) = 1max(j - 1) * b(j - 1)
w(j) = w(j - 1) / b(j)
NEXT j
FOR j - 1 TO jmax
PRINT #1, USING "Mask for residue ##"; j: PRINT #1,
PRINT #1, USING "   Number of stripes=###"; 1max(j)
PRINT #1, USING "   Width of each stripe=###"; w(j)
FOR 1 = 1 TO 1max(j)
a = 1 + (1 - 1) * w(j - 1)
ae = a + w(j) - 1
PRINT #1, USING "   Stripe ## begins at location ###
and ends at ###"; 1; a; ae
NEXT 1
PRINT #1,
PRINT #1, USING "   For each of ## building blocks,
translate mask by ## cell(s)"; b(j); w(j),
PRINT #1, : PRINT #1, : PRINT #1,
NEXT j

TABLE 5

Masking Strategy Output

Number of residues= 3
    Residue  1    3 building blocks
    Residue  2    4 building blocks
    Residue  3    5 building blocks
Number of cells= 60
Mask for residue 1
    Number of stripes= 1
    Width of each stripe= 20
    Stripe 1 begins at location 1 and ends at 20
    For each of 3 building blocks, translate mask by 20 cell(s)
Mask for residue 2
    Number of stripes= 3
    Width of each stripe= 5
    Stripe 1 begins at location 1 and ends at 5
    Stripe 2 begins at location 21 and ends at 25
    Stripe 3 begins at location 41 and ends at 45
    For each of 4 building blocks, translate mask by 5 cell(s)
Mask for residue 3
    Number of stripes= 12
    Width of each stripe= 1
    Stripe 1 begins at location 1 and ends at 1
    Stripe 2 begins at location 6 and ends at 6
    Stripe 3 begins at location 11 and ends at 11
    Stripe 4 begins at location 16 and ends at 16
    Stripe 5 begins at location 21 and ends at 21
    Stripe 6 begins at location 26 and ends at 26
    Stripe 7 begins at location 31 and ends at 31
    Stripe 8 begins at location 36 and ends at 36
    Stripe 9 begins at location 41 and ends at 41
    Stripe 10 begins at location 46 and ends at 46
    Stripe 11 begins at location 51 and ends at 51
    Stripe 12 begins at location 56 and ends at 56
    For each of 5 building blocks, translate mask by 1 cell(s)

V. Details of One Embodiment of a Fluorescent Detection Device

Figure 13:
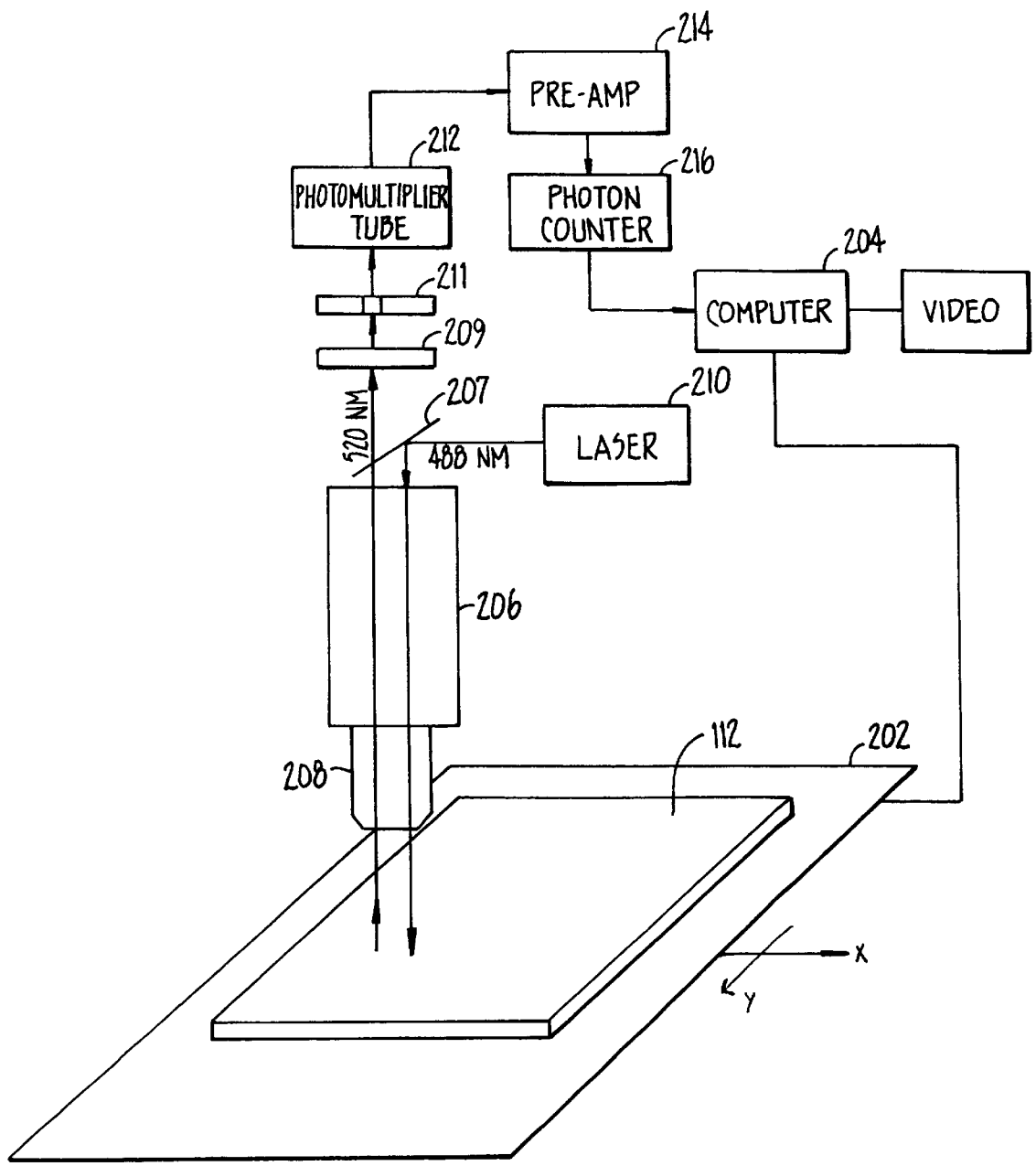
FIG. 13 illustrates a detection apparatus for locating fluorescent markers on the substrate.

FIG. 13 illustrates a fluorescent detection device for detecting fluorescently labeled receptors on a substrate. A substrate 112 is placed on an x/y translation table 202. In a preferred embodiment the x/y translation table is a model no. PM500-A1 manufactured by Newport Corporation. The x/y translation table is connected to and controlled by an appropriately programmed digital computer 204 which may be, for example, an appropriately programmed IBM PC/AT or AT compatible computer. Of course, other computer systems, special purpose hardware, or the like could readily be substituted for the AT computer used herein for illustration. Computer software for the translation and data collection functions described herein can be provided based on commercially available software including, for example, "Lab Windows" licensed by National Instruments, which is incorporated herein by reference for all purposes.

The substrate and x/y translation table are placed under a microscope 206 which includes one or more objectives 208. Light (about 488 nm) from a laser 210, which in some embodiments is a model no. 2020-05 argon ion laser manufactured by Spectraphysics, is directed at the substrate by a dichroic mirror 207 which passes greater than about 520 nm light but reflects 488 nm light. Dichroic mirror 207 may be, for example, a model no. FT510 manufactured by Carl Zeiss. Light reflected from the mirror then enters-the microscope 206 which may be, for example, a model no. Axioscop 20 manufactured by Carl Zeiss. Fluorescein-marked materials on the substrate will fluoresce>488 nm light, and the fluoresced light will be collected by the microscope and passed through the mirror. The fluorescent light from the substrate is then directed through a wavelength filter 209 and, thereafter through an aperture plate 211. Wavelength filter 209 may be, for example, a model no. OG530 manufactured by Melles Griot and aperture plate 211 may be, for example, a model no. 477352/477380 manufactured by Carl Zeiss.

The fluoresced light then enters a photomultiplier tube 212 which in some embodiments is a model no. R943-02 manufactured by Hamamatsu, the signal is amplified in preamplifier 214 and photons are counted by photon counter 216. The number of photons is recorded as a function of the location in the computer 204. Pre-Amp 214 may be, for example, a model no. SR440 manufactured by Stanford Research Systems and photon counter 216 may be a model no. SR400 manufactured by Stanford Research Systems. The substrate is then moved to a subsequent location and the process is repeated. In preferred-embodiments the data are acquired every 1 to 100 $\mu$m with a data collection diameter of about 0.8 to 10 $\mu$m preferred. In embodiments with sufficiently high fluorescence, a CCD detector with broad-field illumination is utilized.

By counting the number of photons generated in a given area in response to the laser, it is possible to determine where fluorescent marked molecules are located on the substrate. Consequently, for a slide which has a matrix of polypeptides, for example, synthesized on the surface thereof, it is possible to determine which of the polypeptides is complementary to a fluorescently marked receptor.

According to preferred embodiments, the intensity and duration of the light applied to the substrate is controlled by varying the laser power and scan stage rate for improved signal-to-noise ratio by maximizing fluorescence emission and minimizing background noise.

While the detection apparatus has been illustrated primarily herein with regard to the detection of marked receptors, the invention will find application in other areas. For example, the detection apparatus disclosed herein could be used in the fields of catalysis, DNA or protein gel scanning, and the like.

In the use of autoradiography, the marker is a radioactive label, such as $^{32}$P. The marker is exposed to a film, which is developed, then read out on a scanner. An exposure time of about 1 hour would be required for autoradiography in one embodiment. Fluorescence detection using, for example, a fluorophore such as fluorescene attached to the receptor will usually require shorter exposure e.g., 1 second or less.

VI. Determination of Relative Binding Strength of Receptors

The signal-to-noise ratio of the present invention is sufficiently high that not only can the presence or absence of a receptor on a ligand be detected, but also the relative binding affinity of receptors to a variety of sequences can be determined.

In practice it is found that a receptor will bind to several peptide sequences in an array, but will bind much more strongly to some sequences than others. Strong binding affinity will be evidenced herein by a strong fluorescent or radiographic signal since many receptor molecules will bind in a region of a strongly bound ligand. Conversely, a weak binding affinity will be evidenced by a weak fluorescent or radiographic signal due to the relatively small number of receptor molecules which bind in a particular region of a substrate having a ligand with a weak binding affinity for the receptor. Consequently, it becomes possible to determine relative binding avidity (or affinity in the case of univalent interactions) of a ligand herein by way of the intensity of a fluorescent or radiographic signal in a region containing that ligand.

Semiquantitative data on affinities might also be obtained by varying washing conditions and concentrations of the receptor. This would be done by comparison to known ligand receptor pairs, for example.

VII. Examples

The following examples are provided to illustrate the efficacy of the inventions herein. All operations were conducted at about ambient temperatures and pressures unless indicated to the contrary.

A. Slide Preparation

Before attachment of reactive groups it is preferred to clean the substrate which is, in a preferred embodiment a glass substrate such as a microscope slide or cover slip. According to one embodiment the slide is soaked in an alkaline bath consisting of, for example, 1 liter of 95% ethanol with 120 ml of water and 120 grams of sodium hydroxide for 12 hours. The slides are then washed under running water and allowed to air dry, and rinsed once with a solution of 95% ethanol.

The slides are then aminated with, for example, aminopropyltriethoxysilane for the purpose of attaching amino groups to the glass surface on linker molecules, although any omega functionalized silane could also be used for this purpose. In one embodiment 0.1% aminopropyltriethoxysilane is utilized, although solutions with concentrations from $10^{-7}\%$ to 10% may be used, with about $10^{-3}\%$ to 2% preferred. A 0.1% mixture is prepared by adding to 100 ml of a 95% ethanol/5% water mixture, 100 microliters ($\mu$l) of aminopropyltriethoxysilane. The mixture is agitated at about ambient temperature on a rotary shaker for about 5 minutes. 500 $\mu$l of this mixture is then applied to the surface of one side of each cleaned slide. After 4 minutes, the slides are decanted of this solution and rinsed three times by dipping in, for example, 100% ethanol.

After the plates dry, they are placed in a 110–1200° C. vacuum oven for about 20 minutes, and then allowed to cure at room temperature for about 12 hours in an argon environment. The slides are then dipped into DMF (dimethylformamide) solution, followed by a thorough washing with methylene chloride.

The aminated surface of the slide is then exposed to about 500 $\mu$l of, for example, a 30 millimolar (mM) solution of NVOC-GABA (gamma amino butyric acid) NHS (N-hydroxysuccinimide) in DMF for attachment of a NVOC-GABA to each of the amino groups.

The surface is washed with, for example, DMF, methylene chloride, and ethanol.

Any unreacted aminopropyl silane on the surface—that is, those amino groups which have not had the NVOC-GABA attached—are now capped with acetyl groups (to prevent further reaction) by exposure to a 1:3 mixture of acetic anhydride in pyridine for 1 hour. Other materials which may perform this residual capping function include trifluoroacetic anhydride, formicacetic anhydride, or other reactive acylating agents. Finally, the slides are washed again with DMF, methylene chloride, and ethanol.

B. Synthesis of Eight Trimers of "A" and "B"

FIG. 14 illustrates a possible synthesis of the eight trimers of the two-monomer set: gly, phe (represented by "A" and "B," respectively). A glass slide bearing silane groups terminating in 6-nitro-veratryloxycarboxamide (NVOC-UH) residues is prepared as a substrate. Active esters (pentafluorophenyl, OBt, etc.) of gly and phe protected at the amino group with NVOC are prepared as reagents. While not pertinent to this example, if side chain protecting groups are required for the monomer set, these must not be photoreactive at the wavelength of light used to protect the primary chain.

For a monomer set of size n, n×l cycles are required to synthesize all possible sequences of length l. A cycle consists of:

1. Irradiation through an appropriate mask to expose the amino groups at the sites where the next residue is to be added, with appropriate washes to remove the by-products of the deprotection.

2. Addition of a single activated and protected (with the same photochemically-removable group) monomer, which will react only at the sites addressed in step 1, with appropriate washes to remove the excess reagent from the surface.

The above cycle is repeated for each member of the monomer set until each location on the surface has been extended by one residue in one embodiment. In other embodiments, several residues are sequentially added at one location before moving on to the next location. Cycle times will generally be limited by the coupling reaction rate, now as short as 20 min in automated peptide synthesizers. This step is optionally followed by addition of a protecting group to stabilize the array for later testing. For some types of polymers (e.g., peptides), a final deprotection of the entire surface (removal of photoprotective side chain groups) may be required.

Figure 14A:
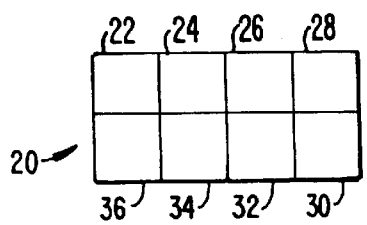
FIGS. 14A–14M illustrate the method as it is applied to the production of the trimers of monomers "A" and "B"
Figure 14B:
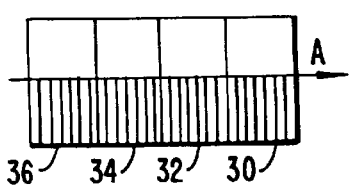
Figure 14C:
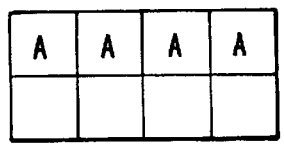
Figure 14D:
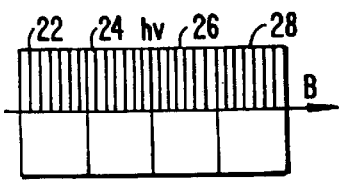
Figure 14E:
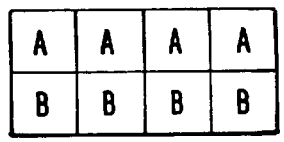
Figure 14F:
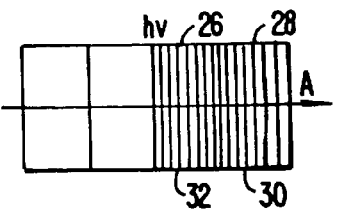
Figure 14G:
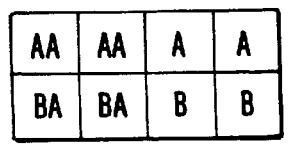
Figure 14H:
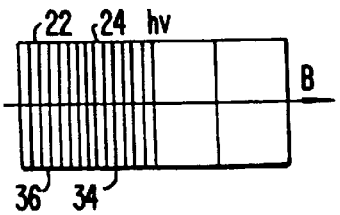
Figure 14I:
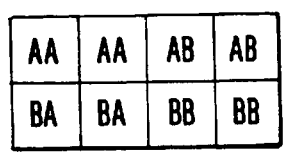
Figure 14J:
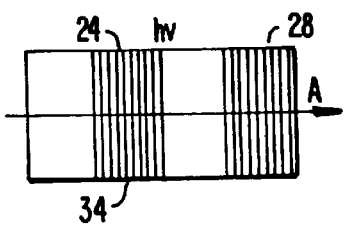
Figure 14K:
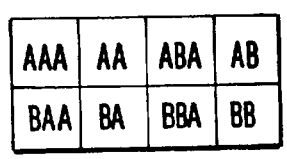
Figure 14L:
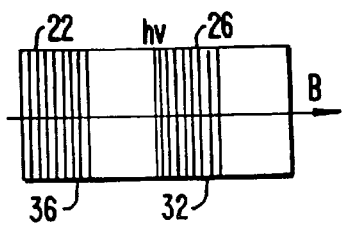
Figure 14M:
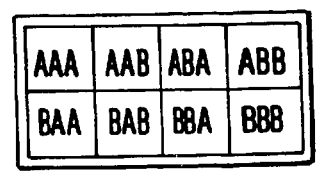

More particularly, as shown in FIG. 14A, the glass 20 is provided with regions 22, 24, 26, 28, 30, 32, 34, and 36. Regions 30, 32, 34, and 36 are masked, as shown in FIG. 14B and the glass is irradiated and exposed to a reagent containg "A" (e.g., gly), with the resulting structure shown in FIG. 14C. Thereafter, regions 22, 24, 26, and 28 are masked, the glass is irradiated (as shown in FIG. 14D) and exposed to a reagent containing "B" (e.g., phe), with the resulting structure shown in FIG. 14E. The process proceeds, consecutively masking and exposing the sections as shown until the structure shown in FIG. 14M is obtained. The glass is irradiated and the terminal groups are, optionally, capped by acetylation. As shown, all possible trimers of gly/phe are obtained.

In this example, no side chain protective group removal is necessary. If it is desired, side chain deprotection may be accomplished by treatment with ethanedithiol and trifluoroacetic acid.

In general, the number of steps needed to obtain a particular polymer chain is defined by:

$$n \times l \quad (1)$$

where:
n=the number of monomers in the basis set of monomers, and
l=the number of monomer units in a polymer chain.

Conversely, the synthesized number of sequences of length l will be:

$$n^l. \quad (2)$$

Of course, greater diversity is obtained by using masking strategies which will also include the synthesis of polymers having a length of less than l. If, in the extreme case, all polymers having a length less than or equal to l are synthesized, the number of polymers synthesized will be:

$$n^l + n^{l-1} + \ldots + n^1. \quad (3)$$

The maximum number of lithographic steps needed will generally be n for each "layer" of monomers, i.e., the total number of masks (and, therefore, the number of lithographic steps) needed will be n×l. The size of the transparent mask regions will vary in accordance with the area of the substrate available for synthesis and the number of sequences to be formed. In general, the size of the synthesis areas will be:

size of synthesis areas=(A)/(S)

where:
A is the total area available for synthesis; and
S is the number of sequences desired in the area.

It will be appreciated by those of skill in the art that the above method could readily be used to simultaneously produce thousands or millions of oligomers on a substrate using the photolithographic techniques disclosed herein. Consequently, the method results in the ability to practically test large numbers of, for example, di, tri, tetra, penta, hexa, hepta, octapeptides, dodecapeptides, or larger polypeptides (or correspondingly, polynucleotides).

The above example has illustrated the method by way of a manual example. It will of course be appreciated that automated or semi-automated methods could be used. The substrate would be mounted in a flow cell for automated addition and removal of reagents, to minimize the volume of reagents needed, and to more carefully control reaction conditions. Successive masks could be applied manually or automatically.

C. Synthesis of a Dimer of an Aminopropyl Group and a Fluorescent Group

In synthesizing the dimer of an aminopropyl group and a fluorescent group, a functionalized durapore membrane was used as a substrate. The durapore membrane was a polyvinylidine difluoride with aminopropyl groups. The aminopropyl groups were protected with the DDZ group by reaction of the carbonyl chloride with the amino groups, a reaction readily known to those of skill in the art. The surface bearing these groups was placed in a solution of THF and contacted with a mask bearing a checkerboard pattern of 1 mm opaque and transparent regions. The mask was exposed to ultraviolet light having a wavelength down to at least about 280 nm for about 5 minutes at ambient temperature, although a wide range of exposure times and temperatures may be appropriate in various embodiments of the invention. For example, in one embodiment, an exposure time of between about 1 and 5000 seconds may be used at process temperatures of between −70 and +500° C.

In one preferred embodiment, exposure times of between about 1 and 500 seconds at about ambient pressure are used. In some preferred embodiments, pressure above ambient is used to prevent evaporation.

The surface of the membrane was then washed for about 1 hour with a fluorescent label which included an active ester bound to a chelate of a lanthanide. Wash times will vary over a wide range of values from about a few minutes to a few hours. These materials fluoresce in the red and the green visible region. After the reaction with the active ester in the fluorophore was complete, the locations in which the fluorophore was bound could be visualized by exposing them to ultraviolet light and observing the red and the green fluorescence. It was observed that the derivatized regions of the substrate closely corresponded to the original pattern of the mask.

D. Demonstration of Signal Capability

Signal detection capability was demonstrated using a low-level standard fluorescent bead kit manufactured by Flow Cytometry Standarda and having model no. 824. This kit includes 5.8 μm diameter beads, each impregnated with a known number of fluorescein molecules.

Figure 9:
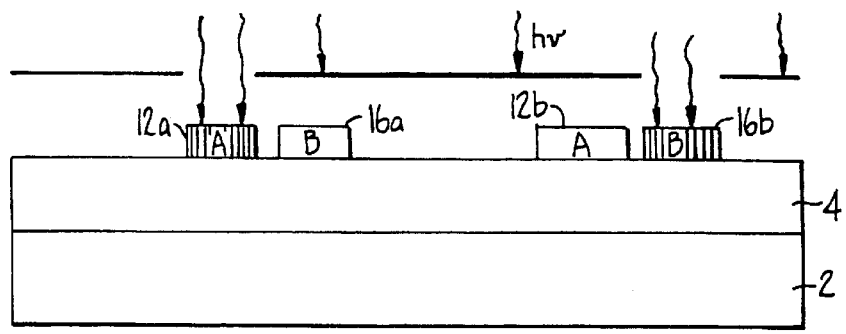
FIG. 9 illustrates irradiation of the "A" monomer.

One of the beads was placed in the illumination field on the scan stage as shown in FIG. 9 in a field of a laser spot which was initially shuttered. After being positioned in the illumination field, the photon detection equipment was turned on. The laser beam was unblocked and it interacted with the particle bead, which then fluoresced. Fluorescence curves of beads impregnated with 7,000; 13,000; and 29,000 fluorescein molecules, are shown in FIGS. 11A, 11B, and 11C respectively. On each curve, traces for beads without fluorescein molecules are also shown. These experiments were performed with 488 nm excitation, with 100 μW of laser power. The light was focused through a 40 power 0.75 NA objective.

The fluorescence intensity in all cases started off at a high value and then decreased exponentially. The fall-off in intensity is due to photobleaching of the fluorescein molecules. The traces of beads without fluorescein molecules are used for background subtraction. The difference in the initial exponential decay between labeled and nonlabeled beads is integrated to give the total number of photon counts, and this number is related to the number of molecules per bead. Therefore, it is possible to deduce the number of photons per fluorescein molecule that can be detected. For the curves illustrated in FIG. 11, this calculation indicates the radiation of about 40 to 50 photons per fluorescein molecule are detected.

E. Determination of the Number of Molecules Per Unit Area

Aminopropylated glass microscope slides prepared according to the methods discussed above were utilized in order to establish the density of labeling of the slides. The free amino termini of the slides were reacted with FITC (fluorescein isothiocyanate) which forms a covalent linkage with the amino group. The slide is then scanned to count the number of fluorescent photons generated in a region which, using the estimated 40–50 photons per fluorescent molecule, enables the calculation of the number of molecules which are on the surface per unit area.

A slide with aminopropyl silane on its surface was immersed in a 1 mM solution of FITC in DMF for 1 hour at about ambient temperature. After reaction, the slide was washed twice with DMF and then washed with ethanol, water, and then ethanol again. It was then dried and stored in the dark until it was ready to be examined.

Figure 15A:
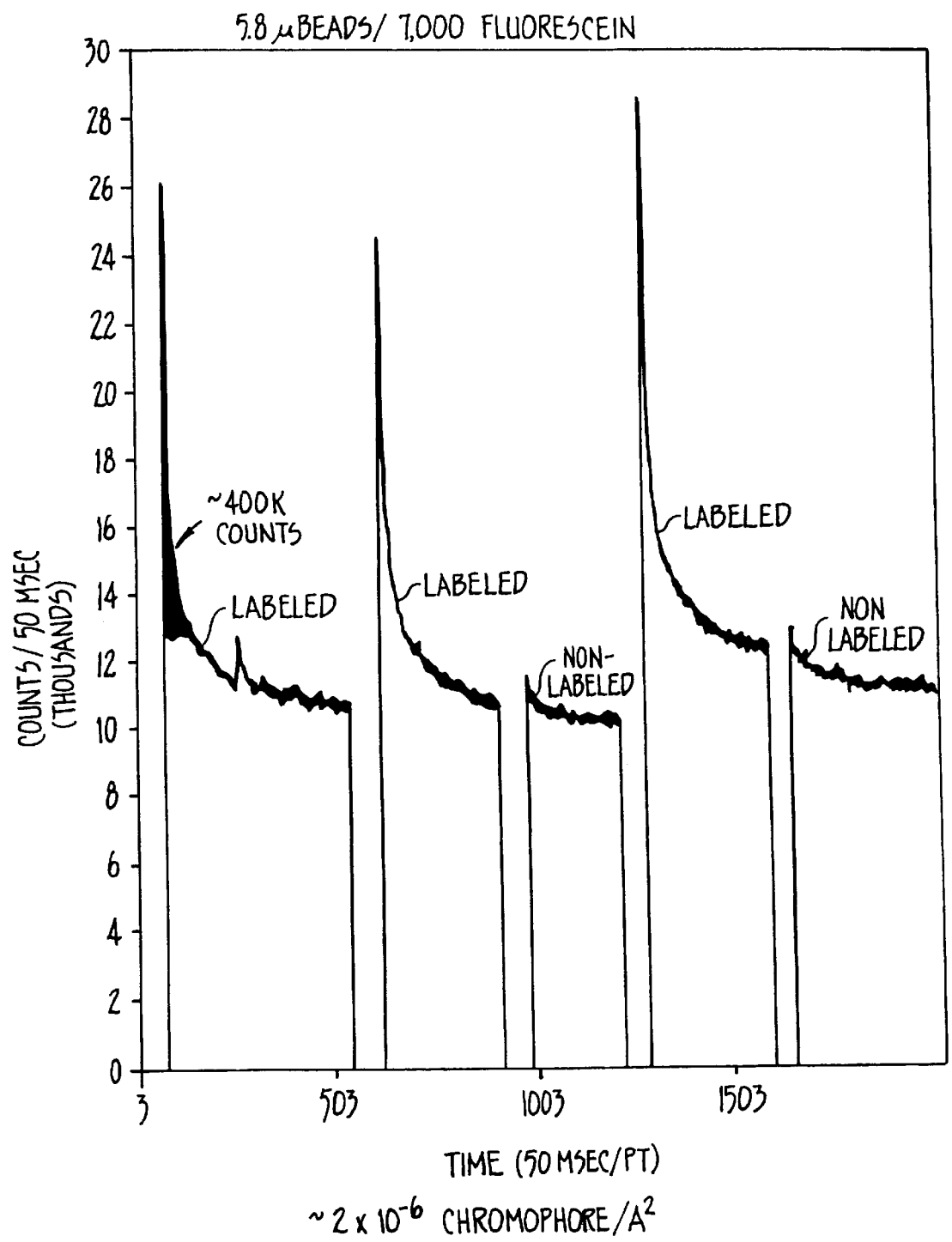
FIGS. 15A and 15B are fluorescence traces for standard fluorescent beads.
Figure 15B:
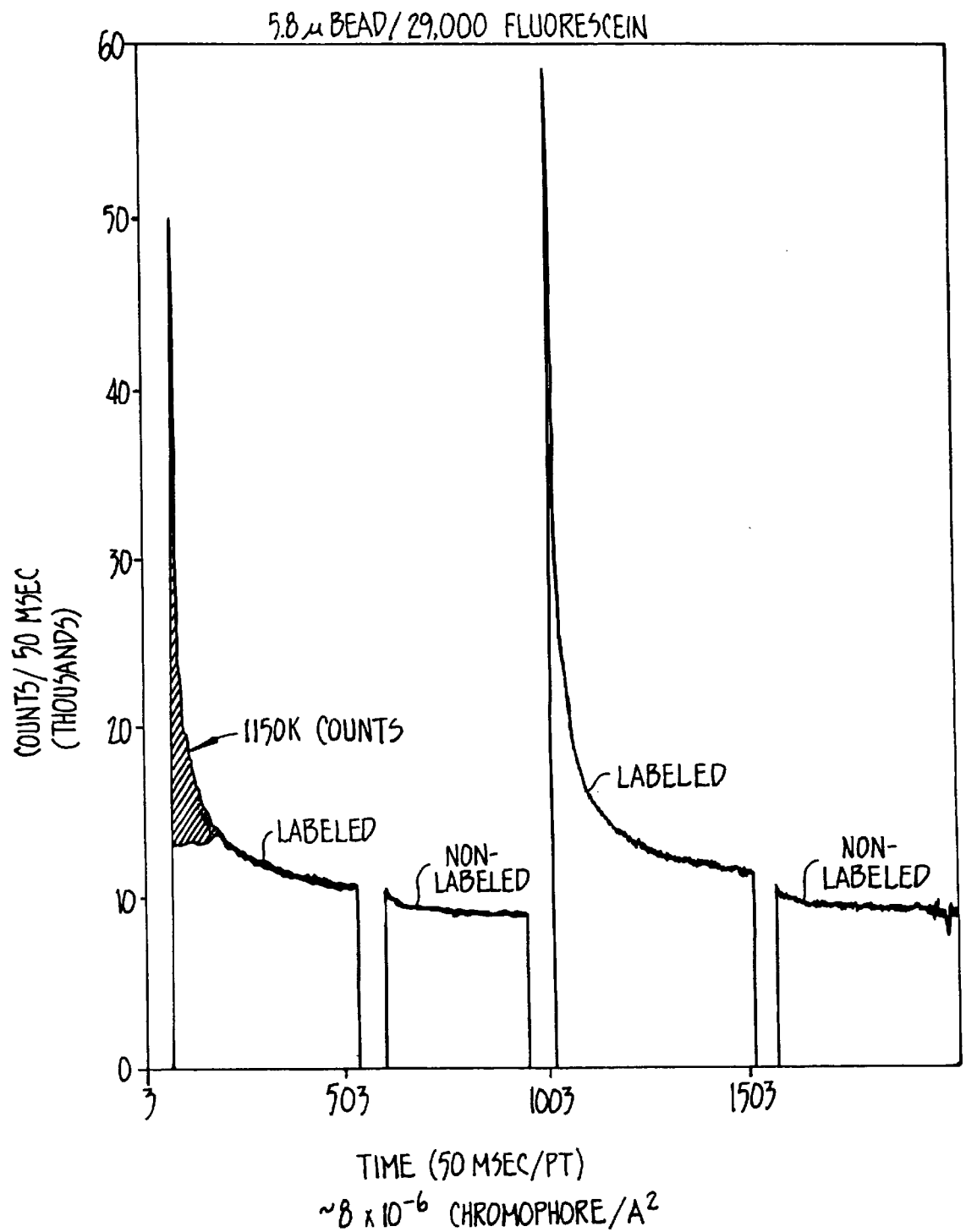

Through the use of curves similar to those shown in FIG. 15, and by integrating the fluorescent counts under the exponentially decaying signal, the number of free amino groups on the surface after derivitization was determined. It was determined that slides with labeling densities of 1 fluoroscein per $10^3 \times 10^3$ to ~2×2 nm could be reproducibly made as the concentration of aminopropyltriethoxysilane varied from $10^{-5}\%$ to $10^{-1}\%$.

F. Removal of NVOC and Attachment of a Fluorescent Marker

NVOC-GABA groups were attached as described above. The entire surface of one slide was exposed to light so as to expose a free amino group at the end of the gamma amino butyric acid. This slide, and a duplicate which was not exposed, were then exposed to fluorescein isothiocyanate (FITC).

Figure 16A:
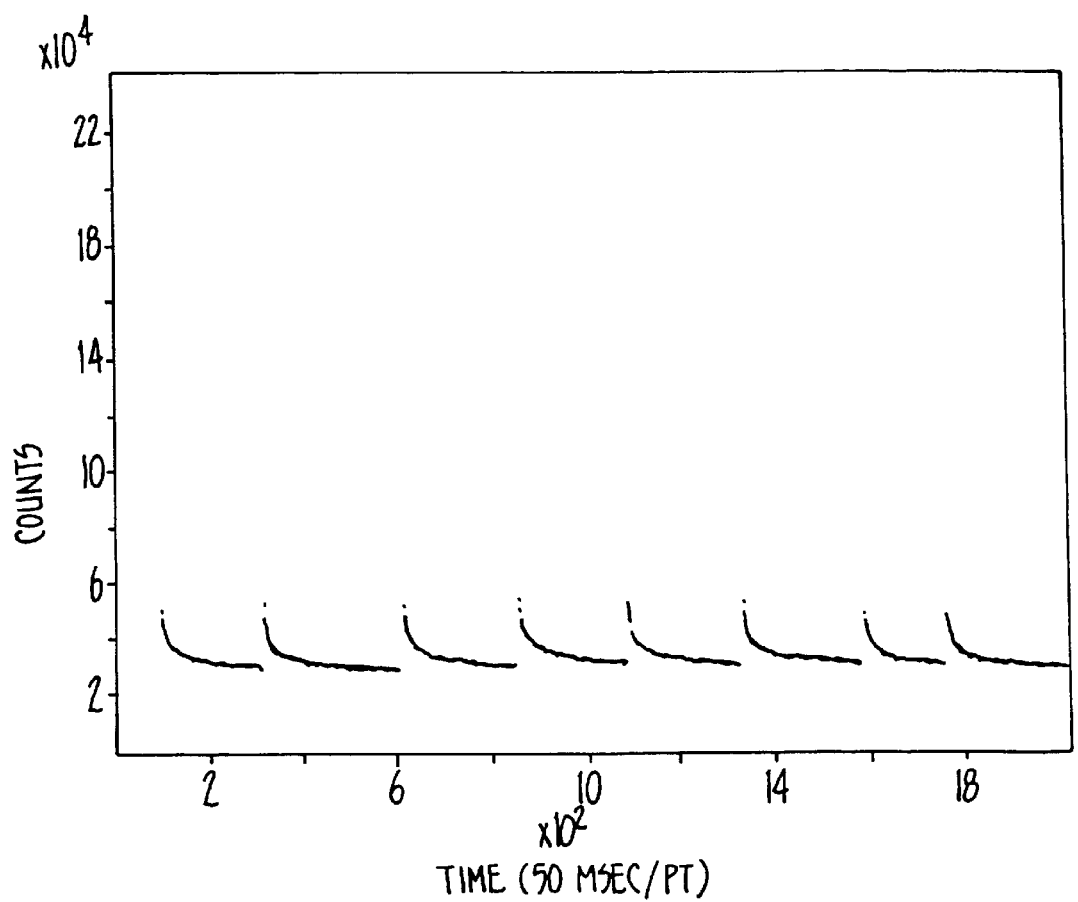
FIGS. 16A and 16B are fluorescence curves for NVOC slides not exposed and exposed to light respectively.
Figure 16B:
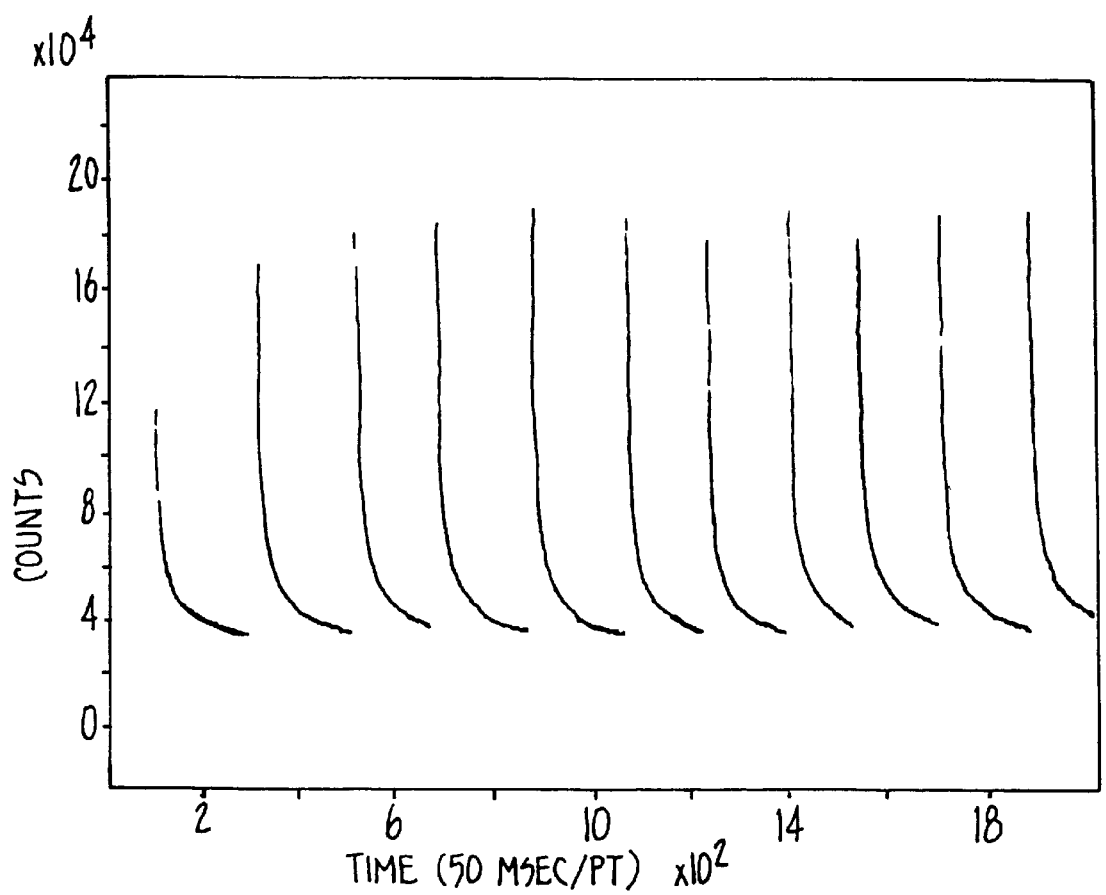

FIG. 16A illustrates the slide which was not exposed to light, but which was exposed to FITC. The units of the x axis are time and the units of the y axis are counts. The trace contains a certain amount of background fluorescence. The duplicate slide was exposed to 350 nm broadband illumination for about 1 minute (12 mW/cm$^2$, ~350 nm illumination), washed and reacted with FITC. The fluorescence curves for this slide are shown in FIG. 16B. A large increase in the level of fluorescence is observed, which indicates photolysis has exposed a number of amino groups on the surface of the slides for attachment of a fluorescent marker.

G. Use of a Mask in Removal of NVOC

The next experiment was performed with a 0.1% aminopropylated slide. Light from a Hg—Xe arc lamp was imaged onto the substrate through a laser-ablated chrome-on-glass mask in direct contact with the substrate.

Figure 17A:
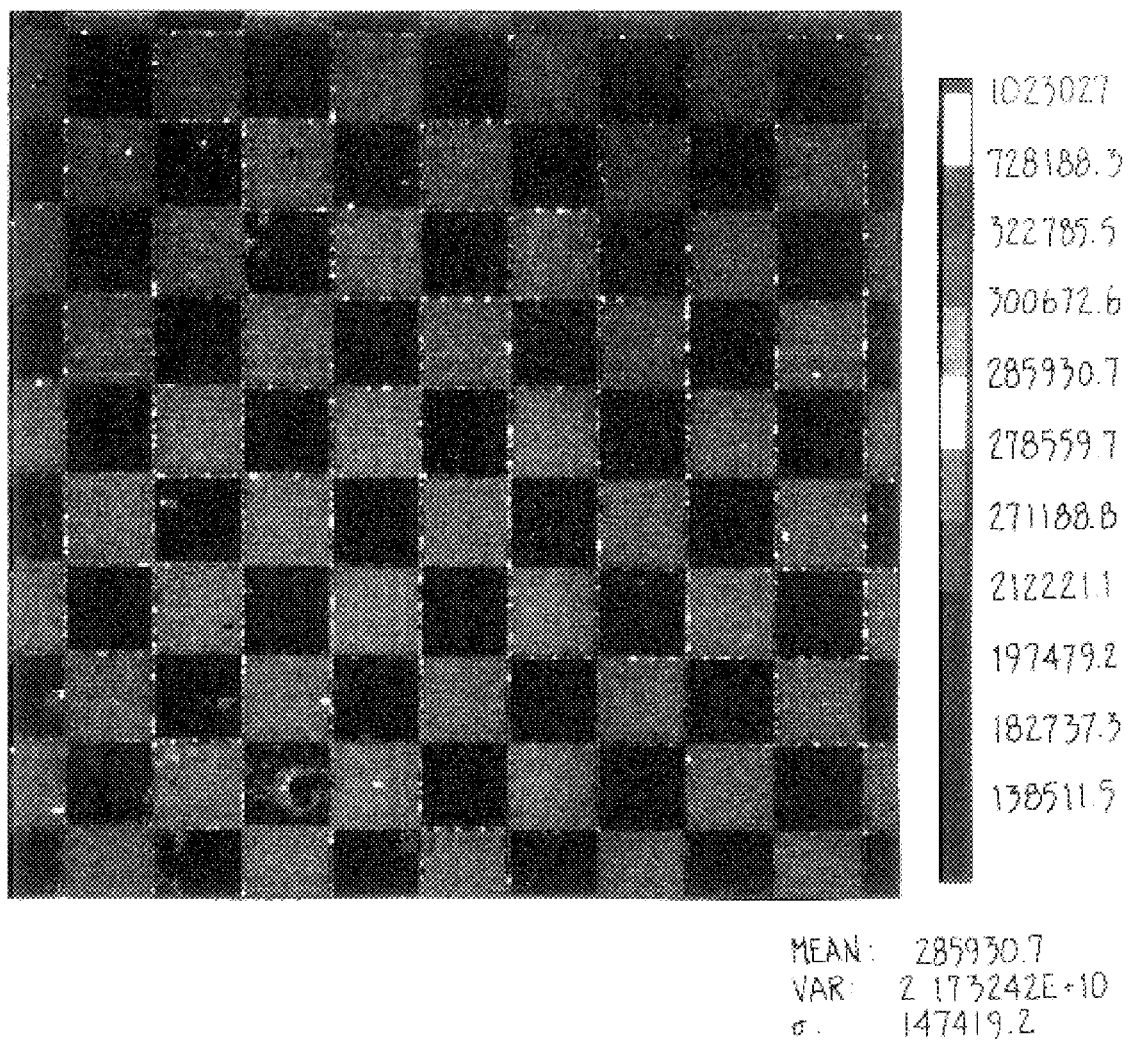
FIGS. 17A to 17D are fluorescence plots of slides exposed through 100 µm, 50 µm, 20 µm, and 10 µm masks.

This slide was illuminated for approximately 5 minutes, with 12 mW of 350 nm broadband light and then reacted with the 1 mM FITC solution. It was put on the laser detection scanning stage and a graph was plotted as a two-dimensional representation of position color-coded for fluorescence intensity. The fluorescence intensity (in counts) as a function of location is given on the color scale to the right of FIG. 17A for a mask having 100×100 µm squares.

Figure 17B:
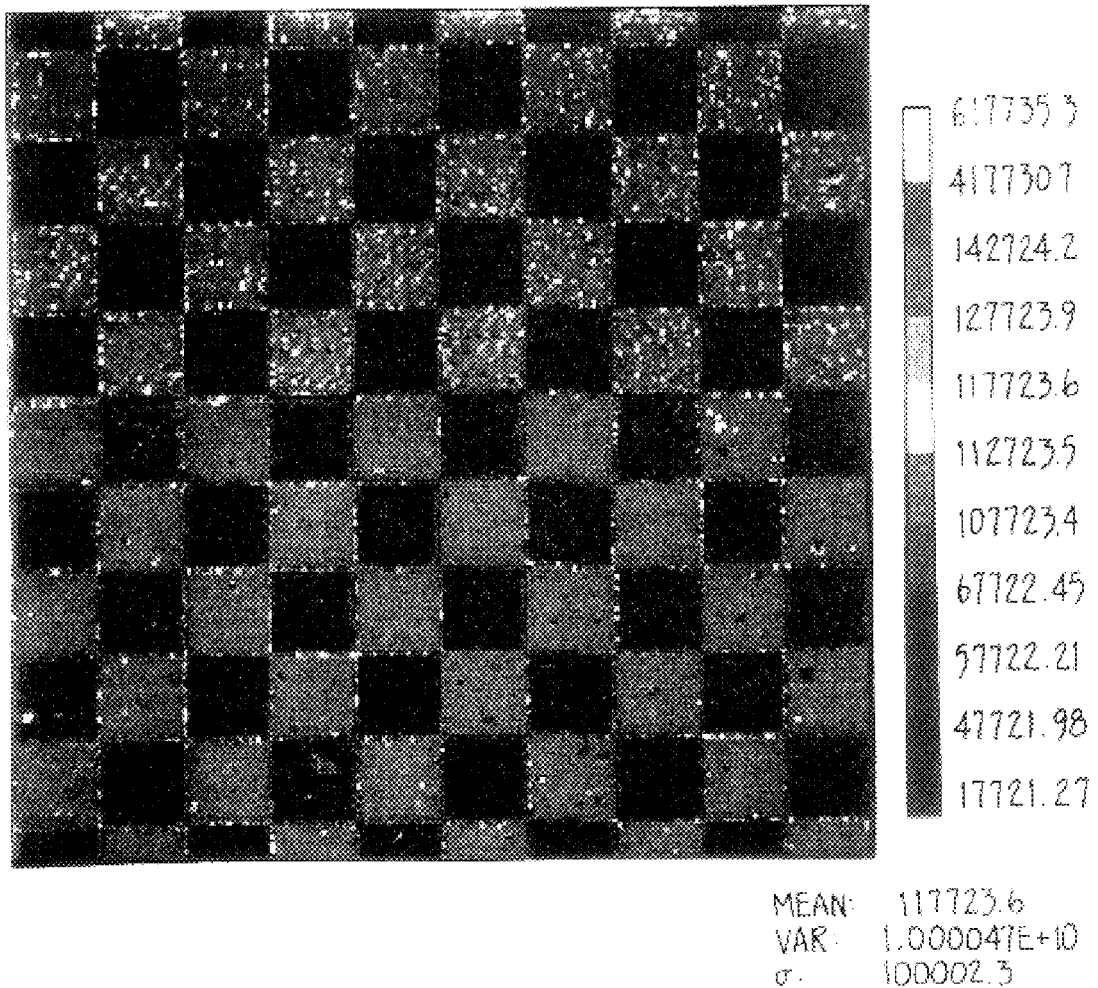
Figure 17C:
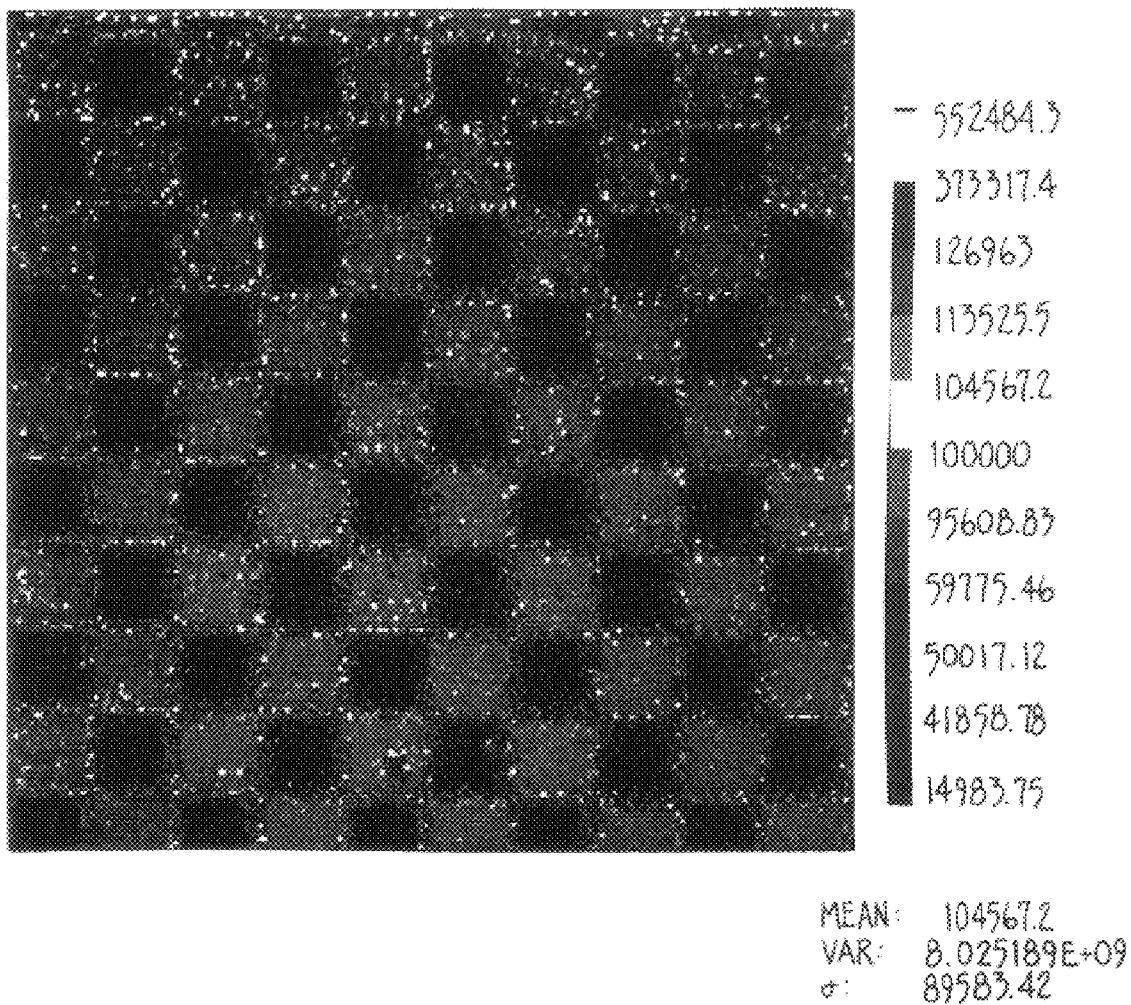
Figure 17D:
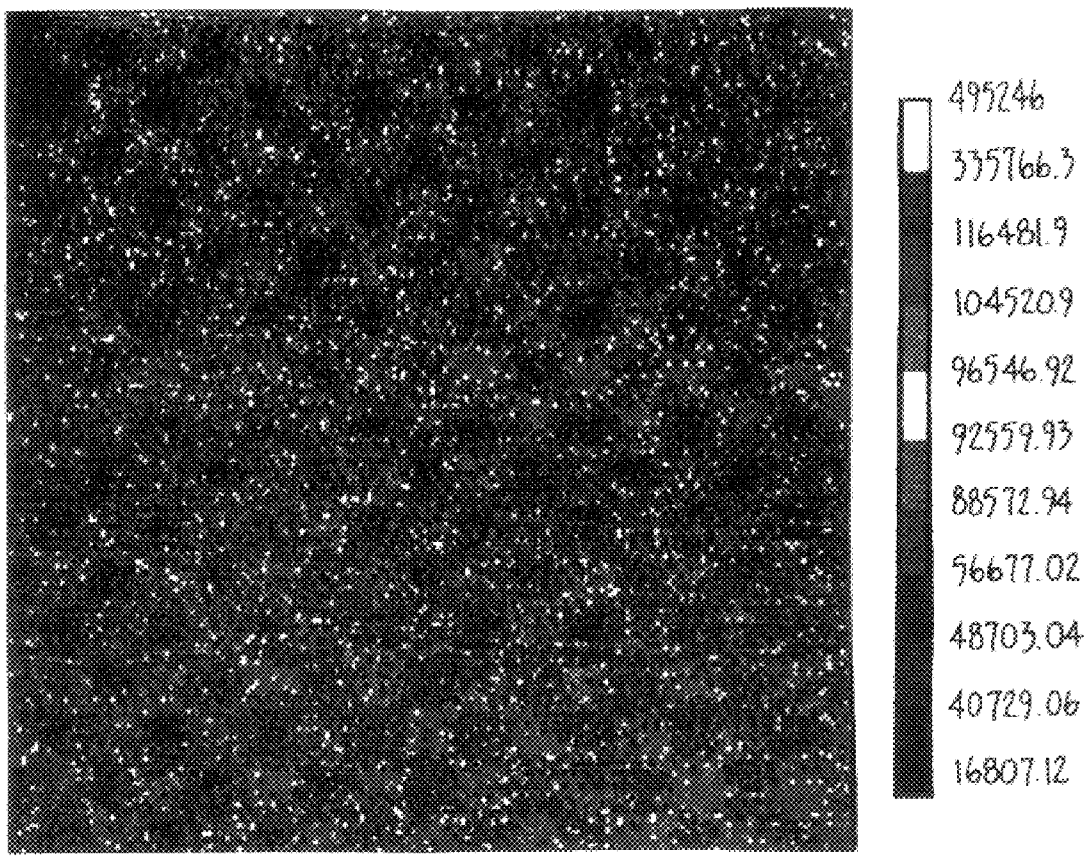

The experiment was repeated a number of times through various masks. The fluorescence pattern for a 50 µm mask is illustrated in FIG. 17B, for a 20 µm mask in FIG. 17C, and for a 10 µm mask in FIG. 17D. The mask pattern is distinct down to at least about 10 µm squares using this lithographic technique.

H. Attachment of YGGFL and Subsequent Exposure to Herz Antibody and Goat Antimouse In order to establish that receptors to a particular polypeptide sequence would bind to a surface-bound peptide and be detected, Leu enkephalin was coupled to the surface and recognized by an antibody. A slide was derivatized with 0.1% amino propyl-triethoxysilane and protected with NVOC. A 500 µm checkerboard mask was used to expose the slide in a flow cell using backside contact printing. The Leu enkephalin sequence (H$_2$N-tyrosine,glycine,glycine, phenylalanine,leucine-CO$_2$H, otherwise referred to herein as YGGFL) was attached via its carboxy end to the exposed amino groups on the surface of the slide. The peptide was added in DMF solution with the BOP/HOBT/DIEA coupling reagents and recirculated through the flow cell for 2 hours at room temperature.

A first antibody, known as the Herz antibody, was applied to the surface of the slide for 45 minutes at 2 µg/ml in a supercocktail (containing 1% BSA and 1% ovalbumin also in this case). A second antibody, goat anti-mouse fluorescein conjugate, was then added at 2 µg/ml in the supercocktail buffer, and allowed to incubate for 2 hours.

Figure 18:
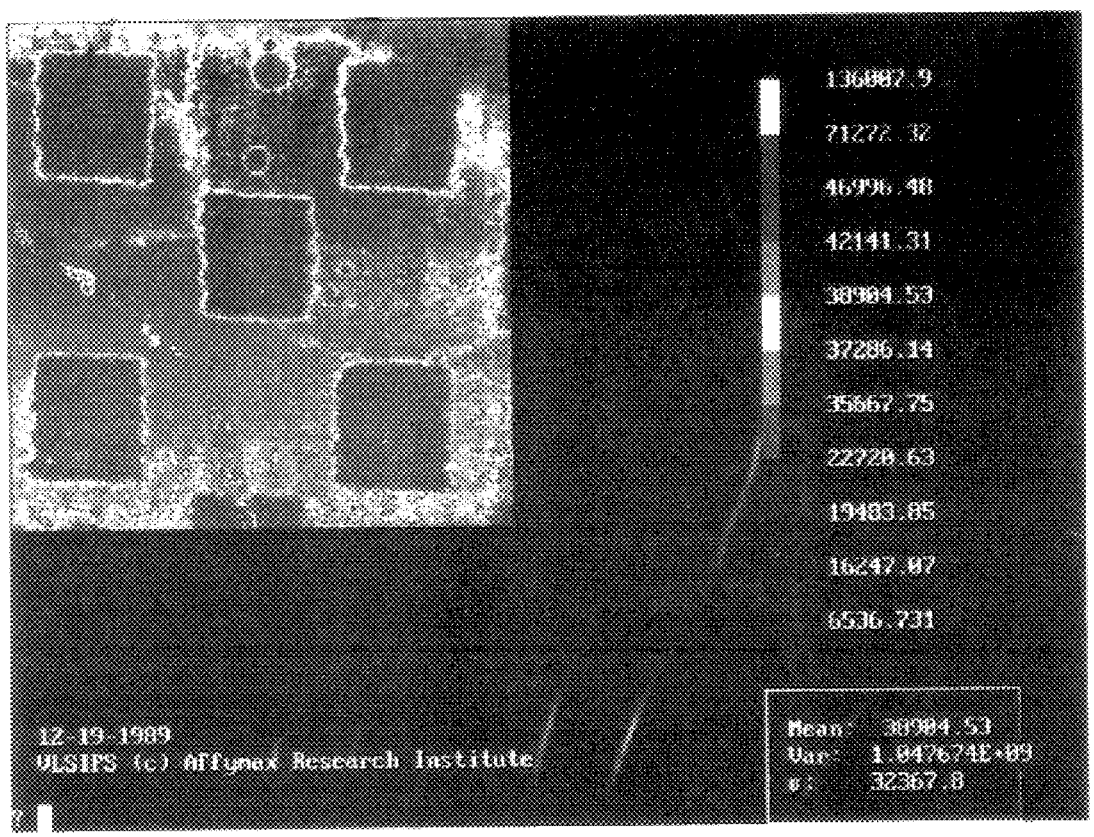
FIG. 18 illustrates fluorescence of a slide with the peptide YGGFL on selected regions of its surface which has been exposed to labeled Herz antibody specific for this sequence.

The results of thins experiment are provided in FIG. 18. Again, this figure illustrates fluorescence intensity as a function of position. The fluorescence scale is shown on the right, according to the color coding. This image was taken at 10 µm steps. This figure indicates that not only can deprotection be carried out in a well defined pattern, but also that (1) the method provides for successful coupling of peptides to the surface of the substrate, (2) the surface of a bound peptide is available for binding with an antibody, and (3) that the detection apparatus capabilities are sufficient to detect binding of a receptor.

I. Monomer-by-Monomer Formation of YGGFL and Subsequent Exposure to Labeled Antibody Monomer-by-monomer synthesis of YGGFL and GGFL in alternate squares was performed on a slide in a checkerboard pattern and the resulting slide was exposed to the Herz antibody. This experiment and the results thereof are illustrated in FIGS. 19A, 19B, 19C, and 19D.

Figure 19A:
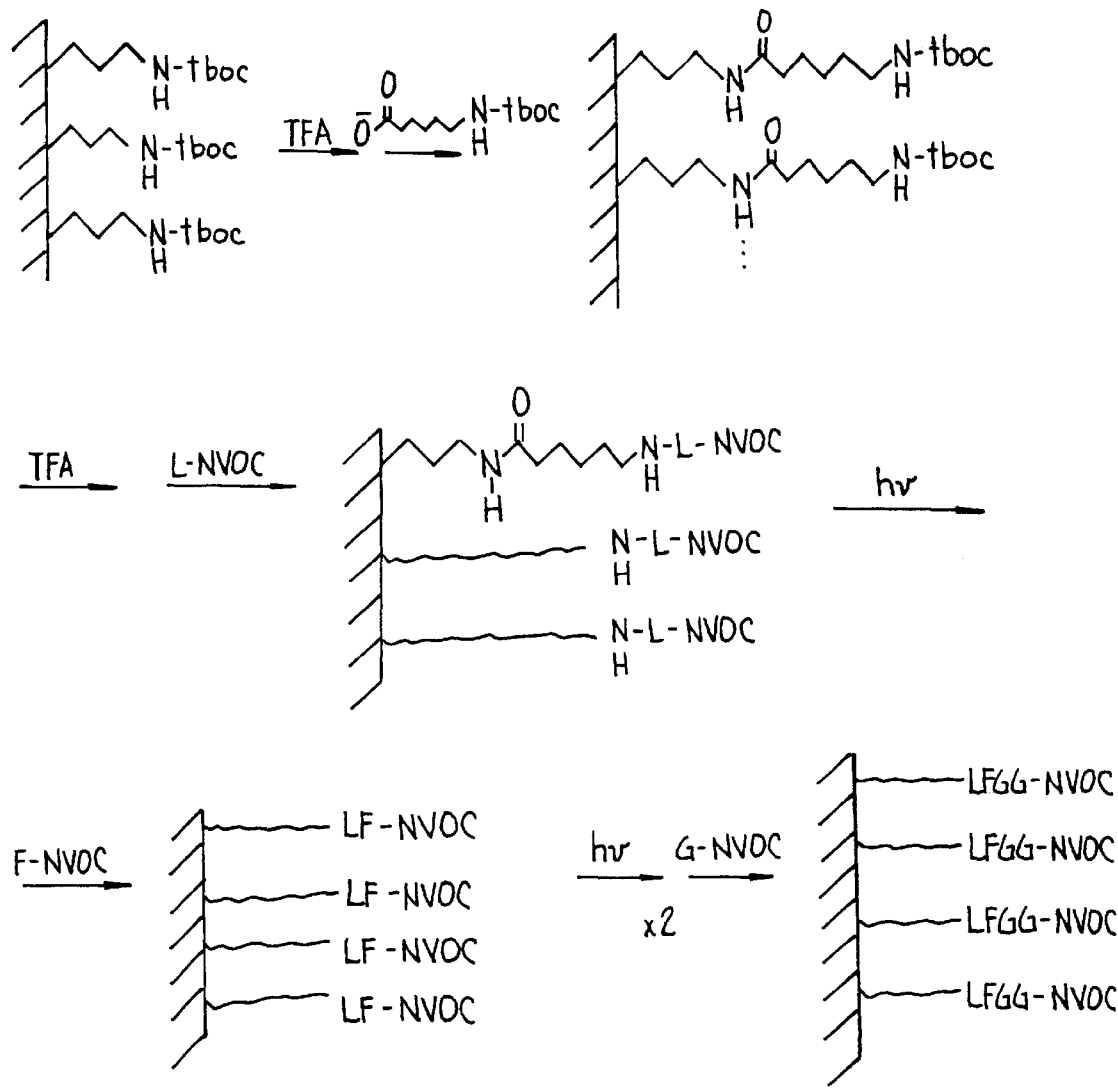
FIGS. 19A to 19D illustrate formation of and a flourescence plot of a slide with a checkerboard pattern of YGGFL and GGFL exposed to labeled Herz antibody.

In FIG. 19A, a slide is shown which is derivatized with the aminopropyl group, protected in this case with t-BOC (t-butoxycarbonyl). The slide was treated with TFA to remove the t-BOC protecting group. E-aminocaproic acid, which was t-BOC protected at its amino group, was then coupled onto the aminopropyl groups. The aminocaproic acid serves as a spacer between the aminopropyl group and the peptide to be synthesized. The amino end of the spacer was deprotected and coupled to NVOC-leucine. The entire slide was then illuminated with 12 mW of 325 nm broadband illumination. The slide was then coupled with NVOC-phenylalanine and washed. The entire slide was again illuminated, then coupled to NVOC-glycine and washed. The slide was again illuminated and coupled to NVOC-glycine to form the sequence shown in the last portion of FIG. 19A.

Figure 19B:
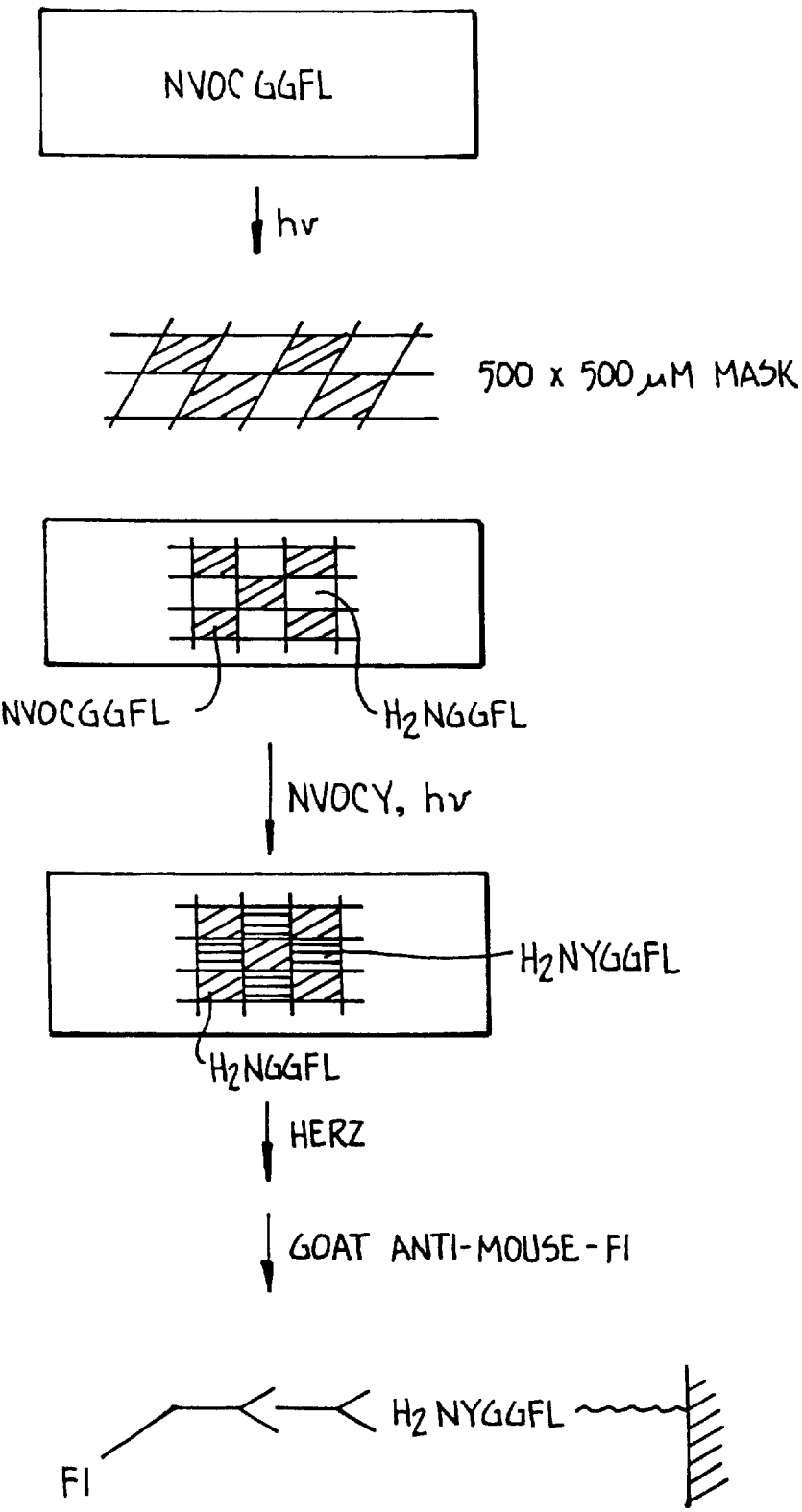

As shown in FIG. 19B, alternating regions of the slide were then illuminated using a projection print using a 500×500 µm checkerboard mask; thus, the amino group of glycine was exposed only in the lighted areas. When the next coupling chemistry step was carried out, NVOC-tyrosine was added, and it coupled only at those spots which had received illumination. The entire slide was then illuminated to remove all the NVOC groups, leaving a checkerboard of YGGFL in the lighted areas and in the other areas, GGFL. The Herz antibody (which recognizes the YGGFL, but not GGFL) was then added, followed by goat anti-mouse fluorescein conjugate.

Figure 19C:
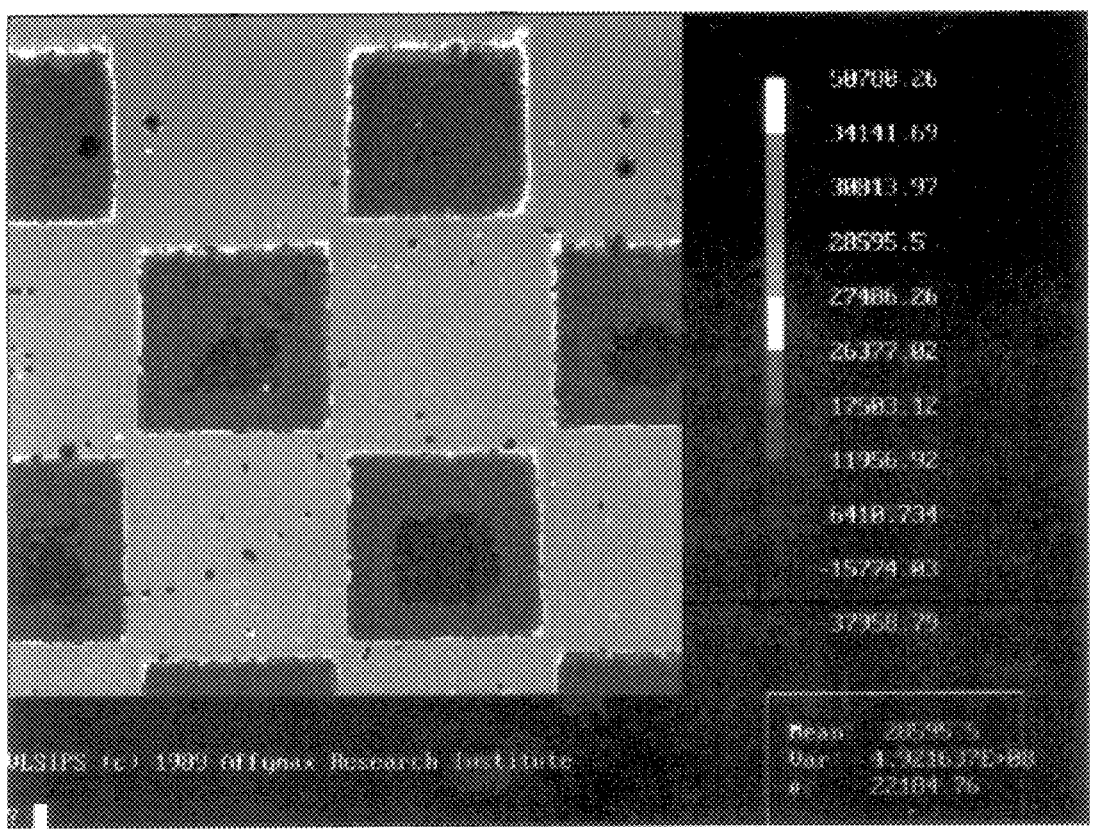

The resulting fluorescence scan is shown in FIG. 19C, and the color coding for the fluorescence intensity is again given on the right. Dark areas contain the tetrapeptide GGFL, which is not recognized by the Herz antibody (and thus there is no binding of the goat anti-mouse antibody with fluorescein conjugate), and in the red areas YGGFL is present. The YGGFL pentapeptide is recognized by the Herz antibody and, therefore, there is antibody in the lighted regions for the fluorescein-conjugated goat anti-mouse to recognize.

Figure 19D:
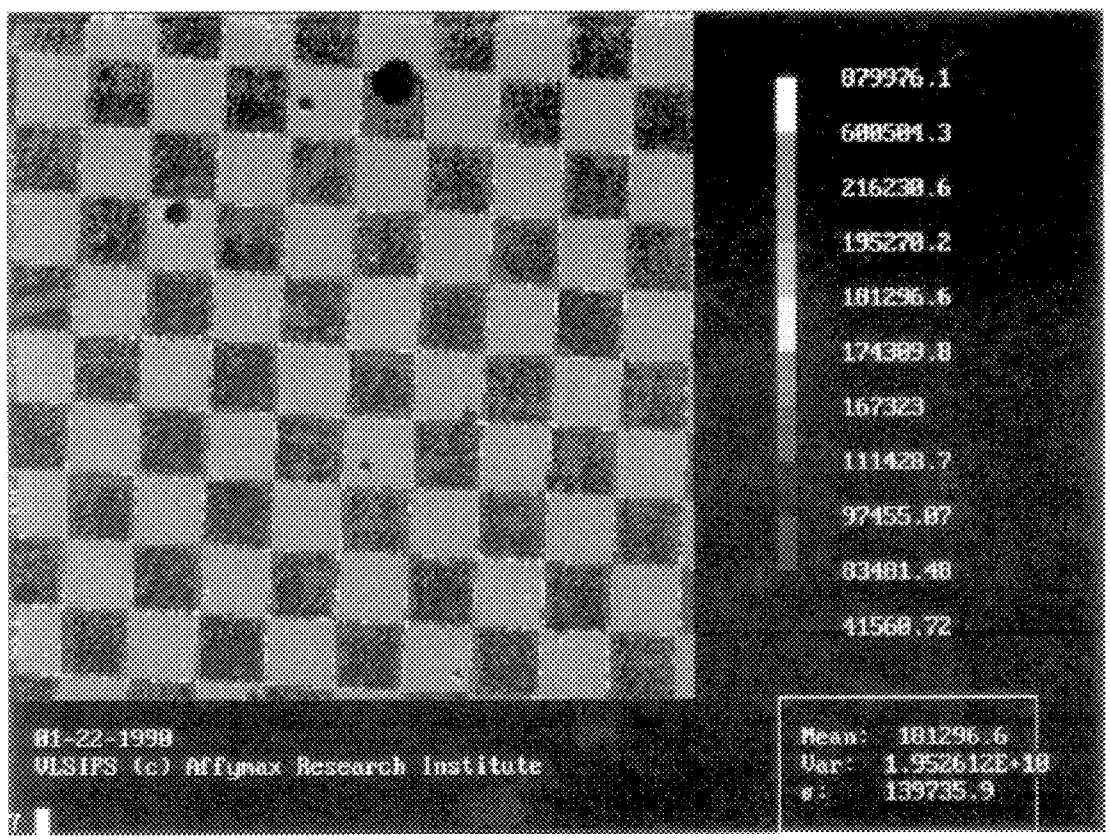

Similar patterns are shown for a 50 µm mask used in direct contact ("proximity print") with the substrate in FIG. 19D. Note that the pattern is more distinct and the corners of the checkerboard pattern are touching when the mask is placed in direct contact with the substrate (which reflects the increase in resolution using this technique).

J. Monomer-by-Monomer Synthesis of YGGFL and PGGFL

A synthesis using a 50 µm checkerboard mask similar to that shown in FIG. 19 was conducted. However, P was added to the GGFL sites on the substrate through an additional coupling step. P was added by exposing protected GGFL to light through a mask, and subsequence exposure to P in the manner set forth above. Therefore, half of the regions on the substrate contained YGGFL and the remaining half contained PGGFL.

Figure 20:
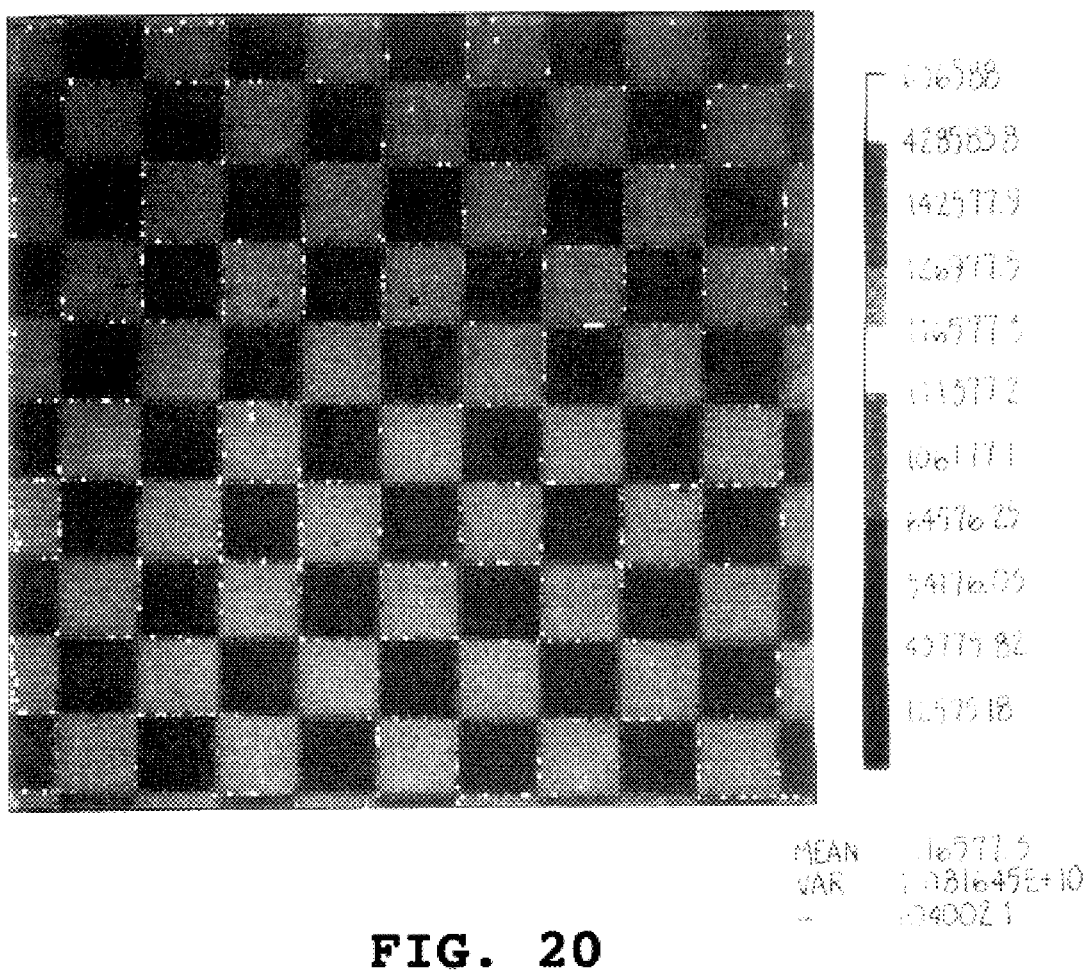
FIG. 20 is a fluorescence plot of YGGFL and PGGFL synthesized in a 50 µm checkerboard pattern.

The fluorescence plot for this experiment is provided in FIG. 20. As shown, the regions are again readily discernable. This experiment demonstrates that antibodies are able to recognize a specific sequence and that the recognition is not length-dependent.

K. Monomer-by-Monomer Synthesis of YGGFL and YPGGFL

Figure 21:
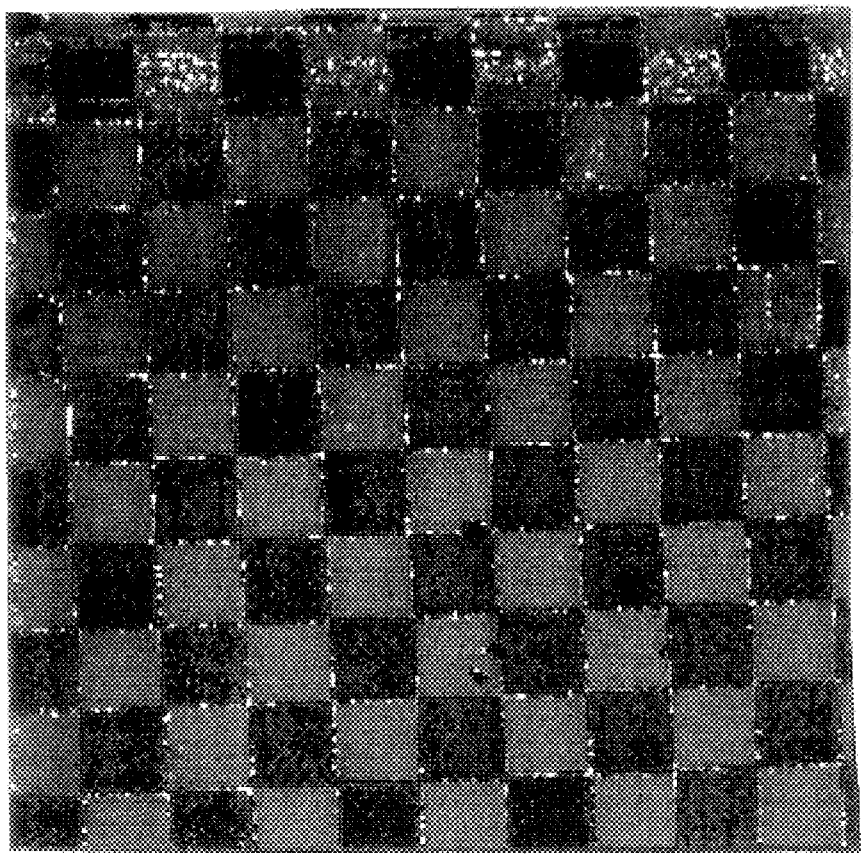
FIG. 21 is a fluorescence plot of YPGGFL and YGGFL synthesized in a 50 µm checkerboard pattern.

In order to further demonstrate the operability of the invention, a 50 μm checkerboard pattern of alternating YGGFL and YPGGFL was synthesized on a substrate using techniques like those set forth above. The resulting fluorescence plot is provided in FIG. 21. Again, it is seen that the antibody is clearly able to recognize the YGGFL sequence and does not bind significantly at the YPGGFL regions.

L. Synthesis of an Array or Sixteen Different Amino Acid Sequences and Estimation of Relative Binding Affinity to Herz Antibody Using techniques similar to those set forth above, an array of 16 different amino acid sequences (replicated four times) was synthesized on each of two glass substrates. The sequences were synthesized by attaching the sequence NVOC-GFL across the entire surface of the slides. Using a series of masks, two layers of amino acids were then selectively applied to the substrate. Each region had dimensions of 0.25 cm×0.0625 cm. The first slide contained amino acid sequences containing only L amino acids while the second slide contained selected D amino acids. FIGS. 18A and 18B illustrate a map of the various regions on the first and second slides, respectively. The patterns shown in FIGS. 22A and 22B were duplicated four times on each slide. The slides were then exposed to the Herz antibody and fluorescein-labeled goat anti-mouse.

Figure 23:
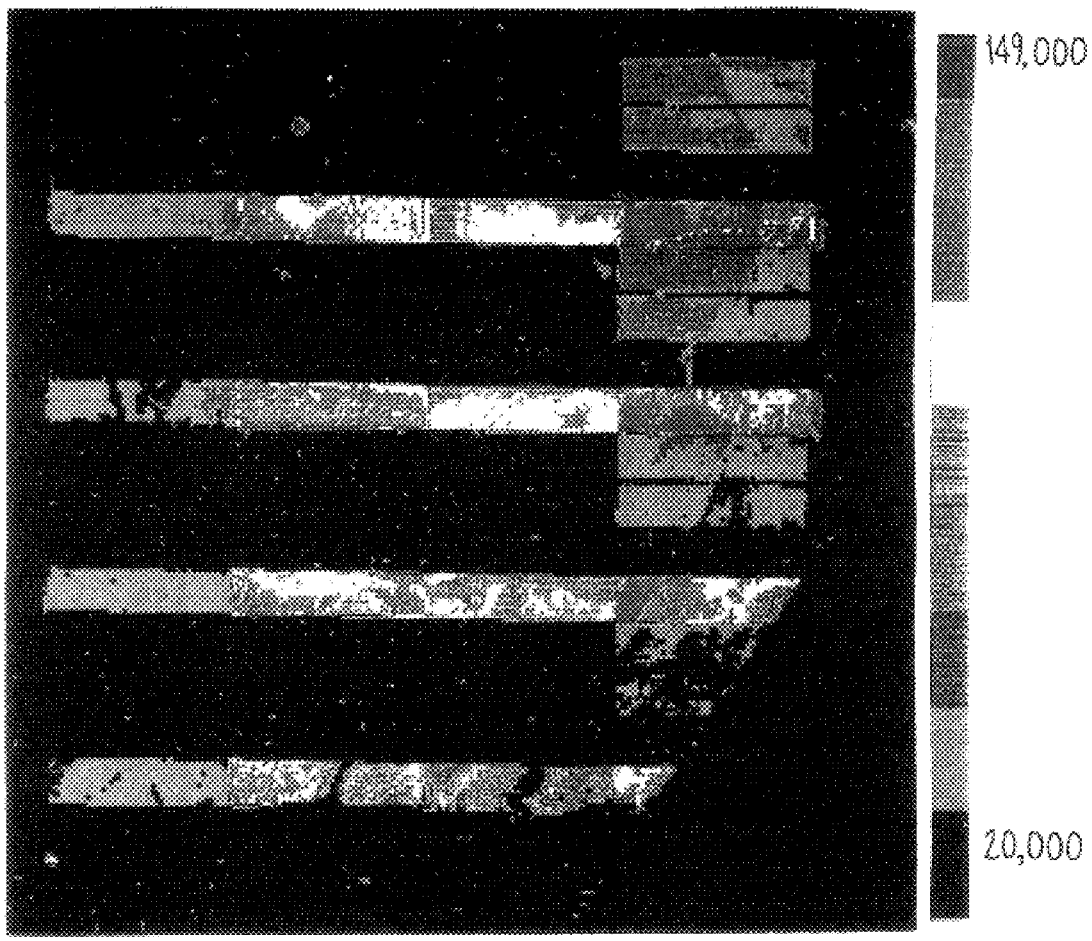
FIG. 23 is a fluorescence plot of the slide illustrated in FIG. 22A.

FIG. 23 is a fluorescence plot of the first slide, which contained only L amino acids. Red indicates strong binding (149,000 counts or more) while black indicates little or no binding of the Herz antibody (20,000 counts or less). The bottom right-hand portion of the slide appears "cut off" because the slide was broken during processing. The sequence YGGFL is clearly most strongly recognized. The sequences YAGFL and YSGFL also exhibit strong recognition of the antibody. By contrast, most of the remaining sequences show little or no binding. The four duplicate portions of the slide are extremely consistent in the amount of binding shown therein.

Figure 24:
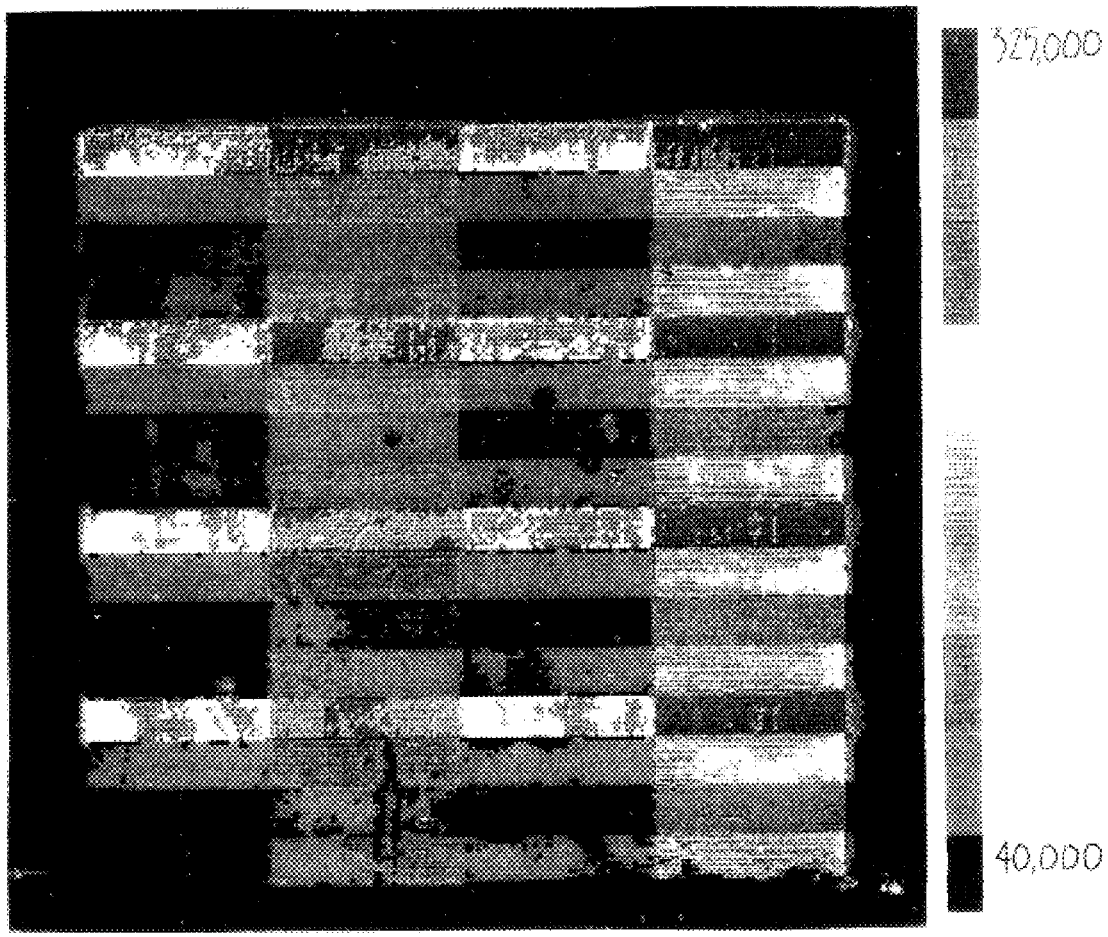
FIG. 24 is a fluorescence plot of the slide illustrated in FIG. 14B.

FIG. 24 is a fluorescence plot of the second slide. Again, strongest binding is exhibited by the YGGFL sequence. Significant binding is also detected to YaGFL, YsGFL, and YpGFL. The remaining sequences show less binding with the antibody. Note the low binding efficiency of the sequence yGGFL.

Table 6 lists the various sequences tested in order of relative fluorescence, which provides information regarding relative binding affinity.

TABLE 6

Apparent Binding to Herz Ab

| L-a.a. Set | D-a.a. Set |
| --- | --- |
| YGGFL | YGGFL |
| YAGFL | YaGFL |
| YSGFL | YsGFL |
| LGGFL | YpGFL |
| FGGFL | fGGFL |

TABLE 6-continued

Apparent Binding to Herz Ab

| L-a.a. Set | D-a.a. Set |
| --- | --- |
| YPGFL | yGGFL |
| LAGFL | faGFL |
| FAGFL | wGGFL |
| WGGFL | yaGFL |
|  | fpGFL |
|  | waGFL |

VIII. Illustrative Alternative Embodiment

According to an alternative embodiment of the invention, the methods provide for attaching to the surface a caged binding member which in its caged form has a relatively low affinity for other potentially binding species, such as receptors and specific binding substances. Such techniques are more fully described in copending application Ser. No. 404,920, filed Sep. 8, 1989, and incorporated herein by reference for all purposes.

According to this alternative embodiment, the invention provides methods for forming predefined regions on a surface of a solid support, wherein the predefined regions are capable of immobilizing receptors. The methods make use of caged binding members attached to the surface to enable selective activation of the predefined regions. The caged binding members are liberated to act as binding members ultimately capable of binding receptors upon selective activation of the predefined regions. The activated binding members are then used to immobilize specific molecules such as receptors on the predefined region of the surface. The above procedure is repeated at the same or different sites on the surface so as to provide a surface prepared with a plurality of regions on the surface containing, for example, the same or different receptors. When receptors immobilized in this way have a differential affinity for one or more ligands, screenings and assays for the ligands can be conducted in the regions of the surface containing the receptors.

The alternative embodiment may make use of novel caged binding members attached to the substrate. Caged (unactivated) members have a relatively low affinity for receptors of substances that specifically bind to uncaged binding members when compared with the corresponding affinities of activated binding members. Thus, the binding members are protected from reaction until a suitable source of energy is applied to the regions of the surface desired to be activated. Upon application of a suitable energy source, the caging groups labilize, thereby presenting the activated binding member. A typical energy source will be light.

Once the binding members on the surface are activated they may be attached to a receptor. The receptor chosen may be a monoclonal antibody, a nucleic acid sequence, a drug receptor, etc. The receptor will usually, though not always, be prepared so as to permit attaching it, directly or indirectly, to a binding member. For example, a specific binding substance having a strong binding affinity for the binding member and a strong affinity for the receptor or a conjugate of the receptor may be used to act as a bridge between binding members and receptors if desired. The method uses a receptor prepared such that the receptor retains its activity toward a particular ligand.

Preferably, the caged binding member attached to the solid substrate will be a photoactivatable biotin complex, i.e., a biotin molecule that has been chemically modified with photoactivatable protecting groups so that it has a significantly reduced binding affinity for avidin or avidin analogs than does natural biotin. In a preferred embodiment, the protecting groups localized in a predefined region of the surface will be removed upon application of a suitable source of radiation to give binding members, that are biotin or a functionally analogous compound having substantially the same binding affinity for avidin or avidin analogs as does biotin.

In another preferred embodiment, avidin or an avidin analog is incubated with activated binding members on the surface until the avidin binds strongly to the binding members. The avidin so immobilized on predefined regions of the surface can then be incubated with a desired receptor or conjugate of a desired receptor. The receptor will preferably be biotinylated, e.g., a biotinylated antibody, when avidin is immobilized on the predefined regions of the surface. Alternatively, a preferred embodiment will present an avidin/biotinylated receptor complex, which has been previously prepared, to activated binding members on the surface.

IX. Conclusion

The present inventions provide greatly improved methods and apparatus for synthesis of polymers on substrates. It is to be understood that the above description is intended to be illustrative and not restrictive. Many embodiments will be apparent to those of skill in the art upon reviewing the above description. By way of example, the invention has been described primarily with reference to the use of photoremovable protective groups, but it will be readily recognized by those of skill in the art that sources of radiation other than light could also be used. For example, in some embodiments it may be desirable to use protective groups which are sensitive to electron beam irradiation, x-ray irradiation, in combination with electron beam lithograph, or x-ray lithography techniques. Alternatively, the group could be removed by exposure to an electric current.

A preferred class of photoremovable protecting groups has the general formula:

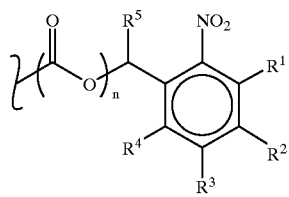

where $R^1$, $R^2$, $R^3$, and $R^4$ independently are a hydrogen atom, a lower alkyl, aryl, benzyl, halogen, hydroxyl, alkoxyl, thiol, thioether, amino, nitro, carboxyl, formate, formamido or phosphido group, or adjacent substituents (i.e., $R^1$-$R^2$, $R^2$-$R^3$, $R^3$-$R^4$) are substituted oxygen groups that together form a cyclic acetal or ketal; $R^5$ is a hydrogen atom, a alkoxyl, alkyl, hydrogen, halo, aryl, or alkenyl group, and n=0 or 1.

A preferred protecting group, 6-nitroveratryl (NV), which is used for protecting the carboxyl terminus of an amino acid or the hydroxyl group of a nucleotide, for example, is formed when $R^2$ and $R^3$ are each a methoxy group, $R^1$, $R^4$ and $R^5$ are each a hydrogen atom, and n=0:

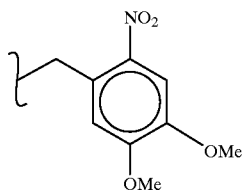

A preferred protecting group, 6-nitroveratryloxycarbonyl (NVOC), which is used to protect the amino terminus of an amino acid, for example, is formed when $R^2$ and $R^3$ are each a methoxy group, $R^1$, $R^4$ and $R^5$ are each a hydrogen atom, and n=1:

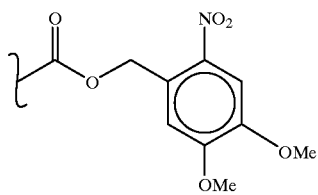

Another preferred protecting group, 6-nitropiperonyl (NP), which is used for protecting the carboxyl terminus of an amino acid or the hydroxyl group of a nucleotide, for example, is formed when $R^2$ and $R^3$ together form a methylene acetal, $R^1$, $R^4$ and $R^5$ are each a hydrogen atom, and n=0:

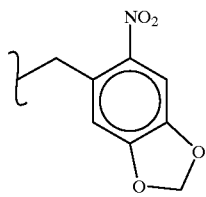

Another preferred protecting group, 6-nitropiperonyloxycarbonyl (NPOC), which is used to protect the amino terminus of an amino acid, for example, is formed when $R^2$ and $R^3$ together form a methylene acetal, $R^1$, $R^4$ and $R^5$ are each a hydrogen atom, and n=1:

A most preferred protecting group, methyl-6-nitroveratryl (MeNV), which is used for protecting the carboxyl terminus of an amino acid or the hydroxyl group of a nucleotide, for example, is formed when $R^2$ and $R^3$ are each a methoxy group, $R^1$ and $R^4$ are each a hydrogen atom, $R^5$ is a methyl group, and n=0:

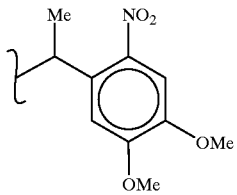

Another most preferred protecting group, methyl-6-nitroveratryloxycarbonyl (MeNVOC), which is used to protect the amino terminus of an amino acid, for example, is formed when $R^2$ and $R^3$ are each a methoxy group, $R^1$ and $R^4$ are each a hydrogen atom, $R^5$ is a methyl group, and n=1:

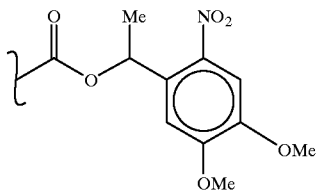

Another most preferred protecting group, methyl-6-nitropiperonyl (MeNP), which is used for protecting the carboxyl terminus of an amino acid or the hydroxyl group of a nucleotide, for example, is formed when $R^2$ and $R^3$ together form a methylene acetal, $R^1$ and $R^4$ are each a hydrogen atom, $R^5$ is a methyl group, and n=0:

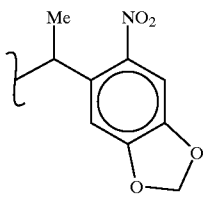

Another most preferred protecting group, methyl-6-nitropiperonyloxycarbonyl (MeNPOC), which is used to protect the amino terminus of an amino acid, for example, is formed when $R^2$ and $R^3$ together form a methylene acetal, $R^1$ and $R^4$ are each a hydrogen atom, $R^5$ is a methyl group, and n=1:

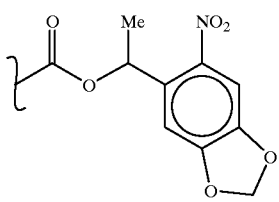

A protected amino acid having a photoactivatable oxycarbonyl protecting group, such NVOC or NPOC or their corresponding methyl derivatives, MeNVOC or MeNPOC, respectively, on the amino terminus is formed by acylating the amine of the amino acid with an activated oxycarbonyl ester of the protecting group. Examples of activated oxycarbonyl esters of NVOC and MeNVOC have the general formula:

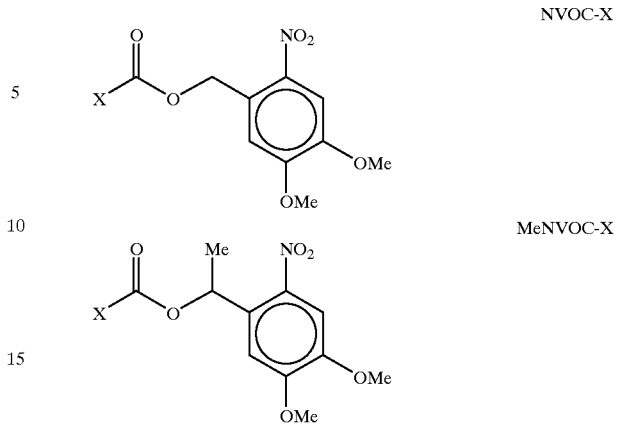

where X is halogen, mixed anhydride, phenoxy, p-nitrophenoxy, N-hydroxysuccinimide, and the like.

A protected amino acid or nucleotide having a photoactivatable protecting group, such as NV or NP or their corresponding methyl derivatives, MeNV or MeNP, respectively, on the carboxy terminus of the amino acid or 5'-hydroxy terminus of the nucleotide, is formed by acylating the carboxy terminus or 5'-OH with an activated benzyl derivative of the protecting group. Examples of activated benzyl derivatives of MeNV and MeNP have the general formula:

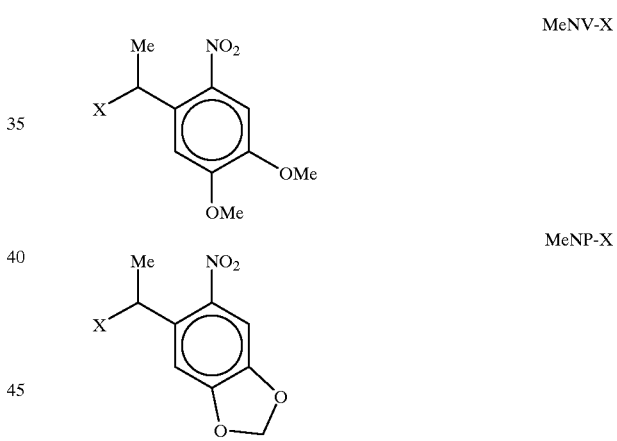

where X is halogen, hydroxyl, tosyl, mesyl, trifluormethyl, diazo, azido, and the like.

Another method for generating protected monomers is to react the benzylic alcohol derivative of the protecting group with an activated ester of the monomer. For example, to protect the carboxyl terminus of an amino acid, an activated ester of the amino acid is reacted with the alcohol derivative of the protecting group, such as 6-nitroveratrol (NVOH). Examples of activated esters suitable for such uses include halo-formate, mixed anhydride, imidazoyl formate, acyl halide, and also includes formation of the activated ester in situ the use of common reagents such as DCC and the like. See Atherton et al. for other examples of activated esters.

A further method for generating protected monomers is to react the benzylic alcohol derivative of the protecting group with an activated carbon of the monomer. For example, to protect the 5'-hydroxyl group of a nucleic acid, a derivative having a 5'-activated carbon is reacted with the alcohol derivative of the protecting group, such as methyl-6- nitropiperonol (MePyROH). Examples of nucleotides having activating groups attached to the 5'-hydroxyl group have the general formula:

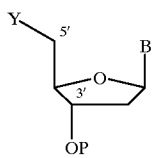

where Y is a halogen atom, a tosyl, mesyl, trifluoromethyl, azido, or diazo group, and the like.

Another class of preferred photochemical protecting groups has the formula:

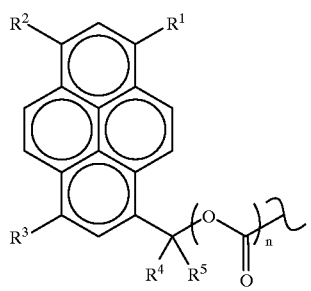

where $R^1$, $R^2$, and $R^3$ independently are a hydrogen atom, a lower alkyl, aryl, benzyl, halogen, hydroxyl, alkoxyl, thiol, thioether, amino, nitro, carboxyl, formate, formamido, sulfanates, sulfido or phosphido group, $R^4$ and $R^5$ independently are a hydrogen atom, an alkoxy, alkyl, halo, aryl, hydrogen, or alkenyl group, and n=0 or 1.

A preferred protecting group, 1-pyrenylmethyloxycarbonyl (PyROC), which is used to protect the amino terminus of an amino acid, for example, is formed when $R^1$ through $R^5$ are each a hydrogen atom and n=1:

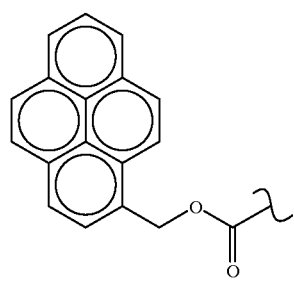

Another preferred protecting group, 1-pyrenylmethyl (PyR), which is used for protecting the carboxy terminus of an amino acid or the hydroxyl group of a nucleotide, for example, is formed when $R^1$ through $R^5$ are each a hydrogen atom and n=0:

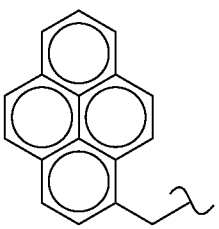

An amino acid having a pyrenylmethyloxycarbonyl protecting group on its amino terminus is formed by acylation of the free amine of amino acid with an activated oxycarbonyl ester of the pyrenyl protecting group. Examples of activated oxycarbonyl esters of PYROC have the general formula:

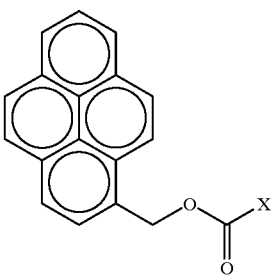

where X is halogen, or mixed anhydride, p-nitrophenoxy, or N-hydroxysuccinimide group, and the like.

A protected amino acid or nucleotide having a photoactivatable protecting group, such as PyR, on the carboxy terminus of the amino acid or 5'-hydroxy terminus of the nucleic acid, respectively, is formed by acylating the carboxy terminus or 5'-OH with an activated pyrenylmethyl derivative of the protecting group. Examples of activated pyrenylmethyl derivatives of PyR have the general formula:

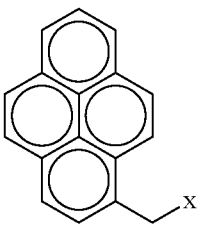

where X is a halogen atom, a hydroxyl, diazo, or azido group, and the like.

Another method of generating protected monomers is to react the pyrenylmethyl alcohol moiety of the protecting group with an activated ester of the monomer. For example, an activated ester of an amino acid can be reacted with the alcohol derivative of the protecting group, such as pyrenylmethyl alcohol (PyROH), to form the protected derivative of the carboxy terminus of the amino acid. Examples of activated esters include halo-formate, mixed anhydride, imidazoyl formate, acyl halide, and also includes formation of the activated ester in situ and the use of common reagents such as DCC and the like.

Clearly, many photosensitive protecting groups are suitable for use in the present invention.

In preferred embodiments, the substrate is irradiated to remove the photoremovable protecting groups and create regions having free reactive moieties and side products resulting from the protecting group. The removal rate of the protecting groups depends on the wavelength and intensity of the incident radiation, as well as the physical and chemical properties of the protecting group itself. Preferred protecting groups are removed at a faster rate and with a lower intensity of radiation. For example, at a given set of conditions, MeNVOC and MeNPOC are photolytically removed from the N-terminus of a peptide chain faster than their unsubstituted parent compounds, NVOC and NPOC, respectively.

Removal of the protecting group is accomplished by irradiation to liberate the reactive group and degradation products derived from the protecting group. Not wishing to be bound by theory, it is believed that irradiation of an NVOC- and MeNVOC-protected oligomers occurs by the following reaction schemes:

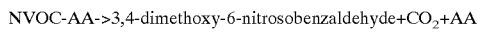

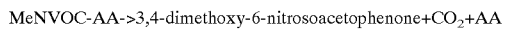

where AA represents the N-terminus of the amino acid oligomer.

Along with the unprotected amino acid, other products are liberated into solution: carbon dioxide and a 2,3-dimethoxy-6-nitrosophenylcarbonyl compound, which can react with nucleophilic portions of the oligomer to form unwanted secondary reactions. In the case of an NVOC-protected amino acid, the degradation product is a nitrosobenzaldehyde, while the degradation product for the other is a nitrosophenyl ketone. For instance, it is believed that the product aldehyde from NVOC degradation reacts with free amines to form a Schiff base (imine) that affects the remaining polymer synthesis. Preferred photoremovable protecting groups react slowly or reversibly with the oligomer on the support.

Again not wishing to be bound by theory, it is believed that the product ketone from irradiation of a MeNVOC-protected oligomer reacts at a slower rate with nucleophiles on the oligomer than the product aldehyde from irradiation of the same NVOC-protected oligomer. Although not unambiguously determined, it is believed that this difference in reaction rate is due to the difference in general reactivity between aldehyde and ketones towards nucleophiles due to steric and electronic effects.

The photoremovable protecting groups of the present invention are readily removed. For example, the photolysis of N-protected L-phenylalanine in solution and having different photoremovable protecting groups was analyzed, and the results are presented in the following table:

TABLE

Photolysis of Protected L-Phe-OH

| Sovlent | $t_{1/2}$ in seconds | | | |
|---|---|---|---|---|
| | NBOC | NVOC | MeNVOC | MeNPOC |
| Dioxane | 1288 | 110 | 24 | 19 |
| 5mM H$_2$SO$_4$/Dioxane | 1575 | 98 | 33 | 22 |

The half life, $t_{1/2}$, is the time in seconds required to remove 50% of the starting amount of protecting group. NBOC is the 6-nitrobenzyloxycarbonyl group, NVOC is the 6-nitroveratryloxycarbonyl group, MeNVOC is the methyl-6-nitroveratryloxycarbonyl group, and MeNPOC is the methyl-6-nitropiperonyloxycarbonyl group. The photolysis was carried out in the indicated solvent with 362/364 nm-wavelength irradiation having an intensity of 10 mW/cm$^2$, and the concentration of each protected phenylalanine was 0.10 mM.

The table shows that deprotection of NVOC-, MeNVOC-, and MeNPOC-protected phenylalanine proceeded faster than the deprotection of NBOC. Furthermore, it shows that the deprotection of the two derivatives that are substituted on the benzylic carbon, MeNVOC and MeNPOC, were photolyzed at the highest rates in both dioxane and acidified dioxane.

1. Use of Photoremovable Groups During Solid-Phase Synthesis of Peptides

The formation of peptides on a solid-phase support requires the stepwise attachment of an amino acid to a substrate-bound growing chain. In order to prevent unwanted polymerization of the monomeric amino acid under the reaction conditions, protection of the amino terminus of the amino acid is required. After the monomer is coupled to the end of the peptide, the N-terminal protecting group is removed, and another amino acid is coupled to the chain. This cycle of coupling and deprotecting is continued for each amino acid in the peptide sequence. See Merrifield, *J. Am. Chem. Soc.* (1963) 85:2149, and Atherton et al., "Solid Phase Peptide Synthesis" 1989, IRL Press, London, both incorporated herein by reference for all purposes. As described above, the use of a photoremovable protecting group allows removal of selected portions of the substrate surface, via patterned irradiation, during the deprotection cycle of the solid phase synthesis. This selectively allows spatial control of the synthesis—the next amino acid is coupled only to the irradiated areas.

In one embodiment, the photoremovable protecting groups of the present invention are attached to an activated ester of an amino acid at the amino terminus:

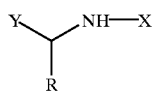

where R is the side chain of a natural or unnatural amino acid, X is a photoremovable protecting group, and Y is an activated carboxylic acid derivative. The photoremovable protecting group, X, is preferably NVOC, NPOC, PyROC, MeNVOC, MeNPOC, and the like as discussed above. The activated ester, Y, is preferably a reactive derivative having a high coupling efficiency, such as an acyl halide, mixed anhydride, N-hydroxysuccinimide ester, perfluorophenyl ester, or urethane protected acid, and the like. Other activated esters and reaction conditions are well known (See Atherton et al.).

2. Use of Photoremovable Groups During Solid-Phase Synthesis of Oligonucleotides The formation of oligonucleotides on a solid-phase support requires the stepwise attachment of a nucleotide to a substrate-bound growing oligomer. In order to prevent unwanted polymerization of the monomeric nucleotide under the reaction conditions, protection of the 5'-hydroxyl group of the nucleotide is required. After the monomer is coupled to the end of the oligomer, the 5'-hydroxyl protecting group is removed, and another nucleotide is coupled to the chain. This cycle of coupling and deprotecting is continued for each nucleotide in the oligomer sequence. See Gait, "Oligonucleotide Synthesis: A Practical Approach" 1984, IRL Press, London, incorporated herein by reference for all purposes. As described above, the use of a photoremovable protecting group allows removal, via patterned irradiation, of selected portions of the substrate surface during the deprotection cycle of the solid phase synthesis. This selectively allows spatial control of the synthesis—the next nucleotide is coupled only to the irradiated areas.

Oligonucleotide synthesis generally involves coupling an activated phosphorous derivative on the 3'-hydroxyl group of a nucleotide with the 5'-hydroxyl group of an oligomer bound to a solid support. Two major chemical methods exist to perform this coupling: the phosphate-triester and phosphoamidite methods (See Gait). Protecting groups of the present invention are suitable for use in either method.

In a preferred embodiment, a photoremovable protecting group is attached to an activated nucleotide on the 5'-hydroxyl group:

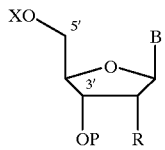

where B is the base attached to the sugar ring; R is a hydrogen atom when the sugar is deoxyribose or R is a hydroxyl group when the sugar is ribose; P represents an activated phosphorous group; and X is a photoremovable protecting group. The photoremovable protecting group, X, is preferably NV, NP, PyR, MeNV, MeNP, and the like as described above. The activated phosphorous group, P, is preferably a reactive derivative having a high coupling efficiency, such as a phosphate-triester, phosphoamidite or the like. Other activated phosphorous derivatives, as well as reaction conditions, are well known (See Gait).

E. Amino Acid N-Carboxy Anhydrides Protected With a Photoremovable Group

During Merrifield peptide synthesis, an activated ester of one amino acid is coupled with the free amino terminus of a substrate-bound oligomer. Activated esters of amino acids suitable for the solid phase synthesis include halo-formate, mixed anhydride, imidazoyl formate, acyl halide, and also includes formation of the activated ester in situ and the use of common reagents such as DCC and the like (See Atherton et al.). A preferred protected and activated amino acid has the general formula:

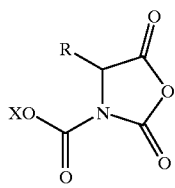

where R is the side chain of the amino acid and X is a photoremovable protecting group. This compound is a urethane-protected amino acid having a photoremovable protecting group attach to the amine. A more preferred activated amino acid is formed when the photoremovable protecting group has the general formula:

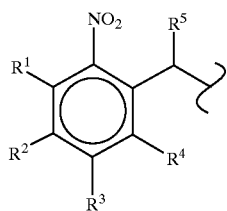

where $R^1$, $R^2$, $R^3$, and $R^4$ independently are a hydrogen atom, a lower alkyl, aryl, benzyl, halogen, hydroxyl, alkoxyl, thiol, thioether, amino, nitro, carboxyl, formate, formamido or phosphido group, or adjacent substituents (i.e., $R^1$-$R^2$, $R^2$-$R^3$, $R^3$-$R^4$) are substituted oxygen groups that together form a cyclic acetal or ketal; and $R^5$ is a hydrogen atom, a alkoxyl, alkyl, hydrogen, halo, aryl, or alkenyl group.

A preferred activated amino acid is formed when the photoremovable protecting group is 6-nitroveratryloxycarbonyl. That is, $R^1$ and $R^4$ are each a hydrogen atom, $R^2$ and $R^3$ are each a methoxy group, and $R^5$ is a hydrogen atom. Another preferred activated amino acid is formed when the photoremovable group is 6-nitropiperonyl: $R^1$ and $R^4$ are each a hydrogen atom, $R^2$ and $R^3$ together form a methylene acetal, and $R^5$ is a hydrogen atom. Other protecting groups are possible. Another preferred activated ester is formed when the photoremovable group is methyl-6-nitroveratryl or methyl-6-nitropiperonyl.

Another preferred activated amino acid is formed when the photoremovable protecting group has the general formula:

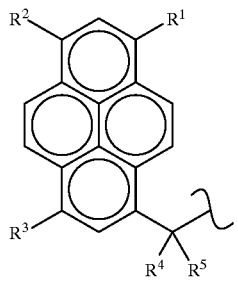

where $R^1$, $R^2$, and $R^3$ independently are a hydrogen atom, a lower alkyl, aryl, benzyl, halogen, hydroxyl, alkoxyl, thiol, thioether, amino, nitro, carboxyl, formate, formamido, sulfanates, sulfido or phosphido group, and $R^4$ and $R^5$ independently are a hydrogen atom, an alkoxy, alkyl, halo, aryl, hydrogen, or alkenyl group. The resulting compound is a urethane-protected amino acid having a pyrenylmethyloxycarbonyl protecting group attached to the amine. A more preferred embodiment is formed when $R^1$ through $R^5$ are each a hydrogen atom.

The urethane-protected amino acids having a photoremovable protecting group of the present invention are prepared by condensation of an N-protected amino acid with an acylating agent such as an acyl halide, anhydride, chloroformate and the like (See Fuller et al., U.S. Pat. No. 4,946,942 and Fuller et al., J. Amer. Chem. Soc. (1990) 112:7414–7416, both herein incorporated by reference for all purposes).

Urethane-protected amino acids having photoremovable protecting groups are generally useful as reagents during solid-phase peptide synthesis, and because of the spatially selectivity possible with the photoremovable protecting group, are especially useful for the spatially addressing peptide synthesis. These amino acids are difunctional: the urethane group first serves to activate the carboxy terminus for reaction with the amine bound to the surface and, once the peptide bond is formed, the photoremovable protecting group protects the newly formed amino terminus from further reaction. These amino acids are also highly reactive to nucleophiles, such as deprotected amines on the surface of the solid support, and due to this high reactivity, the solid-phase peptide coupling times are significantly reduced, and yields are typically higher.

1. Example

Light activated formation of a thymidine-cytidine dimer was carried out. A three dimensional representation of a fluorescence scan showing a checkboard pattern generated by the light-directed synthesis of a dinucleotide is shown in FIG. 8. 5'-nitroveratryl thymidine was attached to a synthesis substrate through the 3' hydroxyl group. The nitroveratryl protecting groups were removed by illumination through a 500 mm checkerboard mask. The substrate was then treated with phosphoramidite activated 2'-deoxycytidine. In order to follow the reaction fluorometrically, the deoxycytidine had been modified with an FMOC protected aminohexyl linker attached to the After removal of the FMOC protecting group with base, the regions which contained the dinucleotide were fluorescently labelled by treatment of the substrate with 1 mM FITC in DMF for one hour.

The three-dimensional representation of the fluorescent intensity data in FIG. 14 clearly reproduces the checkerboard illumination pattern used during photolysis of the substrate. This result demonstrates that oligonucleotidesas well as peptides can be synthesized by the light-directed method.

C. Binary Masking

In fact, the means for producing a substrate useful for these techniques are explained in U.S. Ser. No. 07/492,462 (VLSIPS CIP), which is hereby incorporated herein by reference. However, there are various particular ways to optimize the synthetic processes. Many of these methods are described in U.S. Ser. No. 07/624,120 (automated VLSIPS).

Briefly, the binary synthesis strategy refers to an ordered strategy for parallel synthesis of diverse polymer sequences by sequential addition of reagents which may be represented by a reactant matrix, and a switch matrix, the product of which is a product matrix. A reactant matrix is a 1× n matrix of the building blocks to be added. The switch matrix is all or a subset of the binary numbers from 1 to n arranged in columns. In preferred embodiments, a binary strategy is one in which at least two successive steps illuminate half of a region of interest on the substrate. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme, but will still be considered to be a binary masking scheme within the definition herein. A binary "masking" strategy is a binary synthesis which uses light to remove protective groups from materials for addition of other materials such as nucleotides or amino acids.

In particular, this procedure provides a simplified and highly efficient method for saturating all possible sequences of a defined length polymer. This masking strategy is also particularly useful in producing all possible oligonucleotide sequence probes of a given length.

D. Applications

The technology provided by the present invention has very broad applications. Although described specifically for polynucleotide sequences, similar sequencing, fingerprinting, mapping, and screening procedures can be applied to polypeptide, carbohydrate, or other polymers. In particular, the present invention may be used to completely sequence a given target sequence to subunit resolution. This may be for de novo sequencing, or may be used in conjunction with a second sequencing procedure to provide independent verification. See, e.g., (1988) *Science* 242:1245. For example, a large polynucleotide sequence defined by either the Maxam and Gilbert technique or by the Sanger technique may be verified by using the present invention.

In addition, by selection of appropriate probes, a polynucleotide sequence can be fingerprinted. Fingerprinting is a less detailed sequence analysis which usually involves the characterization of a sequence by a combination of defined features. Sequence fingerprinting is particularly useful because the repertoire of possible features which can be tested is virtually infinite. Moreover, the stringency of matching is also variable depending upon the application. A Southern Blot analysis may be characterized as a means of simple fingerprint analysis.

Fingerprinting analysis may be performed to the resolution of specific nucleotides, or may be used to determine homologies, most commonly for large segments. In particular, an array of oligonucleotide probes of virtually any workable size may be positionally localized on a matrix and used to probe a sequence for either absolute complementary matching, or homology to the desired level of stringency using selected hybridization conditions.

In addition, the present invention provides means for mapping analysis of a target sequence or sequences. Mapping will usually involve the sequential ordering of a plurality of various sequences, or may involve the localization of a particular sequence within a plurality of sequences. This may be achieved by immobilizing particular large segments onto the matrix and probing with a shorter sequence to determine which of the large sequences contain that smaller sequence. Alternatively, relatively shorter probes of known or random sequence may be immobilized to the matrix and a map of various different target sequences may be determined from overlaps. Principles of such an approach are described in some detail by Evans et al. (1989) "Physical Mapping of Complex Genomes by Cosmid Multiplex Analysis," *Proc. Natl. Acad. Sci. USA* 86:5030–5034; Michiels et al. (1987) "Molecular Approaches to Genome Analysis: A Strategy for the Construction of Ordered Overlap Clone Libraries," *CABIOS* 3:203–210; Olsen et al. (1986) "Random-Clone Strategy for Genomic Restriction Mapping in Yeast," *Proc. Natl. Acad. Sci. USA* 83:7826–7830; Craig, et al. (1990) "Ordering of Cosmid Clones Covering the Herpes Simplex Virus Type I (HSV-I) Genome: A Test Case for Fingerprinting by Hybridization," *Nuc. Acids Res.* 18:2653–2660; and Coulson, et al. (1986) "Toward a Physical Map of the Genome of the Nematode Caenorhabditis elegans," *Proc. Natl. Acad. Sci. USA* 83:7821–7825; each of which is hereby incorporated herein by reference.

Fingerprinting analysis also provides a means of identification. In addition to its value in apprehension of criminals from whom a biological sample, e.g., blood, has been collected, fingerprinting can ensure personal identification for other reasons. For example, it may be useful for identification of bodies in tragedies such as fire, flood, and vehicle crashes. In other cases the identification may be useful in identification of persons suffering from amnesia, or of missing persons. Other forensics applications include establishing the identity of a person, e.g., military identification "dog tags", or may be used in identifying the source of particular biological samples. Fingerprinting technology is described, e.g., in Carrano, et al. (1989) "A High-Resolution, Fluorescence-Based, Semi-automated method for DNA Fingerprinting,"Genomics 4: 129–136, which is hereby incorporated herein by reference. See, e.g., table I, for nucleic acid applications, and corresponding applications may be accomplished using polypeptides.

TABLE I

VLSIPS PROJECT IN NUCLEIC ACIDS

I. Construction of Chips
II. Applications
  A. Sequencing
    1. Primary sequencing
    2. Secondary sequencing (sequence checking)
    3. Large scale mapping
    4. Fingerprinting
  B. Duplex/Triplex formation
    1. Antisense
    2. Sequence specific function modulation
      (e.g. promoter inhibition
  C. Diagnosis
    1. Genetic markers
    2. Type markers
      a. Blood donors
      b. Tissue transplants
  D. Microbiology
    1. Clinical microbiology
    2. Food microbiology
III. Instrumentation
  A. Chip machines
  B. Detection
IV. Software Development
  A. Instrumentation software
  B. Data reduction software
  C. Sequence analysis software The fingerprinting analysis may be used to perform various types of genetic screening. For example, a single substrate may be generated with a plurality of screening probes, allowing for the simultaneous genetic screening for a large number of genetic markers. Thus, prenatal or diagnostic screening can be simplified, economized, and made more generally accessible.

In addition to the sequencing, fingerprinting, and mapping applications, the present invention also provides means for determining specificity of interaction with particular sequences. Many of these applications were described in U.S. Ser. No. 07/362,901 (VLSIPS parent), U.S. Ser. No. 07/492,462 (VLSIPS CIP), U.S. Ser. No. 07/435,316 (caged biotin parent), and U.S. Ser. No. 07/612,671 (caged biotin CIP).

E. Detection Methods and Apparatus

An appropriate detection method applicable to the selected labeling method can be selected. Suitable labels include radionucleotides, enzymes, substrates, cofactors, inhibitors, magnetic particles, heavy metal atoms, and particularly fluorescers, chemiluminescers, and spectroscopic labels. Patents teaching the use of such labels include U.S. Pat. Nos. 3,817,837; 3,850,752; 3,939,350; 3,996,345; 4,277,437; 4,275,149; and 4,366,241.

With an appropriate label selected, the detection system best adapted for high resolution and high sensitivity detection may be selected. As indicated above, an optically detectable system, e.g., fluorescence or chemiluminescence would be preferred. Other detection systems may be adapted to the purpose, e.g., electron microscopy, scanning electron microscopy (SEM), scanning tunneling electron microscopy (STEM), infrared microscopy, atomic force microscopy (AFM), electrical condutance, and image plate transfer.

With a detection method selected, an apparatus for scanning the substrate will be designed. Apparatus, as described in U.S. Ser. No. 07/362,901 (VLSIPS parent); or U.S. Ser. No. 07/492,462 (VLSIPS CIP); or U.S. Ser. No. 07/624,120, (automated VLSIPS), are particularly appropriate. Design modifications may also be incorporated therein.

F. Data Analysis

Data is analyzed by processes similar to those described below in the section describing theoretical analysis. More efficient algorithms will be mathematically devised, and will usually be designed to be performed on a computer. Various computer programs which may more quickly or efficiently make measurement samples and distinguish signal from noise will also be devised. See, particularly, U.S. Ser. No. 07/624,120, (automated VLSIPS).

The initial data resulting from the detection system is an array of data indicative of fluorescent intensity versus location on the substrate. The data are typically taken over regions substantially smaller than the area in which synthesis of a given polymer has taken place. Merely by way of example, if polymers were synthesized in squares on the substrate having dimensions of 500 microns by 500 microns, the data may be taken over regions having dimensions of 5 microns by 5 microns. In most preferred embodiments, the regions over which florescence data are taken across the substrate are less than about ½ the area of the regions in which individual polymers are synthesized, preferably less than $1/10$ the area in which a single polymer is synthesized, and most preferably less than $1/100$ the area in which a single polymer is synthesized. Hence, within any area in which a given polymer has been synthesized, a large number of fluorescence data points are collected.

A plot of number of pixels versus intensity for a scan should bear a rough resemblance to a bell curve, but spurious data are observed, particularly at higher intensities. Since it is desirable to use an average of fluorescent intensity over a given synthesis region in determining relative binding affinity, these spurious data will tend to undesirably skew the data.

Accordingly, in one embodiment of the invention the data are corrected for removal of these spurious data points, and an average of the data points is thereafter utilized in determining relative binding efficiency. In general the data are fitted to a base curve and statistically measures are used to remove spurious data.

In an additional analytical tool, various degeneracy reducing analogues may be incorporated in the hybridization probes. Various aspects of this strategy are described, e.g., in Macevicz, S. (1990) PCT publication number WO 90/04652, which is hereby incorporated herein by reference.

II. Theorethical Analysis

The principle of the hybridization sequencing procedure is based, in part, upon the ability to determine overlaps of short segments. The VLSIPS technology provides the ability to generate reagents which will saturate the possible short subsequence recognition possibilities. The principle is most easily illustrated by using a binary sequence, such as a sequence of zeros and ones. Once having illustrated the application to a binary alphabet, the principle may easily be understood to encompass three letter, four letter, five or more. letter, even 20 letter alphabets. A theoretical treatment of analysis of subsequence information to reconstruction of a target sequence is provided, e.e., in Lysov, Yu., et al. (1988) *Doklady Akademi. Nauk. SSR* 303:1508–1511; Khropko K., et al. (1989) *FEBS Letters* 256:118–122; Pevzner, P. (1989) *J. of Biomolecular Structure and Dynamics* 7:63–69; and Drmanac, R. et al. (1989) *Genomics* 4:114–128; each of which is hereby incorporated herein by reference.

The reagents for recognizing the subsequences will usually be specific for recognizing a particular polymer subsequence anywhere within a target polymer. It is preferable that conditions may be devised which allow absolute discrimination between high fidelity matching and very low levels of mismatching. The reagent interaction will preferably exhibit no sensitivity to flanking sequences, to the subsequence position within the target, or to any other remote structure within the sequence. For polynucleotide sequencing, the specific reagents can be oligonucleotide probes; for polypeptides and carbohydrates, antibodies will be useful reagents. Antibody reagents should also be useful for other types of polymers.

A. Simple n-mer Structure: Theory

1. Simple Two Letter Alphabet: Example

A simple example is presented below of how a sequence of ten digits comprising zeros and ones would be sequenceable using short segments of five digits. For example, consider the sample ten digit sequence:

1010011100.

A VLSIPS substrate could be constructed, as discussed elsewhere, which would have reagents attached in a defined matrix pattern which specifically recognize each of the possible five digit sequences of ones and zeros. The number of possible five digit subsequences is $2^5$=32. The number of possible different sequences 10 digits long is $2^{10}$=1,024. The five contiguous digit subsequences within a ten digit sequence number six, i.e., positioned at digits 1–5, 2–6, 3–7, 4–8, 5–9, and 6–10. It will be noted that the specific order of the digits in the sequence is important and that the order is directional, e.g., running left to right versus right to left. The first five digit sequence contained in the target sequence is 10100. The second is 01001, the third is 10011, the fourth is 00111, the fifth is 01110, and the sixth is 11100.

The VLSIPS substrate would have a matrix pattern of positionally attached reagents which recognize each of the different 5-mer subsequences. Those reagents which recognize each of the 6 contained 5-mers will bind the target, and a label allows the positional determination of where the sequence specific interaction has occurred. By correlation of the position in the matrix pattern, the corresponding bound subsequences can be determined.

In the above-mentioned sequence, six different 5-mer sequences would be determined to be present. They would be:

```
10100
 01001
  10011
   00111
    01110
     11100
```

Any sequence which contains the first five digit sequence, 10100, already narrows the number of possible sequences (e.g., from 1024 possible sequences) which contain it to less than about 192 possible sequences.

This 192 is derived from the observation that with the subsequence 10100 at the far left of the sequence, in positions 1–5, there are only 32 possible sequences. Likewise, for that particular subsequence in positions 2–6, 3–7, 4–8, 5–9, and 6–10. So, to sum up all of the sequences that could contain 10100, there are 32 for each position and 6 positions for a total of about 192 possible sequences. However, some of these 10 digit sequences will have been counted twice. Thus, by virtue of containing the 10100 subsequence, the number of possible 10-mer sequences has been decreased from 1024 sequences to less than about 192 sequences.

In this example, not only do we know that sequence contains 10100, but we also know that it contains the second five character sequence, 01001. By virtue of knowing that the sequence contains 10100, we can look specifically to determine whether the sequence contains a subsequence of five characters which contains the four leftmost digits plus a next digit to the left. For example, we would look for a sequence of X1010, but we find that there is none. Thus, we know that the 10100 must be at the left end of the 10-mer. We would also look to see whether the sequence contains the rightmost four digits plus a next digit to the right, e.g., 0100X. We find that the sequence also contains the sequence 01001, and that X is a 1. Thus, we know at least that our target sequence has an overlap of 0100 and has the left terminal sequence 101001.

Applying the same procedure to the second 5-mer, we also know that the sequence must include a sequence of five digits having the sequence 1001Y where Y must be either 0 or 1. We look through the fragments and we see that we have a 10011 sequence within our target, thus Y is also 1. Thus, we would know that our sequence has a sequence of the first seven being 1010011.

Moving to the next 5-mer, we know that there must be sequence of 0011Z, where Z must be either 0 or 1. We look at the fragments produced above and see that the target sequence contains a 00111 subsequence and Z is 1. Thus, we know the sequence must start with 10100111.

The next 5-mer must be of the sequence 0111W where W must be 0 or 1. Again, looking up at the fragments produced, we see that the target sequence contains a 01110 subsequence, and W is a 0.Thus, our sequence to this point is 101001110. We know that the last 5-mer must be either 11100 or 11101. Looking above, we see that it is 11100 and that must be the last of our sequence. Thus, we have determined that our sequence must have been 1010011100.

However, it will be recognized from the example above with the sequences provided therein, that the sequence analysis can start with any known positive probe subsequence. The determination may be performed by moving linearly along the sequence checking the known sequence with a limited number of next positions. Given this possibility, the sequence may be determined, besides by scanning all possible oligonucleotide probe positions, by specifically looking only where the next possible positions would be. This may increase the complexity of the scanning but may provide a longer time span dedicated towards scanning and detecting specific positions of interest relative to other sequence possibilities. Thus, the scanning apparatus could be set up to work its way along a sequence from a given contained oligonucleotide to only look at those positions on the substrate which are expected to have a positive signal.

It is seen that given a sequence, it can be de-constructed into n-mers to produce a set of internal contiguous subsequences. From any given target sequence, we would be able to determine what fragments would result. The hybridization sequence method depends, in part, upon being able to work in the reverse, from a set of fragments of known sequences to the full sequence. In simple cases, one is able to start at a single position and work in either or both directions towards the ends of the sequence as illustrated in the example.

The number of possible sequences of a given length increases very quickly with the length of that sequence. Thus, a 10-mer of zeros and ones has 1024 possibilities, a 12-mer has 4096. A 20-mer has over a million possibilities, and a 30-mer has over a billion. However, a given 30-mer has, at most, 26 different internal 5-mer sequences. Thus, a 30 character target sequence having over a million possible sequences can be substantially defined by only 26 different 5-mers. It will be recognized that the probe oligonucleotides will preferably, but need not necessarily, be of identical length, and that the probe sequences need not necessarily be contiguous in that the overlapping subsequences need not differ by only a single subunit. Moreover, each position of the matrix pattern need not be homogeneous, but may actually contain a plurality of probes of known sequence. In addition, although all of the possible subsequence specifications would be preferred, a less than full set of sequences specifications could be used. In particular, although a substantial fraction will preferably be at least about 70%, it may be less than that. About 20% would be preferred, more preferably at least about 30% would be desired. Higher percentages would be especially preferred.

2. Example of Four Letter Alphabet

A four letter alphabet may be conceptualized in at least two different ways from the two letter alphabet. One way, is to consider the four possible values at each position and to analogize in a similar fashion to the binary example each of the overlaps. A second way is to group the binary digits into groups.

Using the first means, the overlap comparisons are performed with a four letter alphabet rather than a two letter alphabet. Then, in contrast to the binary system with 10 positions where $2^{10}$=1024 possible sequences, in a 4-character alphabet with 10 positions, there will actually be $4^{10}$=1,048,576 possible sequences. Thus, the complexity of a four character sequence has a much larger number of possible sequences compared to a two character sequence. Note, however, that there are still only 6 different internal 5-mers. For simplicity, we shall examine a 5 character string with 3 character subsequences. Instead of only 1 and 0, the characters may be designated, e.g., A, C, G, and T. Let us take the sequence GGCTA. The 3-mer subsequences are:

```
GGC
 GCT
  CTA
```

Given these subsequences, there is one sequence, or at most only a few sequences which would produce that combination of subsequences, i.e., GGCTA.

Alternatively, with a four character universe, the binary system can be looked at in pairs of digits. The pairs would be 00, 01, 10, and 11. In this manner, the earlier used sequence 1010011100 is looked at as 10,10,01,11,00. Then the first character of two digits is selected from the possible universe of the four representations 00, 01, 10, and 11. Then a probe would be in an even number of digits, e.g., not five digits, but, three pairs of digits or six digits. A similar comparison is performed and the possible overlaps determined. The 3-pair subsequences are:

```
10, 10, 01
  10, 01, 11
    01, 11, 00
``` and the overlap reconstruction produces 10,10,01,11,00.

The latter of the two conceptual views of the 4 letter alphabet provides a representation which is similar to what would be provided in a digital computer. The applicability to a four nucleotide alphabet is easily seen by assigning, e.g., 00 to A, 01 to C, 10 to G, and 11 to T. And, in fact, if such a correspondence is used, both examples for the 4 character sequences can be seen to represent the same target sequence. The applicability of the hybridization method and its analysis for determining the ultimate sequence is easily seen if A is the representation of adenine, C is the representation of cytosine, G is the representation of guanine, and T is the representation of thymine or uracil.

3. Generalization to m-letter Alphabet

This reconstruction process may be applied to polymers of virtually any number of possible characters in the alphabet, and for virtually any length sequence to be sequenced, though limitations, as discussed below, will limit its efficiency at various extremes of length. It will be recognized that the theory can be applied to a large diversity of systems where sequence is important.

For example, the method could be applied to sequencing of a polypeptide. A polypeptide can have any of twenty natural amino acid possibilities at each position. A twenty letter alphabet is amenable to sequencing by this method so long as reagents exist for recognizing shorter subsequences therein. A preferred reagent for achieving that goal would be a set of monoclonal antibodies each of which recognizes a specific three contiguous amino acid subsequence. A complete set of antibodies which recognize all possible subsequences of a given length, e.g., 3 amino acids, and preferably with a uniform affinity, would be $20^3$=8000 reagents.

It will also be recognized that each target sequence which is recognized by the specific reagents need not have homogeneous termini. Thus, fragments of the entire target sequence will also be useful for hybridizing appropriate subsequences. It is, however, preferable that there not be a significant amount of labeled homogeneous contaminating extraneous sequences. This constraint does usually require the purification of the target molecule to be sequenced, but a specific label technique would dispense with a purification requirement if the unlabeled extraneous sequences do not interfere with the labeled sequences.

In addition, conformational effects of target polypeptide folding may, in certain embodiments, be negligible if the polypeptide is fragmented into sufficiently small peptides, or if the interaction is performed under conditions where conformation, but not specific interaction, is disrupted.

B. Complications

Two obvious complications exist with the method of sequence analysis by hybridization. The first results from a probe of inappropriate length while the second relates to internally repeated sequences.

The first obvious complication is a problem which arises from an inappropriate length of recognition sequence, which causes problems with the specificity of recognition. For example, if the recognized sequence is too short, every sequence which is utilized will be recognized by every probe sequence. This occurs, e.g., in a binary system where the probes are each of sequences which occur relatively frequently, e.g., a two character probe for the binary system. Each possible two character probe would be expected to appear ¼ of the time in every single two character position. Thus, the above sequence example would be recognized by each of the 00, 10, 01, and 11. Thus, the sequence information is virtually lost because the resolution is too low and each recognition reagent specifically binds at multiple sites on the target sequence.

The number of different probes which bind to a target depends on the relationship between the probe length and the target length. At the extreme of short probe length, the just mentioned problem exists of excessive redundancy and lack of resolution. The lack of stability in recognition will also be a problem with extremely short probes. At the extreme of long probe length, each entire probe sequence is on a different position of a substrate. However, a problem arises from the number of possible sequences, which goes up dramatically with the length of the sequence. Also, the specificity of recognition begins to decrease as the contribution to binding by any particular subunit may become sufficiently low that the system fails to distinguish the fidelity of recognition. Mismatched hybridization may be a problem with the polynucleotide sequencing applications, though the fingerprinting and mapping applications may not be so strict in their fidelity requirements. As indicated above, a thirty position binary sequence has over a million possible sequences, a number which starts to become unreasonably large in its required number of different sequences, even though the target length is still very short. Preparing a substrate with all sequence possibilities for a long target may be extremely difficult due to the many different oligomer s which must be synthesized.

The above example illustrates how a long target sequence may be reconstructed with a reasonably small number of shorter subsequences. Since the present day resolution of the regions of the substrate having defined oligomer probes attached to the substrate approaches about 10 microns by 10 microns for resolvable regions, about $10^6$, or 1 million, positions can be placed on a one centimeter square substrate. However, high resolution systems may have particular disadvantages which may be outweighed using the lower density substrate matrix pattern. For this reason, a sufficiently large number of probe sequences can be utilized so that any given target sequence may be determined by hybridization to a relatively small number of probes.

A second complication relates to convergence of sequences to a single subsequence. This will occur when a particular subsequence is repeated in the target sequence. This problem can be addressed in at least two different ways. The first, and simpler way, is to separate the repeat sequences onto two different targets. Thus, each single target will not have the repeated sequence and can be analyzed to its end. This solution, however, complicates the analysis by requiring that some means for cutting at a site between the repeats can be located. Typically a careful sequencer would want to have two intermediate cut points so that the intermediate region can also be sequenced in both directions across each of the cut points. This problem is inherent in the hybridization method for sequencing but can be minimized by using a longer known probe sequence so that the frequency of probe repeats is decreased.

Knowing the sequence of flanking sequences of the repeat will simplify the use of polymerase chain reaction (PCR) or a similar technique to further definitively determine the sequence between sequence repeats. Probes can be made to hybridize to those known sequences adjacent the repeat sequences, thereby producing new target sequences for analysis. See, e.g., Innis et al., (eds.) (1990) *PCR Protocols: A Guide to Methods and Applications*, Academic Press; and methods for synthesis of oligonucleotide probes, see, e.g., Gait (1984) *Oligonucleotide Synthesis: A Practical Approach*, IRL Press, Oxford.

Other means for dealing with convergence problems include using particular longer probes, and using degeneracy reducing analogues, see, e.g., Macevicz, S. (1990) PCT publication number WO 90/04652, which is hereby incorporated herein by reference. By use of stretches of the degeneracy reducing analogues with other probes in particular combinations, the number of probes necessary to fully saturate the possible oligomer probes is decreased. For example, with a stretch of 12-mers having the central 4-mer of degenerate nucleotides, in combination with all of the possible 8-mers, the collection numbers twice the number of possible 8-mers, e.g. 65,536+65,536=131,072, but the population provides screening equivalent to all possible 12-mers.

By way of further explanation, all possible oligonucleotide 8-mers may be depicted in the fashion:

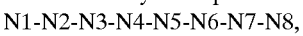

in which there are $4^8$=65,536 possible 8-mers. As described in U.S. Ser. No. 07/624,120 (automated VLSIPS), producing all possible 8-mers requires 4×8=32 chemical binary synthesis steps to produce the entire matrix pattern of 65,536 8-mer possibilities. By incorporating degeneracy reducing nucleotides, D's, which hybridize nonselectively to any corresponding complementary nucleotide, new oligonucleotides 12-mers can be made in the fashion:

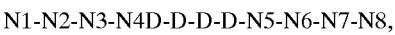

in which there are again, as above, only $4^8$=65,536 possible "12-mers", which in reality only have 8 different nucleotides.

However, it can be seen that each possible 12-mer probe could be represented by a group of the two 8-mer types. Moreover, repeats of less than 12 nucleotides would not converge, or cause repeat problems in the analysis. Thus, instead of requiring a collection of probes corresponding to all 12-mers, or $4^{12}$=16,777,216 different 12-mers, the same information can be derived by making 2 sets of "8-mers" consisting of the typical 8-mer collection of $4^8$=65,536 and the "12-mer" set with the degeneracy reducing analogues, also requiring making $4^8$=65,536. The combination of the two sets, requires making 65,536+65,536=131,072 different molecules, but giving the information of 16,777,216 molecules. Thus, incorporating the degeneracy reducing analogue decreases the number of molecules necessary to get 12-mer resolution by a factor of about 128fold.

C. Non-polynucleotide Embodiments

The above example is directed towards a polynucleotide embodiment. This application is relatively easily achieved because the specific reagents will typically be complementary oligonucleotides, although in certain embodiments other specific reagents may be desired. For example, there may be circumstances where other than complementary base pairing will be utilized. The polynucleotide targets, will usually be single strand, but may be double or triple stranded in various applications. However, a triple stranded specific interaction might be sometimes desired, or a protein or other specific binding molecule may be utilized. For example, various promoter or DNA sequence specific binding proteins might be used, including, e.g., restriction enzyme binding domains, other binding domains, and antibodies. Thus, specific recognition reagents besides oligonucleotides may be utilized.

For other polymer targets, the specific reagents will often be polypeptides. These polypeptides may be protein binding domains from enzymes or other proteins which display specificity for binding. Usually an antibody molecule may be used, and monoclonal antibodies may be particularly desired. Classical methods may be applied for preparing antibodies, see, e.g., Harlow and Lane (1988) *Antibodies: A Laboratory Manual* Cold Spring Harbor Press, New York; and Goding (1986) *Monoclonal Antibodies: Principles and Practice* (2d Ed.) Academic Press, San Diego. Other suitable techniques for in vitro exposure of lymphocytes to the antigens or selection of libraries of antibody binding sites are described, e.g., in Huse et al. (1989) *Science* 246:1275–1281; and Ward et al. 91989) *Nature* 341:544–546, each of which is hereby incorporated herein by reference. Unusual antibody production methods are also described, e.g., in Hendricks et al. (1989) *BioTechnology* 7:1271–1274; and Hiatt et al. (1989) *Nature* 342:76–78, each of which is hereby incorporated herein by reference. Other molecules which may exhibit specific binding interaction may be useful for attachment to a VLSIPS substrate by various methods, including the caged biotin methods, see, e.g., U.S. Ser. No. 07/435,316 (caged biotin parent), and U.S. Ser. No. 07/612,671 (caged biotin CIP).

The antibody specific reagents should be particularly useful for the polypeptide, carbohydrate, and synthetic polymer applications. Individual specific reagents might be generated by an automated process to generate the number of reagents necessary to advantageously use the high density positional matrix pattern. In an alternative approach, a plurality of hybridoma cells may be screened for their ability to bind to a VISIPS matrix possessing the desired sequences whose binding specificity is desired. Each cell might be individually grown up and its binding specificity determined by VLSIPS apparatus and technology. An alternative strategy would be to expose the same VLSIPS matrix to a polyclonal serum of high titer. By a successively large volume of serum and different animals, each region of the VLSIPS substrate would have attached to it a substantial number of antibody molecules with specificity of binding. The substrate, with non-covalently bound antibodies could be derivatized and the antibodies transferred to an adjacent second substrate in the matrix pattern in which the antibody molecules had attached to the first matrix. If the sensitivity of detection of binding interaction is sufficiently high, such a low efficiency transfer of antibody molecules may produce a sufficiently high signal to be useful for many purposes, including the sequencing applications.

In another embodiment, capillary forces may be used to transfer the selected reagents to a new matrix, to which the reagents would be positionally attached in the pattern of the recognized sequences. Or, the reagents could be transversely electrophoresed, magnetically transferred, or otherwise transported to a new substrate in their retained positional pattern.

III. Polynucleotide Sequencing

In principle, the making of a substrate having a positionally defined matrix pattern of all possible oligonucleotides of a given length involves a conceptually simple method of synthesizing each and every different possible oligonucleotide, and affixed to a definable position. Oligonucleotide synthesis is presently mechanized and enabled by current technology, see, e.g., U.S. Ser. No. 07/362,901 (VLSIPS parent); U.S. Ser. No. 07/492,462 (VLSIPS CIP); and instruments supplied by Applied Biosystems, Foster City, Calif.

A. Preparation of Substrate Matrix

The production of the collection of specific oligonucleotides used in polynucleotide sequencing may be produced in at least two different ways. Present technology certainly allows production of ten nucleotide oligomers on a solid phase or other synthesizing system. See, e.g., instrumentation provided by Applied Biosystems, Foster City, Calif. Although a single oligonucleotide can be relatively easily made, a large collection of them would typically require a fairly large amount of time and investment. For example, there are $4^{10}$=1,048,576 possible ten nucleotide oligomers. Present technology allows making each and every one of them in a separate purified form though such might be costly and laborious.

Once the desired repertoire of possible oligomer sequences of a given length have been synthesized, this collection of reagents may be individually positionally attached to a substrate, thereby allowing a batchwise hybridization step. Present technology also would allow the possibility of attaching each and every one of these 10-mers to a separate specific position on a solid matrix. This attachment could be automated in any of a number of ways, particularly use of a caged biotin type linking. This would produce a matrix having each of different possible 10-mers.

A batchwise hybridization is much preferred because of its reproducibility and simplicity. An automated process of attaching various reagents to positionally defined sites on a substrate is provided in U.S. Ser. No. 07/492,462 (VLSIPS CIP); U.S. Ser. No. 07/624,120 (automated VLSIPS); and U.S. Ser. No. 07/612,671 (caged biotin CIP), each of which is hereby incorporated herein by reference.

Instead of separate synthesis of each oligonucleotide, these oligonucleotides are conveniently synthesized in parallel by sequential synthetic processes on a defined matrix pattern as provided in U.S. Ser. No. 07/492,462 (VLSIPS CIP); and U.S. Ser. No. 07/624.120, (automated VLSIPS), which are incorporated herein by reference. Here, the oligonucleotides are synthesized stepwise on a substrate at positionally separate and defined positions. Use of photosensitive blocking reagents allows for defined sequences of synthetic steps over the surface of a matrix pattern. By use of the binary masking strategy, the surface of the substrate can be positioned to generate a desired pattern of regions, each having a defined sequence oligonucleotide synthesized and immobilized thereto.

Although the prior art technology can be used to generate the desired repertoire of oligonucleotide probes, an efficient and cost effective means would be to use the VLSIPS technology described in U.S. Ser. No. 07/492,462 (VLSIPS CIP) and U.S. Ser. No. 07/624,120, (automated VLSIPS). In this embodiment, the photosensitive reagents involved in the production of such a matrix are described below.

The regions for synthesis may be very small, usually less than about 100 $\mu$m×100 $\mu$m, more usually less than about 50 $\mu$m×50 $\mu$m. The photolithography technology allows synthetic regions of less than about 10 $\mu$m×10 $\mu$m, about 3 $\mu$m×3 $\mu$m, or less. The detection also may detect such sized regions, though larger areas are more easily and reliably measured.

At a size of about 30 microns by 30 microns, one million regions would take about 11 centimeters square or a single wafer of about 4 centimeters by 4 centimeters. Thus the present technology provides for making a single matrix of that size having all one million plus possible oligonucleotides. Region size are sufficiently small to correspond to densities of at least about 5 regions/cm$^2$, 20 regions/cm$^2$, 50 regions/cm$^2$, 100 regions/cm$^2$, and greater, including 300 regions/cm$^2$, 1000 regions/cm$^2$, 3K regions/cm$^2$,10K regions/cm$^2$, 30K regions/cm$^2$, 100K regions/cm$^2$300K regions/cm$^2$ or more, even in excess of one million regions/cm$^2$.

Although the pattern of the regions which contain specific sequences is theoretically not important, for practical reasons certain patterns will be preferred in synthesizing the oligonucleotides. The application of binary masking algorithms for generating the pattern of known oligonucleotide probes is described in related U.S. Ser. No. 07/624,120 (automated VLSIPS) which was filed simultaneously with this application. By use of these binary masks, a highly efficient means is provided for producing the substrate with the desired matrix pattern of different sequences. Although the binary masking strategy allows for the synthesis of all lengths of polymers, the strategy may be easily modified to provide only polymers of a given length. This is achieved by omitting steps where a subunit is not attached.

The strategy for generating a specific pattern may take any of a number of different approaches. These approaches are well described in related application U.S. Ser. No. 07/624,120, (automated VLSIPS) and include a number of binary masking approaches which will not be exhaustively discussed herein. However, the binary masking and binary synthesis approaches provide a maximum of diversity with a minimum number of actual synthetic steps.

The length of oligonucleotides used in sequencing applications will be selected on criteria determined to some extent by the practical limits discussed above. For example, if probes are made as oligonucleotides, there will be 65,536 possible eight nucleotide sequences. If a nine subunit oligonucleotide is selected, there are 262,144 possible permeations of sequences. If a ten-mer oligonucleotide is selected, there are 1,048,576 possible permeations of sequences. As the number gets larger, the required number of positionally defined subunits necessary to saturate the possibilities also increases. With respect to hybridization conditions, the length of the matching necessary to converse stability of the conditions selected can be compensated for. See, e.g., Kanehisa, M. (1984) *Nuc. Acids Res.* 12:203–213, which is hereby incorporated herein by reference.

Although not described in detail here, but below for oligonucleotide probes, the VLSIPS technology would typically use a photosensitive protective group on an oligonucleotide. Sample oligonucleotides are shown in FIG. 1. In particular, the photoprotective group on the nucleotide molecules may be selected from a wide variety of positive light reactive groups preferably including nitro aromatic compounds such as o-nitro-benzyl derivatives or benzylsulfonyl. See, e.g., Gait (1984) *Oligonucleotide Synthesis: A Practical Approach*, IRL Press, Oxford, which is hereby incorporated herein by reference. In a preferred embodiment, 6-nitroveratryl oxycarbony (NVOC), 2-nitrobenzyl oxycarbonyl (NBOC), or α,α-dimethyl-dimethoxybenzyl oxycarbonyl (DEZ) is used. Photoremovable protective groups are described in, e.g., Patchornik (1970) *J. Amer. Chem. Soc.* 92:6333–6335; and Amit et al. (1974) *J. Organic Chem.* 39:192–196; each of which is hereby incorporated herein by reference.

Figure 2:
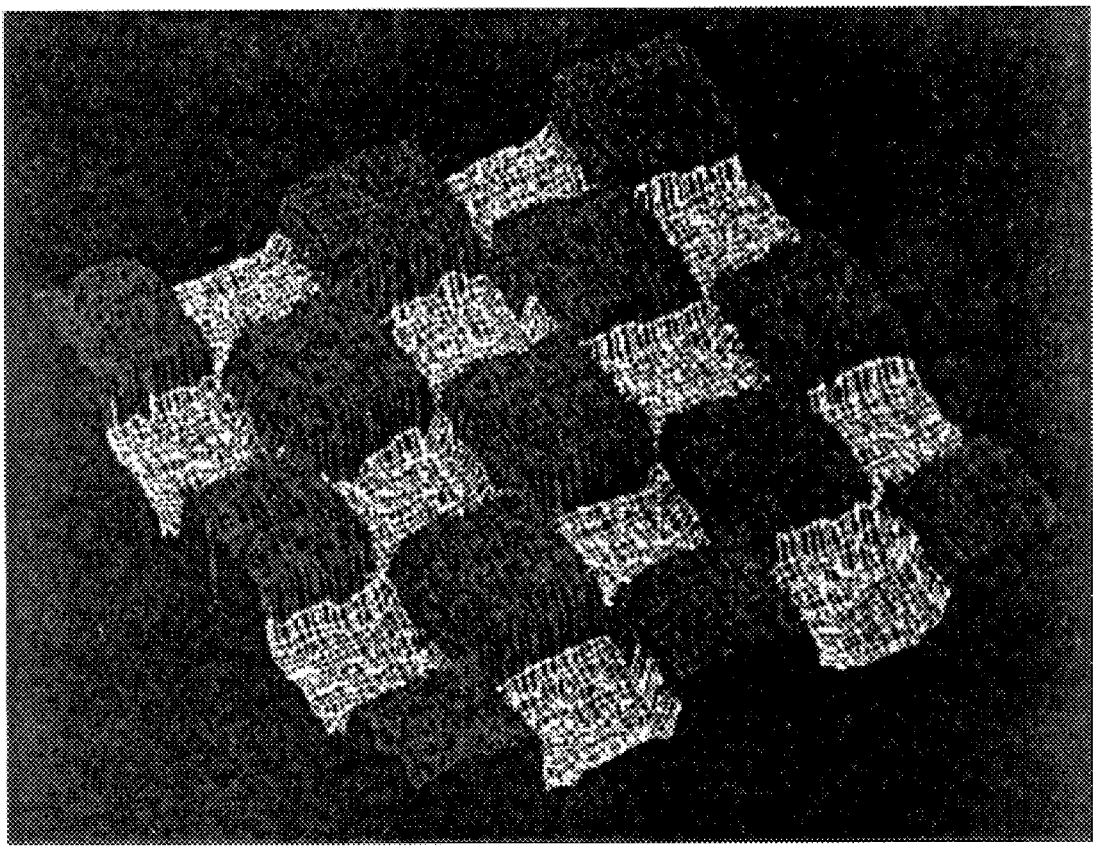
FIG. 2 illustrates the proper function of a VLSIPS peptide synthesis.

A preferred linker for attaching the oligonucleotide to a silicon matrix is illustrated in FIG. 2. A more detailed description is provided below. A photosensitive blocked nucleotide may be attached to specific locations of unblocked prior cycles of attachments on the substrate and can be successively built up to the correct length oligonucleotide probe.

It should be noted that multiple substrates may be simultaneously exposed to a single target sequence where each substrate is a duplicate of one another or where, in combination, multiple substrates together provide the complete or desired subset of possible subsequences. This provides the opportunity to overcome a limitation of the density of positions on a single substrate by using multiple substrates. In the extreme case, each probe might be attached to a single bead or substrate and the beads sorted by whether there is a binding interaction. Those beads which do bind might be encoded to indicate the subsequence specificity of reagents attached thereto.

Then, the target may be bound to the whole collection of beads and those beads that have appropriate specific reagents on them will bind to target. Then a sorting system may be utilized to sort those beads that actually bind the target from those that do not. This may be accomplished by presently available cell sorting devices or a similar apparatus. After the relatively small number of beads which have bound the target have been collected, the encoding scheme may be read off to determine the specificity of the reagent on the bead. An encoding system may include a magnetic system, a shape encoding system, a color encoding system, or a combination of any of these, or any other encoding system. Once again, with the collection of specific interactions that have occurred, the binding may be analyzed for sequence information, fingerprint information, or mapping information.

The parameters of polynucleotide sizes of both the probes and target sequences are determined by the applications and other circumstances. The length of the oligonucleotide probes used will depend in part upon the limitations of the VLSIPS technology to provide the number of desired probes. For example, in an absolute sequencing application, it is often useful to have virtually all of the possible oligonucleotides of a given length. As indicated above, there are 65,536 8-mers, 262,144 9-mers, 1,048,576 10-mers, 4,194,304 11-mers, etc. As the length of the oligomer increases the number of different probes which must be synthesized also increases at a rate of a factor of 4 for every additional nucleotide. Eventually the size of the matrix and the limitations in the resolution of regions in the matrix will reach the point where an increase in number of probes becomes disadvantageous. However, this sequencing procedure requires that the system be able to distinguish, by appropriate selection of hybridization and washing conditions, between binding of absolute fidelity and binding of complementary sequences containing mismatches. On the other hand, if the fidelity is unnecessary, this discrimination is also unnecessary and a significantly longer probe may be used significantly longer probes would typically be useful in fingerprinting or mapping applications.

The length of the probe is selected for a length that it will bind with specificity to possible targets. The hybridization conditions are also very important in that they will determine how close the homology of complementary binding will be detected. In fact, a single target may be evaluated at a number of different conditions to determine its spectrum of specificity for binding particular probes. This may find use in a number of other applications besides the polynucleotide sequencing fingerprinting or mapping. For example, it will be desired to determine the spectrum of binding affinities and specificities of cell surface antigens with binding by particular antibodies immobilized on the substrate surface, particularly under different interaction conditions. In a related fashion, different regions with reagents having differing affinities or levels of specificity may allow such a spectrum to be defined using a single incubation, where various regions, at a given hybridization condition, show the binding affinity. For example, fingerprint probes of various lengths, or with specific defined nonmatches may be used. Unnatural nucleotides or nucleotides exhibiting modified specificity of complementary binding are described in greater detail in Macevicz (1990) PCT pub. No. WO 90/04652; and see the section on modified nucleotides in the Sigma chemical company catalogue.

B. Labeling Target Nucleotide

The label used to detect the target sequences will be determined, in part, by the detection methods being applied. Thus, the labeling method and label used are selected in combination with the actual detecting systems being used.

Once a particular label has been selected, appropriate labeling protocols will be applied, as described below for specific embodiments. Standard labeling protocols for nucleic acids are described, e.g., in Sambrook et al.; Kambara, H. et al. (1988) *BioTechnology* 6:816–821; Smith, L. et al. (1985) *Nuc. Acids Res.* 13:2399–2412; for polypeptides, see, e.g., Allen G. (1989) *Sequencing of Proteins and Peptides*, Elsevier, New York, especially chapter 5, and Greenstein and Winitz (1961) *Chemistry of the Amino Acids*, Wiley and Sons, New York. Carbohydrate labeling is described, e.g., in Chaplin and Kennedy (1986) *Carbohydrate Analysis: A Practical Approach*, IRL Press, Oxford. Labeling of other polymers will be performed by methods applicable to them as recognized by a person having ordinary skill in manipulating the corresponding polymer.

In some embodiments, the target need not actually be labeled if a means for detecting where interaction takes place is available. As described below, for a nucleic acid embodiment, such may be provided by an intercalating dye which intercalates only into double stranded segments, e.g., where interaction occurs. See, e.g., Sheldon et al. U.S. Pat. No. 4,582,789.

In many uses, the target sequence will be absolutely homogeneous, both with respect to the total sequence and with respect to the ends of each molecule. Homogeneity with respect to sequence is important to avoid ambiguity. It is preferable that the target sequences of interest not be contaminated with a significant amount of labeled contaminating sequences. The extent of allowable contamination will depend on the sensitivity of the detection system and the inherent signal to noise of the system. Homogeneous contamination sequences will be particularly disruptive of the sequencing procedure.

However, although the target polynucleotide must have a unique sequence, the target molecules need not have identical ends. In fact, the homogeneous target molecule preparation may be randomly sheared to increase the numerical number of molecules. Since the total information content remains the same, the shearing results only in a higher number of distinct sequences which may be labeled and bind to the probe. This fragmentation may give a vastly superior signal relative to a preparation of the target molecules having homogeneous ends. The signal for the hybridization is likely to be dependent on the numerical frequency of the target-probe interactions. If a sequence is individually found on a larger number of separate moleules a better signal will result. In fact, shearing a homogeneous preparation of the target may often be preferred before the labeling procedure is performed, thereby producing a large number of labeling groups associated with each subsequence.

C. Hybridiation Conditions

The hybridization conditions between probe and target should be selected such that the specific recognition interaction, i.e., hybridization, of the two molecules is both sufficiently specific and sufficiently stable. See, e.g., Hames and Higgins (1985) *Nucleic Acid Hybridisation: A Practical Approach*, IRL Press, Oxford. These conditions will be dependent both on the specific sequence and often on the guanine and cytosine (GC) content of the complementary hybrid strands. The conditions may often be selected to be universally equally stable independent of the specific sequence involved. This typically will make use of a reagent such as an arylammonium buffer. See, Wood et al. (1985) "Base Composition-independent Hybridization in Tetramethylammonium Chloride: A Method for oligonucleotide screening of Highly Complex Gene Libraries," *Proc. Natl. Acad. Sci. USA,* 82:1585–1588; and Krupov et al. (1989) "An Oligonucleotide Hybridization Approach to DNA Sequencing," *FEBS Letters,* 256:118–122; each of which is hereby incorporated herein by reference. An arylammonium buffer tends to minimize differences in hybridization rate and stability due to GC content. By virtue of the fact that sequences then hybridize with approximately equal affinity and stability, there is relatively little bias in strength or kinetics of binding for particular sequences. Temperature and salt conditions along with other buffer parameters should be selected such that the kinetics of renaturation should be essentially independent of the specific target subsequence or oligonucleotide probe involved. In order to ensure this, the hybridization reactions will usually be performed in a single incubation of all the substrate matrices together exposed to the identical same target probe solution under the same conditions.

Alternatively, various substrates may be individually treated differently. Different substrates may be produced, each having reagents which bind to target subsequences with substantially identical stabilities and kinetics of hybridization. For example, all of the high GC content probes could be synthesized on a single substrate which is treated accordingly. In this embodiment, the arylammonium buffers could be unnecessary. Each substrate is then treated in a manner that the collection of substrates show essentially uniform binding and the hybridization data of target binding to the individual substrate matrix is combined with the data from other substrates to derive the necessary subsequence binding information. The hybridization conditions will usually be selected to be sufficiently specific that the fidelity of base matching will be properly discriminated. Of course, control hybridizations should be included to determine the stringency and kinetics of hybridization.

D. Detection; VLSIPS Scanning

The next step of the sequencing process by hybridization involves labeling of target polynucleotide molecules. A quickly and easily detectable signal is preferred. The VLZIPS apparatus is designed to easily detect a fluorescent label, so fluorescent tagging of the target sequence is preferred. Other suitable labels include heavy metal labels, magnetic probes, chromogenic labels (e.g., phosphorescent labels, dyes, and fluorophores) spectroscopic labels, enzyme linked labels, radioactive labels, and labeled binding proteins. Additional labels are described in U.S. Pat. No. 4,366,241, which is incorporated herein by reference.

The detection methods used to determine where hybridization has taken place will typically depend upon the label selected, above. Thus, for a fluorescent label a fluorescent detection step will typically be used. U.S. Ser. No. 07/492, 462 (VLSIPS CIP) and U.S. Ser. No. 07/624,120 (automated VLSIPS) describe apparatus and mechanisms for scanning a substrate matrix using fluorescence detection, but a similar apparatus is adaptable for other optically detectable labels.

The detection method provides a positional localization of the region where hybridization has taken place. However, the position is correlated with the specific sequence of the probe since the probe has specifically been attached or synthesized at a defined substrate matrix position. Having collected all of the data indicating the subsequences present in the target sequence, this data may be aligned by overlap to reconstruct the entire sequence of the target, as illustrated above.

It is also possible to dispense with actual labeling if some means for detecting the positions of interaction between the sequence specific reagent and the target molecule are available. This may take the form of an additional reagent which can indicate the sites either of interaction, or the sites of lack of interaction, e.g., a negative label. For the nucleic acid embodiments, locations of double strand interaction may be detected by the incorporation of intercalating dyes, or other reagents such as antibody or other reagents that recognize helix formation, see, e.g., Sheldon, et al. (1986) U.S. Pat. No. 4,582,789, which is hereby incorporated herein by reference.

E. Analysis

Although the reconstruction can be performed manually as illustrated above, a computer program will typically be used to perform the overlap analysis. A program may be written and run on any of a large number of different computer hardware systems. The variety of operating systems and languages useable will be recognized by a computer software engineer. Various different languages may be used, e.g., BASIC; C; PASCAL; etc. A simple flow chart of data analysis is illustrated in FIG. 4.

F. Substrate Reuse

Finally, after a particular sequence has been hybridized and the pattern of hybridization analyzed, the matrix substrate should be reusable and readily prepared for exposure to a second or subsequent target polynucleotides. In order to do so, the hybrid duplexes are disrupted and the matrix treated in a way which removes all traces of the original target. The matrix may be treated with various detergents or solvents to which the substrate, the oligonucleotide probes, and the linkages to the substrate are inert. This treatment may include an elevated temperature treatment, treatment with organic or inorganic solvents, modifications in pH, and other means for disrupting specific interaction. Thereafter, a second target may actually be applied to the recycled matrix and analyzed as before.

G. Non-Polynucleotide Aspects

Although the sequencing, fingerprinting, and mapping functions will make use of the natural sequence recognition property of complementary nucleotide sequences, the non-polynucleotide sequences typically require other sequence recognition reagents. These reagents will take the form, typically, of proteins exhibiting binding specificity, e.g., enzyme binding sites or antibody binding sites.

Enzyme binding sites may be derived from promoter proteins, restriction enzymes, and the like. See, e.g., Stryer, L. (1988) *Biochemistry*, W. H. Freeman, Palo Alto. Antibodies will typically be produced using standard procedures, see, e.g., Harlow and Lane (1988) *Antibodies; A Laboratory Manual*, Cold Spring Harbor Press, New York; and Goding (1986) *Monoclonal Antibodies: Principles and Practice*, (2d Ed.) Academic Press, San Diego.

Typically, an antigen, or collection of antigens are presented to an immune system. This may take the form of synthesized short polymers produced by the VLSIPS technology, or by the other synthetic means, or from isolation of natural products. For example, antigen for the polypeptides may be made by the VLSIPS technology, by standard peptide synthesis, by isolation of natural proteins with or without degradation to shorter segments, or by expression of a collection of short nucleic acids of random or defined sequences. See, eg., Tuerk and Gold (1990) *Science* 249:505–510, for generation of a collection of randomly mutagenized oligonucleotides useful for expression.

The antigen or collection is presented to an appropriate immune system, e.g., to a whole animal as in a standard immunization protocol, or to a collection of immune cells or equivalent. In particular, see Ward et al. (1989) *Nature* 341:544–546; and Huse et al. (1989) *Science* 246:1275–1281, each of which is hereby incorporated herein by reference.

A large diversity of antibodies will be generated, some of which have specificities for the desired sequences. Antibodies may be purified having the desired sequence specificities by isolating the cells producing them. For example, a VLSIPS substrate with the desired antigens synthesized thereon may be used to isolate cells with cell surface reagents which recognize the antigens. The VLSIPS substrate may be used as an affinity reagent to select and recover the appropriate cells. Antibodies from those cells may be attached to a substrate using the caged biotin methodology, or by attaching a targeting molecule, e.g., an oligonucleotide. Alternatively, the supernatants from antibody producing cells can be easily assayed using a VLSIPS substrate to identify the cells producing the appropriate antibodies.

Although cells may be isolated, specific antibody molecules which perform the sequence recognition will also be sufficient. Preferably populations of antibody with a known specificity can be isolated. Supernatants from a large population of producing cells may be passed over a VLSIPS substrate to bind to the desired antigens attached to the substrate. When a sufficient density of antibody molecules are attached, they may be removed by an automated process, preferably as antibody populations exhibiting specificity of binding.

In one particular embodiment, a VLSIPS substrate, e.g., with a large plurality of fingerprint antigens attached thereto, is used to isolate antibodies from a supernatant of a population of cells producing antibodies to the antigens. Using the substrate as an affinity reagent, the antibodies will attach to the appropriate positionally defined antigens. The antibodies may be carefully removed therefrom, preferably by an automated system which retains their homogeneous specificities. The isolated antibodies can be attached to a new substrate in a positionally defined matrix pattern.

In a further embodiment, these spatially separated antibodies may be isolated using a specific targeting method for isolation. In this embodiment, a linker molecule which attaches to a particular portion of the antibody, preferably away from the binding site, can be attached to the antibodies. Various reagents will be used, including staphylococcus protein A or antibodies which bind to domains remote from the binding site. Alternatively, the antibodies in the population, before affinity purification, may be derivatized with an appropriate reagent compatible with new VLSIPS synthesis. A preferred reagent is a nucleotide which can serve as a linker to synthetic VLSIPS steps for synthesizing a specific sequence thereon. Then, by successive VLSIPS cycles, each of the antibodies attached to the defined antigen regions can have a defined oligonucleotide synthesized thereon and corresponding in area to the region of the substrate having each antigen attached. These defined oligonucleotides will be useful as targeting reagents to attach those antibodies possessing the same target sequence specificity at defined positions on a new substrate, by virtue of having bound to the antigen region, to a new VLSIPS substrate having the complementary target oligonucleotides positionally located on it. In this fashion, a VLSIPS substrate having the desired antigens attached thereto can be used to generate a second VLSIPS substrate with positionally defined reagents which recognize those antigens.

The selected antigens will typically be selected to be those which define particular functionalities or properties, so as to be useful for fingerprinting and other uses. They will also be useful for mapping and sequencing embodiments.

IV. Fingerprinting

A. General

Many of the procedures and techniques used in the polynucleotide sequencing section are also appropriate for fingerprinting applications. See, e.g., Poustka, et al. (1986) *Cold Spring Harbor Symposia on Quant. Biol.*, vol. LI, 131–139, Cold Spring Harbor Press, New York; which is hereby incorporated herein by reference. The fingerprinting method provided herein is based, in part, upon the ability to positionally localize a large number of different specific probes onto a single substrate. This high density matrix pattern provides the ability to screen for, or detect, a very large number of different sequences simultaneously. In fact, depending upon the hybridization conditions, fingerprinting to the resolution of virtually absolute matching of sequence is possible thereby approaching an absolute sequencing embodiment. And the sequencing embodiment is very useful in identifying the probes useful in further fingerprinting uses. For example, characteristic features of genetic sequences will be identified as being diagnostic of the entire sequence. However, in most embodiments, longer probe and target will be used, and for whichs light mismatching may not need to be resolved.

B. Preparation of Substrate Matrix

A collection of specific probes may be produced by either of the methods described above in the section on sequencing. Specific oligonucleotide probes of desired lengths may be individually synthesized on a standard oligonucleotide synthesizer. The length of these probes is limited only by the length of the ability of the synthesizer to continue to accurately synthesize a molecule. Oligonucleotides or sequence fragments may also be isolated from natural sources. Biological amplification methods may be coupled with synthetic synthesizing procedures such as, e.g., polymerase chain reaction.

In one embodiment, the individually isolated probes may be attached to the matrix at defined positions. These probe reagents may be attached by an automated process making use of the caged biotin methodology described in U.S. Ser. No. 07/612,671 (caged biotin CIP), or using photochemical reagents, see, e.g., Dattagupta et al. (1985) U.S. Pat. No. 4,542,102 and (1987) U.S. Pat. No. 4,713,326. Each individual purified reagent can be attached individually at specific locations on a substrate.

In another embodiment, the VLSIPS synthesizing technique may be used to synthesize the desired probes at specific positions on a substrate. The probes may be synthesized by successively adding appropriate monomer subunits, e.g., nucleotides, to generate the desired sequences.

In another embodiment, a relatively short specific oligonucleotide is used which serves as a targeting reagent for positionally directing the sequence recognition reagent. For example, the sequence specific reagents having a separate additional sequence recognition segment (usually of a different polymer from the target sequence) can be directed to target oligonucleotides attached to the substrate. By use of non-natural targeting reagents, e.g., unusual nucleotide analogues which pair with other unnatural nucleotide analogues and which do not interfere with natural nucleotide interactions, the natural and non-natural portions can coexist on the same molecule without interfering with their individual functionalities. This can combine both a synthetic and biological production system analogous to the technique for targeting monoclonal antibodies to locations on a VLSIPS substrate at defined positions. Unnatural optical isomers of nucleotides may be useful unnatural reagents subject to similar chemistry, but incapable of interfering with the natural biological polymers. See also, U.S. Ser. No. 07/626,730, (sequencing by synthesis); which is hereby incorporated herein by reference.

After the separate substrate attached reagents are attached to the targeting segment, the two are crosslinked, thereby permanently attaching them to the substrate. Suitable crosslinking reagents are known, see, e.g., Dattagupta et al. (1985) U.S. Pat. No. 4,542,102 and (1987) "Coupling of nucleic acids to solid support by photochemical methods," U.S. Pat. No. 4,713,326, each of which is hereby incorporated herein by reference. Similar linkages for attachment of proteins to a solid substrate are provided, e.g., in Merrifield (1986) *Science* 232:341-347, which is hereby incorporated herein by reference.

C. Labeling Target Nucleotides

The labeling procedures used in the sequencing embodiments will also be applicable in the fingerprinting embodiments. However, since the fingerprinting embodiments often will involve relatively large target molecules and relatively short oligonucleotide probes, the amount of signal necessary to incorporate into the target sequence may be less critical than in the sequencing applications. For example, a relatively long target with a relatively small number of labels per molecule may be easily amplified or detected because of the relatively large target molecule size.

In various embodiments, it may be desired to cleave the target into smaller segments as in the sequencing embodiments. The labeling procedures and cleavage techniques described in the sequencing embodiments would usually also be applicable here.

D. Hybridization Conditions

The hybridization conditions used in fingerprinting embodiments will typically be less critical than for the sequencing embodiments. The reason is that the amount of mismatching which may be useful in providing the fingerprinting information would typically be far greater than that necessary in sequencing uses. For example, Southern hybridizations do not typically distinguish between slightly mismatched sequences. Under these circumstances, important and valuable information may be arrived at with less stringent hybridization conditions while providing valuable fingerprinting information. However, since the entire substrate is typically exposed to the target molecule at one time, the binding affinity of the probes should usually be of approximately comparable levels. For this reason, if oligonucleotide probes are being used, their lengths should be approximately comparable and will be selected to hybridize under conditions which are common for most of the probes on the substrate. Much as in a southern hybridization, the target and oligonucleotide probes are of lengths typically greater than about 25 nucleotides. Under appropriate hybridization conditions, e.g., typically higher salt and lower temperature, the probes will hybridize irrespective of imperfect complementarity. In fact, with probes of greater than, e.g., about fifty nucleotides, the difference in stability of different sized probes will be relatively minor.

Typically the fingerprinting is merely for probing similarity or homology. Thus, the stringency of hybridization can usually be decreased to fairly low levels. See, e.g., Wetmur and Davidson (1968) "Kinetics of Renaturation of DNA," *J. Mol. Biol.*, 31:349–370; and Kanehisa, M. (1984) *Nuc. Acids Res.*, 12:203–213.

E. Detection; VLSIPS Scanning

Detection methods will be selected which are appropriate for the selected label. The scanning device need not necessarily be digitized or placed into a specific digital database, though such would most likely be done. For example, the analysis in fingerprinting could be photographic. Where a standardized fingerprint substrate matrix is used, the pattern of hybridizations may be spatially unique and may be compared photographically. In this manner, each sample may have a characteristic pattern of interactions and the likelihood of identical patterns will preferably be such low frequency that the fingerprint pattern indeed becomes a characteristic pattern virtually as unique as an individual's fingertip fingerprint. With a standardized substrate, every individual could be, in theory, uniquely identifiable on the basis of the pattern of hybridizing to the substrate.

Of course, the VLSIPS scanning apparatus may also be useful to generate a digitized version of the fingerprint pattern. In this way, the identification pattern can be provided in at linear string of digits. This sequence could also be used for a standardized identification system providing significant useful medical transferability of specific data. In one embodiment, the probes used are selected to be of sufficiently high resolution to measure the antigens of the major histo compatibility complex, it might even be possible to provide transplantation matching data in a linear stream of data. The fingerprinting data may provide a condensed version, or summary, of the linear genetic data, or any other information data base.

F. Analysis

The analysis of the fingerprint will often be much simpler than a total sequence determination. However, there may be particular types of analysis which will be substantially simplified by a selected group of probes. For example, probes which exhibit particular populational heterogeneity may be selected. In this way, analysis may be simplified and practical utility enhanced merely by careful selection of the specific probes and a careful matrix layout of those probes.

G. Substrate Reuse

As with the sequencing application, the fingerprinting usages may also take advantage of the reusability of the substrate. In this way, the interactions can be disrupted, the substrate treated, and the renewed substrate is equivalent to an unused substrate.

H. Non-polynucleotide Aspects

Besides polynucleotide applications, the fingerprinting analysis may be applied to other polymers, especially polypeptides, carbohydrates, and other polymers, both organic and inorganic. Besides using the fingerprinting method for analyzing a particular polymer, the fingerprinting method may be used to characterize various samples. For example, a cell or population of cells may be tested for their expression of specific antigens or their mRA sequence intent. For example, a T-cell may be classified by virtue of its combination of expressed surface antigens. With specific reagents which interact with these antigens, a cell or a population of cells or a lysed cell may be exposed to a VLSIPS substrate. The biological sample may be classified or characterized by analyzing the pattern of specific interaction. This may be applicable to a cell or tissue type, to the expressed messenger RNA population expressed by a cell to the genetic content of a cell, or to virtually any sample which can be classified and/or identified by its combination of specific molecular properties.

The ability to generate a high density means for screening the presence or absence of specific interactions allows for the possibility of screening for, if not saturating, all of a very large number of possible interactions. This is very powerful in providing the means for testing the combinations of molecular properties which can define a class of samples. For example, a species of organism may be characterized by its DNA sequences, e.g., a genetic fingerprint. By using a fingerprinting method, it may be determined that all members of that species are sufficiently similar in specific sequences that they can be easily identified as being within a particular group. Thus, newly defined classes may be resolved by their similarity in fingerprint patterns. Alternatively, a non-member of that group will fail to share those many identifying characteristics. However, since the technology allows testing of a very large number of specific interactions, it also provides the ability to more finely distinguish between closely related different cells or samples. This will have important applications in diagnosing viral, bacterial, and other pathological on nonpathological infections.

In particular, cell classification may be defined by any of a number of different properties. For example, a cell class may be defined by its DNA sequences contained therein. This allows species identification for parasitic or other infections. For example, the human cell is presumably genetically distinguishable from a monkey cell, but different human cells will share many genetic markers. At higher resolution, each individual human genome will exhibit unique sequences that can define it as a single individual.

Likewise, a developmental stage of a cell type may be definable by its pattern of expression of messenger RNA. For example, in particular stages of cells, high levels of ribosomal RNA are found whereas relatively low levels of other types of messenger RNAs may be found. The high resolution distinguishability provided by this fingerprinting method allows the distinction between cells which have relatively minor differences in its expressed mRNA population. Where a pattern is shown to be characteristic of a stage, a stage may be defined by that particular pattern of messenger RNA expression.

In a similar manner, the antigenic determinants found on a protein may very well define the cell class. For example, immunological T-cells are distinguishable from B-cells because, in part, the cell surface antigens on the cell types are distinguishable. Different T-cell subclasses can be also distinguished from one another by whether they contain particular T-cell antigens. The present invention provides the possibility for high resolution testing of many different interactions simultaneously, and the definition of new cell types will be possible.

The high resolution VLSIPS substrate may also be use as a very powerful diagnostic tool to test the combination of presence, of a plurality of different assays from a biological sample. For example, a cancerous condition may be indicated by a combination of various different properties found in the blood. For example, a cancerous condition may be indicated by a combination of expression of various soluble antigens found in the blood along with a high number of various cellular antigens found on lymphocytes and/or particular cell degradation products. With a substrate as provided herein, a large number of different features can be simultaneously performed on a biological sample. In fact, the high resolution of the test will allow more complete characterization of parameters which define particular diseases. Thus, the power of diagnostic tests may be limited by the extent of statistical correlation with a particular condition rather than with the number of antigens or interactions which are tested. The present invention provides the means to generate this large universe of possible reagents and the ability to actually accumulate that correlative data.

In another embodiment, a substrate as provided herein may be used for genetic screening. This would allow for simultaneous screening of thousands of genetic markers. As the density of the matrix is increased, many more molecules can be simultaneously tested. Genetic screening then becomes a simpler method as the present invention provides the ability to screen for thousands, tens of thousands, and hundreds of thousands, even millions of different possible genetic features. However, the number of high correlation genetic markers for conditions numbers only in the hundreds. Again, the possibility for screening a large number of sequences provides the opportunity for generating the data which can provide correlation between sequences and specific conditions or susceptibility. The present invention provides the means to generate extremely valuable correlations useful for the genetic detection of the causative mutation leading to medical conditions. In still another embodiment, the present invention would be applicable to distinguishing two individuals having identical genetic compositions. The antibody population within an individual is dependent both on genetic and historical factors. Each individual experiences a unique exposure to various infectious agents, and the combined antibody expression is partly determined thereby. Thus, individuals may also be fingerprinted by their immunological content, either of actively expressed antibodies, or their immunological memory. Similar sorts of immunological and environmental histories may be useful for fingerprinting, perhaps in combination with other screening properties. In particular, the present invention may be useful for screening allergic reactions or susceptibilities, a simple IgE specificity test may be useful in determining a spectrum of allergies.

With the definition of new classes of cells, a cell sorter will be used to purify them. Moreover, new markers for defining that class of cells will be identified. For example, where the class is defined by its RNA content, cells may be screened by antisense probes which detect the presence or absence of specific sequences therein. Alternatively, cell lysates may provide information useful in correlating intracellular properties with extracellular markers which indicate functional differences. Using standard cell sorter technology with a fluorescence or labeled antisense probe which recognizes the internal presence of the specific sequences of interest, the cell sorter will be able to isolate a relatively homogeneous population of cells possessing the particular marker. Using successive probes the sorting process should be able to select for cells having a combination of a large number of different markers.

In a nonpolynucleotide embodiment, cells may be defined by the presence of other markers. The markers may be carbohydrates, proteins, or other molecules. Thus, a substrate having particular specific reagents, e.g., antibodies, attached to it should be able to identify cells having particular patterns of marker expression. Of course, combinations of these made be utilized and a cell class may be defined by a combination of its expressed mRNA, its carbohydrate expression, its antigens, and other properties. This fingerprinting should be useful in determining the physiological state of a cell or population of cells.

Having defined a cell type whose function or properties are defined by the reagents attachable to a VLSIPS substrate, such as cellular antigens, these structural manifestations of function may be used to sort cells to generate a relatively homogeneous population of that class of cells. Standard cell sorter technology may be applied to purify such a population, see, e.g.; Dangl, J. and Herzenberg (1982) "Selection of hybridomas and hybridoma variants using the fluorescence activated cell sorter," *J. Immunological Methods* 52:1–14; and Becton Dickinson, Fluorescence Activated Cell Sorter Division, San Jose, Calif., and Coulter Diagnostics, Hialeah, Florida.

With the fingerprinted method as in identification means arises from mosaism problems in an organism. A mosaic organism is one whose genetic content in different cells is significantly different. Various clonal populations should have similar genetic fingerprints, though different clonal populations may have different genetic contents. See, for example, Suzuki et al. *An Introduction to Genetic Analysis* (4th Ed.), Freeman and Co., New York, which is hereby incorporated herein by reference. However, this problem should be a relatively rare problem and could be more carefully evaluated with greater experience using the fingerprinting methods.

The invention will also find use in detecting changes, both genetic and antigenic, e.g., in a rapidly "evolving" protozoa infection, or similarly changing organism.

V. Mapping

A. General

The use of the present invention for mapping parallels its use for fingerprinting and sequencing. Where a polymer is a linear molecule, the mapping provides the ability to locate particular segments along the length of the polymer. Branched polymers can be treated as a series of individual linear polymers. The mapping provides the ability to locate, in a relative sense, the order of various subsequences. This may be achieved using at least two different approaches.

The first approach is to take the large sequence and fragment it at specific points. The fragments are then ordered and attached to a solid substrate. For example, the clones resulting from a chromosome walking process may be individually attached to the substrate by methods, e.g., caged biotin techniques, indicated earlier. Segments of unknown map position will be exposed to the substrate and will hybridize to the segment which contains that particular sequence. This procedure allows the rapid determination of a number of different labeled segments, each mapping requiring only a single hybridization step once the substrate is generated. The substrate may be regenerated by removal of the interaction, and the next mapping segment applied.

In an alternative method, a plurality of subsequences can be attached to a substrate. Various short probes may be applied to determine which segments may contain particular overlaps. The theoretical basis and a description of this mapping procedure is contained in, e.g., Evans et al. 1989 "Physical Mapping of Complex Genomes by Cosmid Multiplex Analysis," *Proc. Natl. Acad. Sci. USA* 86:5030–5034, and other references cited above in the Section labeled "Overall Description." Using this approach, the details of the mapping embodiment are very similar to those used in the fingerprinting embodiment.

B. Preparation of Substrate Matrix

The substrate may be generated in either of the methods generally applicable in the sequencing and fingerprinting embodiments. The substrate may be made either synthetically, or by attaching otherwise purified probes or sequences to the matrix. The probes or sequences may be derived either from synthetic or biological means. As indicated above, the solid phase substrate synthetic methods may be utilized to generate a matrix with positionally defined sequences. In the mapping embodiment, the importance of saturation of all possible subsequences of a preselected length is far less important than in the sequencing embodiment, but the length of the probes used may be desired to be much longer. The processes for making a substrate which has longer oligonucleotide probes should not be significantly different from those described for the sequencing embodiments, but the optimization parameters may be modified to comply with the mapping needs.

C. Labeling

The labeling methods will be similar to those applicable in sequencing and fingerprinting embodiments. Again, the target sequences may be desired to be fragmented.

D. Hybridization/Specific Interaction

The specificity of interaction between the targets and probe would typically be closer to those used for fingerprinting embodiments, where homology is more important than absolute distinguishability of high fidelity complementary hybridization. Usually, the hybridization conditions will be such that merely homologous segments will interact and provide a positive signal. Much like the fingerprinting embodiment, it may be useful to measure the extent of homology by successive incubations at higher stringency conditions. Or, a plurality of different probes, each having various levels of homology may be used. In either way, the spectrum of homologies can be measured.

Where non-nucleic acid hybridization is involved, the specific interactions may also be compared in a fingerprint-like manner. The specific reagents may have less specificity, e.g., monoclonal antibodies which recognize a broader spectrum of sequences may be utilized relative to a sequencing embodiment. Again, the specificity of interaction may be measured under various conditions of increasing stringency to determine the spectrum of matching across the specific probes selected, or a number of different stringency reagents may be included to indicate the binding affinity.

E. Detection

The detection methods used in the mapping procedure will be virtually identical to those used in the fingerprinting embodiment. The detection methods will be selected in combination with the labeling methods.

F. Analysis

The analysis of the data in a mapping embodiment will typically be somewhat different from that in fingerprinting. The fingerprinting embodiment will test for the presence or absence of specific or homologous segments. However, in the mapping embodiment, the existence of an interaction is coupled with some indication of the location of the interaction. The interaction is mapped in some manner to the physical polymer sequence. Some means for determining the relative positions of different probes is performed. This may be achieved by synthesis of the substrate in pattern, or may result from analysis of sequences after they have been attached to the substrate.

For example, the probes may be randomly positioned at various locations on the substrate. However, the relative positions of the various reagents in the original polymer may be determined by using short fragments, e.g., individually, as target molecules which determine the proximity of different probes. By an automated system of testing each different short fragment of the original polymer, coupled with proper analysis, it will be possible to determine which probes are adjacent one another on the original target sequence and correlate that with positions on the matrix. In this way, the matrix is useful for determining the relative locations of various new segments in the original target molecule. This sort of analysis is described in Evans, and the related references described above.

G. Substrate Reuse

The substrate should be reusable in the manner described in the fingerprinting section. The substrate is renewed by removal of the specific interactions and is washed and prepared for successive cycles of exposure to new target sequences.

H. Non-polynucleotide Aspects

The mapping procedure may be used on other molecules than polynucleotides. Although hybridization is one type of specific interaction which is clearly useful for use in this mapping embodiment, antibody reagents may also be very useful. In the same way that polypeptide sequencing or other polymers may be sequenced by the reagents and techniques described in the sequencing section and fingerprinting section, the mapping embodiment may also be used similarly.

In another form of mapping, as described above in the fingerprinting section, the developmental map of a cell or biological system may be measured using fingerprinting type technology. Thus, the mapping may be along a temporal dimension rather than along a polymer dimension. The mapping or fingerprinting embodiments may also be used in determining the genetic rearrangements which may be genetically important, as in lymphocyte and B-cell development. In another example, various rearrangements or chromosomal dislocations may be tested by either the fingerprinting or mapping methods. These techniques are similar in many respects and the fingerprinting and mapping embodiments may overlap in many respects.

VI. Additional Screening and Applications

A. Specific Interactions

As originally indicated in the parent filing of VISIPS, the production of a high density plurality of spatially segregated polymers provides the ability to generate a very large universe or repertoire of individually and distinct sequence possibilities. As indicated above, particular oligonucleotides may be synthesized in automated fashion at specific locations on a matrix. In fact, these oligonucleotides may be used to direct other molecules to specific locations by linking specific oligonucleotides to other reagents which are in batch exposed to the matrix and hybridized in a complementary fashion to only those locations where the complementary oligonucleotide has been synthesized on the matrix. This allows for spatially attaching a plurality of different reagents onto the matrix instead of individually attaching each separate reagent at each specific location. Although the caged biotin method allows the automated attachment, the speed of the caged biotin attachment process is relatively slow and requires a separate reaction for each reagent being attached. By use of the oligonucleotide method, the specificity of position can be done in an automated and parallel fashion. As each reagent is produced, instead of directly attaching each reagent at each desired position, the reagent may be attached to a specific desired complementary oligonucleotide which will ultimately be specifically directed toward locations on the matrix having a complementary oligonucleotide attached thereat.

In addition, the technology allows screening for specificity of interaction with particular reagents. For example, the oligonucleotide sequence specificity of binding of a potential reagent may be tested by presenting to the reagent all of the possible subsequences available for binding. Although secondary or higher order sequence specific features might not be easily screenable using this technology, it does provide a convenient, simple, quick, and thorough screen of interactions between a reagent and its target recognition sequences. See, e.g., Pfeifer et al. (1989) *Science* 246:810–812.

For example, the interaction of a promoter protein with its target binding sequence may be tested for many different, or all, possible binding sequences. By testing the strength of interactions under various different conditions, the interaction of the promoter protein with each of the different potential binding sites may be analyzed. The spectrum of strength of interactions with each different potential binding site may provide significant insight into the types of features which are important in determining specificity.

An additional example of a sequence specific interaction between reagents is the testing of binding of a double stranded nucleic acid structure with a single stranded oligonucleotide. Often, a triple stranded structure is produced which has significant aspects of sequence specificity. Testing of such interactions with either sequences comprising only natural nucleotides, or perhaps the testing of nucleotide analogs may be very important in screening for particularly useful diagnostic or therapeutic reagents. See, e.g., Häner and Dervan (1990) *Biochemistry* 29:9761–6765, and references therein.

B. Sequence Comparisons

Once a gene is sequenced, the present invention provides means to compare alleles or related sequences to locate and identify differences from the control sequence. This would be extremely useful in further analysis of genetic variability at a specific gene locus.

C. Categorizations

As indicated above in the fingerprinting and mapping embodiments, the present invention is also useful to define specific stages in the temporal sequence of cells, e.g., development, and the resulting tissues within an organism. For example, the developmental stage of a cell, or population of cells, can be dependent upon the expression of particular messenger RNAs or cellular antigens. The screening procedures provided allow for high resolution definition of new classes of cells. In addition, the temporal development of particular cells will be characterized by the presence or expression of various mRNAs. Means to simultaneously screen a plurality or very large number of different sequences as provided. The combination of different markers made available dramatically increases the ability to distinguish fairly closely related cell types. Other markers may be combined with markers and methods made available herein to define new classifications of biological samples, e.g., based upon new combinations of markers.

The presence or absence of particular marker sequences will be used to define temporal developmental stages. Once the stages are defined, fairly simple methods can be applied to actually purify those particular cells. For example, antisense probes or recognition reagents may be used with a cell sorter to select those cells containing or expressing the critical markers. Alternatively, the expression of those sequences may result in specific antigens which may also be used in defining cell classes and sorting those cells away from others. In this way, for example, it should be possible to select a class of omnipotent immune system cells which are able to completely regenerate a human immune system. Based upon the cellular classes defined by the parameters made available by this technology, purified classes of cells having identifiable differences, structural or functional, are made available.

In an alternative embodiment, a plurality of antigens or specific binding proteins attached to the substrate may be used to define particular cell types. For example, subclasses of T-cells are defined, in part, upon the combination of expressed cell surface antigens. The present invention allows for the simultaneous screening of a large plurality of different antigens together. Thus, higher resolution classification of different T-cell subclasses becomes possible and, with the definitions and functional differences which correlate with those antigenic or other parameters, the ability to purify those cell types becomes available. This is applicable not only to T-cells, lymphocyte cells, or even to freely circulating cells. Many of the cells for which this would be most useful will be immobile cells found in particular tissues or organs. Tumor cells will be diagnosed or detected using these fingerprinting techniques. Coupled with a temporal change in structure, developmental classes may also be selected and defined using these technologies. The present invention also provides the ability not only to define new classes of cells based upon functional or structural differences, but it also provides the ability to select or purify populations of cells which share these particular properties. Standard cell sorting procedures using antibody markers may be used to detect extracellular features. Intracellular features would also be amendable by introducing the label reagents into the cell. In particular, antisense DNA or RNA molecules may be introduced into a cell to detect RNA sequences therein. See, e.g., Weintraub (1990) *Scientific American* 262:40–46.

D. Statistical Correlations

In an additional embodiment, the present invention also allows for the high resolution correlation of medical conditions with various different markers. For example, the present technology, when applied to amniocentesis or other genetic screening methods, typically screen for tens of different markers at most. The present invention allows simultaneous screening for tens, hundreds, thousands, tens of thousands, hundreds of thousands, and even millions of different genetic sequences. Thus, applying the fingerprinting methods of the present invention to a sufficiently large population allows detailed statistical analysis to be made, thereby correlating particular medical conditions with particular markers, typically antigenic or genetic. Tumor specific antigens will be identified using the present invention.

Various medical conditions may be correlated against an enormous database of the sequences within an individual. Genetic propensities and correlations then become available and high resolution genetic predictability and correlation become much more easily performed. With the enormous data base, the reliability of the predictions also is better tested. Particular markers which are partially diagnostic of particular medical conditions or medical susceptibilities will be identified and provide direction in further studies and more careful analysis of the markers involved. Of course, as indicated above in the sequencing embodiment, the present invention will find much use in intense sequencing projects. For example, sequencing of the entire human genome in the human genome project will be greatly simplified and enabled by the present invention.

VI. Formation of Substrate

The substrate is provided with a pattern of specific reagents which are positionally localized on the surface of the substrate. This matrix of positions is defined by the automated system which produces the substrate. The instrument will typically be one similar to that described in U.S. Ser. No. 07/492,462 (VLSIPS CIP), and U.S. Ser. No. 07/624,120, (automated VLSIPS). The instrumentation described therein is directly applicable to the applications used here. In particular, the apparatus comprises a substrate, typically a silicon containing substrate, on which positions on the surface may be defined by a coordinate system of positions. These positions can be individually addressed or detected by the VLSIPS apparatus.

Typically, the VLSIPS apparatus uses optical methods used in semiconductor fabrication applications. In this way, masks may be used to photo-activate positions for attachment or synthesis of specific sequences on the substrate. These manipulations may be automated by the types of apparatus described in U.S. Ser. No. 07/462,492 (VLSIPS CIP) and U.S. Ser. No. 07/624,120, (automated VLSIPS).

Selectively removable protecting groups allow creation of well defined areas of substrate surface having differing reactivities. Preferably, the protecting groups are selectively removed from the surface by applying a specific activator, such as electromagnetic radiation of a specific wavelength and intensity. More preferably, the specific activator exposes selected areas of surface to remove the protecting groups in the exposed areas.

Protecting groups of the present invention are used in conjunction with solid phase oligomer syntheses, such as peptide syntheses using natural or unnatural amino acids, nucleotide syntheses using deoxyribonucleic and ribonucleic acids, oligosaccharide syntheses, and the like. In addition to protecting the substrate surface from unwanted reaction, the protecting groups block a reactive end of the monomer to prevent self-polymerization. For instance, attachment of a protecting group to the amino terminus of an activated amino acid, such as the N-hydroxysuccinimide-activated ester of the amino acid prevents the amino terminus of one monomer from reacting with the activated ester portion of another during peptide synthesis.

Alternatively, the protecting group may be attached to the carboxyl group of an amino acid to prevent reaction at this site. Most protecting groups can be attached to either the amino or the carboxyl group of an amino acid, and the nature of the chemical synthesis will dictate which reactive group will require a protecting group. Analogously, attachment of a protecting group to the 5'-hydroxyl group of a nucleoside during synthesis using for example, phosphate-triester coupling chemistry, prevents the 5'-hydroxyl of one nucleoside from reacting with the 3'-activated phosphate-triester of another.

Regardless of the specific use, protecting groups are employed to protect a moiety on a molecule from reacting with another reagent. Protecting groups of the present invention have the following characteristics: they prevent selected reagents from modifying the group to which they are attached; they are stable (that is, they remain attached) to the synthesis reaction conditions; they are removable under conditions that do not adversely affect the remaining structure; and once removed, do not react appreciably with the surface or surface-bound oligomer. The selection of a suitable protecting group will depend, of course, on the chemical nature of the monomer unit and oligomer, as well as the specific reagents they are to protect against.

In a preferred embodiment, the protecting groups will be photoactivatable. The properties and uses of photoreactive protecting compounds have been reviewed. See, McCray et al., *Ann. Rev. of Biophys. and Biophys. Chem.* (1989) 18:239–270, which is incorporated herein by reference. Preferably, the photosensitive protecting groups will be removable by radiation in the ultraviolet (UV) or visible portion of the electromagnetic spectrum. More preferably, the protecting groups will be removable by radiation in the near UV or visible portion of the spectrum. In some embodiments, however, activation may be performed by other methods such as localized heating, electron beam lithography, laser pumping, oxidation or reduction with micro electrodes, and the like. Sulfonyl compounds are suitable reactive groups for electron beam lithography. Oxidative or reductive removal is accomplished by exposure of the protecting group to an electric current source, preferably using microelectrodes directed to the predefined regions of the surface which are desired for activation. A more detailed description of these protective groups is provided in U.S. Ser. No. 07/624,120, (automated VLSIPS), which is hereby incorporated herein by reference.

The density of reagents attached to a silicon substrate may be varied by standard procedures. The surface area for attachment of reagents may be increased by modifying the silicon surface. For example, a matte surface may be machined or etched on the substrate to provide more sites for attachment of the particular reagents. Another way to increase the density of reagent binding sites is to increase the derivitization density of the silicon. Standard procedures for achieving this are described, below.

One method to control the derivatization density is to highly derivatize the substrate with photochemical groups at high density. The substrate is then photolyzed for various predetermined times, which photoactivate the groups at a measurable rate, and react then with a capping reagent. By this method, the density of linker groups may be modulated by using a desired time and intensity of photoactivation.

In many applications, the number of different sequences which may be provided may be limited by the density and the size of the substrate on which the matrix pattern is generated. In situations where the density is insufficiently high to allow the screening of the desired number of sequences, multiple substrates may be used to increase the number of sequences tested. Thus, the number of sequences tested may be increased by using a plurality of different substrates. Because the VLSIPS apparatus is almost fully automated, increasing the number of substrates does not lead to a significant increase in the number of manipulations which must be performed by humans. This again leads to greater reproducibility and speed in the handling of these multiple substrates.

A. Instrumentation

The concept of using VLSIPS generally allows a pattern or a matrix of reagents to be generated. The procedure for making the pattern is performed by any of a number of different methods. An apparatus and instrumentation useful for generating a high density VLSIPS substrate is described in detail in U.S. Ser. No. 07/492,462 (VLSIPS CIP) and U.S. Ser. No. 07/624,120, (automated VLSIPS).

B. Binary Masking

The details of the binary masking are described in an accompanying application filed simultaneously with this, U.S. Ser. No. 07/624.120 (automated VLSIPS) whose specification is incorporated herein by reference.

For example, the binary masking technique allows for producing a plurality of sequences based on the selection of either of two possibilities at any particular location. By a series of binary masking steps, the binary decision may be the determination, on a particular synthetic cycle, whether or not to add any particular one of the possible subunits. By treating various regions of the matrix pattern in parallel, the binary masking strategy provides the ability to carry out spatially addressable parallel synthesis.

C. Synthetic Methods

The synthetic methods in making a substrate are described in the parent application, U.S. Ser. No. 07/492,462. The construction of the matrix pattern on the substrate will typically be generated by the use of photosensitive reagents. By use of photo-lithographic optical methods, particular segments of the substrate can be irradiated with light to activate or deactivate blocking agents, e.g., to protect or deprotect particular chemical groups. By an appropriate sequence of photo-exposure steps at appropriate times with appropriate masks and with appropriate reagents, the substrates can have known polymers synthesized at positionally defined regions on the substrate. Methods for synthesizing various substrates are described in U.S. Ser. No. 07/492,462 (VLSIPS CIP) and U.S. Ser. No. 07/624,120, (automated VLSIPS). By a sequential series of these photo-exposure and reaction manipulations, a defined matrix pattern of known sequences may be generated, and is typically referred to as a VLSIPS substrate. In the nucleic acid synthesis embodiment, nucleosides used in the synthesis of DNA by photolytic methods will typically be one of the two forms shown below:

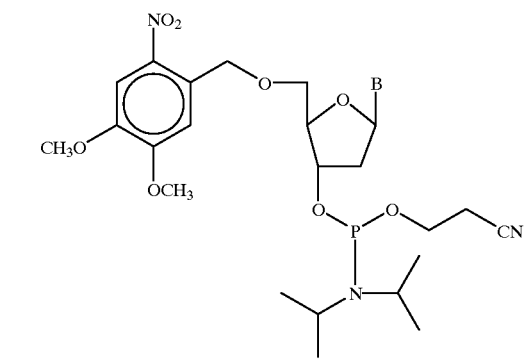

I

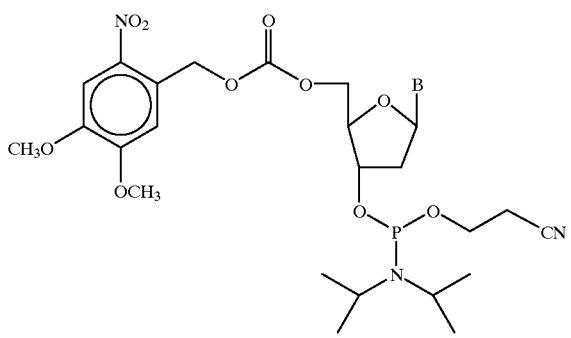

II

B=Adenine, Cytosine, Guanine, or Thymine

In I, the photolabile group at the 5' position is abbreviated NV (nitroveratryl) and in II, the group is abbreviated NVOC (nitroveratryl oxycarbonyl). Although not shown in FIG. C the bases (adenine, cytosine, and guanine) contain exocyclic NH$_2$ groups which must be protected during DNA synthesis. Thymine contains no exocyclic NH$_2$ and therefore requires no protection. The standard protecting groups for these anaines are shown below:

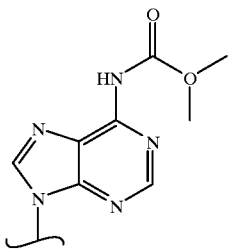

Adenine (A)

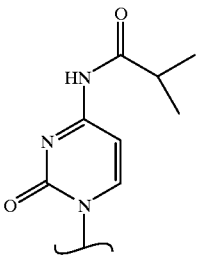

Cytosine (C)

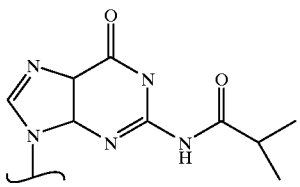

Guanine (G)

Other amides of the general formula

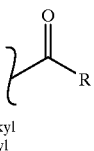

R = alkyl
aryl where R may be alkyl or aryl have been used.

Another type of protecting group FMOC (9-fluorenyl methoxycarbonyl) is currently being used to protect the exocyclic amines of the three bases:

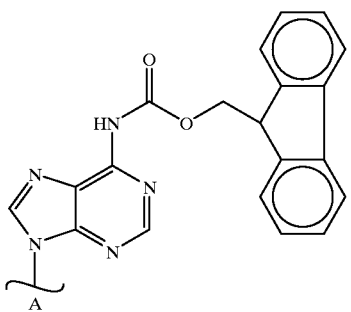

Adenine (A)

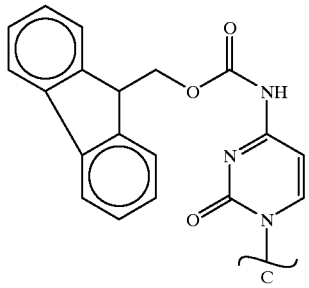

Cytosine (C)

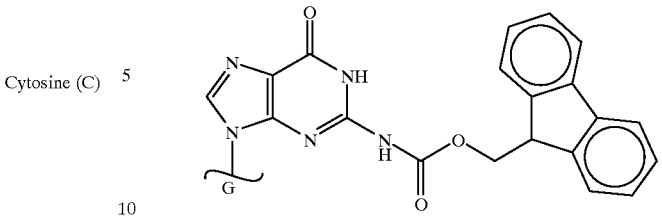

Guanine (G)

The advantage of the FMOC group is that it is removed under mild conditions (dilute organic bases) and can be used for all three bases. The amide protecting groups require more harsh conditions to be removed (NH$_3$/MeOH with heat).

Nucleosides used as 5'-OH probes, useful in verifying correct VLSIPS synthetic function, have been the following:

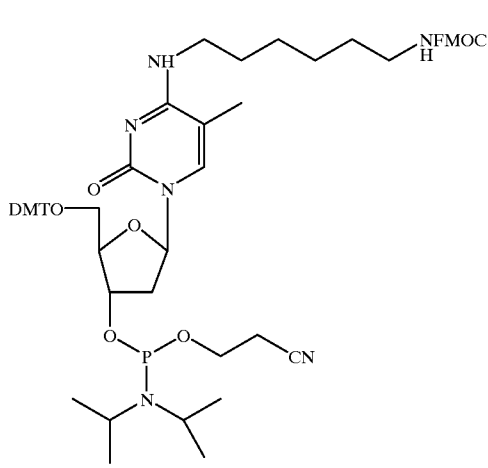

III

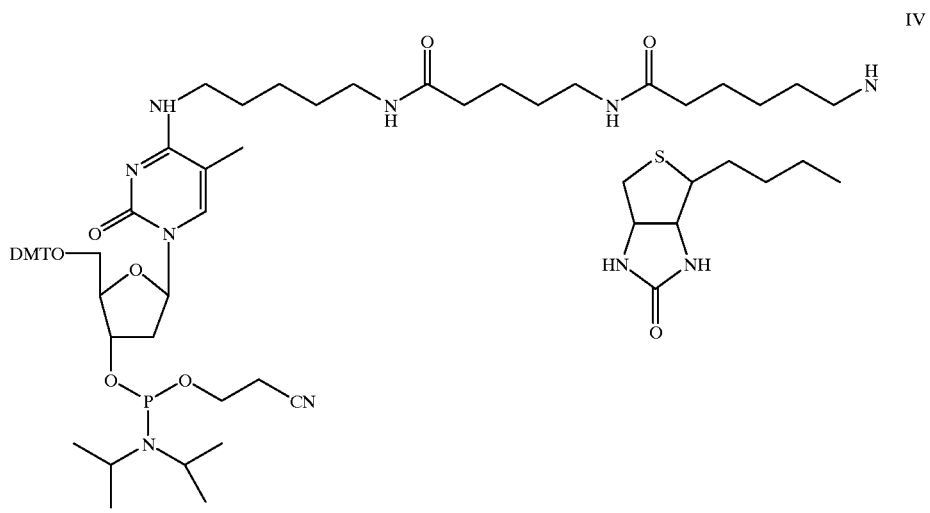

IV

These compounds are used to detect where on a substrate photolysis has occurred by the attachment of either III or V to the newly generated 5'-OH. In the case of III, after the phosphate attachment is made, the substrate is treated with a dilute base to remove the FMOC group. The resulting amine can be reacted with FITC and the substrate examined by fluorescence microscopy. This indicates the proper generation of a 5'-OH. In the case of compound IV, after the phosphate attachment is made, the substrate is treated with FITC labeled streptavidin and the substrate again may be examined by fluorescence microscopy. Other probes, although not nucleoside based, have included the following:

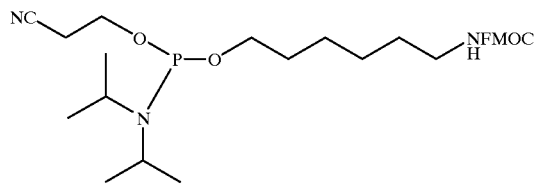

V

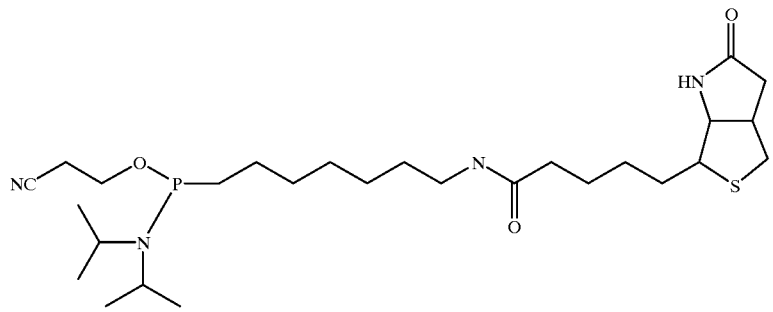

VI

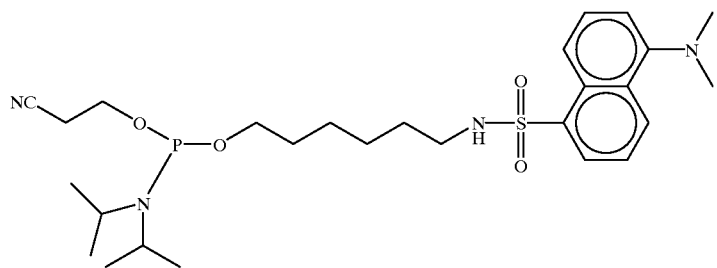

VII

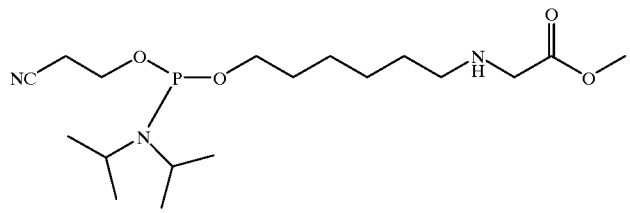

VIII

The method of attachment of the first nucleoside to the surface of the substrate depends on the functionality of the groups at the substrate surface. If the surface is amine functionalized, an amide bond is made (see example below).

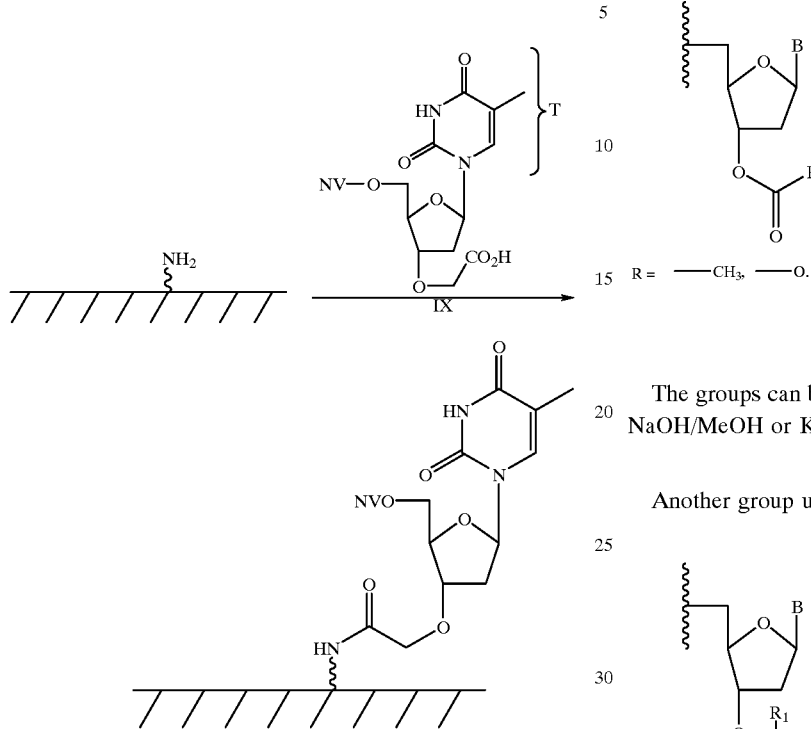

If the surface is hydroxy functionalized a phosphate bond is made (see example below)

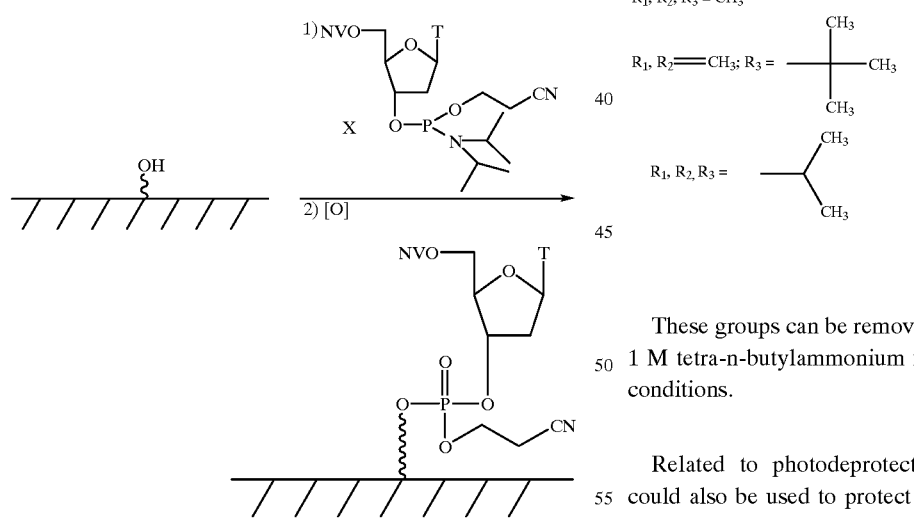

In both cases, the thymidine example is illustrated, but any one of the four phosphoramidite activated nucleosides can be used in the first step.

Photolysis of the photolabile group NV or NVOC on the 5' positions of the nucleosides is carried out at ~362 nm with an intensity of 14 mW/cm$^2$ for 10 minutes with the substrate side (side containing the photolabile group) immersed in dioxane. After the coupling of the next nucleoside is complete, the photolysis is repeated followed by another coupling until the desired oligomer is obtained.

One of the most common 3'-O-protecting group is the ester, in particular the acetate

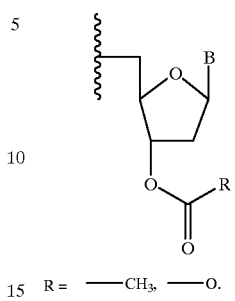

R = —CH$_3$, —O.

The groups can be removed by mild base treatment 0.1N NaOH/MeOH or K$_2$CO$_3$/H$_2$O/MeOH.

Another group used most often is the silyl ether.

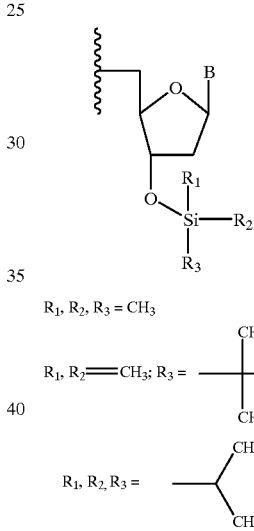

R$_1$, R$_2$, R$_3$ = CH$_3$

R$_1$, R$_2$ = CH$_3$; R$_3$ = —C(CH$_3$)$_3$

R$_1$, R$_2$, R$_3$ = —CH(CH$_3$)$_2$

These groups can be removed by neutral conditions using 1 M tetra-n-butylammonium fluoride in THF or under acid conditions.

Related to photodeprotection, the nitroveratryl group could also be used to protect the 3'-position.

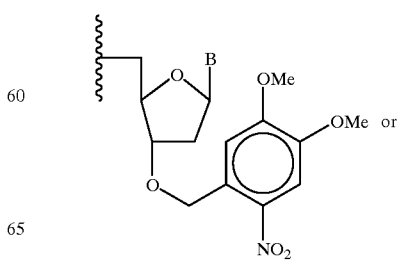

-continued

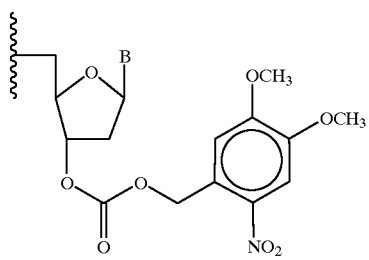

Here, light (photolysis) would be used to remove these protecting groups.

A variety of ethers can also be used in the protection of the 3'-O-position.

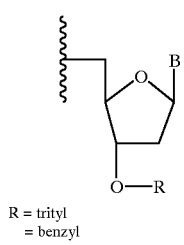

R = trityl
= benzyl

Removal of these groups usually involves acid or catalytic methods.

Note that corresponding linkages and photoblocked amino acids are described in detail in U.S. Ser. No. 07/624,120, which is hereby incorporated herein by reference.

Although the specificity of interactions at particular locations will usually be homogeneous due to a homogeneous polymer being synthesized at each defined location, for certain purposes, it may be useful to have mixed polymers with a commensurate mixed collection of interactions occurring at specific defined locations, or degeneracy reducing analogues, which have been discussed above and show broad specificity in binding. Then, a positive interaction signal may result from any of a number of sequences contained therein.

As an alternative method of generating a matrix pattern on a substrate, preformed polymers may be individually attached at particular sites on the substrate. This may be performed by individually attaching reagents one at a time to specific positions on the matrix, a process which may be automated. See, e.g., U.S. Ser. No. 07/435,316 (caged biotin parent), and U.S. Ser. No. 07/612,671 (caged biotin CIP). Another way of generating a positionally defined matrix pattern on a substrate is to have individually specific reagents which interact with each specific position on the substrate. For example, oligonucleotides may be synthesized at defined locations on the substrate. Then the substrate would have on its surface a plurality of regions having homogeneous oligonucleotides attached at each position.

In particular, at least four different substrate preparation procedures are available for treating a substrate surface. They are the standard VLSIPS method, polymeric substrates, Durapore™, and synthetic beads or fibers. The treatment labeled "standard VLSIPS" method is described in U.S. Ser. No. 07/624,120, (automated VLSIPS), and involves applying amino-propyltriethoxysilane to a glass surface.

The polymeric substrate approach involves either of two ways of generating a polymeric substrate. The first uses a high concentration of aminopropyltriethoxysilane (2–20%) in an aqueous ethanol solution (95%). This allows the silane compound to polymerize both in solution and on the substrate surface, which provides a high density of amines on the surface of the glass. This density is contrasted with the standard VLSIPS method. This polymeric method allows for the deposition on the substrate surface of a monolayer due to the anhydrous method used with the aforementioned silane.

The second polymeric method involves either the coating or covalent binding of an appropriate acrylic acid polymer onto the substrate surface. In particular, e.g., in DNA synthesis, a monomer such as a hydroxypropylacrylate is used to generate a high density of hydroxyl groups on the substrate surface, allowing for the formation of phosphate bonds. An example of such a compound is shown:

41

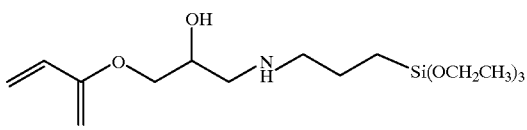

The method using a Durapore™ membrane (Millipore) consists of a polyvinylidine difluoride coating with crosslinked polyhydroxylpropyl acrylate [PVDF-HPA]:

42

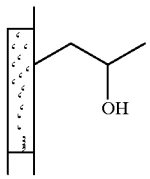

Here the building up of, e.g., a DNA oligomer, can be started immediately since phosphate bonds to the surface can be accomplished in the first step with no need for modification.

A nucleotide dimer (5'-C-T-3') has been successfully made on this substrate in our labs.

The fourth method utilizes synthetic beads or fibers. This would use another substrate, such as a teflon copolymer graft bead or fiber, which is covalently coated with an organic layer (hydrophilic) terminating in hydroxyl sites (commercially available from Molecular Brosystems, Inc.) This would offer the same advantage as the Durapore™ membrane, allowing for immediate phosphate linkages, but would give additional contour by the 3-dimensional growth of oligomers.

A matrix pattern of new reagents may be targeted to each specific oligonucleotide position by attaching a complementary oligonucleotide to which the substrate bound form is complementary. For instance, a number of regions may have homogeneous oligonucleotides synthesized at various locations. Oligonucleotide sequences complementary to each of these can be individually generated and linked to a particular specific reagents. Often these specific reagents will be antibodies. As each of these is specific for finding its complementary oligonucleotide, each of the specific reagents will bind through the oligonucleotide to the appropriate matrix position. A single step having a combination of different specific reagents being attached specifically to a particular oligonucleotide will thereby bind to its complement at the defined matrix position. The oligonucleotides will typically then be covalently attached, using, e.g., an acridine dye, for photocrosslinking. Psoralen is a commonly used acridine dye for photocrosslinking purposes, see, e.g., Song et al. (1979) *Photochem. Photobiol.* 29:1177–1197; Cimino et al. (1985) *Ann. Rev. Biochem.* 54: 1151–1193; Parsons (1980) *Photochem. Photobiol.* 32:813–821; and Dattagupta et al. (1985) U.S. Pat. No. 4,542,102, and (1987) U.S. Pat. No. 4,713,326; each of which is hereby incorporated herein by reference. This method allows a single attachment manipulation to attach all of the specific reagents to the matrix at defined positions and results in the specific reagents being homogeneously located at defined positions. In many embodiments, the specific reagents will be antibodies.

In an alternative embodiment, antibody molecules may be used to specifically direct binding to defined positions on a substrate. The VLSIPS technology may be used to generate specific epitopes at each position on the substrate. Antibody molecules having specificity of interaction may be used to attach oligonucleotides, thereby avoiding the interference of internal polynucleotide sequences from binding to the substrate complementary oligonucleotides. In fact, the specificity of interaction for positional targeting may be achieved by use of nucleotide analogues which do not interact with the natural nucleotides. For example, other synthetic nucleotides have been made which undergo base pairing, thereby providing the specificity of targeting, but the synthetic nucleotides also do not interact with the natural biological nucleotides. Thus, synthetic oligonucleotides would be useful for attachment to biological nucleotides and specific targeting. Moreover, the VLSIPS synthetic processes would be useful in generating the VLSIPS substrate, and standard oligonucleotide synthesis could be applied, with minor modifications, to produce the complementary sequences which would be attached to other specific reagents.

D. Surface Immobilization

1. Caged Biotin

An alternative method of attaching reagents in a positionally defined matrix pattern is to use a caged biotin system. See U.S. Ser. No. 07/612,671 (caged biotin CIP), which is hereby, incorporated herein by reference, for additional details on the chemistry and application of caged biotin embodiments. In short, the caged biotin has a photosensitive blocking moiety which prevents the combination of avidin to biotin. At positions where the photo-lithographic process has removed the blocking group, high affinity biotin sites are generated. Thus, by a sequential series of photolithographic deblocking steps interspersed with exposure of those regions to appropriate biotin containing reagents, only those locations where the deblocking takes place will form an avidin-biotin interaction. Because the avidin-biotin binding is very tight, this will usually be virtually irreversible binding.

2. Crosslinked Interactions

The surface immobilization may also take place by photo crosslinking of defined oligonucleotides linked to specific reagents. After hybridization of the complementary oligonucleotides, the oligonucleotides may be crosslinked by a reagent by psoralen or another similar type of acridine dye. Other useful cross linking reagents are described in Dattagupta et al. (1985) U.S. Pat. No. 4,542,102, and (1987) U.S. Pat. No. 4,713,326.

In another embodiment, colony or phage plaque transfer of biological polymers may be transferred directly onto a silicon substrate. For example, a colony plate may be transferred onto a substrate having a generic oligonucleotide sequence which hybridizes to another generic complementary sequence contained on all of the vectors into which inserts are cloned. This will specifically only bind those molecules which are actually contained in the vectors containing the desired complementary sequence. This immobilization allows for producing a matrix onto which a sequence specific reagent can bind, or for other purposes. In a further embodiment, a plurality of different vectors each having a specific oligonucleotide attached to the vector may be specifically attached to particular regions on a matrix having a complementary oligonucleotide attached thereto.

VIII. Hybridization/Specific Interaction

A. General

As discussed previously in the VLSIPS parent applications, the VLSIPS substrates may be used for screening for specific interactions with sequence specific targets or probes.

In addition, the availability of substrates having the entire repertoire of possible sequences of a defined length opens up the possibility of sequencing by hybridization. This sequence may be de nova determination of an unknown sequence, particularly of nucleic acid, verification of a sequence determined by another method, or an investigation of changes in a previously sequenced gene, locating and identifying specific changes. For example, often Maxam and Gilbert sequencing techniques are applied to sequences which have been determined by Sanger and Coulson. Each of those sequencing technologies have problems with resolving particular types of sequences. Sequencing by hybridization may serve as a third and independent method for verifying other sequencing techniques. See, e.g., (1988) *Science* 242:1245.

In addition, the ability to provide a large repertoire of particular sequences allows use of short subsequence and hybridization as a means to fingerprint a sample. This may be used in a nucleic acid, as well as other polymer embodiments. For example, fingerprinting to a high degree of specificity of sequence matching may be used for identifying highly similar samples, e.g., those exhibiting high homology to the selected probes. This may provide a means for determining classifications of particular sequences. This should allow determination of whether particular genomes of bacteria, phage, or even higher cells might be related to one another.

In addition, fingerprinting may be used to identify an individual source of biological sample. See, e.g., Lander, E. (1989) *Nature,* 339:501–505, and references therein. For example, a DNA fingerprint may be used to determine whether a genetic sample arose from another individual. This would be particularly useful in various sorts of forensic tests to determine, e.g., paternity or sources of blood samples. Significant detail on the particulars of genetic fingerprinting for identification purposes are described in, e.g., Morris et al. (1989) "Biostatistical evolution of evidence from continuous allele frequency distribution DNA probes in reference to disputed paternity of identity," *J. Forensic Science* 34:1311–1317; and Neufeld et al. (1990) *Scientific American* 262:46–53; each of which is hereby incorporated herein by reference.

In another embodiment, a fingerprinting-like procedure may be used for classifying cell types by analyzing a pattern of specific nucleic acids present in the cell. A series of antibodies may be used to identify cell markers, e.g., proteins, usually on the cell surface, but intracellular markers may also be used. Antigens which are extracellularly expressed are preferred so cell lysis is unnecessary in the screening, but intracellular markers may also be useful. The markers will usually be proteins, but may be nucleic acids, lipids, metabolites, carbohydrates, or other cellular components. See, e.g., Winkelgren, I. (1990) *Science News* 136:234–237, which indicates extracellular DNA may common, and suggesting that such might be characteristic of cell types, stage, or physiology. This may also be useful in defining the temporal stage of development of cells, e.g., stem cells or other cells which undergo temporal changes in development. For example, the stage of a cell, or group of cells, may be tested or defined by isolating a sample of mRNA from the population and testing to see what sequences are present in messenger populations. Direct samples, or amplified samples, may be used. Where particular mRNA or other nucleic acid sequences may be characteristic of or shown to be characteristic of particular developmental stages, physiological states, or other conditions, this fingerprinting method may define them. Similar sorts of fingerprinting may be used for determining T-cell classes or perhaps even to generate classification schemes for such proteins as major histocompatibility complex antigens. Thus, the ability to make these substrates allows both the generation of reagents which will be used for defining subclasses or classes of cells or other biological materials, but also provides the mechanisms for selecting those cells which may be found in defined population groups.

Cell classification defined by such a combination of properties, typically expression of extracellular antigens, the present invention also provides the means for isolating homogeneous population of cells. Once the antigenic determinants which define a cell class have been identified, these antigens may be used in a sequential selection process to isolate only those cells which exhibit the combination of defining structural properties.

The present invention may also be used for mapping sequences within a larger segment. This may be performed by at least two methods, particularly in reference to nucleic acids. Often, enormous segments of DNA are subcloned into a large plurality of subsequences. Ordering these subsequences may be important in determining the overlaps of sequences upon nucleotide determinations. Mapping may be performed by immobilizing particularly large segments onto a matrix using the VLSIPS technology. Alternatively, sequences may be ordered by virtue of subsequences shared by overlapping segments. See, e.g., Craig et al. (1990) *Nuc. Acids Res.* 18:2653–2660; Michiels et al. (1987) *CARIOS* 3:203–210; and Olson et al. (1986) *Proc. Natl. Acad. Sci. USA* 83:7826–7830.

B. Important Parameters

The extent of specific interaction between reagents immobilized to the VLSIPS substrate and another sequence specific reagent may be modified by the conditions of the interaction. Sequencing embodiments typically require high fidelity hybridization and the ability to discriminate perfect matching from imperfect matching. Fingerprinting and mapping embodiments may be performed using less stringent conditions, depending upon the circumstances.

For example, the specificity of antibody/antigen interaction may depend upon such parameters as pH, salt concentration, ionic composition, solvent composition, detergent composition and concentration, and chaotropic agent concentration. See, e.g., Harlow and Lane (1988) *Antibodies: A Laboratory Manual*, Cold Spring Harbor Press, New York. By careful control of these parameters, the affinity of binding may be mapped across different sequences.

In a nucleic acid hybridization embodiment, the specificity and kinetics of hybridization have been described in detail by, e.g., Wetmur and Davidson (1968) *J. Mol. Biol.*, 31:349–370, Britten and Kohne (1968) *Science* 161:529–530, and Kanehisa, (1984) *Nuc. Acids Res.* 12:203–213, each of which is hereby incorporated herein by reference. Parameters which are well known to affect specificity and kinetics of reaction include salt conditions, ionic composition of the solvent, hybridization temperature, length of oligonucleotide matching sequences, guanine and cytosine (GC) content, presence of hybridization accelerators, pH, specific bases found in the matching sequences, solvent conditions, and addition of organic solvents.

In particular, the salt conditions required for driving highly mismatched sequences to completion typically include a high salt concentration. The typical salt used is sodium chloride (NaCl), however, other ionic salts may be utilized, e.g., KCl. Depending on the desired stringency hybridization, the salt concentration will often be less than about 3 molar, more often less than 2.5 molar, usually less than about 2 molar, and more usually less than about 1.5 molar. For applications directed towards higher stringency matching, the salt concentrations would typically be lower. Ordinary high stringency conditions will utilize salt concentration of less than about 1 molar, more often less then about 750 millimolar, usually less than about 500 millimolar, and may be as low as about 250 or 150 millimolar.

The kinetics of hybridization and the stringency of hybridization both depend upon the temperature at which the hybridization is performed and the temperature at which the washing steps are performed. Temperatures at which steps for low stringency hybridization are desired would typically be lower temperatures, e.g., ordinarily at least about 15° C., more ordinarily at least about 20° C., usually at least about 25° C., and more usually at least about 30° C. For those applications requiring high stringency hybridization, or fidelity of hybridization and sequence matching, temperatures at which hybridization and washing steps are performed would typically be high. For example, temperatures in excess of about 35° C. would often be used, more often in excess of about 40° C., usually at least about 45° C., and occasionally even temperatures as high as about 50° C. or 60° C. or more. Of course, the hybridization of oligonucleotides may be disrupted by even higher temperatures. Thus, for stripping of targets from substrates, as discussed below, temperatures as high as 80° C., or even higher may be used.

The base composition of the specific oligonucleotides involved in hybridization affects the temperature of melting, and the stability of hybridization as discussed in the above references. However, the bias of GC rich sequences to hybridize faster and retain stability at higher temperatures can be compensated for by the inclusion in the hybridization incubation or wash steps of various buffers. Sample buffers which accomplish this result include the triethly-and trimethyl ammonium buffers. See, e.g., Wood et al. (1987) *Proc. Natl. Acad. Sci. USA*, 82:1585–1588, and Khrapko, K. et al. (1989) *FEBS Letters* 256:118–122.

The rate of hybridization can also be affected by the inclusion of particular hybridization accelerators. These hybridization accelerators include the volume exclusion agents characterized by dextran sulfate, or polyethylene glycol (PEG). Dextran sulfate is typically included at a concentration of between 1% and 40% by weight. The actual concentration selected depends upon the application, but typically a faster hybridization is desired in which the concentration is optimized for the system in question. Dextran sulfate is often included at a concentration of between 0.5% and 2% by weight or dextran sulfate at a concentration between about 0.5% and 5%. Alternatively, proteins which accelerate hybridization may be added, e.g., the recA protein found in *E. coli*) or other homologous proteins.

With respect to those embodiments where specific reagents are not oligonucleotides, the conditions of specific interaction would depend on the affinity of binding between the specific reagent and its target. Typically parameters which would be of particular importance would be pH, salt concentration anion and cation compositions, buffer concentration, organic solvent inclusion, detergent concentration, and inclusion of such reagents such as chaotropic agents. In particular, the affinity of binding may be tested over a variety of conditions by multiple washes and repeat scans or by using reagents with differences in binding affinity to determine which reagents bind or do not bind under the selected binding and washing conditions. The spectrum of binding affinities may provide an additional dimension of information which may be very useful in identification purposes and mapping.

Of course, the specific hybridization conditions will be selected to correspond to a discriminatory condition which provides a positive signal where desired but fails to show a positive signal at affinities where interaction is not desired. This may be determined by a number of titration steps or with a number of controls which will be run during the hybridization and/or washing steps to determine at what point the hybridization conditions have reached the stage of desired specificity.

IX. Detection Methods

Methods for detection depend upon the label selected. The criteria for selecting an appropriate label are discussed below, however, a fluorescent label is preferred because of its extreme sensitivity and simplicity. Standard labeling procedures are used to determine the positions where interactions between a sequence and a reagent take place. For example, if a target sequence is labeled and exposed to a matrix of different probes, only those locations where probes do interact with the target will exhibit any signal. Alternatively, other methods may be used to scan the matrix to determine where interaction takes place. Of course, the spectrum of interactions may be determined in a temporal manner by repeated scans of interactions which occur at each of a multiplicity of conditions. However, instead of testing each individual interaction separately, a multiplicity of sequence interactions may be simultaneously determined on a matrix.

A. Labeling Techniques

The target polynucleotide may be labeled by any of a number of convenient detectable markers. A fluorescent label is preferred because it provides a very strong signal with low background. It is also optically detectable at high resolution and sensitivity through a quick scanning procedure. Other potential labeling moieties include, radioisotopes, chemiluminescent compounds, labeled binding proteins, heavy metal atoms, spectroscopic markers, magnetic labels, and linked enzymes.

Another method for labeling may bypass any label of the target sequence. The target may be exposed to the probes, and a double strand hybrid is formed at those positions only. Addition of a double strand specific reagent will detect where hybridization takes place. An intercalative dye such as ethidium bromide may be used as long as the probes themselves do not fold back on themselves to a significant extent forming hairpin loops. See, e.g., Sheldon et al. (1986) U.S. Pat. No. 4,582,789. However, the length of the hairpin loops in short oligonucleotide probes would typically be insufficient to form a stable duplex.

In another embodiment, different targets may be simultaneously sequenced where each target has a different label. For instance, one target could have a green fluorescent label and a second target could have a red fluorescent label. The scanning step will distinguish sites of binding of the red label from those binding the green fluorescent label. Each sequence can be analyzed independently from one another.

Suitable chromogens will include molecules and compounds which absorb light in a distinctive range of wavelengths so that a color may be observed, or emit light when irradiated with radiation of a particular wave length or wave length range, e.g., fluorescers. Biliproteins, e.g., ficoerythrin, may also serve as labels.

A wide variety of suitable dyes are available, being primary chosen to provide an intense color with minimal absorption by their surroundings. Illustrative dye types include quinoline dyes, triarylmethane dyes, acridine dyes, alizarine dyes, phthaleins, insect dyes, azo dyes, anthraquinoid dyes, cyanine dyes, phenazathionium dyes, and phenazoxonium dyes.

A wide variety of fluorescers may be employed either by themselves or in conjunction with quencher molecules. Fluorescers of interest fall into a variety of categories having certain primary functionalities. These primary functionalities include 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidzaolylphenylamine, 2-oxo-3-chromen, indole, xanthen, 7-hydroxycoumarin, phenoxazine, salicylate, strophanthidin, porphyrins, triarylmethanes and flavin. Individual fluorescent compounds which have functionalities for linking or which can be modified to incorporate such functionalities include, e.g., dansyl chloride; fluoresceins such as 3,6-dihydroxy-9-phenylxanthhydrol; rhodamineisothiocyanate; N-phenyl 1-amino-8-sulfonatonaphthalene; N-phenyl 2-amino-6-sulfonatonaphthalene; 4-acetamido-4-isothiocyanato-stilbene-2,2'-disulfonic acid; pyrene-3-sulfonic acid; 2-toluidinonaphthalene-6-sulfonate; N-phenyl, N-methyl 2-aminoaphthalene-6-sulfonate; ethidium bromide; stebrine; auromine-0,2-(9'-anthroyl)palmitate; dansyl phosphatidyle-thanolamine; N,N'-dioctadecyl oxacarbocyanine; N,N'-dihexyl oxacarbocyanine; merocyanine, 4-(3'pyrenyl) butyrate; d-3-aminodesoxy-equilenin; 12-(9'-anthroyl) stearate; 2-methylanthracene; 9-vinylanthracene; 2,2'-(vinylene-p-phenylene)bisbenzoxazole; p-bis[2-(4-methyl-5-phenyl-oxazolyl)]-benzene; 6-dimethylamino-1,2-benzophenazin; retinol; bis(3'-aminopyridinium) 1,10-decandiyl diiodide; sulfonaphthylhydrazone of hellibrienin; chlorotetracycline; N-(7-dimethylamino-4-methyl-2-oxo-3-chromenyl)maleimide; N-[p-(2-benzimidazolyl)-phenyl] maleimide; N-(4-fluoranthyl)maleimide; bis(homovanillic acid); resazarin; 4-chloro-7-nitro-2,1,3-benzooxadiazole; merocyanine 540; resorufin; rose bengal; and 2,4-diphenyl-3(2H)-furanone.

Desirably, fluorescers should absorb light above about 300 nm, preferably about 350 nm, and more preferably above about 400 nm, usually emitting at wavelengths greater than about 10 nm higher than the wavelength of the light absorbed. It should be noted that the absorption and emission characteristics of the bound dye may differ from the unbound dye. Therefore, when referring to the various wavelength ranges and characteristics of the dyes, it is intended to indicate the dyes as employed and not the dye which is unconjugated and characterized in an arbitrary solvent.

Fluorescers are generally preferred because by irradiating a fluorescer with light, one can obtain a plurality of emissions. Thus, a single label can provide for a plurality of measurable events.

Detectable signal may also be provided by chemiluminescent and bioluminescent sources. Chemiluminescent sources include a compound which becomes electronically excited by a chemical reaction and may then emit light which serves as the detectible signal or donates energy to a fluorescent acceptor. A diverse number of families of compounds have been found to provide chemiluminescence under a variety of conditions. One family of compounds is 2,3-dihydro-1,-4-phthalazinedione. The most popular compound is luminol, which is the 5-amino compound. Other members of the family include the 5-amino-6,7,8-trimethoxy- and the dimethylamino[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminscent analogs include para-dimethylamino and -methoxy substituents. Chemiluminescence may also be obtained with oxalates, usually oxalyl active esters, e.g., p-nitrophenyl and a peroxide, e.g., hydrogen peroxide, under basic conditions. Alternatively, luciferins may be used in conjunction with luciferase or lucigenins to provide bioluminescence.

Spin labels are provided by reporter molecules with an unpaired electron spin which can be detected by electron spin resonance (ESR) spectroscopy. Exemplary spin labels include organic free radicals, transitional metal complexes, particularly vanadium, copper, iron, and manganese, and the like. Exemplary spin labels include nitroxide free radicals.

B. Scanning System

With the automated detection apparatus, the correlation of specific positional labeling is converted to the presence on the target of sequences for which the reagents have specificity of interaction. Thus, the positional information is directly converted to a database indicating what sequence interactions have occurred. For example, in a nucleic acid hybridization application, the sequences which have interacted between the substrate matrix and the target molecule can be directly listed from the positional information. The detection system used is described in U.S. Ser. No. 07/649,642 (VLSIPS CIP); and U.S. Ser. No. 07/624,120, (automated VLSIPS). Although the detection described therein is a fluorescence detector, the detector may be replaced by a spectroscopic or other detector. The scanning system may make use of a moving detector relative to a fixed substrate, a fixed detector with a moving substrate, or a combination. Alternatively, mirrors or other apparatus can be used to transfer the signal directly to the detector. See, e.g, U.S. Ser. No. 07/624,120, VLSIPS), which is hereby incorporated herein by reference.

The detection method will typically also incorporate some signal processing to determine whether the signal at a particular matrix position is a true positive or may be a spurious signal. For example, a signal from a region which has actual positive signal may tend to spread over and provide a positive signal in an adjacent region which actually should not have one. This may occur, e.g., where the scanning system is not properly discriminating with sufficiently high resolution in its pixel density to separate the two regions. Thus, the signal over the spatial region may be evaluated pixel by pixel to determine the locations and the actual extent of positive signal. A true positive signal should, in theory, show a uniform signal at each pixel location. Thus, processing by plotting number of pixels with actual signal intensity should have a clearly uniform signal intensity. Regions where the signal intensities show a fairly wide dispersion, may be particularly suspect and the scanning system may be programmed to more carefully scan those positions.

In another embodiment, as the sequence of a target is determined at a particular location, the overlap for the sequence would necessarily have a known sequence. Thus, the system can compare the possibilities for the next adjacent position and look at these in comparison with each other. Typically, only one of the possible adjacent sequences should give a positive signal and the system might be programmed to compare each of these possibilities and select that one which gives a strong positive. In this way, the system can also simultaneously provide some means of measuring the reliability of the determination by indicating what the average signal to background ratio actually is.

More sophisticated signal processing techniques can be applied to the initial determination of whether a positive signal exists or not. See, e.g., U.S. Ser. No. 07/624,120, (automated VLSIPS).

From a listing of those sequences which interact, data analysis may be performed on a series of sequences. For example, in a nucleic acid sequence application, each of the sequences may be analyzed for their overlap regions and the original target sequence may be reconstructed from the collection of specific subsequences obtained therein. Other sorts of analyses for different applications may also be performed, and because the scanning system directly interfaces with a computer the information need not be transferred manually. This provides for the ability to handle large amounts of data with very little human intervention. This, of course, provides significant advantages over manual manipulations. Increased throughput and reproducibility is thereby provided by the automation of vast majority of steps in any of these applications.

XI. Data Analysis

A. General

Data analysis will typically involve aligning the proper sequences with their overlaps to determine the target sequence. Although the target "sequence" may not specifically correspond to any specific molecule, especially where the target sequence is broken and fragmented up in the sequencing process, the sequence corresponds to a contiguous sequence of the subfragments.

The data analysis can be performed by a computer using an appropriate program. See, e.g., Drmanac, R. et al. (1989) *Genomics* 4:114–128; and a commercially available analysis program available from the Genetic Engineering Center, P.O. Box 794, 11000 Belgrade, Yugoslavia. Although the specific manipulations necessary to reassemble the target sequence from fragments may take many forms, one embodiment uses a sorting program to sort all of the subsequences using a defined hierarchy. The hierarchy need not necessarily correspond to any physical hierarchy, but provides a means to determine, in order, which subfragments have actually been found in the target sequence. In this manner, overlaps can be checked and found directly rather than having to search throughout the entire set after each selection process. For example, where the oligonucleotide probes are 10-mers, the first 9 positions can be sorted. A particular subsequence can be selected as in the examples, to determine where the process starts. As analogous to the theoretical example provided above, the sorting procedure provides the ability to immediately find the position of the subsequence which contains the first 9 positions and can compare whether there exists more than 1 subsequence during the first 9 positions. In fact, the computer can easily generate all of the possible target sequences which contain given combination of subsequences. Typically there will be only one, but in various situations, there will be more.

An exemplary flow chart for a sequencing program is provided in FIG. 4. In general terms, the program provides for automated scanning of the substrate to determine the positions of probe and target interaction. Simple processing of the intensity of the signal may be incorporated to filter out clearly spurious signals. The positions with positive interaction are correlated with the sequence specificity of specific matrix positions, to generate the set of matching subsequences. This information is further correlated with other target sequence information, e.g., restriction fragment analysis. The sequences are then aligned using overlap data, thereby leading to possible corresponding target sequences which will, optimally, correspond to a single target sequence.

B. Hardware

A variety of computer systems may be used to run a sequencing program. The program may be written to provide both the detecting and scanning steps together and will typically be dedicated to a particular scanning apparatus. However, the components and functional steps may be separated and the scanning system may provide an output, e.g., through tape or an electronic connection into a separate computer which separately runs the sequencing analysis program. The computer may be any of a number of machines provided by standard computer manufacturers, e.g., IBM compatible machines, Apple™ machines, VAX machines, and others, which may often use a UNIX™ operating system. Of course, the hardware used to run the analysis program will typically determine what programming language would be used.

C. Software

Software would be easily developed by a person of ordinary skill in the programming art, following the flow chart provided, or based upon the input provided and the desired result.

Of course, an exemplary embodiment is a polynucleotide sequence system. However, the theoretical and mathematical manipulations necessary for data analysis of other linear molecules, such as polypeptides, carbohydrates, and various other polymers are conceptually similar. Simple branching polymers will usually also be sequencable using similar technology. However, where there is branching, it may be desired that additional recognition reagents be used to determine the nature and location of branches. This can easily be provided by use of appropriate specific reagents which would be generated by methods similar to those used to produce specific reagents for linear polymers.

XII. Substrate Reuse

Where a substrate is made with specific reagents that are relatively insensitive to the handling and processing steps involved in a single cycle of use, the substrate may often be reused. The target molecules are usually stripped off of the solid phase specific recognition molecules. Of course, it is preferred that the manipulations and conditions be selected as to be mild and to not affect the substrate. For example, if a substrate is acid labile, a neutral pH would be preferred in all handling steps. Similar sensitivities would be carefully respected where recycling is desired.

A. Removal of Label

Typically for a recycling, the previously attached specific interaction would be disrupted and removed. This will typically involve exposing the substrate to conditions under which the interaction between probe and target is disrupted. Alternatively, it may be exposed to conditions where the target is destroyed. For example, where the probes are oligonucleotides and the target is a polynucleotide, a heating and low salt wash will often be sufficient to disrupt the interactions. Additional reagents may be added such as detergents and organic or inorganic solvents which disrupt the interaction between the specific reagents and target. In an embodiment where the specific reagents are antibodies, the substrate may be exposed to a gentle detergent which will denature the specific binding between the antibody and its target. The conditions are selected to avoid severe disruption or destruction of the structure of the antibody and to maintain the specificity of the antibody binding site. Conditions with specific pH, detergent concentration, salt concentration, ionic concentration, and other parameters may be selected which disrupt the specific interactions.

B. Storage and Preservation

As indicated above, the matrix will typically be maintained under conditions where the matrix itself and the linkages and specific reagents are preserved. Various specific preservatives may be added which prevent degradation. For example, if the reagents are acid or base labile, a neutral pH buffer will typically be added. It is also desired to avoid destruction of the matrix by growth of organisms which may destroy organic reagents attached thereto. For this reason, a preservative such as cyanide or azide may be added. However, the chemical preservative should also be selected to preserve the chemical nature of the linkages and other components of the substrate. Typically, a detergent may also be included.

C. Processes to Avoid Degradation of Oligomers

In particular, a substrate comprising a large number of oligomers will be treated in a fashion which is known to maintain the quality and integrity of oligonucleotides. These include storing the substrate in a carefully controlled environment under conditions of lower temperature, cation depletion (EDTA and EGTA), sterile conditions, and inert argon or nitrogen atmosphere.

XIII. Integrated Sequencing Strategy

A. Initial Mapping Strategy

As indicated above, although the VLSIPS may be applied to sequencing embodiments, it is often useful to integrate other concepts to simply the sequencing. For example, nucleic acids may be easily sequenced by careful selection of the vectors and hosts used for amplifying and generating the specific target sequences. For example, it may be desired to use specific vectors which have been designed to interact most efficiently with the VLSIPS substrate. This is also important in fingerprinting and mapping strategies. For example, vectors may be carefully selected having particular complementary sequences which are designed to attach to a genetic or specific oligomer on the substrate. This is also applicable to situations where it is desired to target particular sequences to specific locations on the matrix.

In one embodiment, unnatural oligomers may be used to target natural probes to specific locations on the VLSIPS substrate. In addition, particular probes may be generated for the mapping embodiment which are designed to have specific combinations of characteristics. For example, the construction of a mapping substrate may depend upon use of another automated apparatus which takes clones isolated from a chromosome walk and attaches them individually or in bulk to the VLSIPS substrate.

In another embodiment, a variety of specific vectors having known and particular "targeting" sequences adjacent the cloning sites may be individually used to clone a selected probe, and the isolated probe will then be targetable to a site on the VLSIPS substrate with a sequence complementary to the "target" sequence.

B. Selection of Smaller Clones

In the fingerprinting and mapping embodiments, the selection of probes may be very important. Significant mathematical analysis may be applied to determine which specific sequences should be used as those probes. Of course, for fingerprinting use, these sequences would be most desired that show significant heterogeneity across the human population. Selection of the specific sequences which would most favorably be utilized will tend to be single copy sequences within the genome.

Various hybridization selection procedures may be applied to select sequences which tend not to be repeated within a genome, and thus would tend to be conserved across individuals. For example, hybridization selections may be made for non-repetitive and single copy sequences. See, .e.g., Britten and Kohne (1968) "Repeated Sequences in DNA," *Science* 161:529–540. On the other hand, it may be desired under certain circumstances to use repeated sequences. For example, where a fingerprint may be used to identify or distinguish different species, or where repetitive sequences may be diagnostic of specific species, repetitive sequences may be desired for inclusion in the fingerprinting probes. In either case, the sequencing capability will greatly assist in the selection of appropriate sequences to be used as probes.

Also as indicated above, various means for constructing an appropriate substrate may involve either mechanical or automated procedures. The standard VLSIPS automated procedure involves synthesizing oligonucleotides or short polymers directly on the substrate. In various other embodiments, it is possible to attach separately synthesized reagents onto the matrix in an ordered array. Other circumstances may lend themselves to transfer a pattern from a petri plate onto a solid substrate. Also, there are methods for site specifically directing collections of reagents to specific locations using unnatural nucleotides or equivalent sorts of targeting molecules.

While a brute force manual transfer process may be utilized sequentially attaching various samples to successive positions, instrumentation for automating such procedures may also be devised. The automated system for performing such would preferably be relatively easily designed and conceptually easily understood.

XIV. Commercial Applications

A. Sequencing

As indicated above, sequencing may be performed either de novo or as a verification of another sequencing method. The present hybridization technology provides the ability to sequence nucleic acids and polynucleotides de novo, or as a means to verify either the Maxam and Gilbert chemical sequencing technique or Sanger and Coulson dideoxy-sequencing techniques. The hybridization method is useful to verify sequencing determined by any other sequencing technique and to closely compare two similar sequences, e.g., to identify and locate sequence differences.

Besides polynucleotide sequencing, the present invention also provides means for sequencing other polymers. This includes polypeptides, carbohydrates, synthetic organic polymers, and other polymers. Again, the sequencing may be either verification or de novo.

Of course, sequencing of can be very important in many different sorts of environments. For example, it will be useful in determining the genetic sequence of particular markers in various individuals. In addition, polymers may be used as markers or for information containing molecules to encode information. For example, a short polynucleotide sequence may be included in large bulk production samples indicating the manufacturer, date, and location of manufacture of a product. For example, various drugs may be encoded with this information with a small number of molecules in a batch. For example, a pill may have somewhere from 10 to 100 to 1,000 or more very short and small molecules encoding this information. When necessary, this information may be decoded from a sample of the material using a polymerase chain reaction (PCR) or other amplification method. This encoding system may be used to provide the origin of large bulky samples without significantly affecting the properties of those samples. For example, chemical samples may also be encoded by this method thereby providing means for identifying the source and manufacturing details of lots. The origin of bulk hydrocarbon samples may be encoded. Production lots of organic compounds such as benzene or plastics may be encoded with a short molecule polymer. Food stuffs may also be encoded using similar marking molecules. Even toxic waste samples can be encoded determining the source or origin. In this way, proper disposal can be traced or more easily enforced.

Similar sorts of encoding may be provided by fingerprinting-type analysis. Whether the resolution is absolute or less so, the concept of coding information on molecules such as nucleic acids, which can be amplified and later decoded, may be a very useful and important application.

This technology also provides the ability to include markers for origins of biological materials. For example, a patented animal line may be transformed with a particular unnatural sequence which can be traced back to its origin. With a selection of multiple markers, the likelihood could be negligible that a combination of markers would have independently arisen from a source other than the patented or specifically protected source. This technique may provide a means for tracing the actual origin of particular biological materials. Bacteria, plants, and animals will be subject to marking by such encoding sequences.

B. Fingerprinting

As indicated above, fingerprinting technology may also be used for data encryption. Moreover, fingerprinting allows for significant identification of particular individuals. Where the fingerprinting technology is standardized, and used for identification of large numbers of people, related equipment and peripheral processing will be developed to accompany the underlying technology. For example, specific equipment may be developed for automatically taking a biological sample and generating or amplifying the information molecules within the sample to be used in fingerprinting analysis. Moreover, the fingerprinting substrate may be mass produced using particular types of automatic equipment. Synthetic equipment may produce the entire matrix simultaneously by stepwise synthetic methods as provided by the VLSIPS technology. The attachment of specific probes onto a substrate may also be automated, e.g., making use of the caged biotin technology. See, e.g., U.S. Ser. No. 07/612,671 (caged biotin CIP). As indicated above, there are automated methods for actually generating the matrix and substrate with distinct sequence reagents positionally located at each of the matrix positions. Where such reagents are, e.g., unnatural amino acids, a targeting function may be utilized which does not interfere with aa natural nucleotide functionality.

In addition, peripheral processing may be important and may be dedicated to this specific application. Thus, automated equipment for producing the substrates may be designed, or particular systems which take in a biological sample and output either a computer readout or an encoded instrument, e.g., a card or document which indicates the information and can provide that information to others. An identification having a short magnetic strip with a few million bits may be used to provide individual identification and important medical information useful in a medical emergency.

In fact, data banks may be set up to correlate all of this information of fingerprinting with medical information. This may allow for the determination of correlations between various medical problems and specific DNA sequences. By collating large populations of medical records with genetic information, genetic propensities and genetic susceptibilities to particular medical conditions may be developed. Moreover, with standardization of substrates, the micro encoding data may be also standardized to reproduce the information from a centralized data bank or on an encoding device carried on an individual person. On the other hand, if the fingerprinting procedure is sufficiently quick and routine, every hospital may routinely perform a fingerprinting operation and from that determine many important medical parameters for an individual.

In particular industries, the VLSIPS sequencing, fingerprinting, or mapping technology will be particularly appropriate. As mentioned above, agricultural livestock suppliers may be able to encode and determine whether their particular strains are being used by others. By incorporating particular markers into their genetic stocks, the markers will indicate origin of genetic material. This is applicable to seed producers, livestock producers, and other suppliers of medical or agricultural biological materials.

This may also be useful in identifying individual animals or plants. For example, these markers may be useful in determining whether certain fish return to their original breeding grounds, whether sea turtles always return to their original birthplaces, or to determine the migration patterns and viability of populations of particular endangered species. It would also provide means for tracking the sources of particular animal products. For example, it might be useful for determining the origins of controlled animal substances such as elephant ivory or particular bird populations whose importation or exportation is controlled.

As indicated above, polymers may be used to encode important information on source and batch and supplier. This is described in greater detail, e.g., "Applications of PCR to industrial problems," (1990) in *Chemical and Engineering News* 68:145, which is hereby incorporated herein by reference. In fact, the synthetic method can be applied to the storage of enormous amounts of information. Small substrates may encode enormous amounts of information, and its recovery will make use of the inherent replication capacity. For example, on regions of 10 $\mu$m×10 $\mu$m, 1 $cm^2$ has $10^6$ regions. An theory, the entire human genome could be attached in 1000 nucleotide segments on a 3 $cm^2$ surface. Genomes of endangered species may be stored on these substrates.

Fingerprinting may also be used for genetic tracing or for identifying individuals for forensic science purposes. See, e.g., Morris, J. et al. (1989) "Biostatistical Evaluation of Evidence From Continuous Allele Frequency Distribution DNA Probes in Reference to Disputed Paternity and Identity," *J. Forensic Science* 34:1311–1317, and references provided therein; each of which is hereby incorporated herein by reference.

In addition, the high resolution fingerprinting allows the distinguishability to high resolution of particular samples. As indicated above, new cell classifications may be defined based on combinations of a large number of properties. Similar applications will be found in distinguishing different species of animals or plants. In fact, microbial identification may become dependent on characterization of the genetic content. Tumors or other cells exhibiting abnormal physiology will be detectable by use of the present invention. Also, knowing the genetic fingerprint of a microorganism may provide very useful information on how to treat an infection by such organism.

Modifications of the fingerprint embodiments may be used to diagnose the condition of the organism. For example, a blood sample is presently used for diagnosing any of a number of different physiological conditions. A multidimensional fingerprinting method made available by the present invention could become a routine means for diagnosing an enormous number of physiological features simultaneously. This may revolutionize the practice of medicine in providing information on an enormous number of parameters together at one time. In another way, the genetic predisposition may also revolutionize the practice of medicine providing a physician with the ability to predict the likelihood of particular medical conditions arising at any particular moment. It also provides the ability to apply preventative medicine.

The present invention might also find application in use for screening new drugs and new reagents which may be very important in medical diagnosis or other applications. For example, a description of generating a population of monoclonal antibodies with defined specificities may be very useful for producing various drugs or diagnostic reagents.

Also available are kits with the reagents useful for performing sequencing, fingerprinting, and mapping procedures. The kits will have various compartments with the desired necessary reagents, e.g., substrate, labeling reagents for target samples, buffers, and other useful accompanying products.

C. Mapping

The present invention also provides the means for mapping sequences within enormous stretches of sequence. For example, nucleotide sequences may be mapped within enormous chromosome size sequence maps. For example, it would be possible to map a chromosomal location within the chromosome which contains hundreds of millions of nucleotide base pairs. In addition, the mapping and fingerprinting embodiments allow for testing of chromosomal translocations, one of the standard problems for which amniocentesis is performed.

Thus, the present invention provides a powerful tool and the means for performing sequencing, fingerprinting, and mapping functions on polymers. Although most easily and directly applicable to polynucleotides, polypeptides, carbohydrates, and other sorts of molecules can be advantageously utilized using the present technology.

The present invention will be better understood by reference to the following illustrative examples. The following examples are offered by way of illustration and not by way of limitation.

EXPERIMENTAL

I. Sequencing
A. polynucleotide
B. polypeptide
C. short peptide
   1. Herz antibody identification II. Fingerprinting
A. polynucleotide fingerprint
B. peptide fingerprint
C. cell classification scheme
D. temporal development scheme
  1. developmental antigens
  2. developmental mRNA expression
E. diagnostic test
  1. viral identification
  2. bacterial identification
  3. other microbiological identifications
  4. allergy test (immobilized antigens)
F. individual (animal/plant) identification
  1. genetic
  2. immunological
G. genetic screen
  1. test alleles with markers
  2. amniocentesis
III. Mapping
A. positionally located clones (caged biotin)
  1. short probes, long targets
  2. long targets, short probes
B. positionally defined clones
IV. Conclusion Relevant applications whose techniques are incorporated herein by reference are Pirrung, et al., U.S. Ser. No. 07/362,901 (VLSIPS parent), filed Jun. 7, 1989; Pirrung et al, U.S. Ser. No. 07/492,462 (VLSIPS CIP), filed Mar. 7, 1990; Barrett, et al., U.S. Ser. No. 07/435,316 (caged biotin) filed Nov. 13, 1989; Barrett, et al., U.S. Ser. No. 07/612,671 (caged biotin CIP), filed Nov. 13, 1990; and commonly assigned and simultaneously filed applications U.S. Ser. No. 07/624,120, (automated VLSIPS) and U.S. Ser. No. 07/626,730, (sequencing by synthesis).

Also, additional relevant techniques are described, e.g., in Sambrook, J., et al. (1989) *Molecular Cloning: a Laboratory Manual*, 2d Ed., vols 1–3, Cold Spring Harbor Press, New York; Greenstein and Winitz (196) *Chemistry of the Amino Acids*, Wiley and Sons, New York; Bodzansky, M. (1988) *Peptide Chemistry: a Practical Textbook*, Springer-Verlag, New York; Harlow and Lane (1988) *Antibodies: A Laboratory Manual*, Cold Spring Harbor Press, New York; Glover, D. (ed.) (1987) *DNA Cloning: A Practical Approach*, vols 1–3, IRL Press, Oxford; Bishop and Rawlings (1987) *Nucleic Acid and Protein Sequence Analysis: A Practical Approach*, IRL Press, Oxford; Hames and Higgins (1985) *Nucleic Acid Hybridisation: A Practical Approach*, IRL Press, Oxford; Wu et al. (1989) *Recombinant DNA Methodology*, Academic Press, San Diego; Goding (1986) *Monoclonal Antibodies: Principles and Practice*, (2ed.), Academic Press, San Diego; Finegold and Barron (1986) *Bailey and Scott's Diagnostic Microbiology*, (7th ed.), Mosby Co., St. Louis; Collins et al. (1989) *Microbiological Methods*, (6th ed.), Butterworth, London; Chaplin and Kennedy (1986) *Carbohydrate Analysis: A Practical Approach*, IRL Press, Oxford; Van Dyke (ed.) (1985) *Bioluminescence and Chemiluminescence: Instruments and Applications*, vol 1, CRC Press, Boca Rotan; and Ausubel et al. (ed.) (1990) *Current Protocols in Molecular Biology*, Greene Publishing and Wiley-Interscience, New York; each of which is hereby incorporated herein by reference.

The following examples are provided to illustrate the efficacy of the inventions herein. All operations were conducted at about ambient temperatures and pressures unless indicated to the contrary.

I. Sequencing

A. Polynucleotide
1. HPLC of the Photolysis of 5'-O-nitroveratryl-thymidine.

In order to determine the time for photolysis of 5'-O-nitrovertryl thymidine to thymidine a 100 μM solution of NV-Thym-OH (5'-O-nitrovertryl thymidine) in dioxane was made and ~200 μl aliquots were irradiated (in a quartz cuvette 1 cm×2 mm) at 362.3 nm for 20 sec, 40 sec, 60 sec, 2 min, 5 min, 10 min, 15 min, and 20 min. The resulting irradiated mixtures were then analyzed by HPLC using a Varian MicroPak SP column ($C_{18}$ analytical) at a flow rate of 1 ml/min and a solvent system of 40% $CH_3CN$ and 60% water. Thymidine has a retention time of 1.2 min and NVO-Thym-OH has a retention time of 2.1 min. It was seen that after 10 min of exposure the deprotection was complete.

2. Preparation and Detection of Thymidine-Cytidine Dimer (FITC)

The reaction is illustrated:

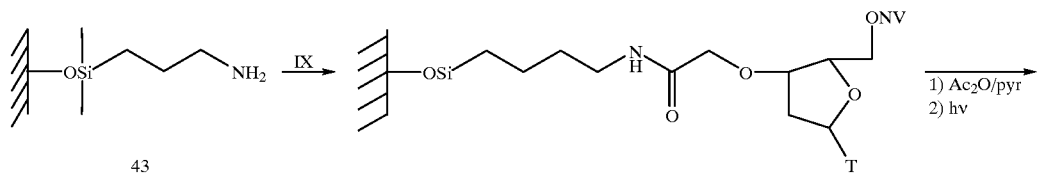

43

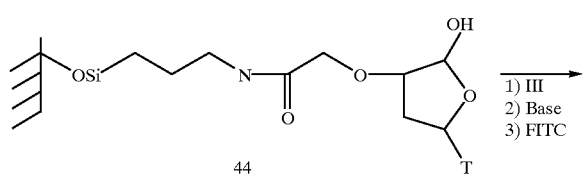

44

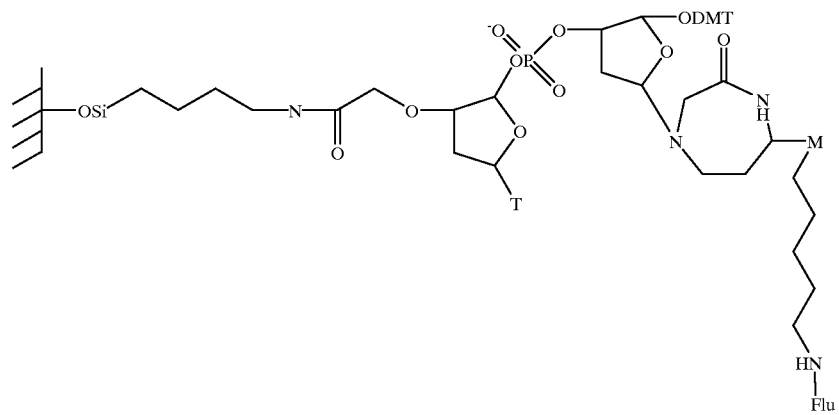

To an aminopropylated glass slide (standard VLSIPS) was added a mixture of the following:
12.2 mg of NVO-Thym-CO$_2$H (IX)
3.4 mg of HOBT (N-hydroxybenztriazal)
8.8 μl DIEA (Diisopropylethylamine)
11.1 mg BOP reagent
2.5 ml DMF After 2 h coupling time (standard VLSIPS) the plate was washed, acetylated with acetic anhydride/pyridine, washed, dried, and photolyzed in dioxane at 362 nm at 14 mW/cm$^2$ for 10 min using a 500 μm checkerboard mask. The slide was then taken and treated with a mixture of the following:

107 mg of FMOC-amine modified C (III)
21 mg of tetrazole
1 ml anhydrous CH$_3$CN After being treated for approximately 8 min, the slide was washed off with CH$_3$CN, dried, and oxidized with I$_2$/H$_2$O/THF/lutidine for 1 min. The slide was again washed, dried, and treated for 30 min with a 20% solution of DBU in DMF. After thorough rinsing of the slide, it was next exposed to a FITC solution (1 mM fluorescein isothiocyanate [FITC] in DMF) for 50 min, then washed, dried, and examined by fluorescence microscopy. This reaction is illustrated:

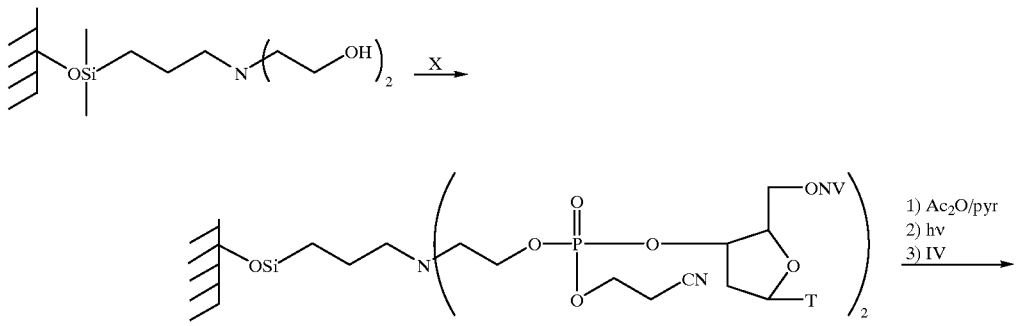

-continued

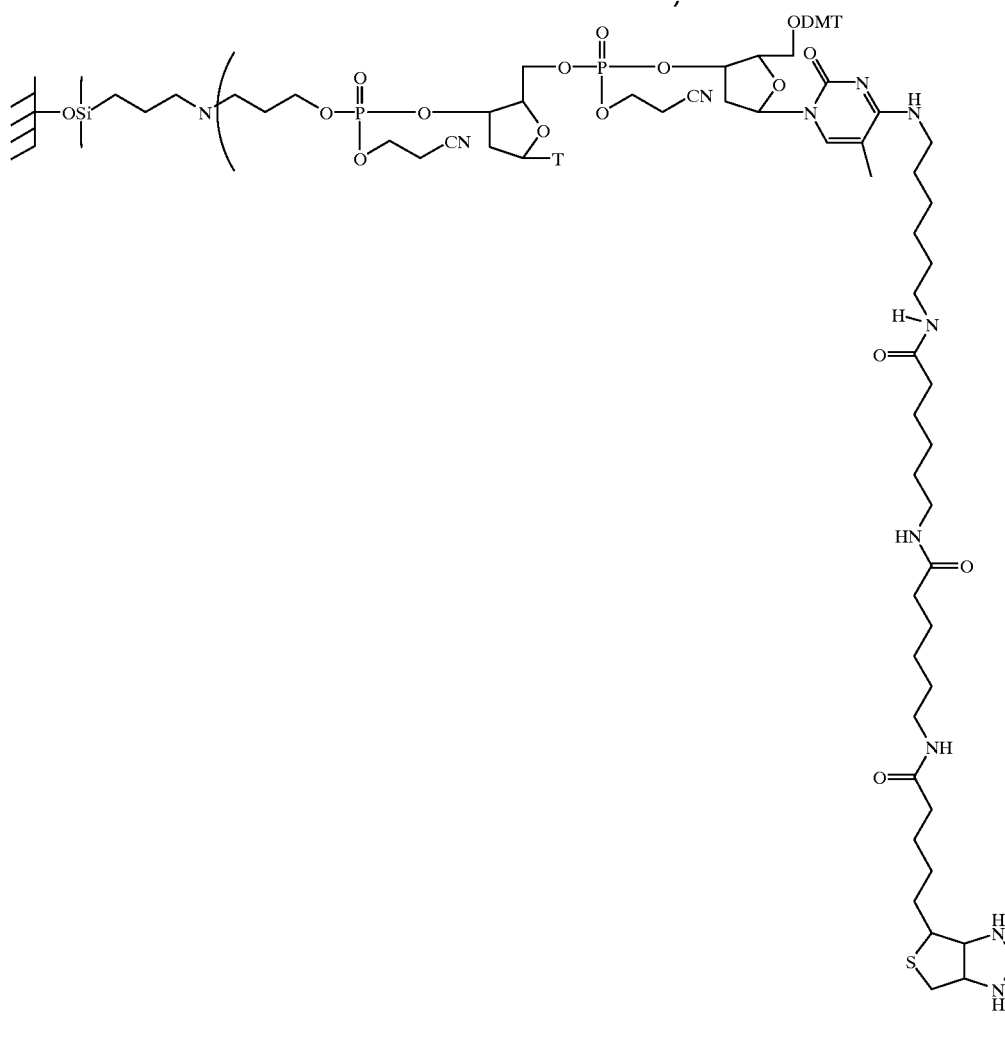

3. Preparation and Detection of Thymidine-Cytidine Dimer (Biotin)

Figure 3:
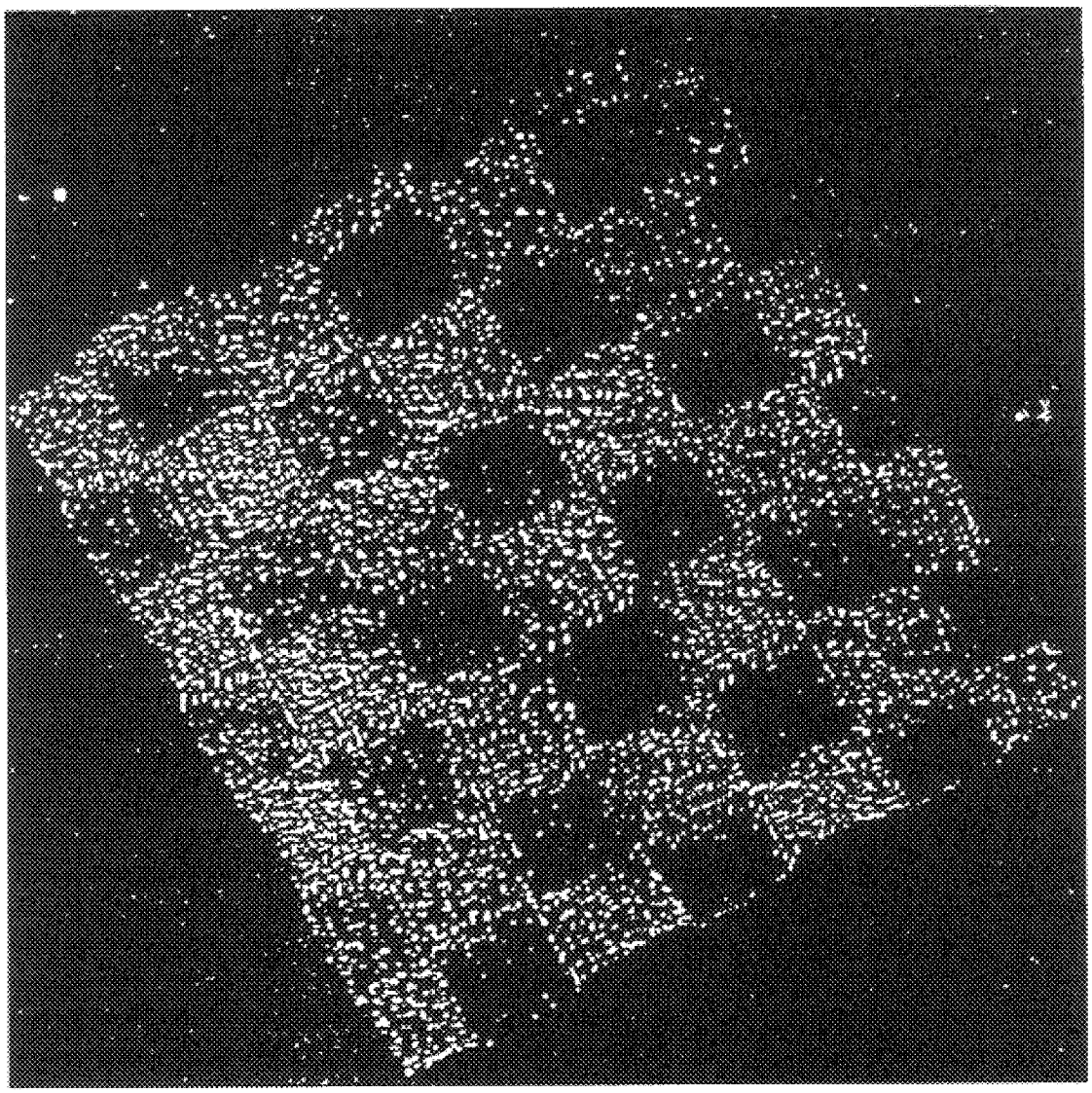
FIG. 3 illustrates the proper function of a VLSIPS dipeptide synthesis.
Figure 4A:
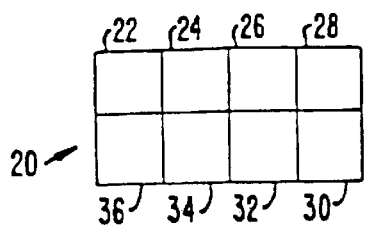
FIG. 4 illustrates the process of a VLSIPS trinucleotide synthesis.
Figure 4B:
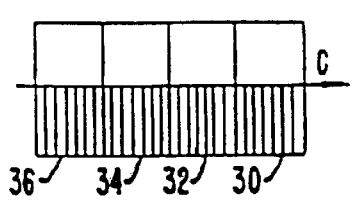
Figure 4C:
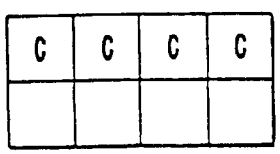
Figure 4D:
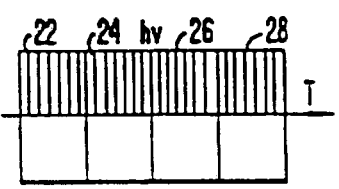
Figure 4E:
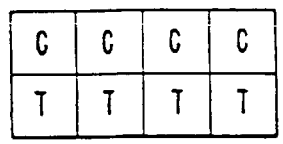
Figure 4F:
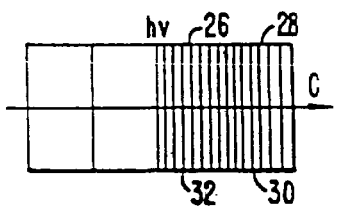
Figure 4G:
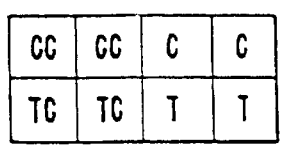
Figure 4H:
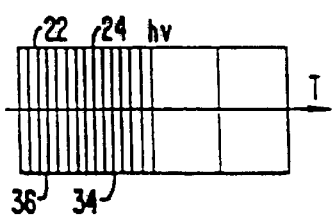
Figure 4I:
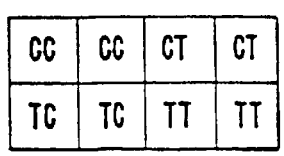
Figure 4J:
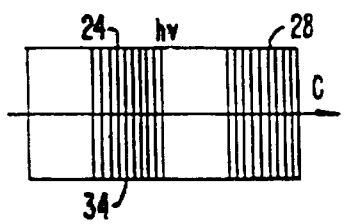
Figure 4K:
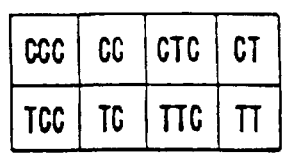
Figure 4L:
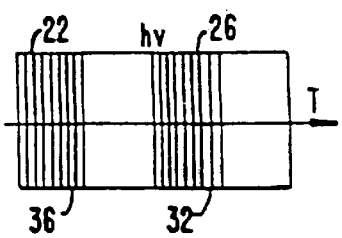
Figure 4M:
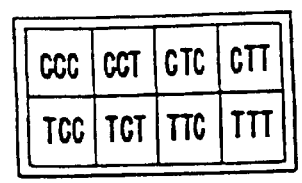

An aminopropyl glass slide, was soaked in a solution of ethylene oxide (20% in DMF) to generate a hydroxylated surface. The slide was added a mixture of the following:
32 mg of NVO-T-OCED (X)
11 mg of tetrazole
0.5 ml of anhydrous $CH_3CN$ After 8 min the plate was then rinsed with acetonitrile, then oxidized with $I_2/H_2O$/THF/lutidine for 1 min, washed and dried. The slide was then exposed to a 1:3 mixture of acetic anhydride:pyridine for 1 h, then washed and dried. The substrate was a then photolyzed in dioxane at 362 nm at 14 mW/cm$^2$ for 10 min using a 500 μm checkerboard mask, dried, and then treated with a mixture of the following:
65 mg of biotin modified C (IV)
11 mg of tetrazole
0.5 ml anhydrous $CH_3CN$ After 8 min the slide was washed with $CH_3CN$ then oxidized with $I_2/H_2O$/THF/lutidine for 1 min, washed, and then dried. The slide was then soaked for 30 min in a PBS/0.05% Tween 20 buffer and the solution then shaken off. The slide was next treated with FITC-labeled streptavidin at 10 μg/ml in the same buffer system for 30 min. After this time the streptavidin-buffer system was rinsed off with fresh PBS/0.05% Tween 20 buffer and then the slide was finally agitated in distilled water for about ½ h. After drying, the slide was examined by fluorescence microscopy (see FIG. 2 and FIG. 3).

4. Substrate Preparation

Before attachment of reactive groups it is preferred to clean the substrate which is, in a preferred embodiment, a glass substrate such as a microscope slide or cover slip. A roughened surface will be useable but a plastic or other solid substrate is also appropriate. According to one embodiment the slide is soaked in an alkaline bath consisting of, e.g., 1 liter of 95% ethanol with 120 ml of water and 120 grams of sodium hydroxide for 12 hours. The slides are washed with a buffer and under running water, allowed to air dry, and rinsed with a solution of 95% ethanol.

The slides are then aminated with, e.g., aminopropyltriethoxysilane for the purpose of attaching amino groups to the glass surface on linker molecules, although other omega functionalized silanes could also be used for this purpose. In one embodiment 0.1% aminopropyltriethoxysilane is utilized, although solutions with concentrations from $10^{-7}$% to 10% may be used, with about $10^{-3}$% to 2% preferred. A 0.1% mixture is prepared by adding to 100 ml of a 95% ethanol/5% water mixture, 100 microliters (µl) of aminopropyltriethoxysilane. The mixture is agitated at about ambient temperature on a rotary shaker for an appropriate amount of time, e.g., about 5 minutes. 500 µl of this mixture is then applied to the surface of one side of each cleaned slide. After 4 minutes or more, the slides are decanted of this solution and thoroughly rinsed three times or more by dipping in 100% ethanol.

After the slides dry, they are heated in a 110–120° C. vacuum oven for about 20 minutes, and then allowed to cure at room temperature for about 12 hours in an argon environment. The slides are then dipped into DMF (dimethylformamide) solution, followed by a thorough washing with methylene chloride.

5. Linker Attachment, Blocking of Free Sites

The aminated surface of the slide is then exposed to about 500 µl of, for example, a 30 millimolar (mM) solution of NVOC-nucleotide-NHS (N-hydroxysuccinimide) in DMF for attachment of a NVOC-nucleotide to each of the amino groups. See, e.g., SIGMA Chemical Company for various nucleotide derivatives. The surface is washed with, for example, DMF, methylene chloride, and ethanol.

Any unreacted aminopropyl silane on the surface, i.e., those amino groups which have not had the NVOC-nucleotide attached, are now capped with acetyl groups (to prevent further reaction) by exposure to a 1:3 mixture of acetic anhydride in pyridine for 1 hour. Other materials which may perform this residual capping function include trifluoroacetic anhydride, formicacetic anhydride, or other reactive acylating agents. Finally, the slides are washed again with DMF, methylene chloride, and ethanol.

6. Synthesis of Eight Trimers of C and T

FIG. 4 illustrates a possible synthesis of the eight trimers of the two-monomer set: cytosine and thymine (represented by C and T, respectively). A glass slide bearing silane groups terminating in 6-nitroveratryloxycarboxamide (NVOC-NH) residues is prepared as a substrate. Active esters (pentafluorophenyl, OBt, etc.) of cytosine and thymine protected at the 5' hydroxyl group with NVOC are prepared as reagents. While not pertinent to this example, if side chain protecting groups are required for the monomer set, these must not be photoreactive at the wavelength of light used to protect the primary chain.

For a monomer set of size n, n×l cycles are required to synthesize all possible sequences of length l. A cycle consists of:

1. Irradiation through an appropriate mask to expose the 5'-OH groups at the sites where the next residue is to be added, with appropriate washes to remove the by-products of the deprotection.

2. Addition of a single activated and protected (with the same photochemically-removable group) monomer, which will react only at the sites addressed in step 1, with appropriate washes to remove the excess reagent from the surface.

The above cycle is repeated for each member of the monomer set until each location on the surface has been extended by one residue in one embodiment. In other embodiments, several residues are sequentially added at one location before moving on to the next location. Cycle times will generally be limited by the coupling reaction rate, now as short as about 10 min in automated oligonucleotide synthesizers. This step is optionally followed by addition of Of course, greater diversity is obtained by using masking strategies which will also include the synthesis of polymers having a length of less than l. If, in the extreme case, all polymers having a length less than or equal to l are synthesized, the number of polymers synthesized will be:

$$n^l + n^{l-1} + \ldots + n^1. \quad (3)$$

The maximum number of lithographic steps needed will generally be n for each "layer" of monomers, i.e., the total number of masks (and, therefore, the number of lithographic steps) needed will be n×l. The size of the transparent mask regions will vary in accordance with the area of the substrate available for synthesis and the number of sequences to be formed. In general, the size of the synthesis areas will be:

size of synthesis areas=$(A)/(S)$ where:

A is the total area available for synthesis; and

S is the number of sequences desired in the area.

It will be appreciated by those of skill in the art that the above method could readily be used to simultaneously produce thousands or millions of oligomers on a substrate using the photolithographic techniques disclosed herein. Consequently, the method results in the ability to practically test large numbers of, for example, di, tri, tetra, penta, hexa, hepta, octa, nona, deca, even dodecanucleotides, or larger polynucleotides (or correspondingly, polypeptides).

The above example has illustrated the method by way of a manual example. It will of course be appreciated that automated or semi-automated methods could be used. The substrate would be mounted in a flow cell for automated addition and removal of reagents, to minimize the volume of reagents needed, and to more carefully control reaction conditions. Successive masks will be applicable manually or automatically. See, e.g., U.S. Ser. No. 07/492,462 (VLSIPS CIP) and U.S. Ser. No. 07/624,120, (automated VLSIPS).

7. Labeling of Target

The target oligonucleotide can be labeled using standard procedures referred to above. As discussed, for certain situations, a reagent which recognizes interaction, e.g., ethidium bromide, may be provided in the detection step. Alternatively, fluorescence labeling techniques may be applied, see, e.g., Smith, et al. (1986) *Nature,* 321: 674–679; and Prober, et al. (1987) *Science,* 238:336–341. The techniques described therein will be followed with minimal modifications as appropriate for the label selected.

8. Dimers of A, C, G, and T

The described technique may be applied, with photosensitive blocked nucleotides corresponding to adenine, cytosine, guanine, and thymine, to make combinations of polynucleotides consisting of each of the four different nucleotides. All 16 possible dimers would be made using a minor modification of the described method.

9. 10-mers of A, C, G, and T

The described technique for making dimers of A, C, G, and T may be further extended to make longer oligonucleotides. The automated system described, e.g., in U.S. Ser. No. 07/492,462 (VLSIPS CIP), and U.S. Ser. No. 07/624,120, (automated VLSIPS), can be adapted to make all possible 10-mers composed of the 4 nucleotides A, C, G, and T. The photosensitive, blocked nucleotide analogues have been described above, and would be readily adaptable to longer oligonucleotides.

10. Specific Recognition Hybridization to 10-mers

The described hybridization conditions are directly applicable to the sequence specific recognition reagents attached to the substrate, produced as described immediately above. The 10-mers have an inherent property of hybridizing to a complementary sequence. For optimum discrimination between full matching and some mismatch, the conditions of hybridization should be carefully selected, as described above. Careful control of the conditions, and titration of parameters should be performed to determine the optimum collective conditions.

11. Hybridization

Hybridization conditions are described in detail, e.g., in Hames and Higgins (1985) *Nucleic Acid Hybridisation: A Practical Approach*; and the considerations for selecting particular conditions are described, e.g., in Wetmur and Davidson, (1988) *J. Mol. Biol.* 31:349–370, and Wood et al. (1985) *Proc. Natl. Acad. Sci. USA* 82:1585–1588. As described above, conditions are desired which can distinguish matching along the entire length of the probe from where there is one or more mismatched bases. The length of incubation and conditions will be similar, in many respects, to the hybridization conditions used in Southern blot transfers. Typically, the GC bias may be minimized by the introduction of appropriate concentrations of the alkylammonium buffers, as described above.

Titration of the temperature and other parameters is desired to determine the optimum conditions for specificity and distinguishability of absolutely matched hybridization from mismatched hybridization.

A fluorescently labeled target or set of targets are generated, as described in Prober, et al. (1987) *Science* 238:336–341, or Smith, et al. (1986) *Nature* 321:674–679. Preferably, the target or targets are of the same length as, or slightly longer, than the oligonucleotide probes attached to the substrate and they will have known sequences. Thus, only a few of the probes hybridize perfectly with the target, and which particular ones did would be known.

The substrate and probes are incubated under appropriate conditions for a sufficient period of time to allow hybridization to completion. The time is measured to determine when the probe-target hybridizations have reached completion. A salt buffer which minimizes GC bias is preferred, incorporating, e.g., buffer, such as tetramethyl ammonium or tetraethyl ammonium ion at between about 2.4 and 3.0 M. See Wood, et al. (1965) *Proc. Nat'l Acad. Sci. USA* 82:1585–1588. This time is typically at least about 30 min, and may be as long as about 1–5 days. Typically very long matches will hybridize more quickly, very short matches will hybridize less quickly, depending upon relative target and probe concentrations. The hybridization will be performed under conditions where the reagents are stable for that time duration.

Upon maximal hybridization, the conditions for washing are titrated. Three parameters initially titrated are time, temperature, and cation concentration of the wash step. The matrix is scanned at various times to determine the conditions at which the distinguishability between true perfect hybrid and mismatched hybrid is optimized. These conditions will be preferred in the sequencing embodiments.

12. Positional Detection of Specific Interaction

As indicated above, the detection of specific interactions may be performed by detecting the positions where the labeled target sequences are attached. Where the label is a fluorescent label, the apparatus described, e.g., in U.S. Ser. No. 07/492,462 (VLSIPS CIP); and U.S. Ser. No. 07/624,120, may be advantageously applied. In particular, the synthetic processes described above will result in a matrix pattern of specific sequences attached to the substrate, and a known pattern of interactions can be converted to corresponding sequences.

In an alternative embodiment, a separate reagent which differentially interacts with the probe and interacted probe/targets can indicate where interaction occurs or does not occur. A single-strand specific reagent will indicate where no interaction has taken place, while a double-strand specific reagent will indicate where interaction has taken place. An intercalating dye, e.g., ethidium bromide, may be used to indicate the positions of specific interaction.

13. Analysis

Conversion of the positional data into sequence specificity will provide the set of subsequences whose analysis by overlap segments, may be performed, as described above. Analysis is provided by the methodology described above, or using, e.g., software available from the Genetic Engineering Center, P.O. Box 794, 11000 Belgrade, Yugoslavia (Yugoslav group). See, also, Macevicz, PCT publication no. WO 90/04652, which is hereby incorporated herein by reference.

B. Polypeptide

The description of the preparation of short peptides on a substrate incorporates by reference sections in U.S. Ser. No. 07/492,462 (VLSIPS CIP), and described below.

1. Slide Preparation

Preparation of the substrate follows that described above for nucleotides.

2. Linker Attachment, Blocking of Free Sites

The aminated surface of the slide is exposed to about 500 µl of, e.g., a 30 millimolar (mM) solution of NVOC-GABA (gamma amino butyric acid) NHS (N-hydroxysuccinimide) in DMF for attachment of a NVOC-GABA to each of the amino groups. The surface is washed with, for example, DMF, methylene chloride, and ethanol. See U.S. Ser. No. 07/624,120, for details on amino acid chemistry.

Any unreacted aminopropyl silane on the surface, i.e., those amino groups which have not had the NVOC-GABA attached, are now capped with acetyl groups (to prevent further reaction) by exposure to a 1:3 mixture of acetic anhydride in pyridine for 1 hour. Other materials which may perform this residual capping function include trifluoroacetic anhydride, formicacetic anhydride, or other reactive acylating agents. Finally, the slides are washed again with DMF, methylene chloride, and ethanol.

3. Synthesis of 8 Trimers of "A" and "B"

See U.S. Ser. No. 07/492,462 (VLSIPS CIP) which describes the preparation of glycine and phenylalanine trimers. The technique is similar to the method described above for making triners of C and T, but substituting photosensitive blocked glycine for the C derivative and photosensitive blocked phenylalamine for the T derivative.

4. Synthesis of a Dimer of an Aminopropyl Group and a Fluorescent Group

In synthesizing the dimer of an aminopropyl group and a fluorescent group, a functionalized durapore membrane was used as a substrate. The Durapore membrane was a polyvinylidine difluoride with aminopropyl groups. The aminopropyl groups were protected with the DDZ group by reaction of the carbonyl chloride with the amino groups, a reaction readily known to those of skill in the art. The surface bearing these groups was placed in a solution of THF and contacted with a mask bearing a checkerboard pattern of 1 mm opaque and transparent regions. The mask was exposed to ultraviolet light having a wavelength down to at least about 280 nm for about 5 minutes at ambient temperature, although a wide range of exposure times and temperatures may be appropriate in various embodiments of the invention. For example, in one embodiment, an exposure time of between about 1 and 5000 seconds may be used at process temperatures of between −70 and +50° C.

In one preferred embodiment, exposure times of between about 1 and 500 seconds at about ambient pressure are used. In some preferred embodiments, pressure above ambient is used to prevent evaporation.

The surface of the membrane was then washed for about 1 hour with a fluorescent label which included an active ester bound to a chelate of a lanthanide. Wash times will vary over a wide range of values from about a few minutes to a few hours. These materials fluoresce in the red and the green visible region. After the reaction with the active ester in the fluorophore was complete, the locations in which the fluorophore was bound could be visualized by exposing them to ultraviolet light and observing the red and the green fluorescence. It was observed that the derivatized regions of the substrate closely corresponded to the original pattern of the mask.

5. Demonstration of Signal Capability

Signal detection capability was demonstrated using a low-level standard fluorescent bead kit manufactured by Flow Cytometry Standards and having model no. 824. This kit includes 5.8 μm diameter beads, each impregnated with a known number of fluorescein molecules.

One of the beads was placed in the illumination field on the scan stage in a field of a laser spot which was initially shuttered. After being positioned in the illumination field, the photon detection equipment was turned on. The laser beam was unblocked and it interacted with the particle bead, which then fluoresced. Fluorescence curves of beads impregnated with 7,000 and 29,000 fluorescein molecules, are shown in FIGS. 11A and 11B, respectively of U.S. Ser. No. 07/492,462 (VLSIPS CIP). On each curve, traces for beads without fluorescein molecules are also shown. These experiments were performed with 488 nm excitation, with 100 μW of laser power. The light was focused through a 40 power 0.75 NA objective.

The fluorescence intensity in all cases started off at a high value and then decreased exponentially. The fall-off in intensity is due to photobleaching of the fluorescein molecules. The traces of beads without fluorescein molecules are used for background subtraction. The difference in the initial exponential decay between labeled and nonlabeled beads is integrated to give the total number of photon counts, and this number is related to the number of molecules per bead. Therefore, it is possible to deduce the number of photons per fluorescein molecule that can be detected. This calculation indicates the radiation of about 40 to 50 photons per fluorescein molecule are detected.

6. Determination of the Number of Molecules Per Unit Area

Aminopropylated glass microscope slides prepared according to the methods discussed above were utilized in order to establish the density of labeling of the slides. The free amino termini of the slides were reacted with FITC (fluorescein isothiocyanate) which forms a covalent linkage with the amino group. The slide is then scanned to count the number of fluorescent photons generated in a region which, using the estimated 40–50 photons per fluorescent molecule, enables the calculation of the number of molecules which are on the surface per unit area.

A slide with aminopropyl silane on its surface was immersed in a 1 mM solution of FITC in DMF for 1 hour at about ambient temperature. After reaction, the slide was washed twice with DMF and then washed with ethanol, water, and then ethanol again. It was then dried and stored in the dark until it was ready to be examined.

Through the use of curves similar to those shown in FIG. 11 of U.S. Ser. No. 07/492,462 (VLSIPS CIP), and by integrating the fluorescent counts under the exponentially decaying signal, the number of free amino groups on the surface after derivitization was determined. It was determined that slides with labeling densities of 1 fluorescein per $10^3 \times 10^3$ to ~$2 \times 2$ nm could be reproducibly made as the concentration of aminopropyltriethoxysilane varied from $10^{-5}\%$ to $10^{-1}\%$.

7. Removal of NOVC and Attachment of a Fluorescent Marker

NVOC-GABA groups were attached as described above. The entire surface of one slide was exposed to light so as to expose a free amino group at the end of the gamma amino butyric acid. This slide, and a duplicate which was not exposed, were then exposed to fluorescein isothiocyanate (FITC).

FIG. 12A of U.S. Ser. No. 07/492,462 (VLSIPS CIP) illustrates the slide which was not exposed to light, but which was exposed to FITC. The units of the x axis are time and the units of the y axis are counts. The trace contains a certain amount of background fluorescence. The duplicate slide was exposed to 350 nm broadband illumination for about 1 minute (12 mW/cm$^2$, ~350 nm illumination), washed and reacted with FITC. A large increase in the level of fluorescence is observed, which indicates photolysis has exposed a number of amino groups on the surface of the slides for attachment of a fluorescent marker.

8. Use of a Mask in Removal of NVOC

The next experiment was performed with a 0.1% aminopropylated slide. Light from a Hg—Xe arc lamp was imaged onto the substrate through a laser-ablated chrome-on-glass mask in direct contact with the substrate.

This slide was illuminated for approximately 5 minutes, with 12 mW of 350 nm broadband light and then reacted with the 1 mM FITC solution. It was put on the laser detection scanning stage and a graph was plotted as a two-dimensional representation of position color-coded for fluorescence intensity. The experiment was repeated a number of times through various masks. The fluorescence patterns for a 100×100 μm mask, a 50 μm mask, a 20 μm mask, and a 10 μm mask indicate that the mask pattern is distinct down to at least about 10 μm squares using this lithographic technique.

9. Attachment of YGGFL and Subsequent Exposure to Herz Antibody and Goat Anti-mouse Antibody In order to establish that receptors to a particular polypeptide sequence would bind to a surface-bound peptide and be detected, Leu enkephalin was coupled to the surface and recognized by an antibody. A slide was derivatized with 0.1% amino propyl-triethoxysilane and protected with NVOC. A 500 μm checkerboard mask was used to expose the slide in a flow cell using backside contact printing. The Leu enkephalin sequence (H$_2$N-tyrosine,glycine,glycine, phenylalanine,leucine-COOH, otherwise referred to herein as YGGFL) was attached via its carboxy end to the exposed amino groups on the surface of the slide. The peptide was added in DMF solution with the BOP/HOBT/DIEA coupling reagents and recirculated through the flow cell for 2 hours at room temperature.

A first antibody, known as the Herz antibody, was applied to the surface of the slide for 45 minutes at 2 μg/ml in a supercocktail (containing 1% BSA and 1% ovalbumin also in this case). A second antibody, goat anti-mouse fluorescein conjugate, was then added at 2 μg/ml in the supercocktail buffer, and allowed to incubate for 2 hours.

The results of this experiment were plotted as fluorescence intensity as a function of position. This image was taken at 10 μm steps and showed that not only can deprotection be carried out in a well defined pattern, but also that (1) the method provided for successful coupling of peptides to the surface of the substrate, (2) the surface of a bound peptide was available for binding with an antibody, and (3) that the detection apparatus-capabilities were sufficient to detect binding of a receptor. Moreover, the Herz antibody is a sequence specific reagent which may be used advantageously as a sequence specific recognition reagent. It may be used, if specificity is high, for sequencing purposes, and, at least, for fingerprinting and mapping uses.

10. Monomer-by-monomer Formation of YGGFL and Subsequent Exposure to Labeled Antibody Monomer-by-monomer synthesis of YGGFL and GGFL in alternate squares was performed on a slide in a checkerboard pattern and the resulting slide was exposed to the Herz antibody.

A slide is derivatized with the aminopropyl group, protected in this case with t-BOC (t-butoxycarbonyl). The slide was treated with TFA to remove the t-BOC protecting group. E-aminocaproic acid, which was t-BOC protected at its amino group, was then coupled onto the aminopropyl groups. The aminocaproic acid serves as a spacer between the aminopropyl group and the peptide to be synthesized. The amino end of the spacer was deprotected and coupled to UVOC-leucine. The entire slide was then illuminated with 12 mW of 325 nm broadband illumination. The slide was then coupled with NVOC-phenylalanine and washed. The entire slide was again illuminated, then coupled to NVOC-glycine and washed. The slide was again illuminated and coupled to NVOC-glycine to form the sequence shown in the last portion of FIG. 13A of U.S. Ser. No. 07/492,462 (VLSIPS CIP).

Alternating regions of the slide were then illuminated using a projection print using a 500×500 µm checkerboard mask; thus, the amino group of glycine was exposed only in the lighted areas. When the next coupling chemistry step was carried out, NVOC-tyrosine was added, and it coupled only at those spots which had received illumination. The entire slide was then illuminated to remove all the NVOC groups, leaving a checkerboard of YGGFL in the lighted areas and in the other areas, GGFL. The Herz antibody (which recognizes the YGGFL, but not GGPL) was then added, followed by goat anti-mouse fluorescein conjugate.

The resulting fluorescence scan showed dark areas containing the tetrapeptide GGFL, which is not recognized by the Herz antibody (and thus there is no binding of the goat anti-mouse antibody with fluorescein conjugate), and red areas in which YGGFL was present. The YGGFL pentapeptide is recognized by the Herz antibody and, therefore, there is antibody in the lighted regions for the fluorescein-conjugated goat anti-mouse to recognize.

Similar patterns for a 50 µm mask used in direct contact ("proximity print") with the substrate provided a pattern which was more distinct and the corners of the checkerboard pattern were touching as a result of the mask being placed in direct contact with the substrate (which reflects the increase in resolution using this technique).

11. Monomer-by-monomer Synthesis of YGGFL and PGGFL

A synthesis using a 50 µm checkerboard mask was conducted. However, P was added to the GGFL sites on the substrate through an additional coupling step. P was added by exposing protected GGFL to light through a mask, and subsequence exposure to P in the manner set forth above. Therefore, half of the regions on the substrate contained YGGFL and the remaining half contained PGGFL.

The fluorescence plot for this experiment showed the regions are again readily discernable between those in which binding did and did not occur. This experiment demonstrated that antibodies are able to recognize a specific sequence and that the recognition is not length-dependent. ps 12. Monomer-by-monomer Synthesis of YGGFL and YPGGFL In order to further demonstrate the operability of the invention, a 50 µm checkerboard pattern of alternating YGGFL and YPGGFL was synthesized on a substrate using techniques like those set forth above. The resulting fluorescence plot showed that the antibody was clearly able to recognize the YGGFL sequence and did not bind significantly at the YPGGFL regions.

13. Synthesis of an Array of Sixteen Different Amino Acid Sequences and Estimation of Relative Binding Affinity to Herz Antibody Using techniques similar to those set forth above, an array of 16 different amino acid sequences (replicated four times) was synthesized on each of two glass substrates. The sequences were synthesized by attaching the sequence NVOC-GFL across the entire surface of the slides. Using a series of masks, two layers of amino acids were then selectively applied to the substrate. Each region had dimensions of 0.25 cm×0.0625 cm. The first slide contained amino acid sequences containing only L-amino acids while the second slide contained selected D-amino acids. Various regions on the first and second slides, were duplicated four times on each slide. The slides were then exposed to the Herz antibody and fluorescein-labeled goat anti-mouse antibodies.

A fluorescence plot of the first slide, which contained only L-amino acids showed red areas (indicating strong binding, i.e., 149,000 counts or more) and black areas (indicating little or no binding of the Herz antibody, i.e., 20,000 counts or less). The sequence YGGFL was clearly most strongly recognized. The sequences YAGFL and YSGFL also exhibited strong recognition of the antibody. By contrast, most of the remaining sequences showed little or no binding. The four duplicate portions of the slide were extremely consistent in the amount of binding shown therein.

A fluorescence plot of the D-amino acid slide indicated that strongest binding was exhibited by the YGGFL sequence. Significant binding was also detected to YaGFL, YsGFL, and YpGFL. The remaining sequences showed less binding with the antibody. Low binding efficiency of the sequence yGGFL was observed.

Table 6 lists the various sequences tested in order of relative fluorescence, which provides information regarding relative binding affinity.

TABLE 6

| Apparent Binding to Herz Ab | |
|---|---|
| L- a.a. Set | D- a.a. Set |
| YGGFL | YGGFL |
| YAGFL | YaGFL |
| YSGFL | YsGFL |
| LGGFL | YpGFL |
| FGGFL | fGGFL |
| YPGFL | yGGFL |
| LAGFL | faGFL |
| FAGFL | wGGFL |
| WGGFL | yaGFL |
| | fpGFL |
| | waGFL |

14. Illustrative Alternative Embodiment

According to an alternative embodiment of the invention, the methods provide for attaching to the surface a caged binding member which, in its caged form, has a relatively low affinity for other potentially binding species, such as receptors and specific binding substances. Such techniques are more fully described in copending application Ser. No. 404,920, filed Sep. 8, 1989, and incorporated herein by reference for all purposes. See also U.S. Ser. No. 07/435,316 (caged biotin parent) and U.S. Ser. No. 07/612,671 (caged biotin CIP), each of which is hereby incorporated herein by reference.

According to this alternative embodiment, the invention provides methods for forming predefined regions on a surface of a solid support, wherein the predefined regions are capable of immobilizing receptors. The methods make use of caged binding members attached to the surface to enable selective activation of the predefined regions. The caged binding members are liberated to act as binding members ultimately capable of binding receptors upon selective activation of the predefined regions. The activated binding members are then used to immobilize specific molecules such as receptors on the predefined region of the surface. The above procedure is repeated at the same or different sites on the surface so as to provide a surface prepared with a plurality of regions on the surface containing, for example, the same or different receptors. When receptors immobilized in this way have a differential affinity for one or more ligands, screenings and assays for the ligands can be conducted in the regions of the surface containing the receptors.

The alternative embodiment may make use of novel caged binding members attached to the substrate. Caged (unactivated) members have a relatively low affinity for receptors of substances that specifically bind to uncaged binding members when compared with the corresponding affinities of activated binding members. Thus, the binding members are protected from reaction until a suitable source of energy is applied to the regions of the surface desired to be activated. Upon application of a suitable energy source, the caging groups labilize, thereby presenting the activated binding member. A typical energy source will be light.

Once the binding members on the surface are activated they may be attached to a receptor. The receptor chosen may be a monoclonal antibody, a nucleic acid sequence, a drug receptor, etc. The receptor will usually, though not always, be prepared so as to permit attaching it, directly or indirectly, to a binding member. For example, a specific binding substance having a strong binding affinity for the binding member and a strong affinity for the receptor or a conjugate of the receptor may be used to act as a bridge between binding members and receptors if desired. The method uses a receptor prepared such that the receptor retains its activity toward a particular ligand.

Preferably, the caged binding member attached to the solid substrate will be a photoactivatable biotin complex, i.e., a biotin molecule that has been chemically modified with photoactivatable protecting groups so that it has a significantly reduced binding affinity for avidin or avidin analogs than does natural biotin. In a preferred embodiment, the protecting groups localized in a predefined region of the surface will be removed upon application of a suitable source of radiation to give binding members, that are biotin or a functionally analogous compound having substantially the same binding affinity for avidin or avidin analogs as does biotin.

In another preferred embodiment, avidin or an avidin analog is incubated with activated binding members on the surface until the avidin binds strongly to the binding members. The avidin so immobilized on predefined regions of the surface can then be incubated with a desired receptor or conjugate of a desired receptor. The receptor will preferably be biotinylated, e.g., a biotinylated antibody, when avidin is immobilized on the predefined regions of the surface. Alternatively, a preferred embodiment will present an avidin/biotinylated receptor complex, which has been previously prepared, to activated binding members on the surface.

II. Fingerprinting

The above section on generation of reagents for sequencing provides specific reagents useful for fingerprinting applications. Fingerprinting embodiments may be applied towards polynucleotide fingerprinting, polypeptide fingerprinting, cell and tissue classification, cell and tissue temporal development stage classification, diagnostic tests, forensic uses for individual identification, classification of organisms, and genetic screening of individuals. Mapping applications are also described below.

A. Polynucleotide Fingerprint

Polynucleotide fingerprinting may use reagents similar to those described above for probing a sequence for the presence of specific subsequences found therein. Typically, the subsequences used for fingerprinting will be longer than the sequences used in oligonucleotide sequencing. In particular, specific long segments may be used to determine the similarity of different samples of nucleic acids. They may also be used to fingerprint whether specific combinations of information are provided therein. Particular probe sequences are selected and attached in a positional manner to a substrate. The means for attachment may be either using a caged biotin method described, e.g., in U.S. Ser. No. 07/612,671 (caged biotin CIP), or by another method using targeting molecules. For example, a short polypeptide of specific sequence may be attached to an oligonucleotide and targeted to specific positions on a substrate having antibodies attached thereto, the antibodies exhibiting specificity for binding to those short peptide sequences. In another embodiment, an unnatural nucleotide or similar complementary binding molecule may be attached to the fingerprinting probe and the probe thereby directed towards complementary sequences on a VLSIPS substrate. Typically, unnatural nucleotides would be preferred, e.g., unnatural optical isomers, which would not interfere with natural nucleotide interactions.

Having produced a substrate with particular fingerprint probes attached thereto at positionally defined regions, the substrate may be used in a manner quite similar to the sequencing embodiment to provide information as to whether the fingerprint probes are detecting the corresponding sequence in a target sequence. This will often provide information similar to a Southern blot hybridization.

B. Polypeptide Fingerprint

A polypeptide fingerprint may be performed using antibodies which recognize specific antigens on the polypeptide. For example, monoclonal antibodies which recognize specific sequences or antigens on a polypeptide may be used to determine whether those epitopes are found on a particular protein. For example, particular patterns of epitopes would be found on various types of proteins. This will lead to the discovery that specific epitopes, or antigenic determinants, which are characteristic of, e.g., beta sheet segments, will be identified as will particular different types of domains in various protein types. Thus, a screening method may be devised which can classify polypeptides, either native or denatured, into various new classes defined by the epitopes existing thereon.

In addition, once the substrate is generated in the manners described above, a target peptide is exposed to the substrate. The target may be either native or denatured, though the conditions used to denature the polypeptide may interfere with the specific interaction between the polypeptide and the recognition reagent. This method is not dependent on the fact that the polypeptide is a single chain, thus protein complexes may also be fingerprinted using this methodology. Structures such as multi-subunit proteins, associations of proteins, ribosomes, nucleosomes, and other small cellular structures may also be fingerprinted and classified according to the presence of specific recognizable features thereon.

Peptide fingerprinting may be useful, for example, in correlating with particular physiological conditions or developmental stages of a cell or organism. Thus, a biological sample may be fingerprinted to determine the presence in that sample of a plurality of different polypeptides which are each individually fingerprinted. In an alternative embodiment, a polypeptide itself is not fingerprinted but a biological sample is fingerprinted searching for specific epitopes, e.g., polypeptide, carbohydrate, nucleic acid, or any of a number of other specific recognizable structural features.

The conditions for the interactions using antibodies is described, e.g., in Harlow and Lane (1988) *Antibodies: A Laboratory Manual*, Cold Spring Harbor Press, New York. The conditions should be titrated for temperature, buffer composition, time, and other important parameters in an antibody interaction.

C. Cell Classification Scheme

The present invention can be used for cell classification using fingerprinting type technology as described above in the polypeptide fingerprint. Classes of cells are typically defined by the presence of common functions which are usually reflected by structural features. Thus, a plant cell is classified differently from an animal cell by a number of structural features. Given an unknown cell, the present invention provides improved means for distinguishing the different cell types. Once a cell classification scheme is developed and the structural features which define it are identified using the present invention, homogeneous cell population expressing these features may be separated from others. Standard cell sorters may be coupled with recognition reagents and labels which can distinguish various cell types.

a. T-Cell Classes

T-cell classes are defined on the basis of expression of particular antigens characteristic of each class. For example, mouse T-cell differentiation markers include the LY antigens. With the plurality of different antigens which may be tested using antibody or other recognition reagents, new populations and classes of cells may be defined. For example, different neural cell types may be defined on the basis of cell surface antigens. Different tissue types will be defined on the basis of tissue specific antigens. Developmental cell classes will be similarly defined. All of these screenings can make use of the VLSIPS substrates with specific recognition molecules attached thereto. The substrates are exposed to the cell types directly, assaying for attachment of cells to specific regions, or are exposed to products of a population of cells, e.g., a supernatant, or a cell lysate.

Once a cell classification scheme has been correlated with specific structural markers therein, reagents which recognize those features may be developed and used in a fluorescence activated cell sorter as described, e.g., in Dangl, J. and Herzenberg (1982) *J. Immunological Methods* 52: 1–14; and Becton Dickinson, Fluorescence Activated Cell Sorters Division, San Jose, Calif. This will provide a homogeneous population of cells whose function has been defined by structure.

b. B-Cell Classes

The present cell classification scheme may also be used to determine specific B-cell classes. For example, B-cells specific for producing IgM, IgG, IgD, IgE, and IgA may be defined by the internal expression of specific mRNA sequences encoding each type of immunoglobulin. The classification scheme may depend on either extracellularly expressed markers which are correlated as being diagnostic of specific stages in development, or intracellular mRNA sequences which indicate particular functions.

D. Temporal Development Scheme

1. Developmental Antigens

The present fingerprinting invention also allows cell classification by expression of developmental antigens. For example, a lymphocyte stem cell expresses a particular combination of antigens. As the lymphocyte develops through a program developmental scheme, at various stages it expresses particular antigens which are diagnostic of particular stages in development. Again, the fingerprinting methodology allows for the definition of specific structural features which are diagnostic of developmental or functional features which will allow classification of cells into temporal developmental classes. Cells, products of those cells, or lysates of those cells will be assayed to determine the developmental stage of the source cells. In this manner, once a developmental stage is defined, specific synchronized populations of cells will be selected out of another population. These synchronized populations may be very important in determining the biological mechanisms of development.

2. Developmental mRNA Expression

Besides expressed antigens, the present invention also allows for fingerprinting of the mRNA population of a cell. In this fashion, the mRNA population, which should be a good determinant of developmental stage, will be correlated with other structural features of the cell. In this manner, cells at specific developmental stages will be characterized by the intracellular environment, as well as the extracellular environment. The present invention also allows the combination of definitions based, in part, upon antigens and, in part, upon mRNA expression.

In one embodiment, the two may be combined in a single incubation step. A particular incubation condition may be found which is compatible with both hybridization recognition non-hybridization recognition molecules. Thus, e.g., an incubation condition may be selected which allows both specificity of antibody binding and specificity of nucleic acid hybridization. This allows simultaneous performance of both types of interactions on a single matrix. Again, where developmental mRNA patterns are correlated with structural features, or with probes which are able to hybridize to intracellular mRNA populations, a cell sorter may be mused to sort specifically those cells having desired mRNA population patterns.

E. Diagnostic Tests

The present invention also provides the ability to perform diagnostic tests. Diagnostic tests typically are based upon a fingerprint type assay, which tests for the presence of specific diagnostic structural features. Thus, the present invention provides means for viral strain identification, bacterial strain identification, and other diagnostic tests using positionally defined specific reagents. The present invention also allows for determining a spectrum of allergies, diagnosing a biological sample for any or all of the above, and testing for many other conditions.

1. Viral Identification

The present invention provides reagents and methodology for identifying viral strains. The specific reagents may be either antibodies or recognition proteins which bind to specific viral epitopes preferably surface exposed, but may make use of internal epitopes, e.g., in a denatured viral sample. In an alternative embodiment, the viral genome may be probed for specific sequences which are characteristic of particular viral strains. As above, a combination of the two may be performed simultaneously in a single interaction step, or in separate tests, e.g., for both genetic characteristics and epitope characteristics.

2. Bacterial Identification

Similar techniques will be applicable to identifying a bacterial source. This may be useful in diagnosing bacterial infections, or in classifying sources of particular bacterial species. For example, the bacterial assay may be useful in determining the natural range of survivability of particular strains of bacteria across regions of the country or in different ecological niches.

3. Other Microbiological Identifications

The present invention provides means for diagnosis of other microbiological and other species, e.g., protozoal species and parasitic species in a biological sample, but also provides the means for assaying a combination of different infections. For example, a biological specimen may be assayed for the presence of any or all of these microbiological species. In human diagnostic uses, typical samples will be blood, sputum, stool, urine, or other samples.

4. Allergy Tests

An immobilized set of antigens may be attached to a solid substrate and, instead of the standard skin reaction tests, a blood sample may be assayed on such a substrate to determine the presence of antibodies, e.g., IgE or other type antibodies, which may be diagnostic of an allergic or immunological susceptibility. A standard radioallergosorbent test (RAST) may be used to check a much larger population of antigens.

In addition, an allergy like test may be used to diagnose the immunological history of a particular individual. For example, by testing the circulating antibodies in a blood sample, which reflects the immunological history and memory of an individual, it may be determined what infections may not have been historically presented to the immune system. In this manner, it may be possible to specifically supplement an immune system for a short period of time with IgG fractions made up of specific types of gamma globulins. Thus, hepatitis gamma globulin injections may be better designed for a particular environment which a person is expected to be exposed. This also provides the ability to identify genetically equivalent individuals who have immunologically different experiences. Thus, a blood sample from an individual who has a particular combination of circulating antibodies will likely be different from the combination of circulating antibodies found in a genetically similar or identical individual. This could allow for the distinction between clones of particular animals, e.g., mice, rats, or other animals.

F. Individual Identification

The present invention provides the ability to fingerprint and identify a genetic individual. This individual may be a bacterial or lower microorganism, as described above in diagnostic tests, or of a plant or animal. An individual may be identified genetically or immunologically, as described.

1. Genetic

Genetic fingerprinting has been utilized in comparing different related species in Southern hybridization blots. Genetic fingerprinting has also been used in forensic studies, see, e.g., Morris et al. (1989) *J. Forensic Science* 34: 1311–1317, and references cited therein. As described above, an individual may be identified genetically by a sufficiently large number of probes. The likelihood that another individual would have an identical pattern over a sufficiently large number of probes may be statistically negligible. However, it is often quite important that a large number of probes be used where the statistical probability of matching is desired to be particularly low. In fact, the probes will optimally be selected for having high heterogeneity among the population. In addition, the fingerprint method may make use of the pattern of homologies indicated by a series of more and more stringent washes. Then, each position has both a sequence specificity and a homology measurement, the combination of which greatly increases the number of dimensions and the statistical likelihood of a perfect pattern match with another genetic individual.

2. Immunological

As indicated above in the diagnostic tests, it is possible to identify a particular immune system within a genetically homogeneous class of organisms by virtue of her immunological history. For example, a large colony of cloned mice may be distinguishable by virtue of each immunological history. For example, one mouse may have had an immunological response to exposure to antigen A to which her genetically identical sibling may have not been exposed. By virtue of this differential history, the first of the pair will likely have a high antibody titer against the antigen A whereas her genetically identical sibling will have not had a response to that antigen by virtue of never having been exposed to it. For this reason, immune systems may be identified by their immunological memories. Thus, immunological experience may also be a means for identifying a particular individual at a particular moment in her lifetime.

This same immunological screening may be used for other sorts of identifiable biological products. For example, an individual may be identified by her combination of expressed proteins. These proteins may reflect a physiological state of the individual, and would thus be useful in certain circumstances where diagnostic tests may be performed. For example, an individual may be identified, in part, by the presence of particular metabolic products.

In fact, a plant origin may be determined by virtue of having within its genome an unnatural sequence introduced to it by genetic breeders. Thus, a marker nucleic acid sequence may be introduced as a means to determine whether a genetic strain of a plant or animal originated from another particular source.

G. Genetic Screening

1. Test Alleles With Markers

The present invention provides for the ability to screen for genetic variations of individuals. For example, a number of genetic diseases are linked with specific alleles. See, e.g., Scriber, C. et al. (eds.) (1989) *The Metabolic Bases of Inherited Disease*, McGraw-Hill, New York. In one embodiment, cystic fibrosis has been correlated with a specific gene, see, Gregory et al. (1990) *Nature* 347: 382–386. A number of alleles are correlated with specific genetic deficiencies. See, e.g., McKusick, V. (1990) *Genetic Inheritance in Man: Catalogs of Autosomal Dominant, Autosomal Recessive, and X-linked Phenotypes*, Johns Hopkins University Press, Baltimore; Ott, J. (1985) *Analysis of Human Genetic Linkage*, Johns Hopkins University Press, Baltimore; Track, R. et al. (1989) *Banbury Report* 32: *DNA Technology and Forensic Science*, Cold Spring Harbor Press, New York; each of which is hereby incorporated herein by reference.

2. Amniocentesis

Typically, amniocentesis is used to determine whether chromosome translocations have occurred. The mapping procedure may provide the means for determining whether these translocations have occurred, and for detecting particular alleles of various markers.

III. Mapping

A. Positionally Located Clones

The present invention allows for the positional location of specific clones useful for mapping. For example, caged biotin may be used for specifically positioning a probe to a location on a matrix pattern.

In addition, the specific probes may be positionally directed to specific locations on a substrate by targeting. For example, polypeptide specific recognition reagents may be attached to oligonucleotide sequences which can be complementarily targeted to specific locations on a VLSIPS substrate. Hybridization conditions, as applied for oligonucleotide probes, will be used to target the reagents to locations on a substrate having complementary oligonucleotides synthesized thereon. In another embodiment, oligonucleotide probes may be attached to specific polypeptide targeting reagents such as an antigen or antibody. These reagents can be directed towards a complementary antigen or antibody already attached to a VLSIPS substrate.

In another embodiment, an unnatural nucleotide which does not interfere with natural nucleotide complementary hybridization may be used to target oligonucleotides to particular positions on a substrate. Unnatural optical isomers of natural nucleotides should be ideal candidates.

In this way, short probes may be used to determine the mapping of long targets or long targets may be used to map the position of shorter probes. See, e.g., Craig et al. 1990 *Nuc. Acids Res.* 18: 2653–2660.

B. Positionally Defined Clones

Positionally defined clones may be transferred to a new substrate by either physical transfer or by synthetic means. Synthetic means may involve either a production of the probe on the substrate using the VLSIPS synthetic methods, or may involve the attachment of a targeting sequence made by VLSIPS synthetic methods which will target that positionally defined clone to a position on a new substrate. Both methods will provide a substrate having a number of positionally defined probes useful in mapping.

IX. Conclusion

The present inventions provide greatly improved methods and apparatus for synthesis of polymers on substrates. It is to be understood that the above description is intended to be illustrative and not restrictive. Many embodiments will be apparent to those of skill in the art upon reviewing the above description. By way of example, the invention has been described primarily with reference to the use of photoremovable protective groups, but it will be readily recognized by those of skill in the art that sources of radiation other than light could also be used. For example, in some embodiments it may be desirable to use protective groups which are sensitive to electron beam irradiation, x-ray irradiation, in combination with electron beam lithograph, or x-ray lithography techniques. Alternatively, the group could be removed by exposure to an electric current. The scope of the invention should, therefore, be determined not with reference to the above description, but should instead be determined with reference to the appended claims, along with the full scope of equivalents to which such claims are entitled.

All publications and patent applications referred to herein are incorporated by reference to the same extent as if each individual publication or patent application was specifically and individually incorporated by reference. The present invention now being fully described, it will be apparent to one of ordinary skill in the art that many changes and modifications can be made thereto without departing from the spirit or scope of the appended claims.

What is claimed is:

1. A method of analyzing a receptor bound to an array of nucleic acids, comprising:

providing an array of different nucleic acids immobilized on a substrate, the different nucleic acids occupying different localized areas on the substrate of less than 0.01 cm$^2$, at least some of the nucleic acids being bound to a fluorescently labeled receptor; and detecting the localized areas of the array with a detector to detect light fluoresced from the labeled receptor bound to the nucleic acids in the localized areas, the detection step being one second or less, to detect which nucleic acids bind to the labeled receptor.

2. The method of claim 1, wherein the detector is a charge coupled device.

3. The method of claim 1, further comprising exposing the array to ultraviolet light.

4. The method of claim 1, wherein each location has an area of less than 10,000 square microns.

5. The method of claim 1, wherein each location has an area of less than 100 square microns.

6. The method of claim 1, wherein the array comprises at least 1000 probes.

7. The method of claim 1, wherein the combined area occupied by the at least 1000 nucleic acids is less than 1 cm$^2$.

8. The method of claim 1, wherein the array comprises at least 10$^6$ nucleic acids per cm$^2$.

9. The method of claim 1, wherein the nucleic acids have lengths of 2–100 nucleotides.

10. The method of claim 1, wherein the labeled receptor is a labeled nucleic acid.

11. The method of claim 1, wherein the labeled receptor is a labeled polypeptide.

12. The method of claim 1, wherein the known locations are squares or rectangles.

13. The method of claim 1, wherein the method further comprises:

directing light from a light source at the surface of the substrate; and storing a pattern of fluoresced light from the different localized areas in a data storage system.

14. The method of claim 1, wherein the method further comprises translating the detector relative to the substrate.

15. The method of claim 1, further comprising analyzing the stored pattern of fluoresced light to determine which nucleic acids bind to the receptor.

16. The method of claim 1, wherein the array comprises more than 10 different nucleic acids.

17. The method of claim 1, wherein the array comprises more than 100 different nucleic acids.

18. The method of claim 1, wherein the array comprises more than 10,000 different nucleic acids.

19. The method of claim 1, wherein the array comprises more than 100,000 different nucleic acids.

20. The method of claim 1, wherein the array comprises more than 1000 different nucleic acids at a density of more than 1000 nucleic acids per cm$^2$.

21. The method of claim 1, wherein the array comprises more than 10,000 different nucleic acids at a density of more than 10,000 nucleic acids per cm$^2$.

22. The method of claim 1, wherein the array comprises more than 1,000,000 different nucleic acids at a density of more than 1,000,000 nucleic acids per cm$^2$.

23. The method of claim 1, further comprising:

illuminating the array with a device comprising:

a point light source to generate an excitation light;

an objective lens to focus the point light source at the surface of the substrate, whereby the fluorescently marked localized areas emit a fluoresced light in response to the excitation light;

a dichroic mirror to reflect light having a wavelength of the excitation light and passing light having a wavelength of the fluoresced light;

a photomultiplier and photon counter to detect the fluoresced light;

moving the substrate relative to the excitation light with an x-y translation stage; and recording the fluoresced light as a function of a position on the surface of the substrate from which the fluoresced light was emitted with an appropriately programmed computer.

24. The method of claim 1, further comprising washing the surface of the substrate to remove unbound labeled receptor.

25. An apparatus for analyzing ligand-receptor binding, comprising:

a substrate that comprises more than 1000 different ligands of known sequence collectively occupying less than 1 cm$^2$, the different ligands occupying different localized areas within the 1 cm$^2$; and a detector capable of detecting light from fluorescently marked localized areas on the substrate.

26. The apparatus of claim 25, wherein the ligands are nucleic acids.

27. The apparatus of claim 25, wherein the ligands are polypeptides.

28. The apparatus of claim 25, wherein the ligands have known sequences.

29. An apparatus for analyzing ligand-receptor binding, comprising:

a substrate that comprises at least 100 different ligands, collectively occupying less than 1 cm$^2$, the different ligands occupying different localized areas; and a detector to detect a label bound to said ligands at said localized areas.

30. The apparatus of claim 29, wherein the different ligands are nucleic acids.

31. The apparatus of claim 29, wherein the different ligands have known sequences.

32. The apparatus of claim 29, wherein the different ligands are peptides.

33. The apparatus of claim 29, wherein the marker is a fluorescent marker.

34. The apparatus of claim 29, wherein the marker is a radiolabelled marker.

35. An apparatus for detecting binding of nucleic acids; comprising:

(a) a substrate having a surface comprising more than 10 different nucleic acids, having known sequences, at localized areas on the surface of the substrate, each of the localized areas having an area of 10$^{-2}$ cm$^2$ or less, at least one of the nucleic acids being bound to a labeled receptor;

(b) an excitation light source;

(c) a detector capable of receiving a signal from fluorescently marked localized areas on the substrate;

(d) a translator to move the substrate relative to the detector; and (e) a data collection system adapted to receive input from the detector.

36. The apparatus of claim 35, wherein the nucleic acids have known sequences.

37. A method of analyzing a receptor bound to an array of polymers, comprising:

providing an array of different polymers immobilized on a substrate, the different polymers occupying different localized areas on the substrate having an area of less than 0.01 cm$^2$, at least some of the nucleic acids being bound to a labeled receptor; and detecting the localized areas of the array with a detector, each localized area being scanned for one second or less, to detect which polymers bind to the labeled receptor.

38. The method of claim 37, wherein the different polymers are different nucleic acids.

39. The method of claim 37, wherein the receptor is a nucleic acid.

40. The method of claim 37, wherein the different polymers are peptides.

41. A method for screening comprising:

exposing a substrate having a ligand in a localized area to a marked receptor; and detecting binding between the ligand and the marked receptor by scanning the substrate for 1 second or less in the localized area.

42. The method of claim 41, wherein the ligand is a nucleic acid.

43. The method of claim 41, wherein the marked receptor is a marked nucleic acid.

44. The method of claim 41, wherein the ligand is a polypeptide.

45. The method of claim 41, wherein the receptor is marked with a fluorescent label.

46. The method of claim 41, wherein the substrate has more than 1000 different ligands in 1000 different localized areas within an area less than 1 cm$^2$.

47. The method of claim 41, wherein the receptor is marked with a fluorescent marker.

48. The apparatus of claim 35, wherein the ten different nucleic acids have lengths up to 100 nucleotides.

49. An apparatus for detection of fluorescent marked locations on a substrate, wherein the substrate comprises a plurality of different polymer sequences coupled to a surface of the substrate and wherein the plurality of different polymer sequences comprises a plurality of different nucleic acid sequences, each of the different polymer sequences being coupled in a different localized area of the surface at a density of more than 1000/cm$^2$, each of the localized areas having an area of 10$^{-3}$ cm$^2$ or less, the apparatus comprising:

(a) a light source constructed and arranged to direct light at a plurality of the localized areas;

(b) a detector constructed and arranged to detect light fluoresced from the plurality of the localized areas in response to the light source;

(c) a translator constructed and arranged to translate the substrate relative to the light source whereby the plurality of the localized areas are exposed to the light; and (d) a data storage system constructed and arranged to store fluoresced light intensity as a function of location on the surface, the data storage system coupled to the translator and the detector.

50. An apparatus for detection of fluorescent markers at a plurality of localized areas on a substrate, comprising:

(a) a light source constructed and arranged to direct light at the plurality of localized areas;

(b) a detector constructed and arranged to detect light fluoresced from the plurality of localized areas in response to the light source;

(c) a translator constructed and arranged to translate the substrate relative to the light source whereby the plurality of localized areas are exposed to the light; and (d) a data storage system constructed and arranged to store fluoresced light intensity as a function of location on the surface, the data storage system coupled to the translator and the detector:

wherein the substrate comprises a plurality of different polymer sequences coupled to a surface of the substrate and wherein the plurality of different polymer sequences comprises a plurality of different nucleic acid sequences, each of the different polymer sequences being coupled in a different of the localized areas, each localized area having an area of $10^{-2}$ cm$^2$ or less.

51. An apparatus for detection of fluorescent markers at a plurality of localized areas on a substrate, comprising:

(a) a light source constructed and arranged to direct light at the plurality of localized areas, wherein the substrate comprises a plurality of different polymer sequences coupled to a surface of the substrate and wherein the plurality of different polymer sequences comprises a plurality of different nucleic acid sequences, each of the different polymer sequences being coupled in a different of the localized areas, each of the localized areas having an area of $10^{-2}$ cm$^2$ or less;

(b) a detector constructed and arranged to detect light fluoresced from the plurality of localized areas in response to the light source;

(c) a translator constructed and arranged to translate the substrate relative to the light source whereby the plurality of localized areas are exposed to the light; and (d) a data storage system constructed and arranged to store fluoresced light intensity as a function of location on the surface, the data storage system coupled to the translator and the detector.

52. A method in accordance with claim 1 further comprising collecting and analyzing data from the detection step using a computer system.

53. A method in accordance with claim 52 wherein the computer system comprises an IBM PC or AT compatible computer.

54. A method in accordance with claim 1 further comprising translating the array using an X/Y translation table.

55. A method in accordance with claim 54 wherein the X/Y translation table is controlled by a digital computer.

56. A method in accordance with claim 1 wherein the detecting step uses a photomultiplier tube.

57. A method in accordance with claim 1 wherein the detecting step uses a pre-amplifier.

58. A method in accordance with claim 1 further comprising displaying data that has been acquired using a video display.

59. A method in accordance with claim 1 further comprising detecting and displaying the output of the detection using a photomultiplier tube, a pre-amplifier, a computer, and a video display.

60. A method in accordance with claim 1 wherein the detecting step involves counting the number of photons per unit area.

61. A method in accordance with claim 1 wherein the detecting step includes acquiring data every 1 to 100 µm.

62. A method in accordance with claim 1 wherein the detection step includes acquiring data with a data collection diameter of about 0.8 to 10 µm.

63. A method in accordance with claim 1 further comprising exposing the array to laser light.

64. A method in accordance with claim 1 further comprising exposing the array to laser light having a wavelength of greater than 520 nm.

65. A method in accordance with claim 1 further comprising translating the array with an X/Y translator under the control of a computer; detecting and displaying the output of the detection using a photomultiplier tube, a pre-amplifier, and a computer; and collecting and analyzing data from the detection step using a computer system.

66. A method in accordance with claim 37 further comprising collecting and analyzing data from the detection step using a computer system.

67. A method in accordance with claim 66 wherein the computer system comprises an IBM PC or AT compatible computer.

68. A method in accordance with claim 37 further comprising translating the array using an X/Y translation table.

69. A method in accordance with claim 37 wherein the X/Y translation table is controlled by a digital computer.

70. A method in accordance with claim 37 wherein the detecting step uses a photomultiplier tube.

71. A method in accordance with claim 37 wherein the detecting step uses a pre-amplifier.

72. A method in accordance with claim 37 further comprising displaying data that has been acquired using a video display.

73. A method in accordance with claim 37 further comprising detecting and displaying the output of the detection using a photomultiplier tube, a pre-amplifier, a computer, and a video display.

74. A method in accordance with claim 37 wherein the detecting step involves counting the number of photons per unit area.

75. A method in accordance with claim 37 wherein the detecting step includes acquiring data every 1 to 100 µm.

76. A method in accordance with claim 37 wherein the detection step includes acquiring data with a data collection diameter of about 0.8 to 10 µm.

77. A method in accordance with claim 37 further comprising exposing the array to laser light.

78. A method in accordance with claim 37 further comprising exposing the array to laser light having a wavelength of greater than 520 nm.

79. A method in accordance with claim 37 further comprising translating the array with an X/Y translator under the control of a computer; detecting and displaying the output of the detection using a photomultiplier tube, a pre-amplifier, and a computer; and collecting and analyzing data from the detection step using a computer system.

80. An apparatus in accordance with claim 37 further comprising a computer system.

81. An apparatus in accordance with claim 80 wherein the computer system comprises an IBM PC or AT compatible computer.

82. An apparatus in accordance with claim 25 further comprising an X/Y translation table.

83. An apparatus in accordance with claim 25 wherein the X/Y translation table is controlled by a digital computer.

84. An apparatus in accordance with claim 25 further comprising a photomultiplier tube.

85. An apparatus in accordance with claim 25 further comprising a pre-amplifier.

86. An apparatus in accordance with claim 25 further comprising a video display.

87. An apparatus in accordance with claim 25 further comprising a photomultiplier tube, a pre-amplifier, a computer, and a video display.

88. An apparatus in accordance with claim 29 further comprising a laser.

89. An apparatus in accordance with claim 29 further comprising an X/Y translator under the control of a computer; a photomultiplier tube, a pre-amplifier, and a computer; and a computer system.

90. An apparatus in accordance with claim 29 further comprising a computer system.

91. An apparatus in accordance with claim 90 wherein the computer system comprises an IBM PC or AT compatible computer.

92. An apparatus in accordance with claim 37 further comprising an X/Y translation table.

93. An apparatus in accordance with claim 92 wherein the X/Y translation table is controlled by a digital computer.

94. An apparatus in accordance with claim 29 further comprising a photomultiplier tube.

95. An apparatus in accordance with claim 29 further comprising a pre-amplifier.

96. An apparatus in accordance with claim 29 further comprising a video display.

97. An apparatus in accordance with claim 29 further comprising a photomultiplier tube, a pre-amplifier, a computer, and a video display.

98. An apparatus in accordance with claim 29 further comprising a laser.

99. An apparatus in accordance with claim 29 further comprising an X/Y translator under the control of a computer; a photomultiplier tube, a pre-amplifier, and a computer; and a computer system.

100. A method in accordance with claim 23 wherein the receptor is a nucleic acid.

101. An apparatus in accordance with claim 25 wherein the receptor is a nucleic acid.

102. An apparatus in accordance with claim 29 wherein the receptor is a nucleic acid.

103. A method in accordance with claim 25 wherein the receptor is a peptide.

104. A method in accordance with claim 37 wherein the receptor is a peptide.

105. A method in accordance with claim 29 wherein the receptor is a peptide.

106. A method for detecting binding between a nucleic acid probe bound to a substrate and a nucleic acid target comprising:
providing an array of positionally distinguishable nucleic acids of known sequence bound to a substrate having a density of more than 300 different nucleic acids/cm$^2$; and
detecting a double stranded nucleic acid.

107. A method in accordance with claim 106 wherein the density of the array is 1,000 different nucleic acids/cm$^2$.

108. A method in accordance with claim 107 wherein the density of the array is more than 10,000 different nucleic acids/cm$^2$.

109. A method of analyzing using an array of nucleic acids, comprising:
providing an array of different nucleic acids of known sequence immobilized on a substrate at a density more than 1,000 nucleic acids/cm$^2$, the different nucleic acids being positionally distinguishable and, at least some of the nucleic acids being bound to a fluorescently labeled receptor;
illuminating an area of the array greater than $10^{-3}$ cm$^2$ with an energy source; and
detecting fluoresced light from the known locations of the array with a detector, the detection step being one second or less, to detect which nucleic acids bind to the labeled receptor.

110. A method in accordance with claim 109 wherein the receptor is a nucleic acid.

111. A method in accordance with claim 109 wherein the receptor is a peptide.

112. A method in accordance with claim 109 wherein the density is more than 10,000 nucleic acids/cm$^2$.

113. A method in accordance with claim 1 wherein the sequences of the nucleic acids are known.

114. An apparatus in accordance with claim 41 wherein the sequence of the ligand is known.

115. An apparatus in accordance with claim 49 wherein the sequences of the nucleic acids are known.

116. An apparatus in accordance with claim 50 wherein the sequences of the nucleic acids are known.

117. An apparatus in accordance with claim 51 wherein the sequences of the nucleic acids are known.

118. An apparatus in accordance with claim 35 wherein the density of the different nucleic acid sequences on the array is more than 1000/cm$^2$.

119. An apparatus in accordance with claim 37 wherein the density of the different nucleic acid sequences on the array is more than 1000/cm$^2$.

120. An apparatus in accordance with claim 41 wherein the density of the different nucleic acid sequences on the array is more than 1000/cm$^2$.

121. An apparatus in accordance with claim 50 wherein the density of the different nucleic acid sequences on the array is more than 1000/cm$^2$.

122. An apparatus in accordance with claim 51 wherein the density of the different nucleic acid sequences on the array is more than 1000/cm$^2$.

123. An apparatus in accordance with claim 1 wherein the density of the different nucleic acid sequences on the array is more than 300/cm$^2$.

124. An apparatus in accordance with claim 1 wherein the density of the different nucleic acid sequences on the array is more than 300/cm$^2$.

125. An apparatus in accordance with claim 35 wherein the density of the different nucleic acid sequences on the array is more than 300/cm$^2$.

126. An apparatus in accordance with claim 29 wherein the density of the different nucleic acid sequences on the array is more than 300/cm$^2$.

127. A method of analyzing using an array of polymers, comprising:
providing an array of different polymers of known sequence immobilized on a substrate at a density more than 1,000 polymers/cm$^2$, the different polymers being positionally distinguishable and at least some of the polymers being bound to a fluorescently labeled target polymers;
illuminating an area of the array greater than $10^{-3}$ cm$^2$ with an energy source; and
detecting fluoresced light from the known locations of the array with a detector, the detection step being one second or less, to detect which polymers on the array bind to the labeled target polymers.

128. A method in accordance with claim 127 wherein the polymers are nucleic acids.

129. A method in accordance with claim 127 wherein the polymers are peptides.

130. A method in accordance with claim 128 the density of the different nucleic acids is more than 10,000/cm$^2$.

131. A method in accordance with claim 129 wherein the density of the different peptides is more than 10,000/cm$^2$.

* * * * *

UNITED STATES PATENT AND TRADEMARK OFFICE
CERTIFICATE OF CORRECTION

PATENT NO.    : 6,403,320 B1
DATED         : June 11, 2002
INVENTOR(S)   : J. Leighton Read et al.

It is certified that error appears in the above-identified patent and that said Letters Patent is hereby corrected as shown below:

Column 1,
Lines 8-9, delete "now U.S. Pat. No. 6,197,506";
Lines 12, 14, 17 and 28, delete "now abandoned"; and
Line 66, after "underlying" delete "the".

Column 2,
Line 8, after "sequence" insert -- of --; and
Line 60, after "VLSIPS" insert -- ™ Technology (Very Large Scale Immobilized Polymer Synthesis) --.

Column 4,
Line 31, after "probes" delete "are".

Column 5,
Line 5, delete "upon".

Column 6,
Line 48, delete "peptide" and insert therefor -- ™ Technology nucleotide --;
Line 50, delete "dipeptide" and insert therefor -- ™ Technology --; and
Line 52, after "VLSIPS" add -- ™ Technology --.

Column 10,
Lines 8, 21 and 30, after "VLSIPS" add -- ™ Technology --.

Column 12,
Line 6, after "VLSIPS" add -- ™ Technology --;
Line 10, delete "(VLSIPS) technology" and insert therefor
-- (VLSIPS ™) Technology --;
Line 23, delete "technology" and insert therefor -- ™ Technology --;
Line 30, delete "U.S. Ser. No. 07/492,462 (VLSIPS CIP)" and insert therefor
-- Pirrung et al. (1992) U.S. Pat. No. 5,143,854 --;
Line 37, after "VLSIPS" add -- ™ Technology --;
Lines 38-39, delete "U.S. Ser. No. 07/492,462 (VLSIPS CIP)" and insert therefor
-- Pirrung et al. (1992) U.S. Pat. No. 5,143,854 --;
Lines 39-40, delete "U.S. Ser. No. 07/624,120 (automated VLSIPS)" and insert therefor
-- U.S. Pat. No. 5,489,678 --;
Line 41, after "VLSIPS" add -- ™ Technology --;
Line 47, delete "technology" and insert therefor -- ™ Technology --;
Line 51, after "10$^2$" add -- /cm$^2$ --; and
Line 62, delete "U.S. Ser. No. 07/624,1200 (automated VLSIPS) and U.S. Ser. No. 07/626,730, (sequencing by synthesis)" and insert therefor -- U.S. Pat. No. 5,489,678 and U.S. Pat. No. 5,427,408 --.

UNITED STATES PATENT AND TRADEMARK OFFICE
CERTIFICATE OF CORRECTION

PATENT NO. : 6,403,320 B1
DATED : June 11, 2002
INVENTOR(S) : J. Leighton Read et al.

It is certified that error appears in the above-identified patent and that said Letters Patent is hereby corrected as shown below:

Column 13,
Line 23, after "VLSIPS" add -- ™ Technology --.

Column 45,
Lines 36-37, delete "U.S. Ser. No. 07/492,462 (VLSIPS CIP)" and insert therefor -- Pirrung et al. (1992) U.S. Pat. No. 5,143,854 --; and
Line 40, delete "U.S. Ser. No. 07/624,120 (automated VLSIPS)" and insert therefor -- U.S. Pat. No. 5,489,678 --.

Column 47,
Line 17, after "VLSIPS" add -- ™ Technology --;
Line 52, delete "(VLSIPS parent)" and insert therefor -- from which CIP --;
Line 53, delete "(VLSIPS CIP,)" and insert therefor -- issued as U.S. Pat. No. 5,143,854, and --;
Lines 53-54, delete "(caged biotin parent), and" and insert therefor -- from which CIP --; and
Lines 54-55, delete "(caged biotin CIP)" and insert therefor -- issued as U.S. Pat. No. 5,252,743 --.

Column 48,
Line 9, delete "(VLSIPS parent); or" and insert therefor -- from which CIP --;
Line 10, delete "(VLSIPS CIP)" and insert therefor -- issued as U.S. Pat. No. 5,143,854 --;
Lines 10-11, delete "U.S. Ser. No. 07/624,120, (automated VLSIPS)" and insert therefor -- U.S. Pat. No. 5,489,678 --;
Lines 20-21, delete "U.S. Ser. No. 07/624,120, (automated VLSIPS)" and insert therefor -- U.S. Pat. No. 5,489,678 --;
Line 57, delete "Theorethical" and insert therefor -- Theoretical --; and
Line 60, delete "technology" and insert therefor -- ™ Technology --.

Column 49,
Line 2, delete "e.e." and insert therefor -- e.g. --;
Line 4, delete "Khropko" and insert therefor -- Khrapko --; and
Lines 29 and 43, after "VLSIPS" add -- ™ Technology --.

Column 50,
Line 10, after "that" add -- the --.

Column 51,
Line 29, after "way" delete -- , --.

UNITED STATES PATENT AND TRADEMARK OFFICE
CERTIFICATE OF CORRECTION

PATENT NO. : 6,403,320 B1  
DATED : June 11, 2002  
INVENTOR(S) : J. Leighton Read et al.

Page 3 of 10

It is certified that error appears in the above-identified patent and that said Letters Patent is hereby corrected as shown below:

Column 54,
Line 21, delete "U.S. Ser. No. 07/624,120 (" and insert therefor
-- U.S. Pat. No. 5,489,678 --; and after "VLSIPS" delete ")" and insert therefor
-- ™ Technology --.

Column 55,
Line 17, after "VLSIPS" add -- ™ Technology --;
Lines 19-20, delete "U.S. Ser. No. 07/435,316 (caged biotin parent), and U.S. Ser. No. 07/612,671 (caged biotin CIP)" and insert therefor -- Barrett et al. (1993) U.S. Pat. No. 5,252,743 --;
Line 28, delete "VISIPS" and insert therefor -- VLSIPS™ Technology --;
Lines 31, 32 and 35, after "VLSIPS" add -- ™ Technology --;
Line 58, delete "affixed" and insert therefor -- affixing them --; and
Lines 60-61, delete "U.S. Ser. No. 07/362,901 (VLSIPS parent); U.S. Ser. No. 07/492,462 (VLSIPS CIP)" and insert therefor -- Pirrung et al. (1992) U.S. Pat. No. 5,143,854 --.

Column 56,
Line 19, after "particularly" add -- through the --;
Lines 24-26, delete "U.S. Ser. No. 07/492,462 (VLSIPS CIP); U.S. Ser. No. 07/624,120 (automated VLSIPS); and U.S. Ser. No. 07/612,671 (caged biotin CIP)" and insert therefor -- Pirrung et al. (1992) U.S. Pat. No. 5,143,854; U.S. Pat. No. 5,489,678; and Barrett et al. (1993) U.S. Pat. No. 5,252,743 --;
Lines 31-32, delete "U.S. Ser. No. 07/492,462 (VLSIPS CIP); and U.S. Ser. No. 07/624,120, (automated VLSIPS)" and insert therefor -- Pirrung et al. (1992) U.S. Pat. No. 5,143,854; and U.S. Pat No. 5,489,678 --;
Lines 45-46, delete "U.S. Ser. No. 07/492,462 (VLSIPS CIP) and U.S. Ser. No. 07/624,120, (automated VLSIPS)" and insert therefor -- U.S. Pat. No. 5,489,678 --; and
Line 61, delete "are" and insert -- is --.

Column 57,
Lines 6-8, delete "U.S. Ser. No. 07/624,120 (automated VLSIPS) which was filed simultaneously with this application" and insert therefor -- U.S. Pat. No. 5,489,678 --;
Lines 17-18, delete "U.S. Ser. No. 07/624,120, (automated VLSIPS)" and insert therefor -- U.S. Pat. No. 5,489,678 --;
Line 34, delete "converse" and insert therefor -- confer --; and
Line 39, delete "technology"and insert therefor -- ™ Technology --.

UNITED STATES PATENT AND TRADEMARK OFFICE
CERTIFICATE OF CORRECTION

PATENT NO. : 6,403,320 B1
DATED : June 11, 2002
INVENTOR(S) : J. Leighton Read et al.

It is certified that error appears in the above-identified patent and that said Letters Patent is hereby corrected as shown below:

Column 58,
Line 10, after "to" add -- the --;
Line 48, after "that" delete -- it --;
Line 48, after "will" add -- allow the probe to --; and
Line 51, delete "close" and insert therefor -- closely --.

Column 60,
Lines 5, 12 and 32, delete "arylammonium" and insert therefor -- alkylammonium --;
Line 33, after "manner" add -- such --;
Line 39, after "specific" add -- such --;
Line 43, after "VLSIPS" add -- $^{TM}$ Technology --;
Lines 46-47, delete "VLZIPS" and insert therefor -- VLSIPS$^{TM}$ Technology --; and
Lines 58-60, delete "U.S. Ser. No. 07/492,462 (VLSIPS CIP) and U.S. Ser. No. 07/624,120 (automated VLSIPS)" and insert therefor -- Pirrung et al. (1992) U.S. Pat. No. 5,143,854 and U.S. Pat. No. 5,489,678 --.

Column 61,
Line 60, after "VLSIPS" add -- $^{TM}$ Technology --;
Line 61, delete "technology"; and
Line 63, delete "technology" and insert therefor -- $^{TM}$ Technology --.

Column 62,
Lines 15, 17, 23, 35, 54, 56, 57, 65 and 67, after "VLSIPS" add -- $^{TM}$ Technology --.

Column 63,
Line 2, after "VLSIPS" add -- $^{TM}$ Technology --;
Line 46, delete "U.S. Ser. No. 07/612,671 (caged biotin CIP)" and insert therefor -- U.S. Pat. No. 5,252,743 --; and
Line 52, after "VLSIPS" add -- $^{TM}$ Technology --.

Column 64,
Line 5, after "VLSIPS" add -- $^{TM}$ Technology --; and
Line 9, delete "U.S. Ser. No. 07/626,730, (sequencing by synthesis);" and insert therefor -- U.S. Pat. No. 5,547,839 --.

Column 65,
Lines 4, 20 and 61, after "VLSIPS" add -- $^{TM}$ Technology --;
Line 28, after "complex" delete ", it" and insert therefor -- . It --; and
Line 64, delete "expressed".

UNITED STATES PATENT AND TRADEMARK OFFICE
CERTIFICATE OF CORRECTION

PATENT NO. : 6,403,320 B1
DATED : June 11, 2002
INVENTOR(S) : J. Leighton Read et al.

It is certified that error appears in the above-identified patent and that said Letters Patent is hereby corrected as shown below:

Column 66,
Line 52, after "VLSIPS" add -- ™ Technology --; and delete "use" and insert -- used --.

Column 67,
Line 35, after "susceptibilities," add -- and --.

Column 68,
Line 9, delete "fingerprinted" and insert therefor -- fingerprinting --; and delete "in" and insert -- an --; and
Line 10, delete "mosaism" and insert therefor -- mosaicism --.

Column 69,
Lines 11-12, delete "Again, the target sequences may be desired to be fragmented" and insert therefor -- Again, it may be desirable to fragment the target sequences --.

Column 70,
Line 31, after "VLSIPS" add -- ™ Technology --; and
Line 46, after "allows" delete "the".

Column 71,
Line 29, delete "to define" and insert therefor -- in defining --;
Line 40, delete "as" and insert therefor -- are --; and
Line 65, delete "upon" and insert therefor -- by --.

Column 72,
Line 19, delete "amendable" and insert therefor -- detectable --;
Line 28, delete "present" and insert therefor -- presently available --;
Line 29, delete "screen" and insert therefor -- screens --;
Line 44, delete "also is" and insert therefor -- is also --;
Lines 59-61, delete "U.S. Ser. No. 07/492,462 (VLSIPS CIP), and U.S. Ser. No. 07/624,120, (automated VLSIPS)" and insert therefor -- Pirrung et al. (1992) U.S. Pat. No. 5,143,854; and U.S. Pat. No. 5,489,678 --; and
Line 67, after "VLSIPS" add -- ™ Technology --.

Column 73,
Line 1, after "VLSIPS" add --™ Technology --; and
Lines 6-7, delete "U.S. Ser. No. 07/462,492 (VLSIPS CIP) and U.S. Ser. No. 07/624,120, (automated VLSIPS)" and insert therefor -- Pirrung et al. (1992) U.S. Pat. No. 5,143,854; and U.S. Pat. No. 5,489,678 --.

UNITED STATES PATENT AND TRADEMARK OFFICE
CERTIFICATE OF CORRECTION

PATENT NO. : 6,403,320 B1
DATED : June 11, 2002
INVENTOR(S) : J. Leighton Read et al.

It is certified that error appears in the above-identified patent and that said Letters Patent is hereby corrected as shown below:

Column 74,
Lines 6-7, delete " U.S. Ser. No. 07/624,120, (automated VLSIPS)" and insert therefor -- U.S. Pat. No. 5,489,678 --;
Line 24, delete "then" and insert therefor -- them --;
Lines 36, 43 and 47, after "VLSIPS" add -- ™ Technology --;
Lines 48-49, delete "U.S. Ser. No. 07/492,462 (VLSIPS CIP) and U.S. Ser. No. 07/624,120, (automated VLSIPS)" and insert therefor -- Pirrung et al. (1992) U.S. Pat. No. 5,143,854 and U.S. Pat. No. 5,489,678 --;
Line 53, delete " U.S. Ser. No. 07/624.120 (automated VLSIPS)" and insert therefor -- U.S. Pat. No. 5,489,678 --; and
Line 66, delete "U.S. Ser. No. 07/492,462" and insert therefor -- which issued as U.S. Pat. No. 5,143,854 --.

Column 75,
Line 11, delete "U.S. Ser. No. 07/492,462 (VLSIPS CIP) and U.S. Ser. No. 07/624,120 (automated VLSIPS)" and insert therefor -- Pirrung et al. (1992) U.S. Pat. No. 5,143,854 and U.S. Pat. No. 5,489,678 --;
Line 16, after "VLSIPS" add -- ™ Technology --; and
Line 66, delete "anaines" and insert therefor -- amines --.

Column 78,
Line 18, after "VLSIPS" add -- ™ Technology --; and delete "have been" and insert therefor -- include, for example --.

Column 81,
Line 34, after "functionalized" add -- , --; and
Line 35, after "(see example below)" add -- : --.

Column 82,
Line 1, delete "group" and insert therefor -- groups --;
Line 2, after "acetate" add -- : --;
Line 24, after "ether" delete "." and insert therefor -- : --; and
Line 54, delete "Related to" and insert therefor -- With respect to --;
Line 62, after "VLSIPS" add -- ™ Technology --; and
Line 63, delete "U.S. Ser. No. 07/624,120, (automated VLSIPS)" and insert therefor -- U.S. Pat. No. 5,489,678 --.

Column 84,
Line 6, after "VLSIPS" add -- ™ Technology --;
Line 44, delete "in our labs"; and
Line 49, delete "Brosystems" and insert therefor -- Biosystems --.

UNITED STATES PATENT AND TRADEMARK OFFICE
CERTIFICATE OF CORRECTION

PATENT NO. : 6,403,320 B1
DATED : June 11, 2002
INVENTOR(S) : J. Leighton Read et al.

It is certified that error appears in the above-identified patent and that said Letters Patent is hereby corrected as shown below:

Column 85,
Line 41, delete "U.S. Ser. No. 07/612,671 (caged biotin CIP)" and insert -- Barrett et al. (1993) U.S. Pat. No. 5,252,743 --.

Column 86,
Lines 13 and 14, after "VLSIPS" add -- ™ Technology --.

Column 87,
Line 24, delete "Cell" and insert therefor -- In addition to cell --;
Line 41, after "VLSIPS" add -- ™ --;
Line 44, delete "CARIOS" and insert therefor -- CABIOS --; and
Line 49, after "VLSIPS" add -- ™ Technology --.

Column 89,
Line 2, after "*coli*" delete ")".

Column 90,
Line 13, delete "ficoerythrin" and insert therefor -- phycoerythrin --; and
Line 15, delete "primary" and insert therefor -- primarily --.

Column 91,
Line 47, delete "U.S. Ser. No. 07/649,642 (VLSIPS CIP); and U.S. Ser. No. 07/624,120, (automated VLSIPS)" and insert therefor -- Pirrung et al. (1992) U.S. Pat. No. 5,143,854 and U.S. Pat. No. 5,489,678 --; and
Line 56, delete "U.S. Ser. No. 07/624,120, (VLSIPS)" and insert therefor -- U.S. Pat. No. 5,489,678 --.

Column 92,
Lines 23-24, delete "U.S. Ser. No. 07/624,120, (automated VLSIPS)" and insert therefor -- U.S. Pat. No. 5,489,678 --;
Line 39, after "of" add -- a --; and
Line 47, after "fragmented" delete "up".

Column 94,
Lines 45, 52, 60 and 67, after "VLSIPS" add -- ™ Technology --; and
Line 47, delete "simply" and insert therefor -- simplify --.

Column 95,
Line 2, after "adjacent" add -- to --;
Lines 5 and 33, after "VLSIPS" add -- ™ Technology --;
Line 44, after "utilized" add -- for --; and
Line 66, after "sequencing" delete "of".

UNITED STATES PATENT AND TRADEMARK OFFICE
CERTIFICATE OF CORRECTION

PATENT NO. : 6,403,320 B1
DATED : June 11, 2002
INVENTOR(S) : J. Leighton Read et al.

It is certified that error appears in the above-identified patent and that said Letters Patent is hereby corrected as shown below:

Column 96,
Line 58, after "VLSIPS" add -- ™ --; and
Lines 60-61, delete "U.S. Ser. No. 07/612,671 (caged biotin CIP)" and insert therefor -- Barrett et al. (1993) U.S. Pat. No. 5,252,743 --.

Column 97,
Line 26, after "VLSIPS" add -- ™ Technology --; and
Line 56, delete "An" and insert therefor -- In --.

Column 98,
Line 26, delete "preventative" and insert -- preventive --.

Column 99,
Line 29, delete "(VLSIPS parent), filed Jun. 7, 1989" and insert therefor -- , from which CIP 07/492,462 issued as U.S. Pat. No. 5,143,854 --;
Lines 29-30, delete "Pirrung et al., U.S. Ser. No. 07/492,462 (VLSIPS CIP), filed Mar. 7, 1990; Barrett et al."; and
Lines 33-36, delete "(caged biotin CIP), filed Nov. 13, 1990; and commonly assigned and simultaneously filed applications U.S. Ser. No. 07/624,120, (automated VLSIPS) and U.S. Ser. No. 07/626,730, (sequencing by synthesis)" and insert therefor -- from which CIP 07/612,671 issued as U.S. Pat. No. 5,252,743 and U.S. Pat. No. 5,489,678 --.

Column 100,
Lines 29-30, delete "5'-O-nitrovertryl" and insert therefor -- 5'-O-nitroveratryl --; and
Line 31, delete "5'-O-nitrovertryl" and insert therefor -- 5'-O-nitroveratryl --.

Column 101,
Line 21, after "VLSIPS" add -- ™ Technology --.

Column 103,
Line 48, after "added" add -- to --; and
Line 56, after "was" delete "a".

Column 106,
Lines 30-31, delete "U.S. Ser. No. 07/492,462 (VLSIPS CIP) and U.S. Ser. No. 07/624,120, (automated VLSIPS)" and insert therefor -- Pirrung et al. (1992) U.S. Pat. No. 5,143,854 and U.S. Pat. No. 5,489,678 --; and
Lines 52-54, delete "U.S. Ser. No. 07/492,462 (VLSIPS CIP), and U.S. Ser. No. 07/624,120, (automated VLSIPS)" and insert therefor -- Pirrung et al. (1992) U.S. Pat. No. 5,143,854 and U.S. Pat. No. 5,489,678 --.

UNITED STATES PATENT AND TRADEMARK OFFICE
CERTIFICATE OF CORRECTION

PATENT NO. : 6,403,320 B1
DATED : June 11, 2002
INVENTOR(S) : J. Leighton Read et al.

It is certified that error appears in the above-identified patent and that said Letters Patent is hereby corrected as shown below:

Column 107,
Lines 56-58, delete "U.S. Ser. No. 07/492,462 (VLSIPS CIP); and U.S. Ser. No. 07/624,120" and insert therefor -- Pirrung et al. (1992) U.S. Pat. No. 5,143,854 --;

Column 108,
Lines 16-17, delete "U.S. Ser. No. 07/492,462 (VLSIPS CIP)" and insert therefor -- Pirrung et al. (1992) U.S. Pat. No. 5,143,854 --;
Lines 27-28, delete "U.S. Ser. No. 07/624,120" and insert therefor -- U.S. Pat. No. 5,489,678 --;
Line 39, delete "U.S. Ser. No. 07/492,462 (VLSIPS CIP)" and insert -- Pirrung et al. (1992) U.S. Pat. No. 5,143,854 --;
Line 48, delete "durapore" and insert -- Durapore$^{TM}$ --; and
Line 49, after "Durapore" add -- $^{TM}$ --.

Column 109,
Lines 26-27, delete "U.S. Ser. No. 07/492,462 (VLSIPS CIP)" and insert therefor -- Pirrung et al. (1992) U.S. Pat. No. 5,143,854 --; and
Line 62, delete "U.S. Ser. No. 07/492,462 (VLSIPS CIP)" and insert therefor -- Pirrung et al. (1992) U.S. Pat. No. 5,143,854 --.

Column 110,
Line 3, delete "NOVC" and insert therefor -- NVOC --;
Line 11, delete "U.S. Ser. No. 07/492,462 (VLSIPS CIP)" and insert therefor -- Pirrung et al. (1992) U.S. Pat. No. 5,143,854 --; and
Line 67, delete "that".

Column 111,
Line 26, delete "U.S. Ser. No. 07/492,462 (VLSIPS CIP)" and insert therefor -- Pirrung et al. (1992) U.S. Pat. No. 5,143,854 --.

Column 113,
Line 2, delete "(caged biotin parent) and" and insert therefor -- from which CIP --;
Lines 2-3, delete "(caged biotin CIP)" and insert therefor -- issued as U.S. Pat. No. 5,252,743 --; and
Line 52, delete "are" and insert -- is --.

UNITED STATES PATENT AND TRADEMARK OFFICE
CERTIFICATE OF CORRECTION

PATENT NO. : 6,403,320 B1
DATED : June 11, 2002
INVENTOR(S) : J. Leighton Read et al.

It is certified that error appears in the above-identified patent and that said Letters Patent is hereby corrected as shown below:

Column 114,
Lines 23-24, delete "U.S. Ser. No. 07/612,671 (caged biotin CIP)" and insert therefor -- Barrett et al. (1993) U.S. Pat. No. 5,252,743 --; and
Line 33, after "VLSIPS" add -- ™ Technology --.

Column 116,
Line 39, before "non-hybridization" add -- and --.

Column 117,
Line 41, after "environment" add -- to --.

Column 118,
Line 14, delete "her" and insert therefor -- their --.

Column 119,
Lines 11, 19, 34 and 36, after "VLSIPS" add -- ™ Technology --.

Column 122,
Line 4, delete "nucleic acids" and insert -- different polymers --.

Column 126,
Line 18, delete "apparatus" and insert therefor -- method --;
Line 18, delete "37" and insert therefor -- 38 --; and
Line 61, after "128" add -- wherein --.

Signed and Sealed this

Second Day of December, 2003

JAMES E. ROGAN
*Director of the United States Patent and Trademark Office*